United States Patent
Kim et al.

(10) Patent No.: US 12,127,474 B2
(45) Date of Patent: Oct. 22, 2024

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

(71) Applicants: SAMSUNG SDI CO., LTD., Yongin-si (KR); SAMSUNG ELECTRONICS CO., LTD., Suwon-si (KR)

(72) Inventors: Jun Seok Kim, Suwon-si (KR); Jinhyun Lui, Suwon-si (KR); Dong Min Kang, Suwon-si (KR); Jongwoo Won, Suwon-si (KR); Byoungkwan Lee, Suwon-si (KR); Sangshin Lee, Suwon-si (KR); Jihun Shin, Suwon-si (KR); Jinseok Jang, Suwon-si (KR); Sung-Hyun Jung, Suwon-si (KR)

(73) Assignees: SAMSUNG SDI CO., LTD., Yongin-si (KR); SAMSUNG ELECTRONICS CO., LTD., Suwon-si (KR)

(*) Notice: Subject to any disclaimer, the term of this patent is extended or adjusted under 35 U.S.C. 154(b) by 830 days.

(21) Appl. No.: 16/973,867

(22) PCT Filed: Feb. 26, 2019

(86) PCT No.: PCT/KR2019/002327
§ 371 (c)(1),
(2) Date: Dec. 10, 2020

(87) PCT Pub. No.: WO2019/240352
PCT Pub. Date: Dec. 19, 2019

(65) Prior Publication Data
US 2021/0184128 A1    Jun. 17, 2021

(30) Foreign Application Priority Data
Jun. 15, 2018 (KR) .................. 10-2018-0069125

(51) Int. Cl.
*H01L 51/50* (2006.01)
*C07D 209/88* (2006.01)
(Continued)

(52) U.S. Cl.
CPC ......... *H10K 85/636* (2023.02); *C07D 209/88* (2013.01); *C07D 251/24* (2013.01);
(Continued)

(58) Field of Classification Search
CPC .. C07D 209/88; C07D 251/24; C07D 405/04; C09K 11/06; C09K 2211/1018;
(Continued)

(56) References Cited

U.S. PATENT DOCUMENTS 9,761,812 B2    8/2017 Osaka et al.
2015/0280136 A1    10/2015 Ryu et al.

FOREIGN PATENT DOCUMENTS

| CN | 104755462 A | 7/2015 |
|---|---|---|
| CN | 104903421 A | 9/2015 |

(Continued)

OTHER PUBLICATIONS

European Search Report dated Apr. 26, 2022.
(Continued)

*Primary Examiner* — Gregory D Clark
(74) *Attorney, Agent, or Firm* — Lee IP Law, P.C.

(57) ABSTRACT

The present invention is related to a first compound for an organic optoelectronic device represented by Chemical Formula 1, a composition for an organic optoelectronic device including the same, an organic optoelectronic device, and a display device.
In Chemical Formula 1, definitions of each substituent are the same as defined in the specification.

19 Claims, 1 Drawing Sheet

(51) Int. Cl.
  *C07D 251/24* (2006.01)
  *C07D 405/04* (2006.01)
  *C07D 405/14* (2006.01)
  *C07D 495/04* (2006.01)
  *C09K 11/06* (2006.01)
  *H10K 85/60* (2023.01)
  *H10K 50/11* (2023.01)
  *H10K 50/15* (2023.01)
  *H10K 101/10* (2023.01)

(52) U.S. Cl.
  CPC ......... *C07D 405/04* (2013.01); *C07D 405/14* (2013.01); *C07D 495/04* (2013.01); *C09K 11/06* (2013.01); *H10K 85/615* (2023.02); *H10K 85/622* (2023.02); *H10K 85/633* (2023.02); *H10K 85/654* (2023.02); *H10K 85/657* (2023.02); *H10K 85/6572* (2023.02); *H10K 85/6574* (2023.02); *C09K 2211/1018* (2013.01); *H10K 50/11* (2023.02); *H10K 50/15* (2023.02); *H10K 2101/10* (2023.02)

(58) Field of Classification Search
  CPC .... C09K 2211/1022; C09K 2211/1029; H10K 85/633; H10K 85/636; H10K 85/654; H10K 85/657; H10K 85/6572; H10K 50/10; H10K 50/15; H10K 50/30; H10K 50/113; H10K 50/622; H10K 50/631; H10K 50/155; H10K 50/852; H10K 50/342; H10K 85/342; H10K 85/6574
  See application file for complete search history.

(56) References Cited

FOREIGN PATENT DOCUMENTS

| | | | |
|---|---|---|---|
| JP | H 4-178670 A | 6/1992 | |
| JP | 5133259 B2 | 11/2012 | |
| JP | 5609256 B2 | 9/2014 | |
| JP | 2016-149558 A | 8/2016 | |
| JP | 6059888 B2 | 12/2016 | |
| KR | 10-0573137 B1 | 4/2006 | |
| KR | 10-1127264 B1 | 3/2012 | |
| KR | 10-1347519 B1 | 1/2014 | |
| KR | 10-1350581 B1 | 1/2014 | |
| KR | 10-2014-0049227 A | 4/2014 | |
| KR | 2014-049227 A * | 4/2014 | ............ H01L 51/00 |
| KR | 10-1395080 B1 | 5/2014 | |
| KR | 10-1443755 B1 | 10/2014 | |
| KR | 10-2014-0135524 A | 11/2014 | |
| KR | 10-1462070 B1 | 11/2014 | |
| KR | 10-2015-0004099 A | 1/2015 | |
| KR | 10-1527181 B1 | 6/2015 | |
| KR | 10-1550429 B1 | 9/2015 | |
| KR | 10-2015-0136942 A | 12/2015 | |
| KR | 10-2016-0053561 A | 5/2016 | |
| KR | 10-1649950 B1 | 8/2016 | |
| KR | 10-2016-0114526 A | 10/2016 | |
| KR | 10-2017-0037522 A | 4/2017 | |
| KR | 10-2017-0083765 A | 7/2017 | |
| KR | 10-2018-0013449 A | 2/2018 | |
| KR | 10-2018-0093354 A | 8/2018 | |
| WO | WO 2016/072691 A1 | 5/2016 | |
| WO | WO 2016/153283 A1 | 9/2016 | |

OTHER PUBLICATIONS

International Search Report dated Jun. 7, 2019 for PCT/KR2019/002327.
EP Partial Supplementary Search Report mailed Jan. 24, 2022 for corresponding European Patent Application No. 19819247.8.
European Office Action dated Jan. 4, 2024, of the corresponding European Patent Application No. 19819247.8.
Chinese Office action dated Jun. 29, 2024.

* cited by examiner

【Figure 1】
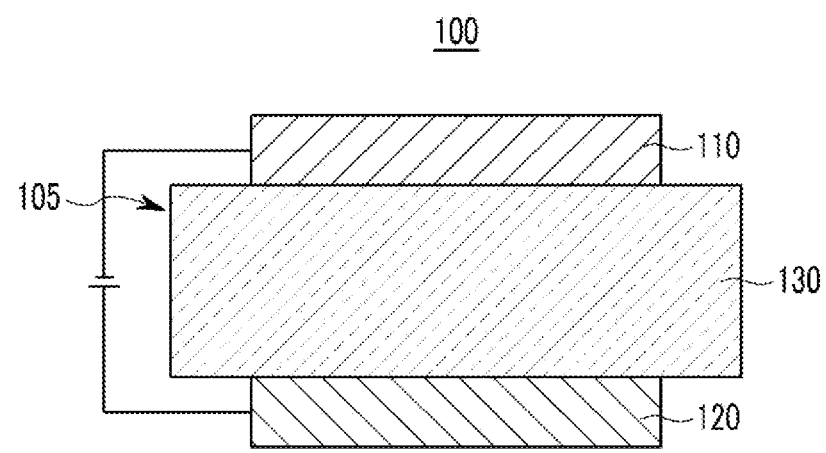
【Figure 2】
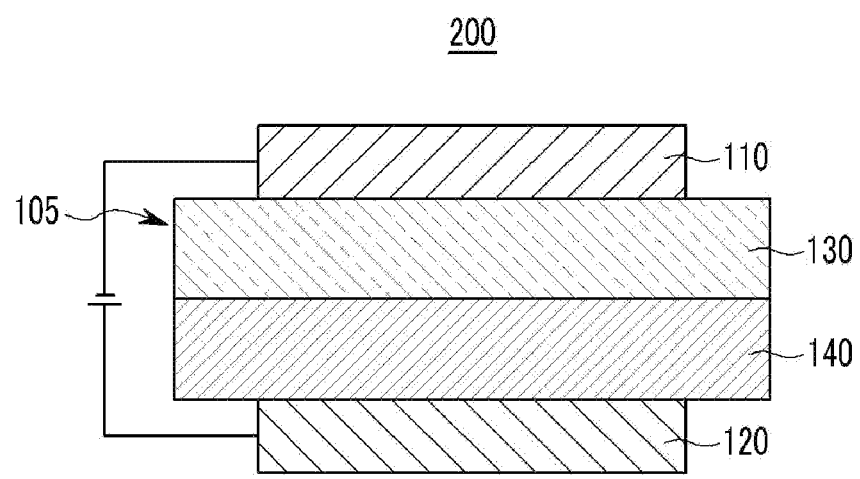

COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

CROSS REFERENCE TO RELATED APPLICATIONS

This is the U.S. national phase application based on PCT Application No. PCT/KR2019/002327, filed Feb. 26, 2019, which is based on Korean Patent Application No. 10-2018-0069125, filed Jun. 15, 2018, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and Performance of an organic light emitting diode may be affected by organic materials disposed between electrodes.

DISCLOSURE

Technical Problem

An embodiment provides a compound for an organic optoelectronic device capable of realizing an organic optoelectronic device having high efficiency and a long life-span.

Another embodiment provides a composition for an organic optoelectronic device including the compound for an organic optoelectronic device.

Yet another embodiment provides an organic optoelectronic device including the composition for an organic optoelectronic device.

Still another embodiment provides a display device including the organic optoelectronic device.

Technical Solution

According to an embodiment, a compound for an organic optoelectronic device represented by Chemical Formula 1 is provided.

[Chemical Formula 1]

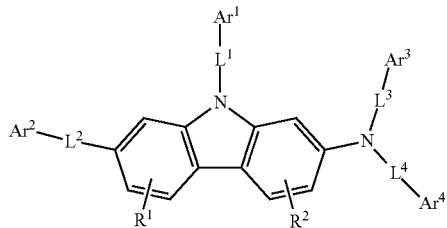

In Chemical Formula 1,
$Ar^1$ and $Ar^2$ are independently a substituted or unsubstituted C6 to C12 aryl group,
$Ar^3$ and $Ar^4$ are independently a substituted or unsubstituted C6 to C30 aryl group,
$L^1$ is a single bond or a phenylene group,
$L^2$ to $L^4$ are independently a single bond or a substituted or unsubstituted C6 to C12 arylene group,
$R^1$ and $R^2$ are independently hydrogen, deuterium, a cyano group, or a substituted or unsubstituted C1 to C10 alkyl group.

According to another embodiment, a composition for an organic optoelectronic device includes the compound for an organic optoelectronic device as a first compound for an organic optoelectronic device, a compound represented by Chemical Formula 2 as a second compound for an organic optoelectronic device.

[Chemical Formula 2]

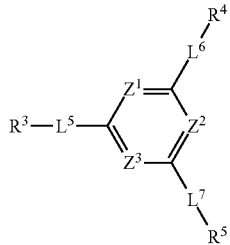

In Chemical Formula 2,
$Z^1$ to $Z^3$ are independently N or $CR^a$,
at least two of $Z^1$ to $Z^3$ are N,
$R^a$ is hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof,
$L^5$ to $L^7$ are independently a single bond, a substituted or unsubstituted C6 to C20 arylene group, a substituted or unsubstituted C2 to C20 heterocyclic group, or a combination thereof,
$R^3$ to $R^5$ are independently substituted or unsubstituted C6 to C30 aryl group, a substituted or unsubstituted C2 to C30 heterocyclic group, or a combination thereof,
at least one of $R^3$ to $R^5$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group, and $R^a$ and $R^3$ to $R^5$ are independently present or adjacent groups thereof are linked with each other to form a substituted or unsubstituted aliphatic, aromatic, or heteroaromatic monocyclic or polycyclic ring.

According to another embodiment, an organic optoelectronic device includes an anode and a cathode facing each other, and at least one organic layer disposed between the anode and the cathode, wherein the organic layer includes the compound for an organic optoelectronic device or the composition for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

DESCRIPTION OF SYMBOLS 100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In examples of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, specific examples of the present invention, the "substituted" refers to replacement of at least one hydrogen of a substituent or a compound by deuterium, a C1 to C5 alkyl group, a C6 to C18 aryl group, a pyridinyl group, quinolinyl group, an isoquinolinyl group, a dibenzofuranyl group, a dibenzothiophenyl group, or a carbazolyl group. In addition, specific examples of the present invention, the "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, specific examples of the present invention, the "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a dibenzofuranyl group, or a dibenzothiophenyl group.

In the present specification when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatom s.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, or a combination thereof, but is not limited thereto.

In the present specification, "adjacent groups thereof are linked with each other to form a substituted or unsubstituted aromatic monocyclic or polycyclic ring, or a substituted or unsubstituted aromatic monocyclic or polycyclic heterocyclic ring" means that any two adjacent substituents directly substituting an aromatic ring or an aromatic heterocyclic ring with a single bond without a linking group are linked to form an additional ring.

For example, adjacent groups are linked with each other to form a substituted or unsubstituted aromatic monocyclic or polycyclic ring and examples may be a substituted or unsubstituted aromatic monocyclic ring.

For example, any two substituents directly substituting a pyrimidine ring are linked with each other to form an additional ring, and thereby a substituted or unsubstituted quinazolinyl group may be formed along with the pyrimidine ring.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

[Chemical Formula 1]

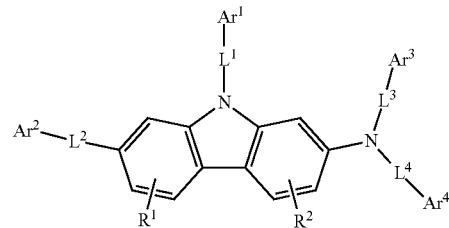

In Chemical Formula 1,
$Ar^1$ and $Ar^2$ are independently a substituted or unsubstituted C6 to C12 aryl group,
$Ar^3$ and $Ar^4$ are independently a substituted or unsubstituted C6 to C30 aryl group,
$L^1$ is a single bond or a phenylene group,
$L^2$ to $L^4$ are independently a single bond or a substituted or unsubstituted C6 to C12 arylene group, and
$R^1$ and $R^2$ are independently hydrogen, deuterium, a cyano group, or a substituted or unsubstituted C1 to C10 alkyl group.

In the compound for an organic optoelectronic device according to an embodiment, one benzene ring of the carbazole is substituted with an aryl group at the 2-position, the other benzene ring is directly substituted with the arylamine group at the 2-position, and the carbazole is substituted with an aryl group having 18 or less carbon atoms in an N-direction.

The compound where one benzene ring of the carbazole is substituted with an aryl group at the 2-position may improve life-span of the device compared with a compound substituted with an aryl group at other positions and unsubstituted compound. The substituted compound at only 2-position may improve driving and life-span of a device compared with the compound that is additionally substituted at other positions.

In addition, a structure in which the other benzene ring of the carbazole is directly substituted with the arylamine group at the 2-position may realize a device having improved in driving and life-span characteristics, compared with a structure in which the other benzene ring is substituted with the arylamine group at other positions and is substituted through a linking group, and in particular, when an aryl group is substituted with the amine group, an appropriate HOMO energy level may be obtained, thereby realizing a device improved in driving and life-span characteristics.

On the other hand, the compound including an aryl group having 18 or less carbon atoms in the N-direction of the carbazole may have a higher HOMO energy level than a compound having a structure including carbon atoms of greater than 18 or a heteroaryl group, and thus a device including the same may exhibit improved life-span and driving.

Accordingly, a device to which the compound according to the present invention is applied may realize improved long life-span characteristics.

For example, $Ar^1$ and $Ar^2$ may independently be a substituted or unsubstituted phenyl group, a substituted or unsubstituted biphenyl group, or a substituted or unsubstituted naphthyl group.

For example, $L^2$ may be a single bond or a phenylene group.

For specific examples, $Ar^1$ and $Ar^2$ may independently be a substituted or unsubstituted phenyl group, and $L^2$ may be a single bond.

For example, $Ar^3$ and $Ar^4$ may independently be a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, or a substituted or unsubstituted phenanthrenyl group.

For example, $L^3$ and $L^4$ may independently be a single bond, a phenylene group, or a naphthylene group.

For specific examples, $Ar^3$ and $Ar^4$ may independently be a substituted or unsubstituted phenyl group, a substituted or unsubstituted biphenyl group, or a substituted or unsubstituted naphthyl group and $L^3$ and $L^4$ may independently be a single bond or a phenylene group.

For example, $R^1$ and $R^2$ may independently be hydrogen or a C1 to C5 alkyl group.

For specific examples, $R^1$ and $R^2$ may independently be hydrogen.

For example, Chemical Formula 1 may be represented by Chemical Formula 1A.

[Chemical Formula 1A]

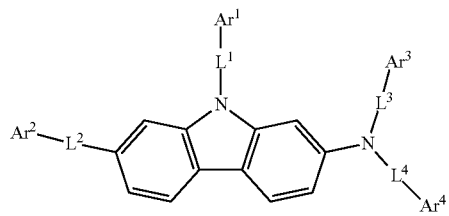

In Chemical Formula 1A, definitions of $Ar^1$ to $Ar^4$, $L^1$ to $L^4$ are the same as described above.

Chemical Formula 1 may be for example one of compounds of Group 1, but is not limited thereto.

[Group 1]

A-1

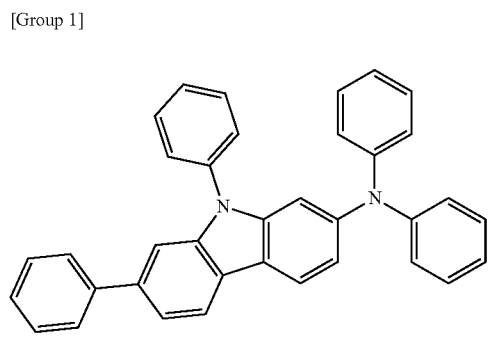

A-2

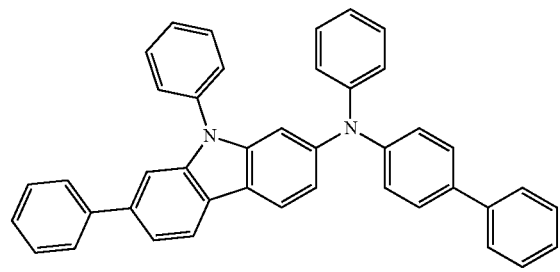

A-3

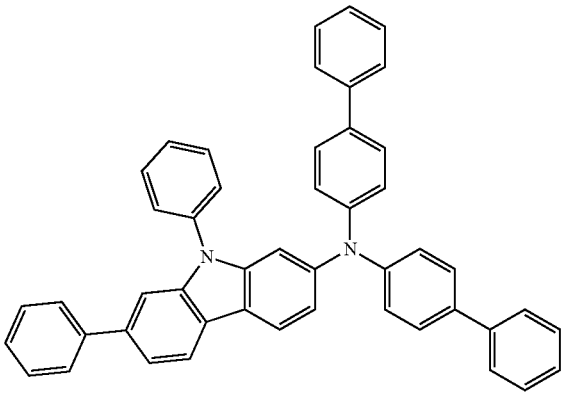

A-4

A-5

A-6

A-7
A-8
A-9
A-10
A-11
A-12
A-13
A-14
A-15
A-16

A-17
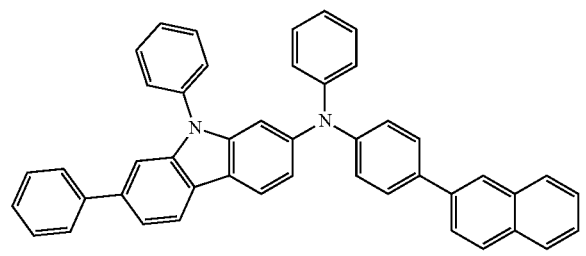
A-18
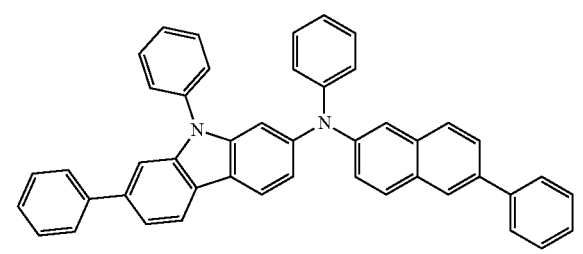
A-19
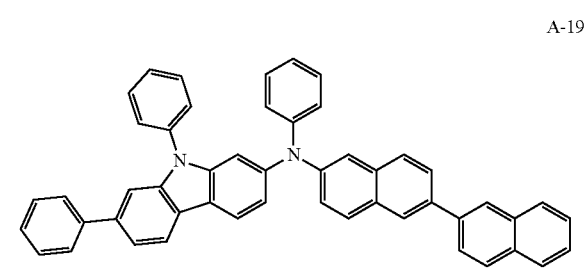
A-20
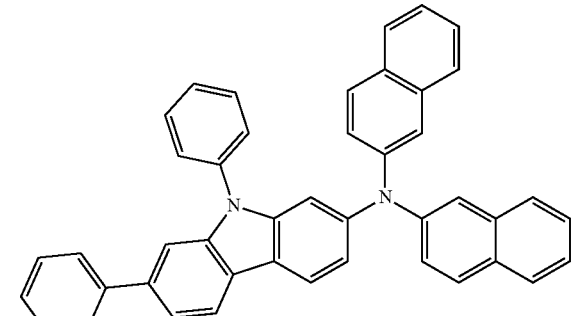
A-21
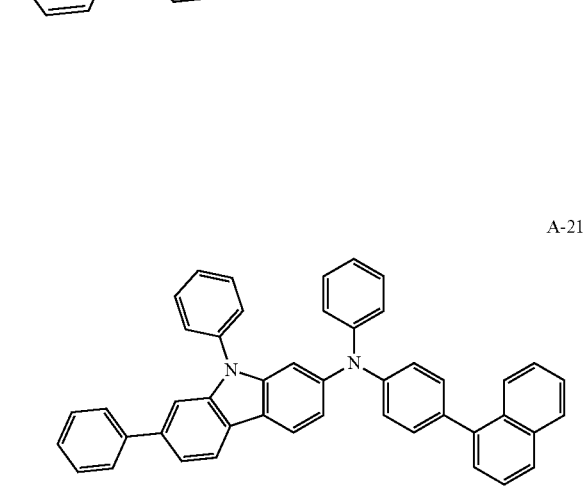
A-22
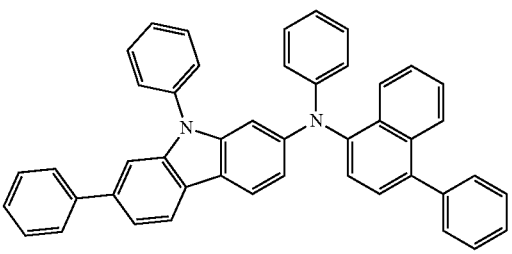
A-23
A-24
A-25

A-26
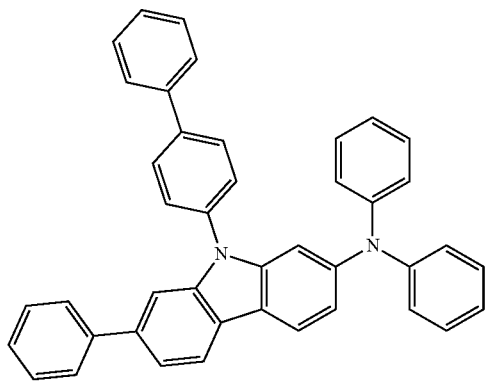
A-27
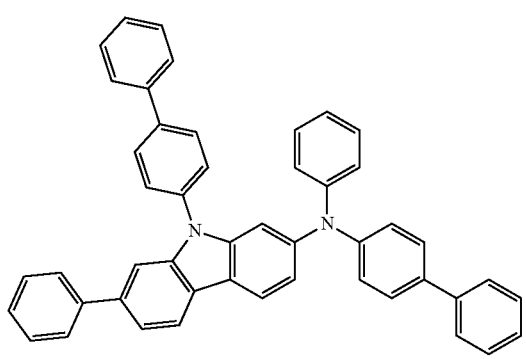
A-28
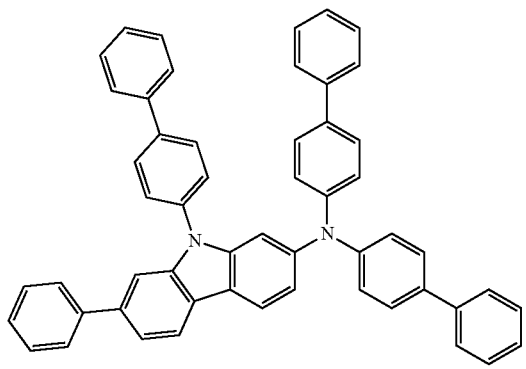
A-29
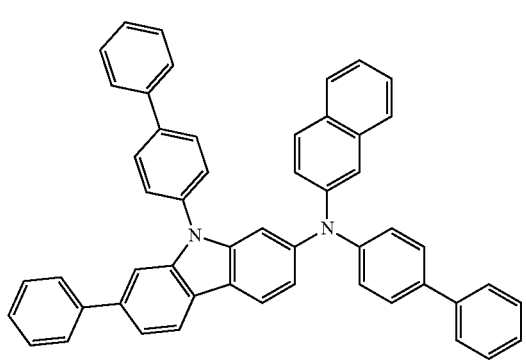
A-30
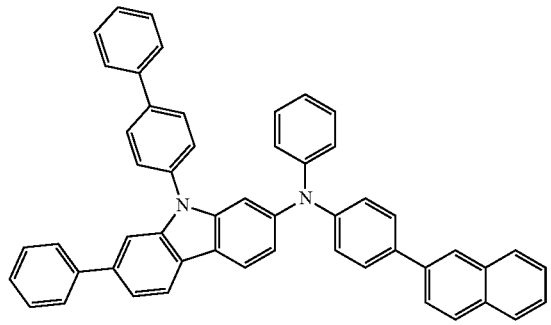
A-31
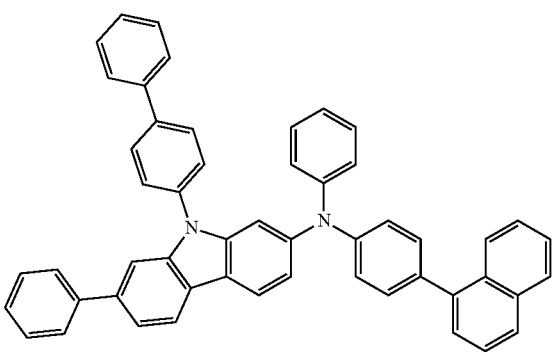
A-32
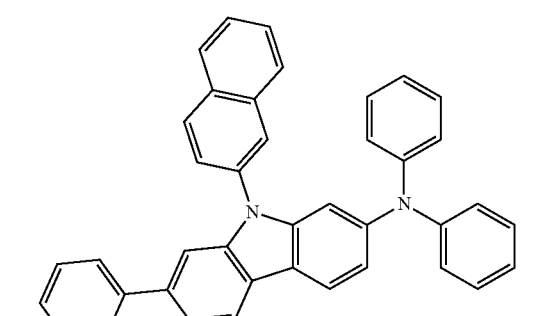
A-33
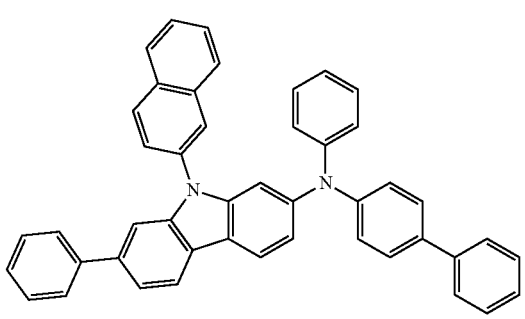

A-34
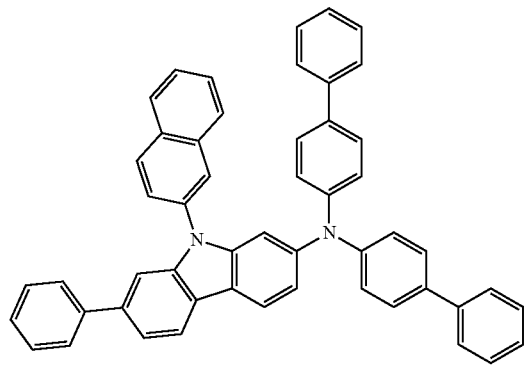
A-35
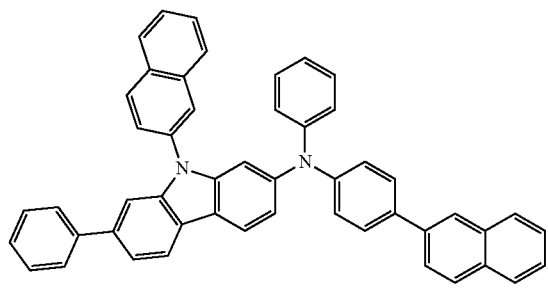
A-36
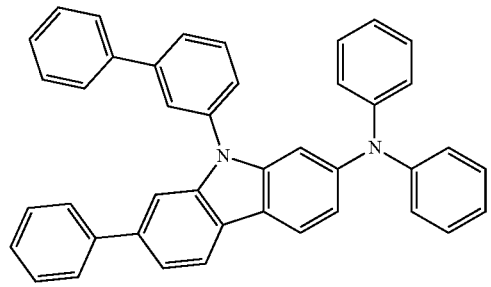
A-37
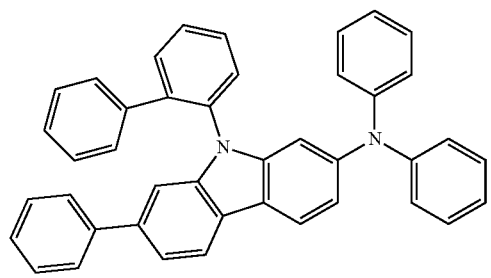
A-38
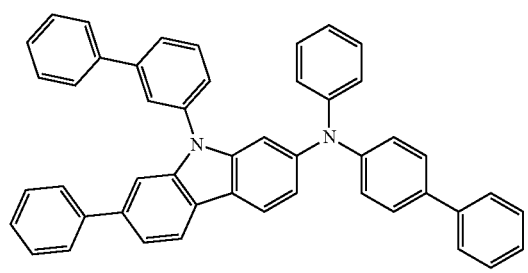
A-39
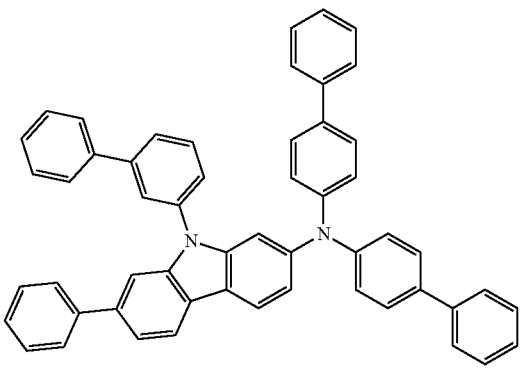
A-40
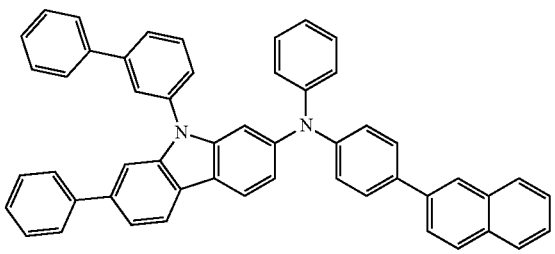
A-41
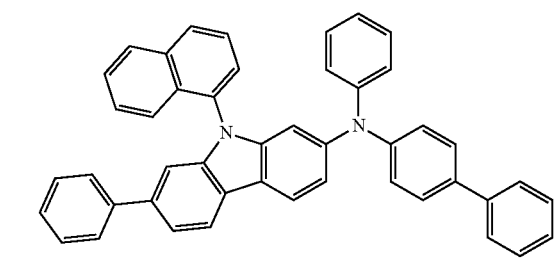
A-42
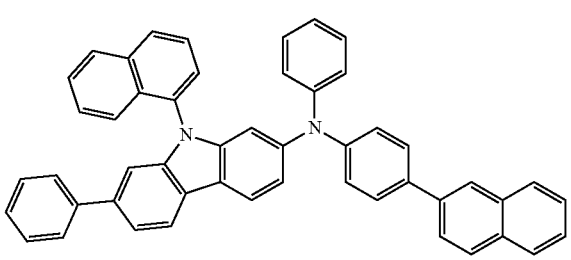
A-43
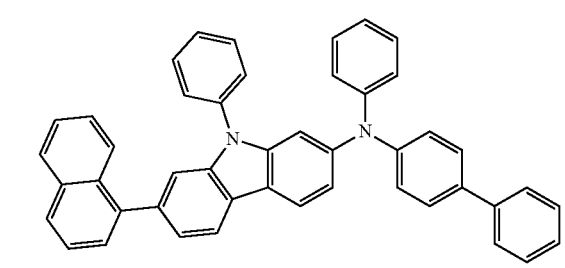

A-44
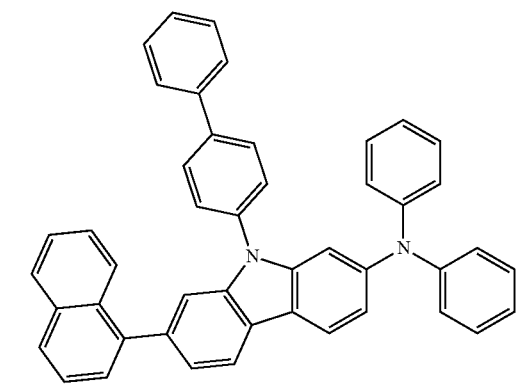
A-45
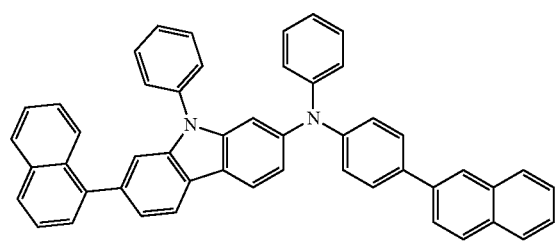
A-46
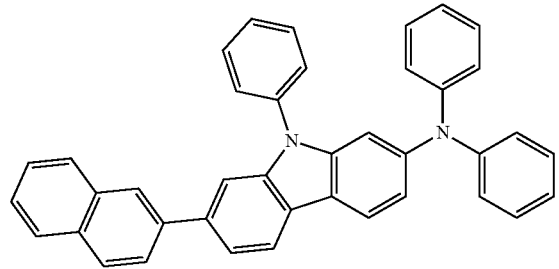
A-47
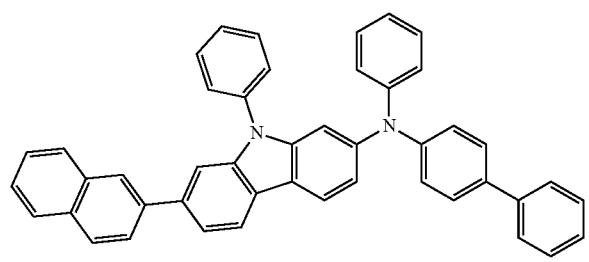
A-48
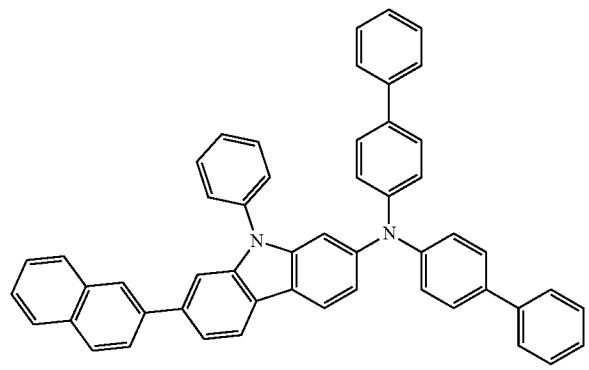
A-49
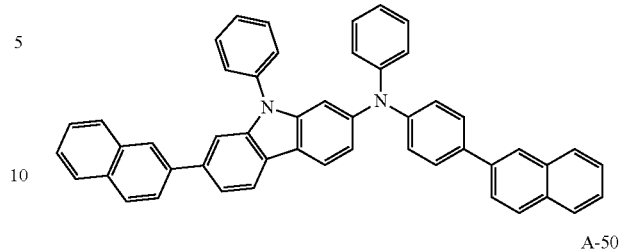
A-50
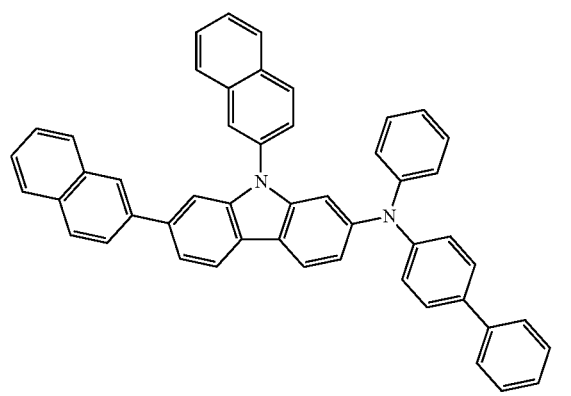
A-51
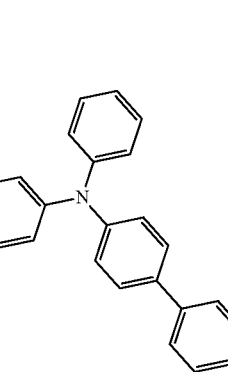
A-52
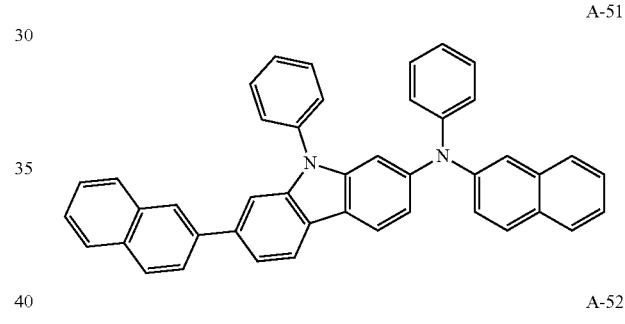
A-53

-continued
A-54
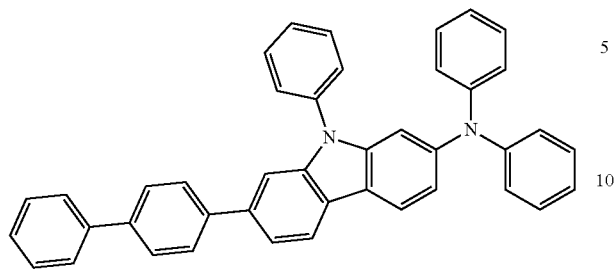
A-55
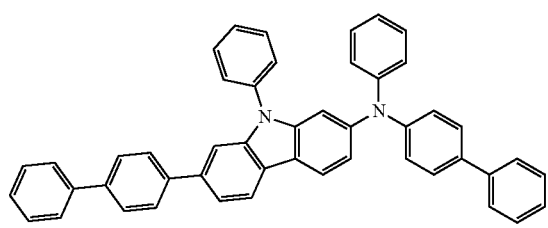
A-56
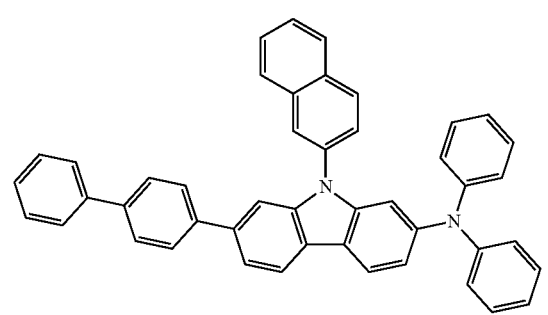
A-57
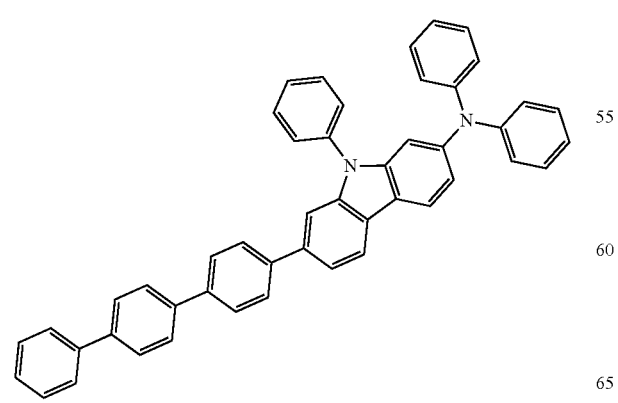
-continued
A-58
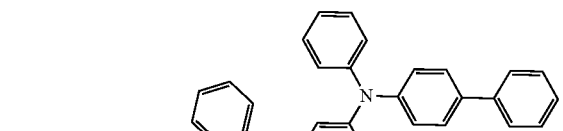
A-59
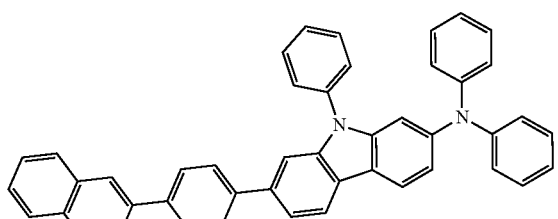
A-60
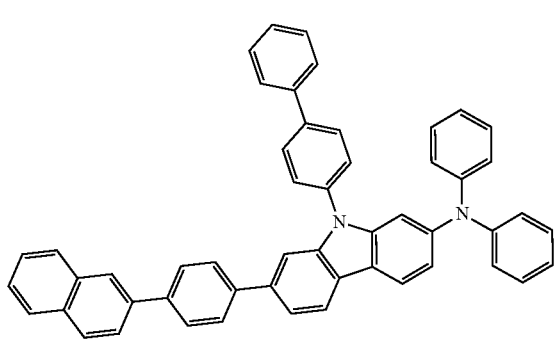
A-61
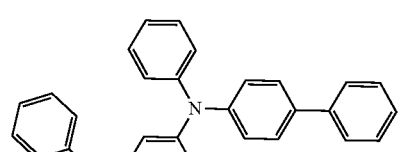

A-62
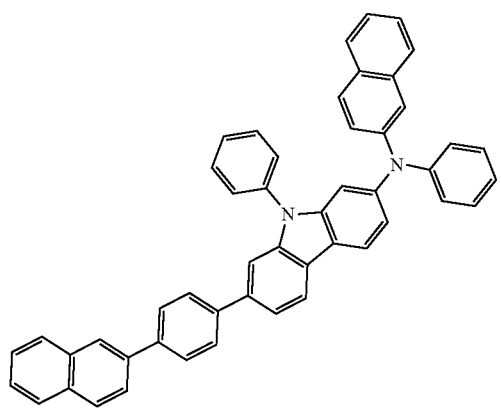
A-63
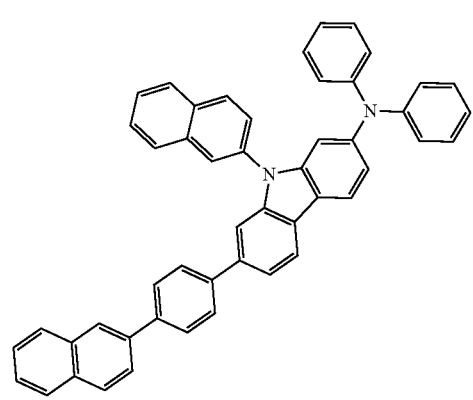
A-64
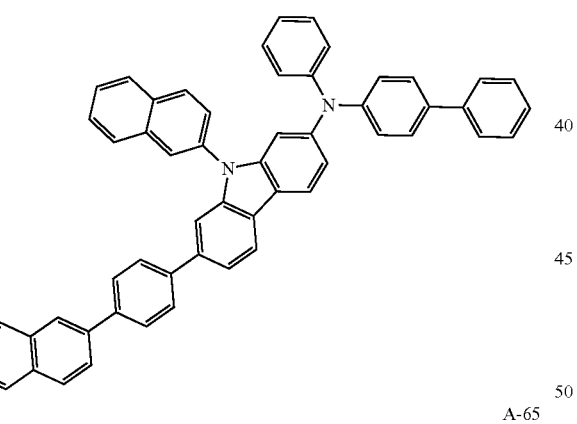
A-65
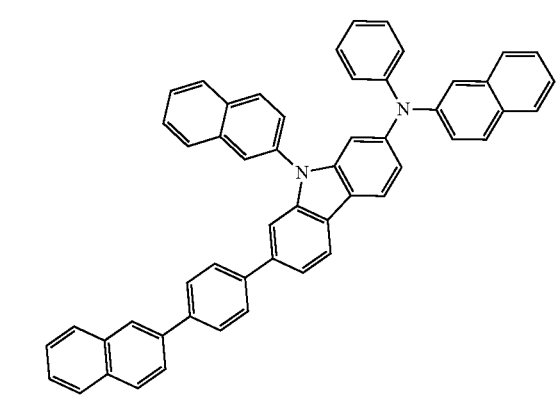
A-66
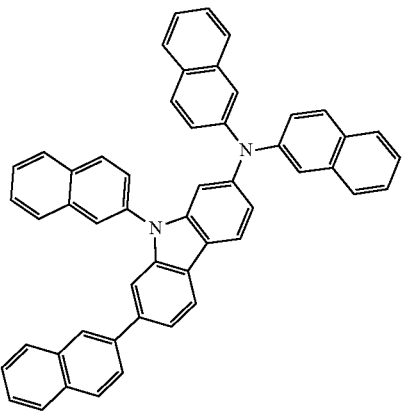
A-67
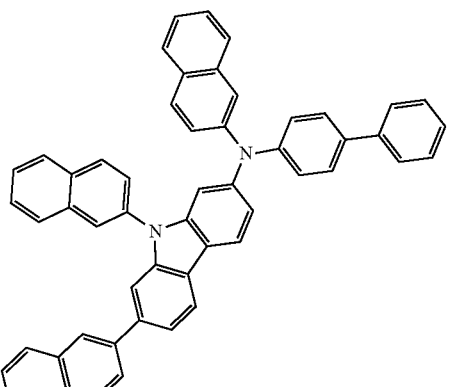
A-68
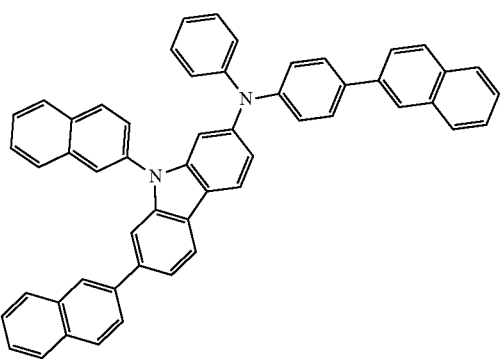
A-69
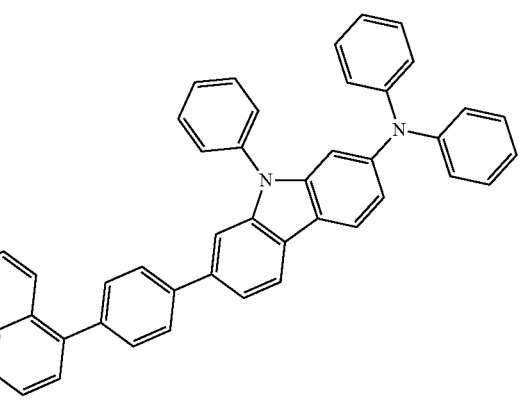

-continued

A-70

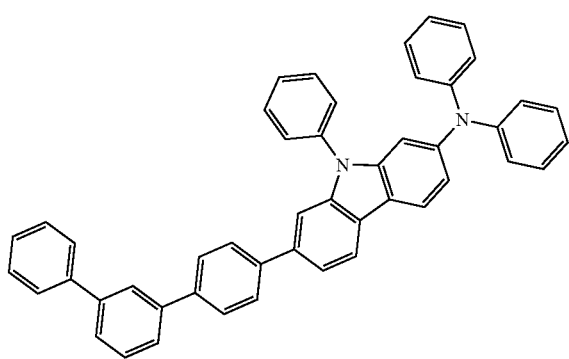

A composition for an organic optoelectronic device according to another embodiment includes the compound for an organic optoelectronic device (hereinafter, "first compound for an organic optoelectronic device") and a second compound for an organic optoelectronic device.

The second compound for an organic optoelectronic device is represented by Chemical Formula 2 and is included with the first compound for an organic optoelectronic device to exhibit good interface characteristics and hole and electron transport performance, to improve life-span characteristics of a device including the same, to increase efficiency, and to lower a driving voltage.

[Chemical Formula 2]

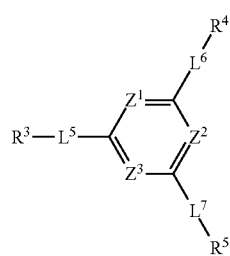

In Chemical Formula 2, $Z^1$ to $Z^3$ are independently N or $CR^a$, at least two of $Z^1$ to $Z^3$ are N, $R^a$ is hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof, $L^5$ to $L^7$ are independently a single bond, a substituted or unsubstituted C6 to C20 arylene group, a substituted or unsubstituted C2 to C20 heterocyclic group, or a combination thereof, $R^3$ to $R^5$ are independently substituted or unsubstituted C6 to C30 aryl group, a substituted or unsubstituted C2 to C30 heterocyclic group, or a combination thereof, at least one of $R^3$ to $R^5$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group, and $R^a$ and $R^3$ to $R^5$ are independently present or adjacent groups thereof are linked with each other to form a substituted or unsubstituted aliphatic, aromatic, or heteroaromatic monocyclic or polycyclic ring.

For example, two of $Z^1$ to $Z^3$ may be nitrogen (N) and one may be $CR^a$.

For example, $Z^1$ and $Z^2$ may be nitrogen and $Z^3$ may be $CR^a$.

For example, $Z^2$ and $Z^3$ may be nitrogen and $Z^1$ may be $CR^a$.

For example, $Z^1$ and $Z^3$ may be nitrogen and $Z^2$ may be $CR^a$.

For example, $Z^1$ to $Z^3$ may be nitrogen (N).

For example, $R^a$ and $R^3$ to $R^5$ may independently be present and at least one of $R^3$ to $R^5$ may be a substituted or unsubstituted dibenzofuranyl group, or a substituted or unsubstituted dibenzothiophenyl group.

For example, it may be represented by one of Chemical Formula 2B-1 to Chemical Formula 2B-3.

[Chemical Formula 2B-1]

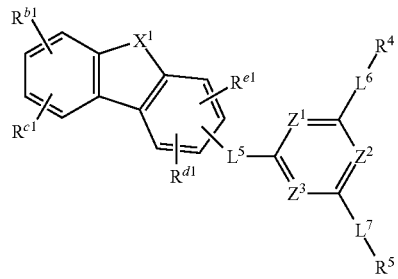

[Chemical Formula 2B-2]

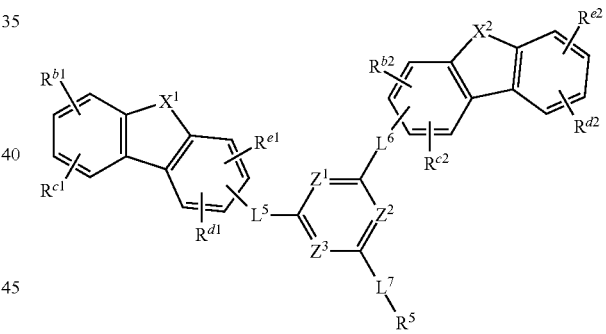

[Chemical Formula 2B-3]

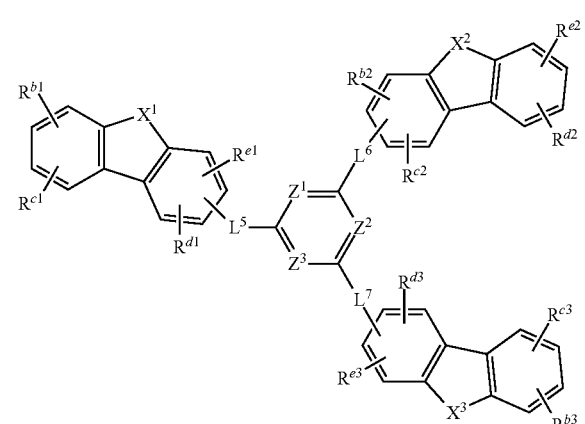

In Chemical Formulae 2B-1 to 2B-3, $Z^1$ to $Z^3$, $R^4$, $R^5$, and $L^5$ to $L^7$ are the same as described above, $X^1$ to $X^3$ are independently O or S, and $R^{b1}$ to $R^{b3}$, $R^{c1}$ to $R^{c3}$, $R^{d1}$ to $R^{d3}$, and $R^{e1}$ to $R^{e3}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

For another example, adjacent groups of $R^a$ and $R^3$ to $R^5$ may be linked with each other to form a substituted or unsubstituted aliphatic, aromatic or heteroaromatic monocyclic or polycyclic ring and at least one of $R^3$ to $R^5$ that does not form a ring may be a substituted or unsubstituted dibenzofuranyl group, or a substituted or unsubstituted dibenzothiophenyl group.

In the present specification "adjacent groups thereof are linked with each other to form a substituted or unsubstituted aliphatic, aromatic, or heteroaromatic monocyclic or polycyclic ring" refers to that any adjacent two substituents are fused to form a ring. For example, adjacent $R^a$ and $R^3$, $R^a$ and $R^4$ or $R^a$ and $R^5$ in Chemical Formula 2 may be fused with each other to form a heteroaromatic polycyclic ring together with the nitrogen-containing hexagonal ring substituted therewith. Herein, examples of the formed heteroaromatic polycyclic ring may be a substituted or unsubstituted benzofuranpyrimidinyl group, a substituted or unsubstituted benzothiophenepyrimidinyl group, a substituted or unsubstituted quinazolinyl group, and the like, for example $R^a$ and $R^3$ of Chemical Formula 2 may be fused to form a substituted or unsubstituted benzofuranpyrimidinyl group, or a substituted or unsubstituted benzothiophenepyrimidinyl group together with the nitrogen-containing hexagonal ring substituted therewith, thereby providing a compound represented by Chemical Formula 2B-4.

[Chemical Formula 2B-4]

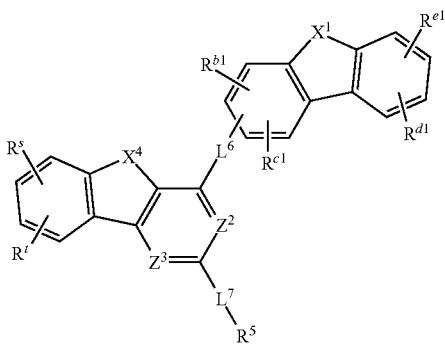

In Chemical Formula 2B-4, $X^1$, $Z^2$, $Z^3$, $L^6$, $L^7$, $R^5$, $R^{b1}$, $R^{c1}$, and $R^{e1}$ are the same as described above, $X^4$ is O or S, and $R^s$ and $R^t$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

For example, in Chemical Formula 2B-2, $X^1$ and $X^2$ may be the same or different.

For example, in Chemical Formula 2B-2, $X^1$ and $X^2$ may be the same and $X^1$ and $X^2$ may independently be O.

For example, in Chemical Formula 2B-2, $X^1$ and $X^2$ may be the same and $X^1$ and $X^2$ may independently be S.

For example, in Chemical Formula 2B-2, $X^1$ and $X^2$ may be different, $X^1$ may be S and $X^2$ may be O, or $X^1$ may be O and $X^2$ may be S.

For example, in Chemical Formula 2B-3, $X^1$ to $X^3$ may be the same or different.

For example, in Chemical Formula 2B-3, $X^1$ to $X^3$ may be the same and $X^1$ to $X^3$ may independently be O.

For example, in Chemical Formula 2B-3, $X^1$ to $X^3$ may be the same and $X^1$ to $X^3$ may independently be S.

For example, in Chemical Formula 2B-3, one of $X^1$ to $X^3$ may be different, two of $X^1$ to $X^3$ may be S and one of $X^1$ to $X^3$ may be O, or two of $X^1$ to $X^3$ may be O and one of $X^1$ to $X^3$ may be S.

For example, in Chemical Formula 2B-1, Chemical Formula 2B-2. and Chemical Formula 2B-4, $R^4$ and $R^5$ may independently be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted pyridinyl group, a substituted or unsubstituted pyrimidinyl group, or a substituted or unsubstituted triazinyl group.

For example, $R^4$ and $R^5$ of Chemical Formula 2B-1, Chemical Formula 2B-2, and Chemical Formula 2B-4 may independently be a substituted or unsubstituted phenyl group, a substituted or unsubstituted biphenyl group, a substituted or unsubstituted naphthyl group, or a substituted or unsubstituted carbazolyl group.

For example, $R^4$ and $R^5$ of Chemical Formula 2B-1, Chemical Formula 2B-2, and Chemical Formula 2B-4 may independently be one of substituents of Group I.

[Group I]

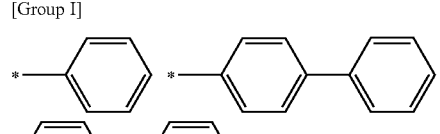

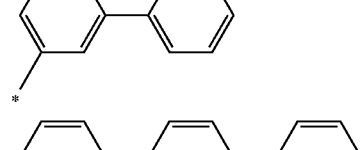

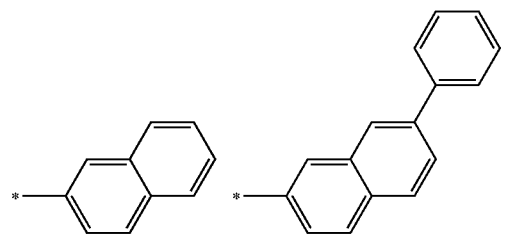

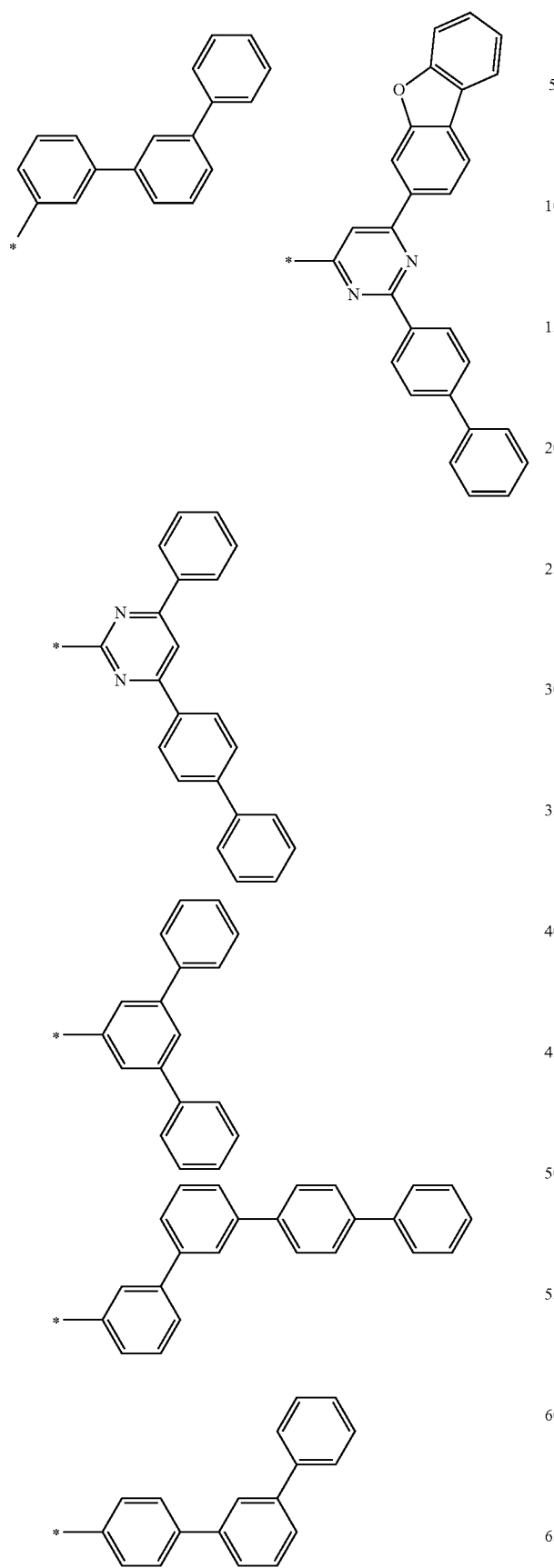
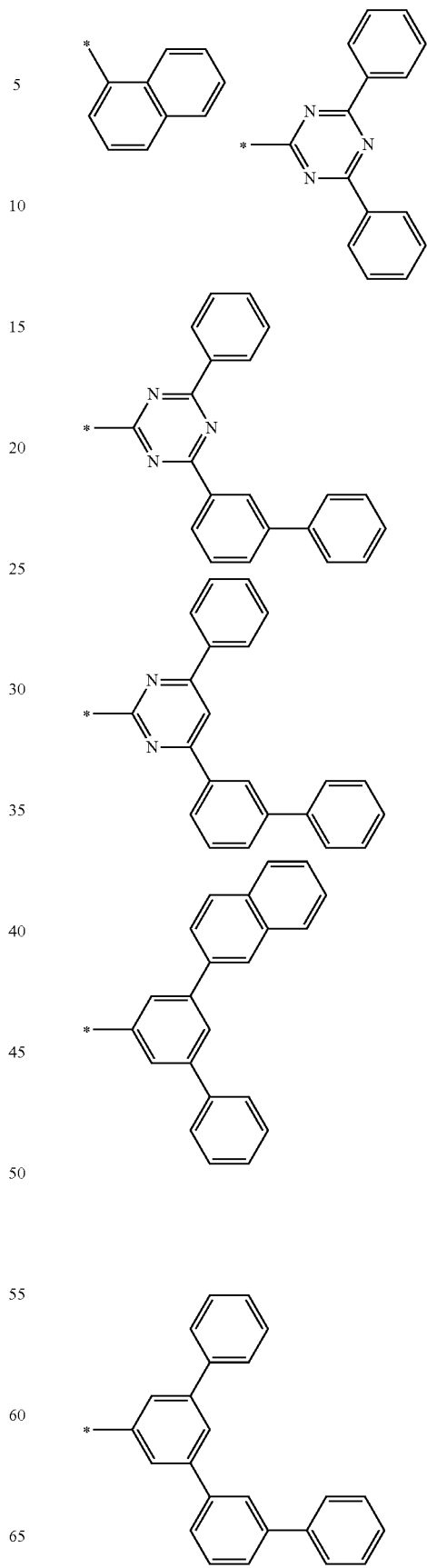

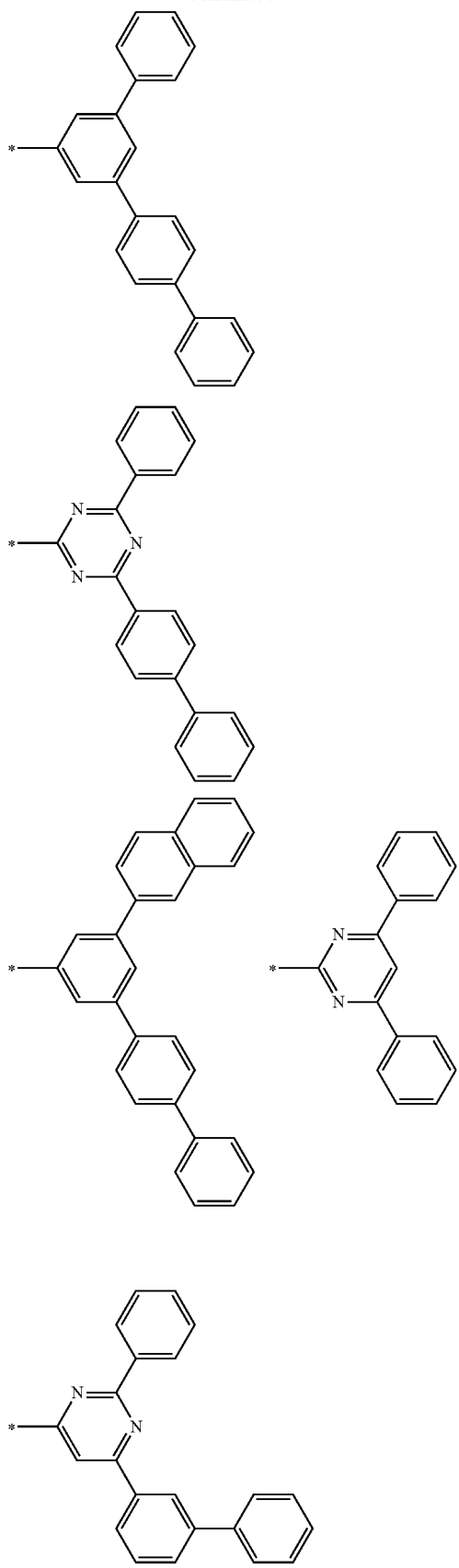
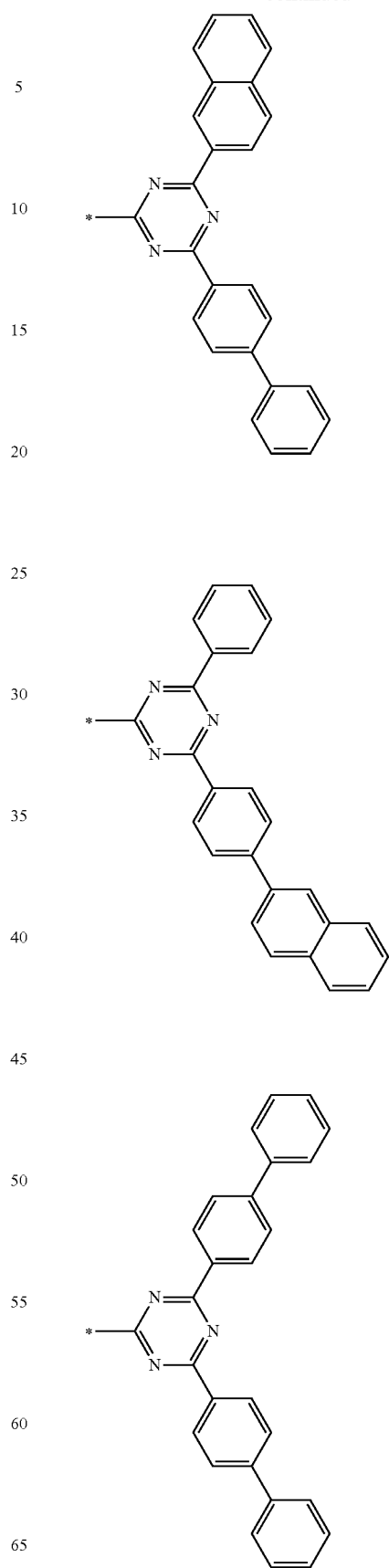

-continued

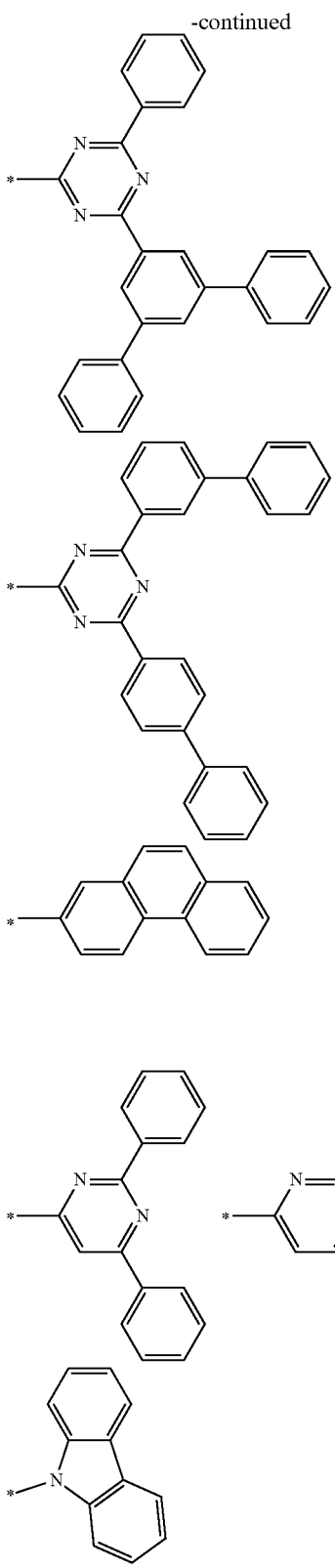

For example, in Chemical Formulae 2B-1 to 2B-4, $L^5$ to $L^7$ may independently be a single bond or a substituted or unsubstituted C6 to C20 arylene group.

For example, $L^5$ to $L^7$ may independently be a single bond, a substituted or unsubstituted phenylene group, a substituted or unsubstituted biphenylene group, a substituted or unsubstituted terphenylene group, or a substituted or unsubstituted naphthylene group.

For example, $L^5$ to $L^7$ may independently be a single bond, a substituted or unsubstituted m-phenylene group, or a substituted or unsubstituted p-phenylene group.

For example, in Chemical Formulae 2B-1 to 2B-4, $R^{b1}$ to $R^{b3}$, $R^{c1}$ to $R^{c3}$, $R^{d1}$ to $R^{d3}$, and $R^{e1}$ to $R^{e3}$ may independently be hydrogen, deuterium, a substituted or unsubstituted C1 to C20 alkyl group, or a substituted or unsubstituted C6 to C20 aryl group.

For example, $R^{b1}$ and $R^{b3}$, $R^{c1}$ to $R^{c3}$, $R^{d1}$ to $R^{d3}$, and $R^{e1}$ to $R^{e3}$ may independently be hydrogen or a substituted or unsubstituted phenyl group.

For specific examples, the dibenzofuranyl group or the dibenzothiophenyl group may be represented by one of Chemical Formula 2-1 to Chemical Formula 2-4 according to a bonding position.

[Chemical Formula 2-1]

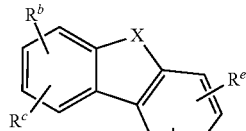

[Chemical Formula 2-2]

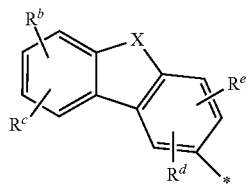

[Chemical Formula 2-3]

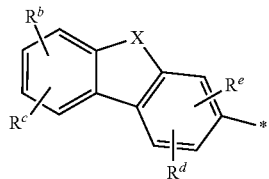

[Chemical Formula 2-4]

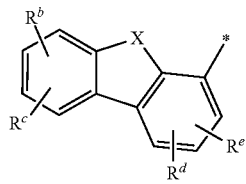

In Chemical Formula 2-1 to Chemical Formula 2-4, X is the same as $X^1$ and $X^3$, $R^b$ to $R^e$ are the same as $R^{b1}$ to $R^{b3}$, $R^{c1}$ to $R^{c3}$, $R^{d1}$ to $R^{d3}$, and $R^{e1}$ to $R^{e3}$.

For example, the dibenzofuranyl group or dibenzothiophenyl group may be represented by Chemical Formula 2-1 or Chemical Formula 2-3.

For example, the second compound for an organic optoelectronic device may be represented by Chemical Formula 2B-1 or Chemical Formula 2B-4.

For example, in Chemical Formula 2B-1, $L^5$ may be a single bond and each of $Z^1$ to $Z^3$ may be N.

For example, Chemical Formula 2B-1 may be represented by Chemical Formula 2B-1-1 or Chemical Formula 2B-1-3.

[Chemical Formula 2B-1-1]

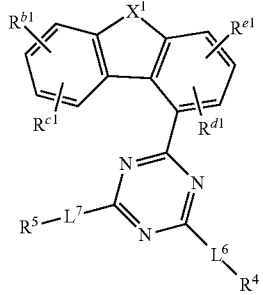

[Chemical Formula 2B-1-3]

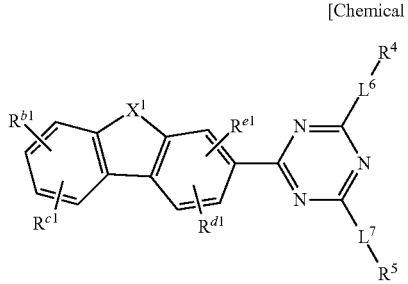

In Chemical Formula 2B-1-1 and Chemical Formula 2B-1-3, $X^1$, $R^4$, $R^5$, $L^6$, $L^7$, $R^{b1}$, $R^{c1}$, $R^{d1}$, and $R^{e1}$ are the same as described above.

The second compound for an organic optoelectronic device represented by Chemical Formula 2B-1-1 and Chemical Formula 2B-1-3 has an effectively expanded LUMO energy band and increased planarity of a molecular structure and thus may have a structure easily accepting electrons, when an electric field is applied. Accordingly, a driving voltage of an organic optoelectronic device including the second compound for an organic optoelectronic device may be lowered. In addition, this expansion of LUMO and the fusion of rings increases stability regarding electrons of the triazine ring and thus effectively improves a life-span of the organic optoelectronic device manufactured by applying the second compound for an organic optoelectronic device.

For specific example, in Chemical Formula 2B-1-1 and Chemical Formula 2B-1-3, $X^1$ may be O, $L^6$ and $L^7$ may independently be a single bond or a p-phenylene group, and $R^4$ and $R^5$ may independently be a substituted or unsubstituted phenyl group, a substituted or unsubstituted biphenyl group, or a substituted or unsubstituted naphthyl group.

For example, in Chemical Formula 2B-4, $L^6$ may be a single bond and $Z^2$ and $Z^3$ may independently N.

For example, Chemical Formula 2B-4 may be represented by Chemical Formula 2B-4-3.

[Chemical Formula 2B-4-3]

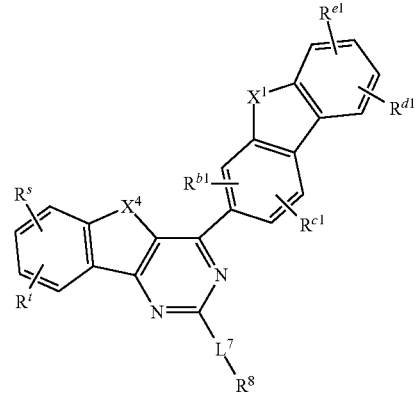

In Chemical Formula 2B-4-3, $X^4$, $R^5$, $L^7$, $R^{b1}$, $R^{c1}$, $R^{d1}$, $R^{e1}$, $R^s$, and $R^t$ are the same as described above.

For specific examples, $R^5$ of Chemical Formula 2B-4-3 may be a substituted or unsubstituted carbazolyl group and for example may be represented by Chemical Formula 2B-4-3a.

[Chemical Formula 2B-4-3a]

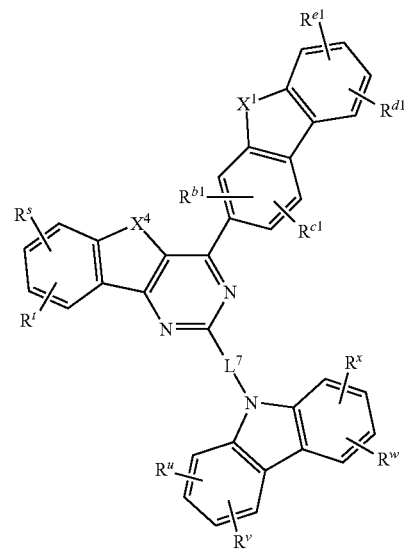

In Chemical Formula 2B-4-3a, $X^4$, $L^7$, $R^{b1}$, $R^{c1}$, $R^{d1}$, $R^{e1}$, $R^s$, and $R^t$ are the same as described above, and $R^u$, $R^v$, $R^w$, and $R^x$ are the same as $R^s$ and $R^t$.

For example, at least one of $R^3$ to $R^5$ may be a substituted or unsubstituted carbazolyl group, a substituted or unsubstituted benzocarbazolyl group, or a substituted or unsubstituted dibenzocarbazolyl group and for example the second compound for an organic optoelectronic device may be represented by one of Chemical Formula 2C-1 to Chemical Formula 2C-12.

[Chemical Formula 2C-1]
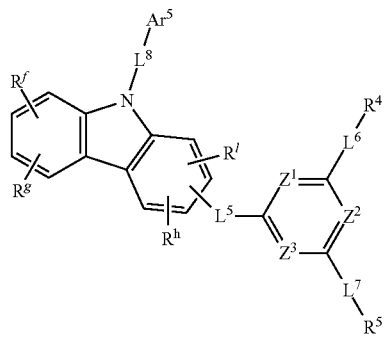
[Chemical Formula 2C-2]
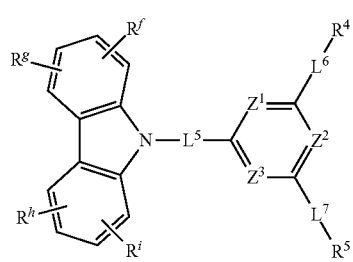
[Chemical Formula 2C-3]
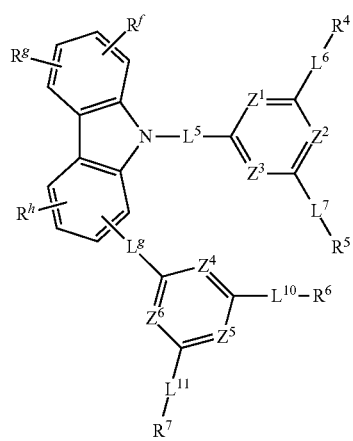
[Chemical Formula 2C-4]
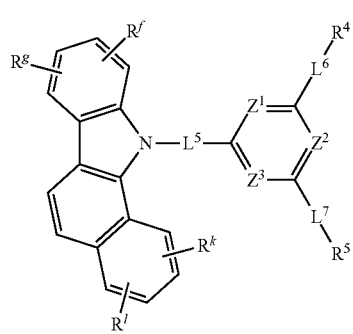
[Chemical Formula 2C-5]
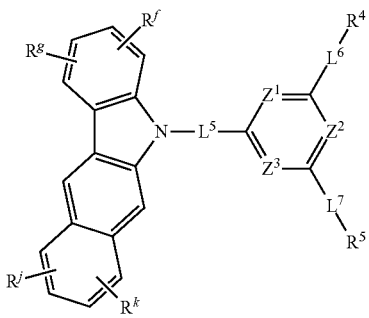
[Chemical Formula 2C-6]
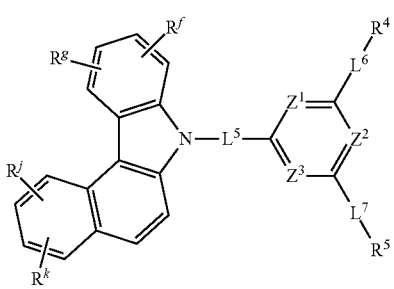
[Chemical Formula 2C-7]
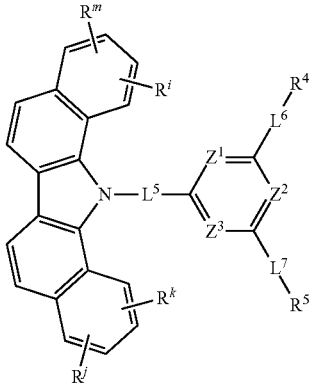
[Chemical Formula 2C-8]
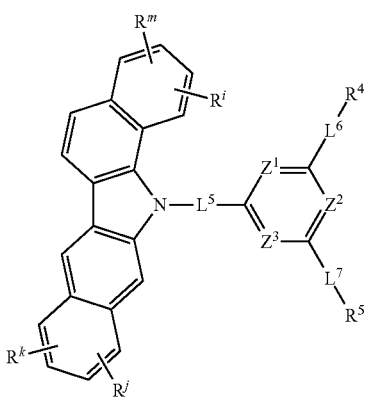

[Chemical Formula 2C-9]

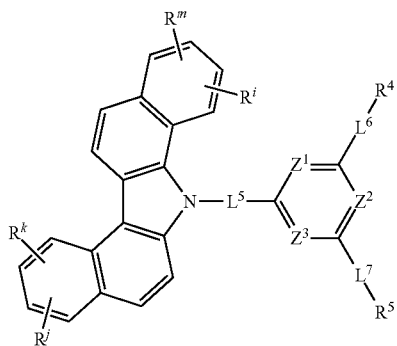

[Chemical Formula 2C-10]

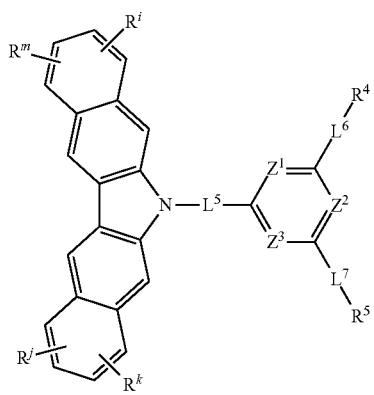

[Chemical Formula 2C-11]

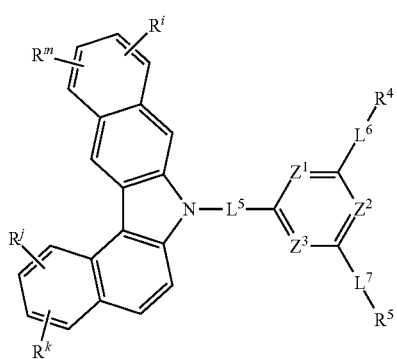

[Chemical Formula 2C-12]

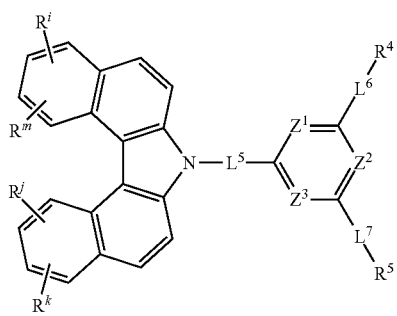

In Chemical Formula 2C-1 to Chemical Formula 2C-12, $Z^1$ to $Z^3$, $R^4$, $R^5$, and $L^5$ to $L^7$ are the same as described above, $Z^4$ to $Z^6$ are the same as $Z^1$ to $Z^3$, $R^6$ and $R^7$ are the same as $R^4$ and $R^5$, $R^f$, $R^g$, $R^h$, $R^i$, $R^j$, $R^k$, $R^l$, and $R^m$ are the same as $R^{b1}$ to $R^{b3}$, $R^{c1}$ to $R^{c3}$, $R^{d1}$ to $R^{d3}$, and $R^{e1}$ to $R^{e3}$, and $L^8$ to $L^{11}$ are the same as $L^5$ to $L^7$.

$Ar^5$ is a substituted or unsubstituted C6 to C30 aryl group, a substituted or unsubstituted C2 to C30 heterocyclic group, or a combination thereof.

For example, $Ar^5$ may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, or a substituted or unsubstituted fluorenyl group.

For example, $Ar^5$ may be a substituted or unsubstituted phenyl group, a substituted or unsubstituted biphenyl group, a substituted or unsubstituted naphthyl group, or a substituted or unsubstituted fluorenyl group, but is not limited thereto.

For example, $R^4$ to $R^7$ of Chemical Formula 2C-1 to Chemical Formula 2C-12 may independently be present and may be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted dibenzofuranyl group, or a substituted or unsubstituted dibenzothiophenyl group.

For example, $R^4$ to $R^7$ may independently be present and may be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted phenanthrenyl group, a substituted or unsubstituted pyrimidinyl group, or a substituted or unsubstituted triazinyl group.

For example, $R^4$ to $R^7$ of Chemical Formula 2C-1 to Chemical Formula 2C-12 are linked with adjacent $R^a$ to form a substituted or unsubstituted heteroaromatic monocyclic or polycyclic ring.

For specific examples, the substituted or unsubstituted heteroaromatic monocyclic or polycyclic ring may be a substituted or unsubstituted benzofuranpyrimidinyl group, a substituted or unsubstituted benzothiophenepyrimidinyl group, or a substituted or unsubstituted quinazolinyl group, for example a substituted or unsubstituted quinazolinyl group.

For example, $L^5$ to $L^7$ of Chemical Formula 2C-1 to Chemical Formula 2C-12 may independently be a single bond, a substituted or unsubstituted C6 to C20 arylene group, or a substituted or unsubstituted C2 to C20 heteroarylene group.

For example, $L^5$ to $L^7$ may independently be a single bond, a substituted or unsubstituted phenylene group, a substituted or unsubstituted biphenylene group, or a substituted or unsubstituted naphthylene group.

For example, $R^f$, $R^g$, $R^h$, $R^i$, $R^j$, $R^k$, $R^l$, and $R^m$ of Chemical Formula 2C-1 to Chemical Formula 2C-12 may independently be hydrogen, deuterium, a substituted or unsubstituted C1 to C10 alkyl group, a substituted or unsubstituted C6 to C20 aryl group, or a substituted or unsubstituted C2 to C20 heteroaryl group.

For example, $R^f$, $R^g$, $R^h$, $R^i$, $R^j$, $R^k$, $R^l$, and $R^m$ are independently hydrogen, a substituted or unsubstituted phenyl group, a substituted or unsubstituted triphenylene group, a substituted or unsubstituted dibenzofuranyl group, or a substituted or unsubstituted dibenzothiophenyl group.

For specific examples, it may be represented by one of Chemical Formula 2-5 to Chemical Formula 2-8 according to a binding position of a carbazolyl group of Chemical Formula 2C-1.

[Chemical Formula 2-5]

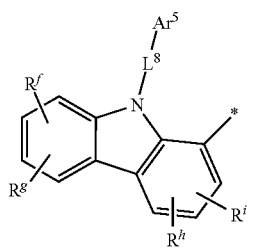

[Chemical Formula 2-6]

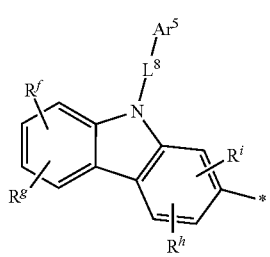

[Chemical Formula 2-7]

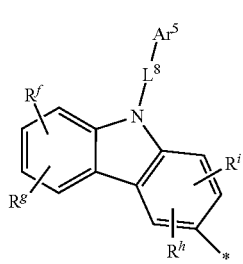

[Chemical Formula 2-8]

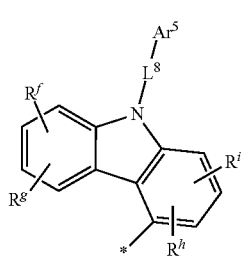

In Chemical Formula 2-5 to Chemical Formula 2-8, $Ar^5$, $R^f$, $R^g$, $R^h$, $R^i$, and $L^8$ are the same as described above.

For example, the second compound for an organic optoelectronic device may be represented by one of Chemical Formula 2C-2 to Chemical Formula 2C-6.

For example, the second compound for an organic optoelectronic device may be represented by Chemical Formula 2C-2 or Chemical Formula 2C-6.

For example, at least one of $R^3$ to $R^5$ may be a substituted or unsubstituted triphenylene group and for example the second compound for an organic optoelectronic device may be represented by one of Chemical Formula 2D-1 or Chemical Formula 2D-2.

[Chemical Formula 2D-1]

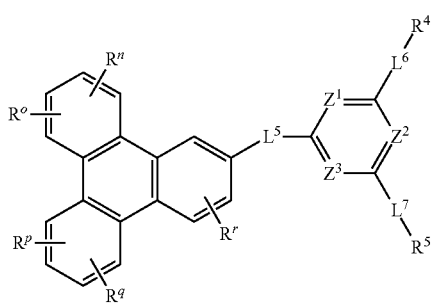

[Chemical Formula 2D-2]

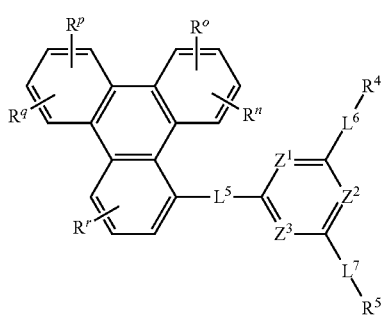

In Chemical Formula 2D-1 and Chemical Formula 2D-2, $Z^1$ to $Z^3$, $R^4$, $R^5$, and $L^5$ to $L^7$ are the same as described above, and $R^n$, $R^o$, $R^p$, $R^q$, and $R^r$ are the same as $R^{b1}$ to $R^{b3}$, $R^{c1}$ to $R^{c3}$, $R^{d1}$ to $R^{d3}$, and $R^{e1}$ to $R^{e3}$.

For example, $R^4$ and $R^5$ of Chemical Formula 2D-1 and Chemical Formula 2D-2 may independently be a substituted or unsubstituted phenyl group, a substituted or unsubstituted biphenyl group, a substituted or unsubstituted terphenyl group, a substituted or unsubstituted naphthyl group, a substituted or unsubstituted pyridinyl group, a substituted or unsubstituted pyrimidinyl group, a substituted or unsubstituted triazinyl group, a substituted or unsubstituted dibenzofuranyl group, a substituted or unsubstituted dibenzothiophenyl group.

For example, $R^4$ and $R^5$ may independently be a substituted or unsubstituted phenyl group, a substituted or unsubstituted biphenyl group, a substituted or unsubstituted terphenyl group, a substituted or unsubstituted naphthyl group, a substituted or unsubstituted pyridinyl group, a substituted or unsubstituted dibenzofuranyl group, or a substituted or unsubstituted dibenzothiophenyl group.

For example, L⁵ to L⁷ of Chemical Formula 2D-1 and Chemical Formula 2D-2 may independently be a single bond, a substituted or unsubstituted C6 to C20 arylene group, or a substituted or unsubstituted C2 to C20 heteroarylene group.

For example, L⁵ to L⁷ may independently be a single bond, a substituted or unsubstituted phenylene group, a substituted or unsubstituted biphenylene group, or a substituted or unsubstituted naphthylene group.

For example, $R^n$, $R^o$, $R^p$, $R^q$, and $R^r$ of Chemical Formula 2D-1 and Chemical Formula 2D-2 may independently be hydrogen, deuterium, a cyano group, a substituted or unsubstituted C1 to C10 alkyl group, a substituted or unsubstituted C6 to C20 aryl group, or a substituted or unsubstituted C2 to C20 heteroaryl group.

For example, $R^n$, $R^o$, $R^p$, $R^q$, and $R^r$ may independently be hydrogen, deuterium, a cyano group, methyl group, or a substituted or unsubstituted phenyl group.

For example, the second compound for an organic optoelectronic device may be represented by Chemical Formula 2D-1 and L⁵ of Chemical Formula 2D-1 may be a single bond and $Z^1$ to $Z^3$ may be N. For example, it may be represented by Chemical Formula 2D-1-1.

[Chemical Formula 2D-1-1]

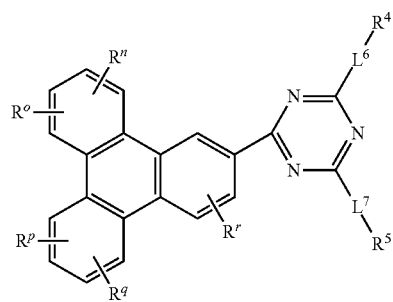

In Chemical Formula 2D-1-1, R⁴, R⁵, L⁵ to L⁷ and $R^n$, $R^o$, $R^p$, $R^q$, and $R^r$ are the same as described above.

In a specific example embodiment, the second compound for an organic optoelectronic device may be represented by one of Chemical Formula 2B-1-1, Chemical Formula 2B-1-3, Chemical Formula 2B-4-3, and Chemical Formula 2D-1-1.

Particularly, the Chemical Formula 2B-4-3 may be represented by Chemical Formula 2B-4-3a.

The second compound for an organic optoelectronic device represented by Chemical Formula 2 may be for example one of the compounds of Group 2, but is not limited thereto.

[Group 2]

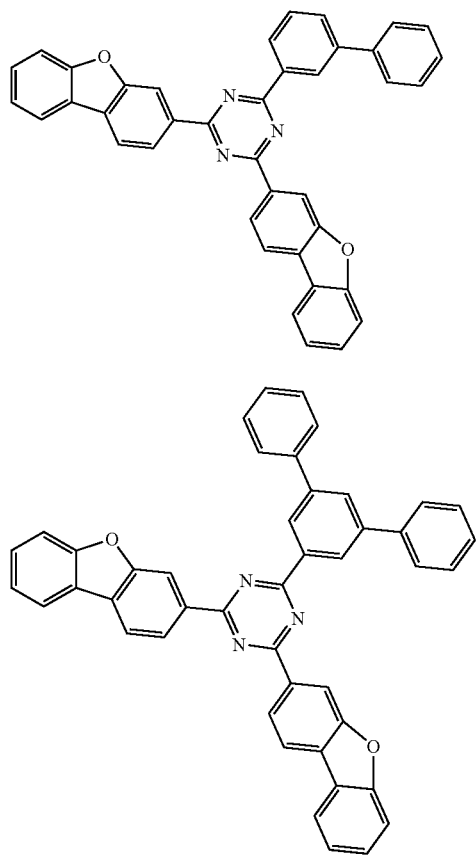

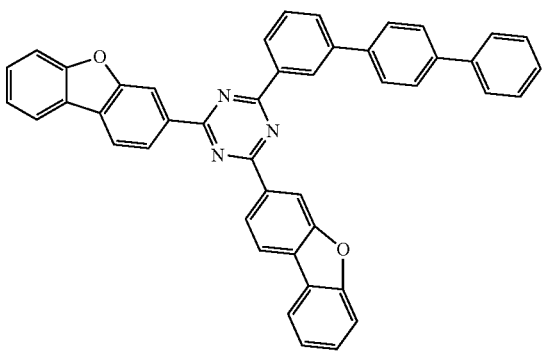

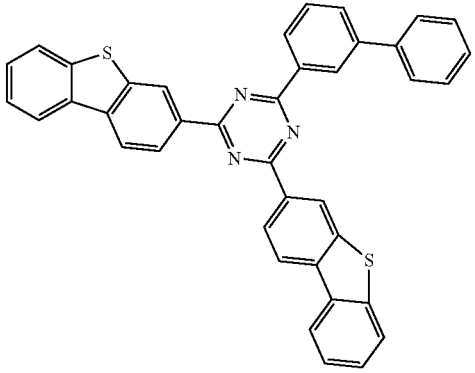

-continued
B-5
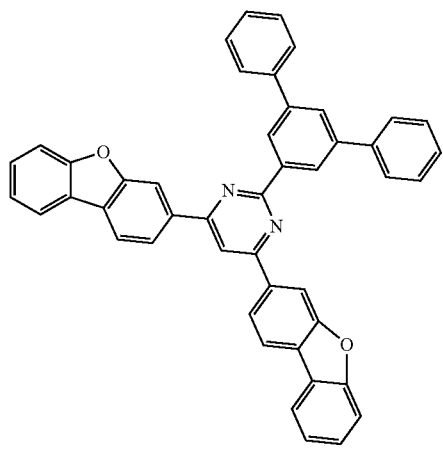
B-6
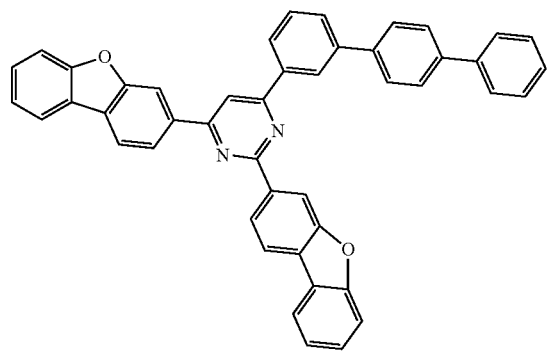
B-7
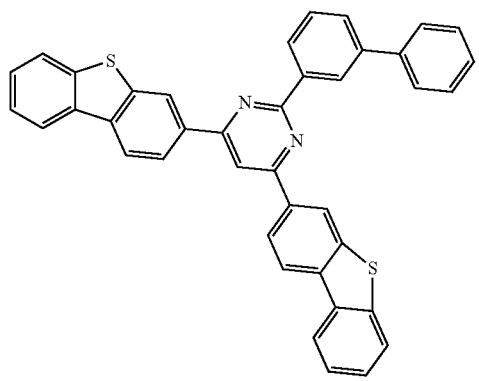
B-8
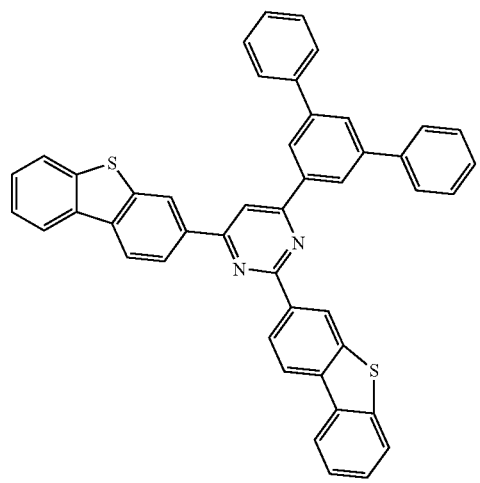
B-9
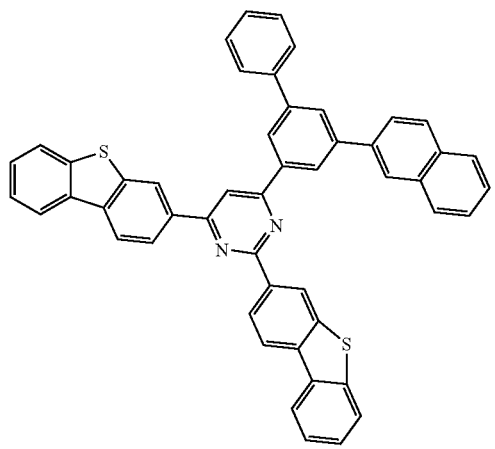
B-10
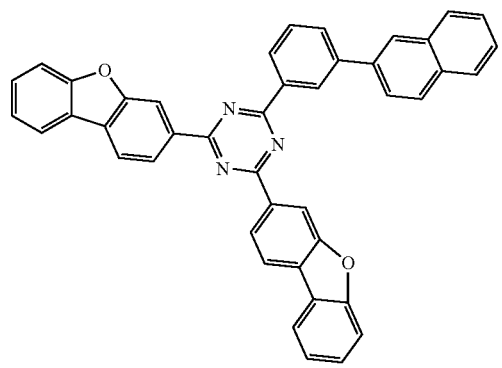

-continued
B-11
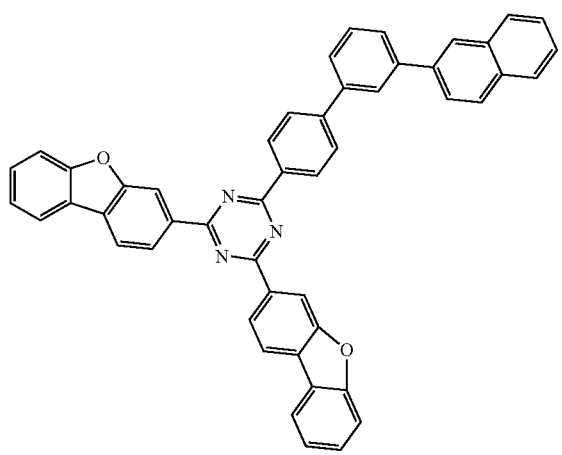
B-12
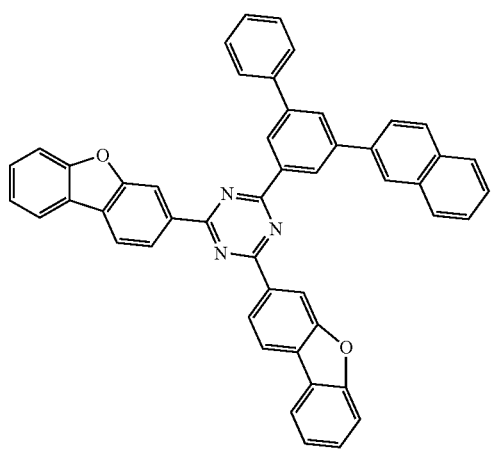
B-13
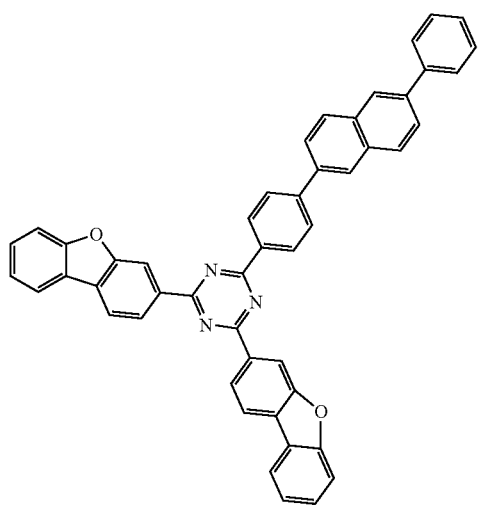
B-14
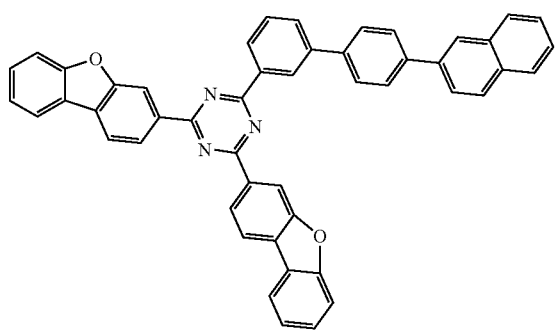
B-15
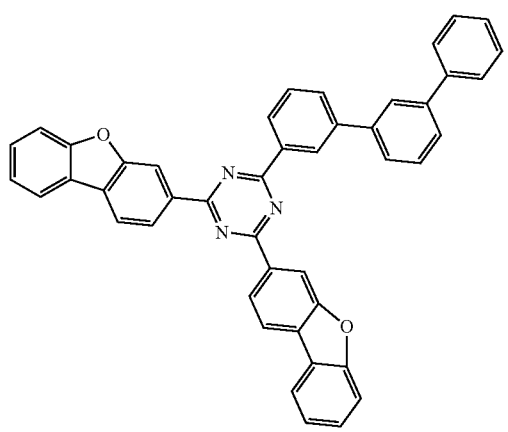
B-16
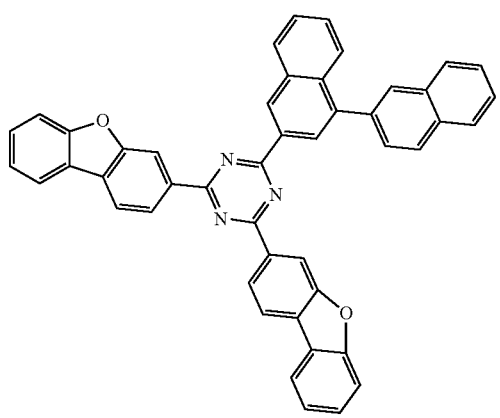

-continued
B-17
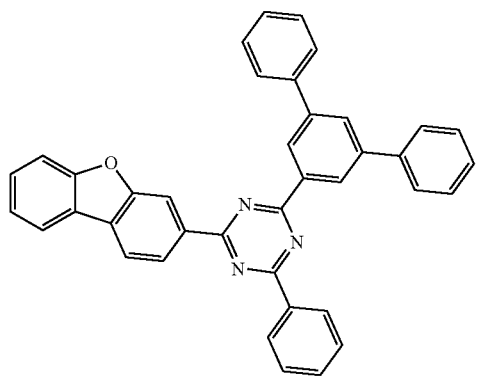
B-18
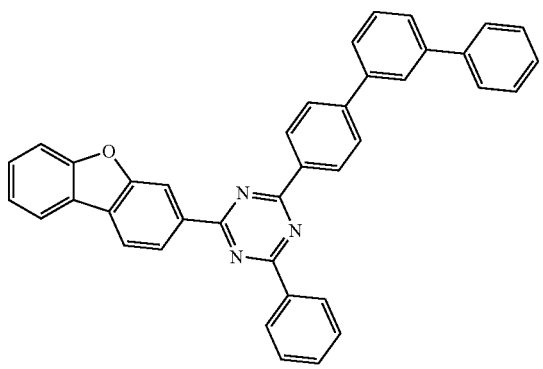
B-19
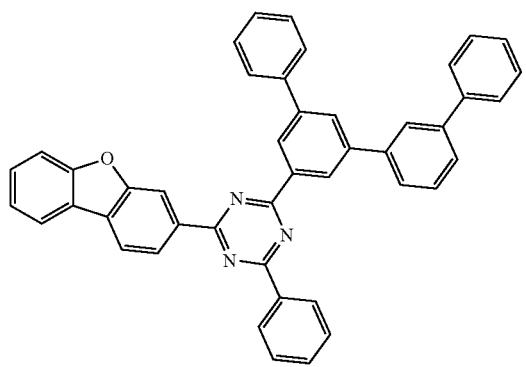
B-20
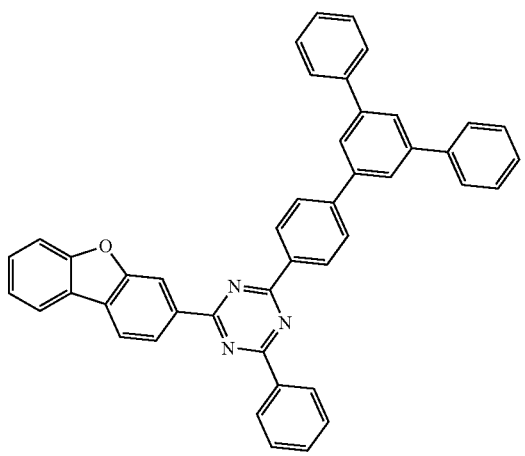
B-21
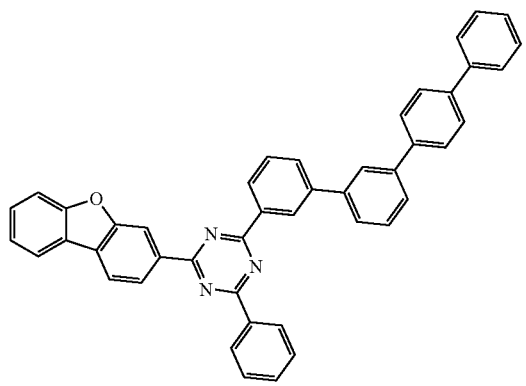
B-22
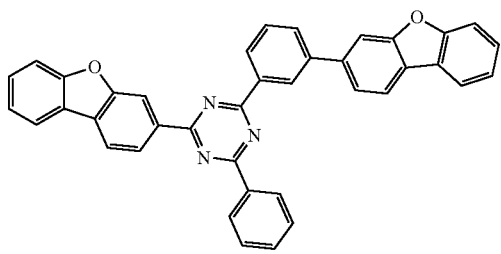

-continued
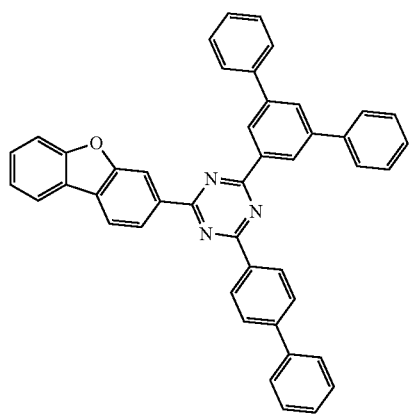
B-23
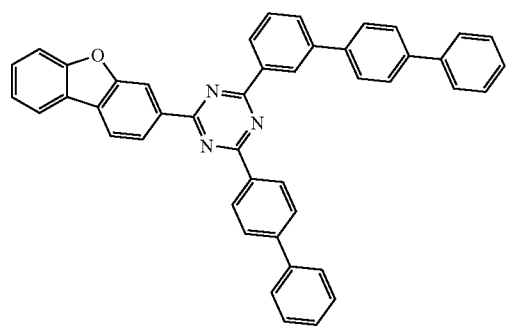
B-24
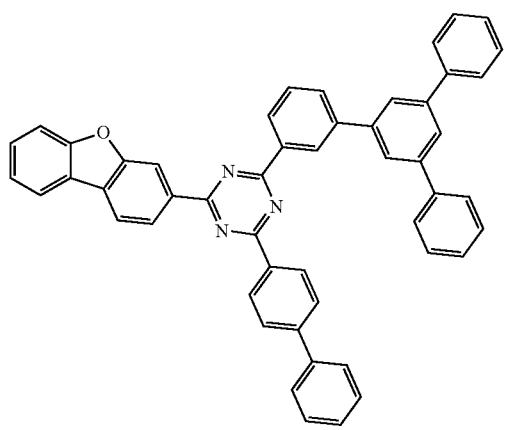
B-25
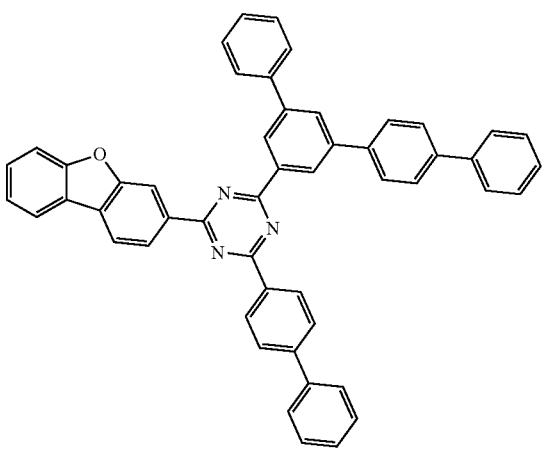
B-26
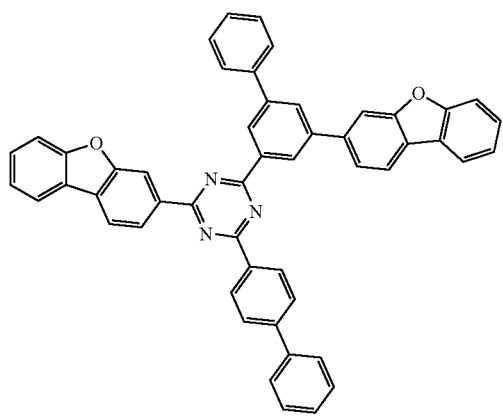
B-27
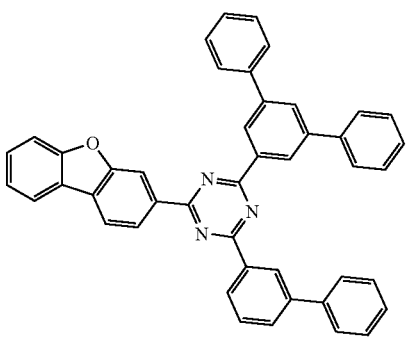
B-28

-continued
B-29
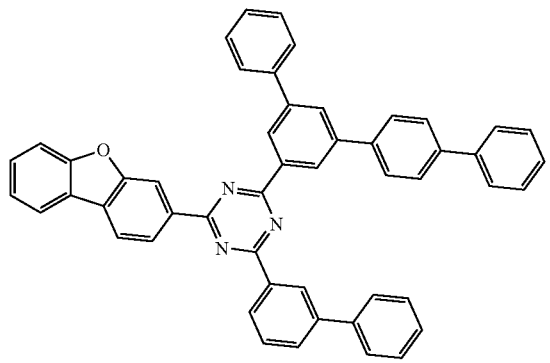
B-30
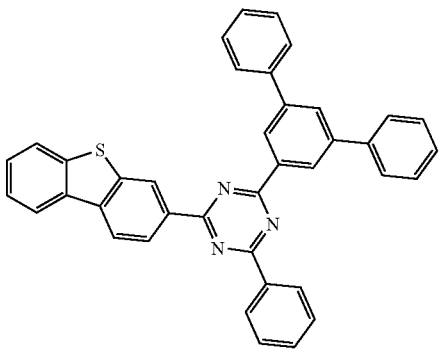
B-31
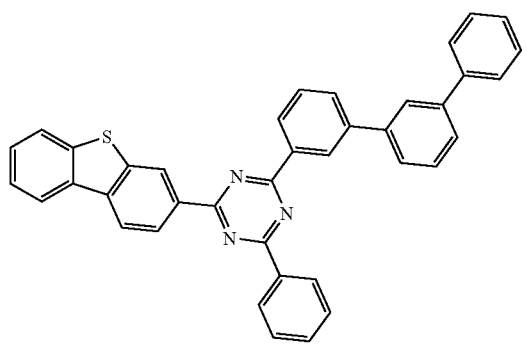
B-32
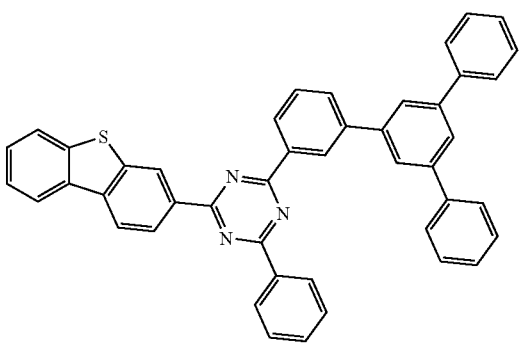
B-33
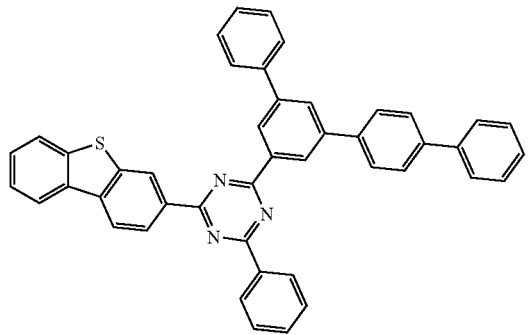
B-34
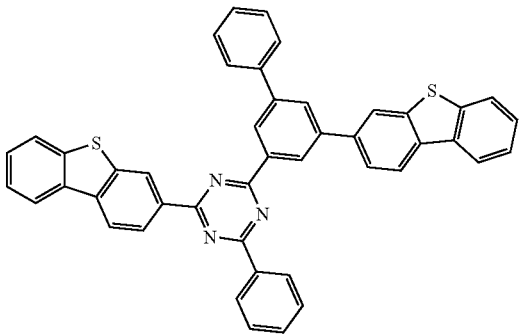
B-35
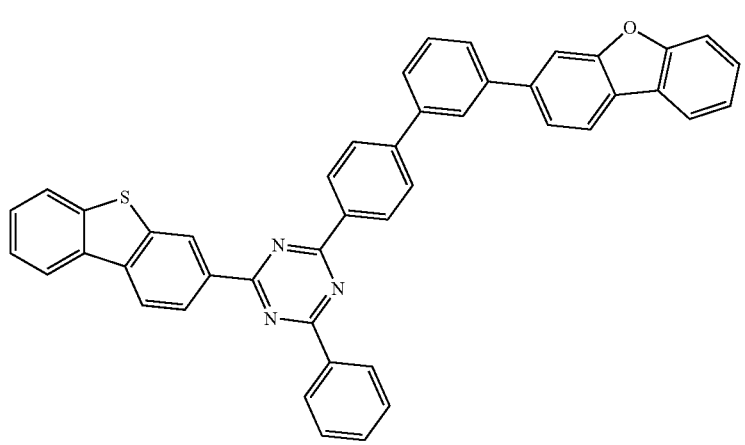

-continued
B-36
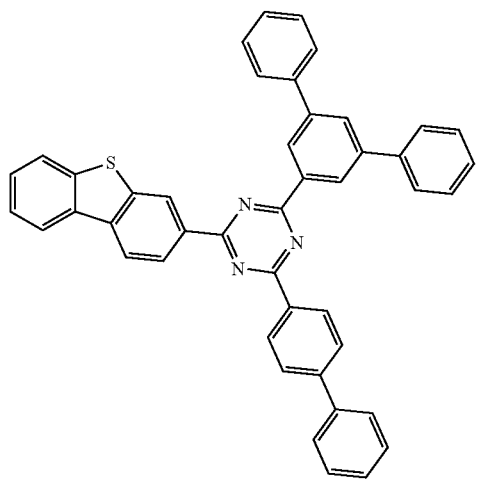
B-37
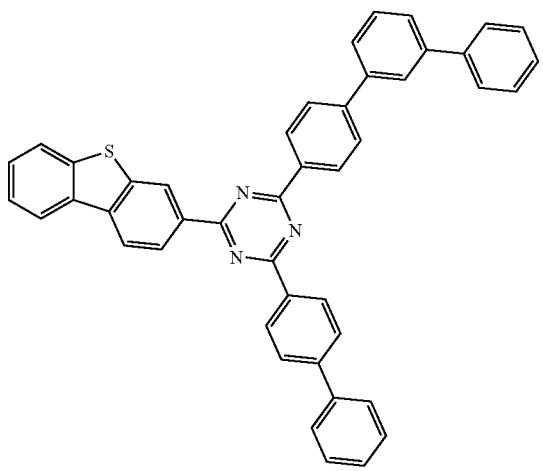
B-38
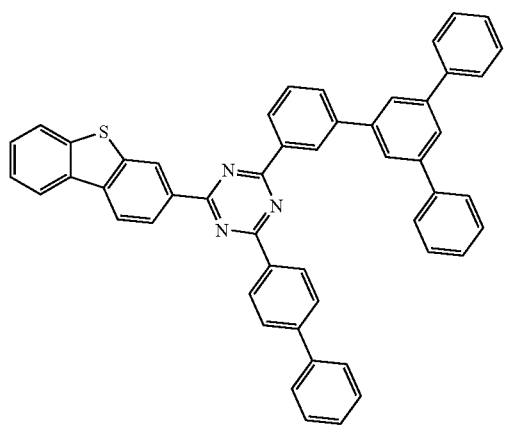
B-39
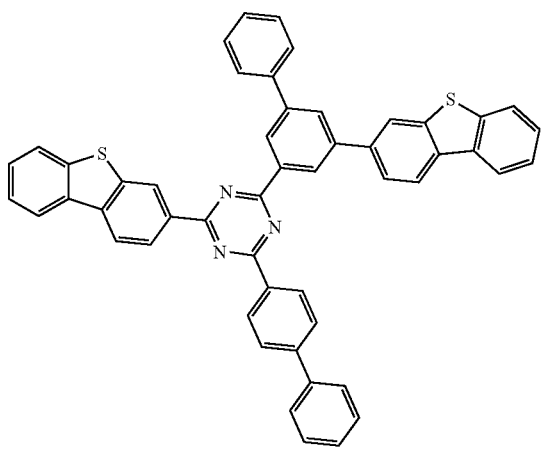
B-40
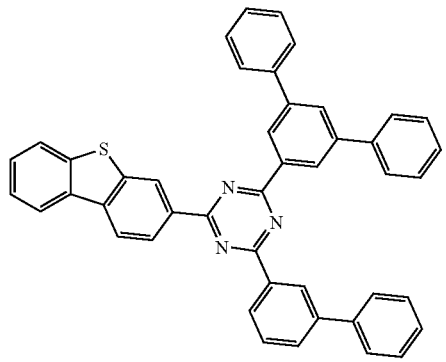
B-41
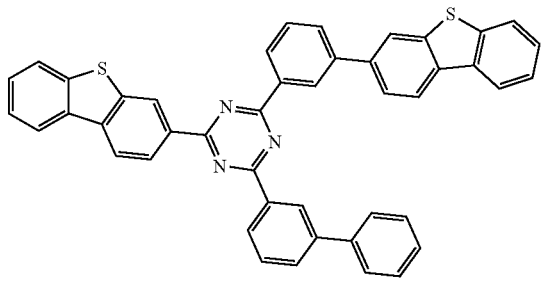

-continued
B-42
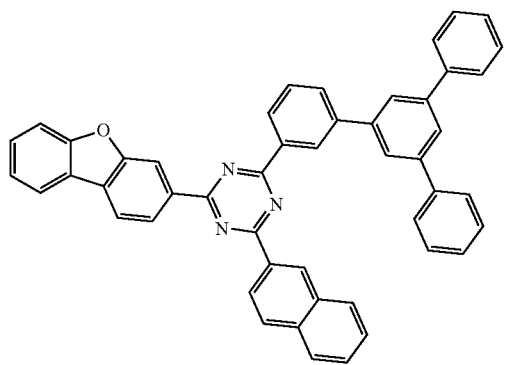
B-43
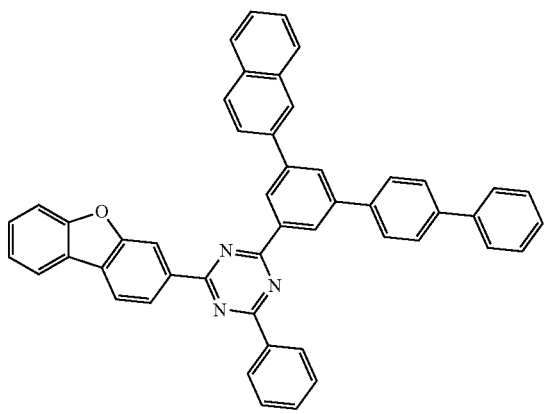
B-44
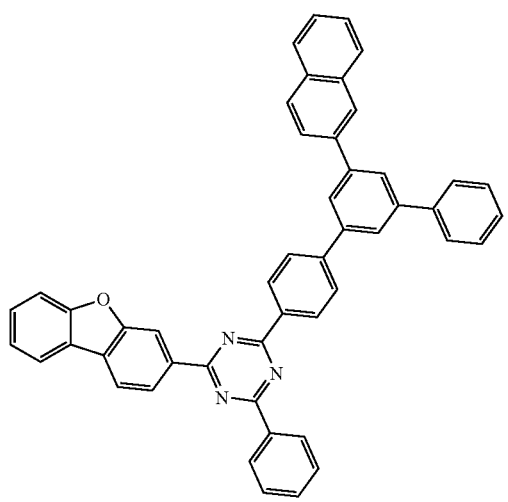
B-45
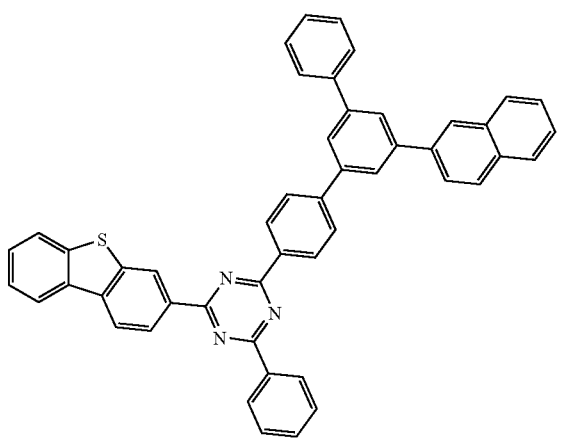
B-46
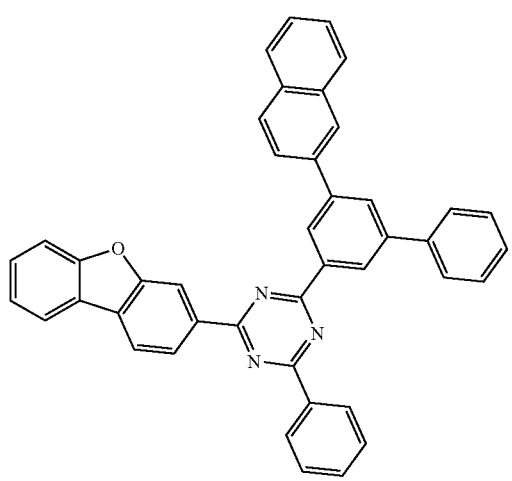

B-47
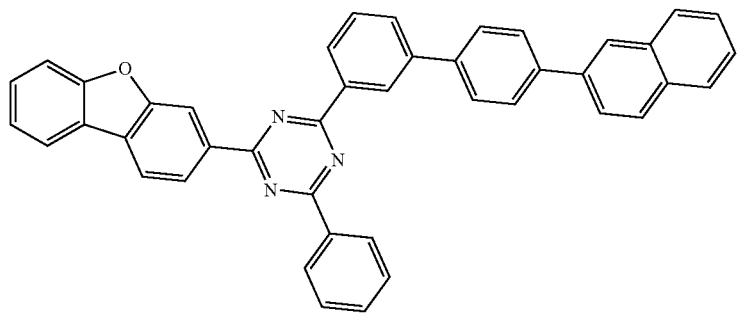
B-48
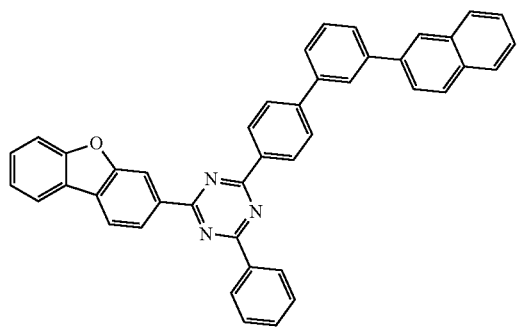
B-49
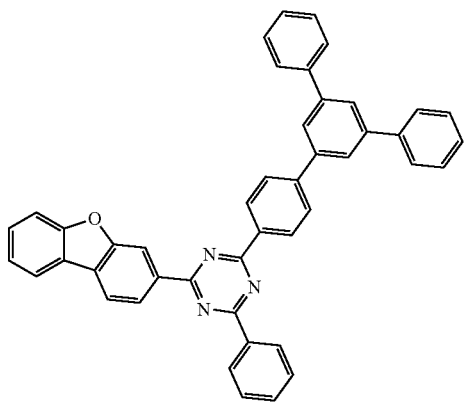
B-50
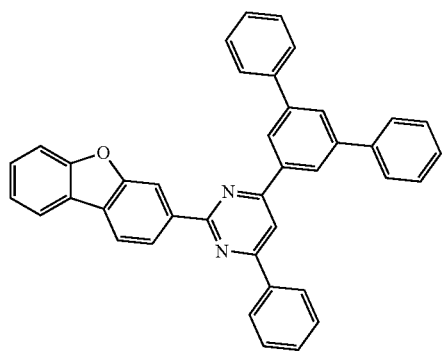
B-51
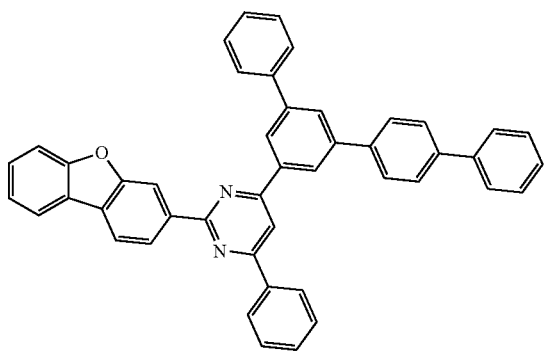
B-52
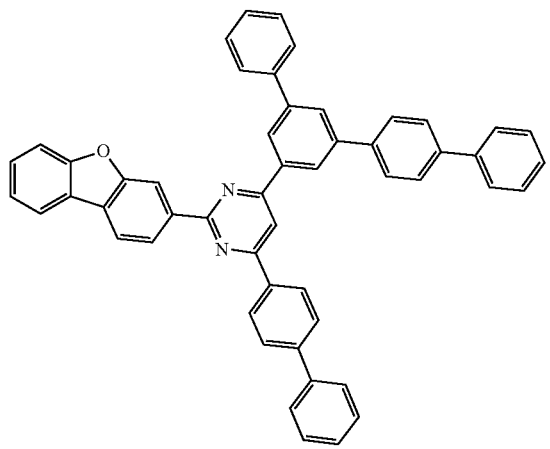
B-53
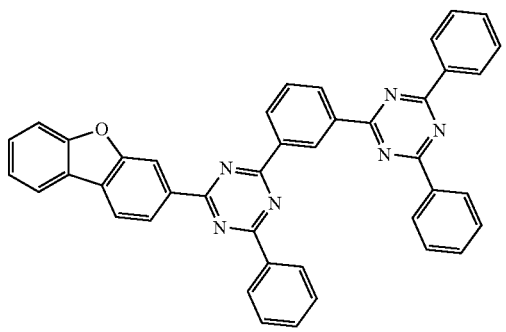

B-54
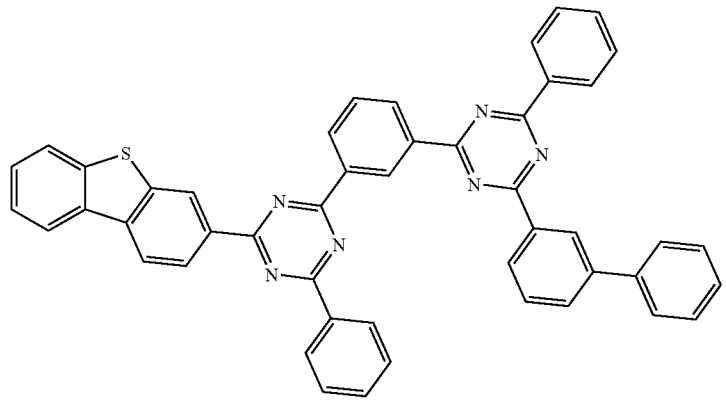
B-55
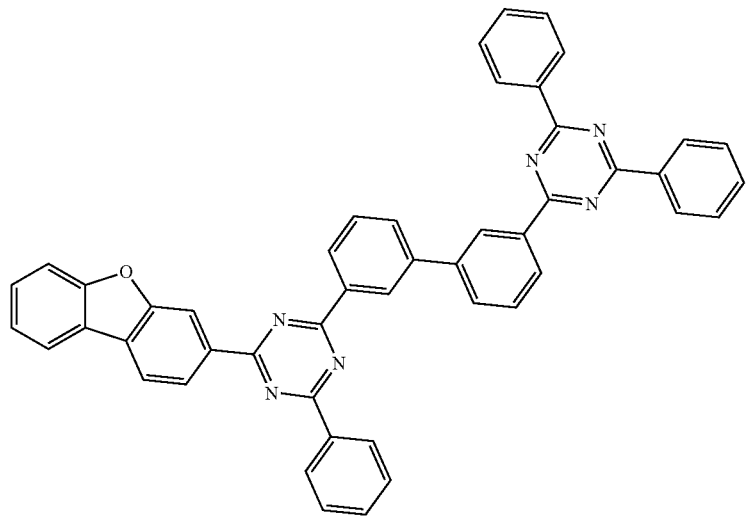
B-56 B-57
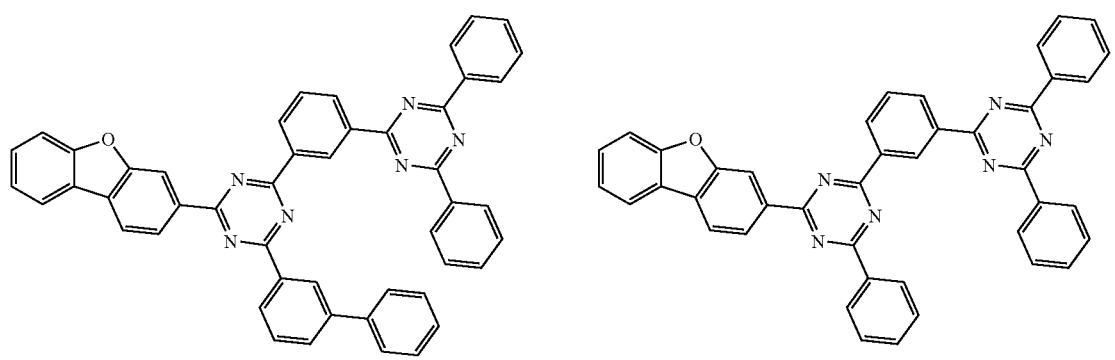

-continued
B-58
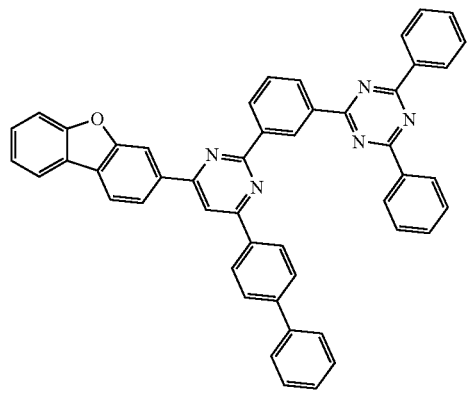
B-59
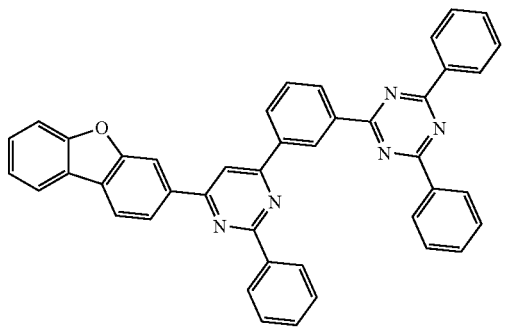
B-60
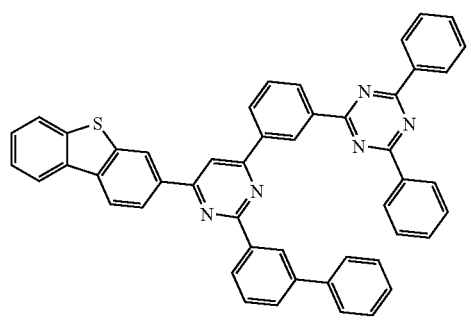
B-61
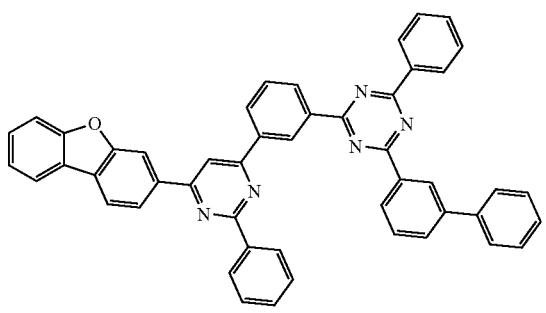
B-62
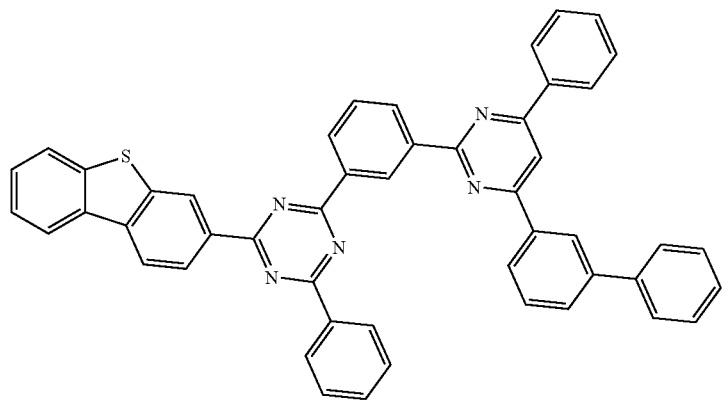
B-63
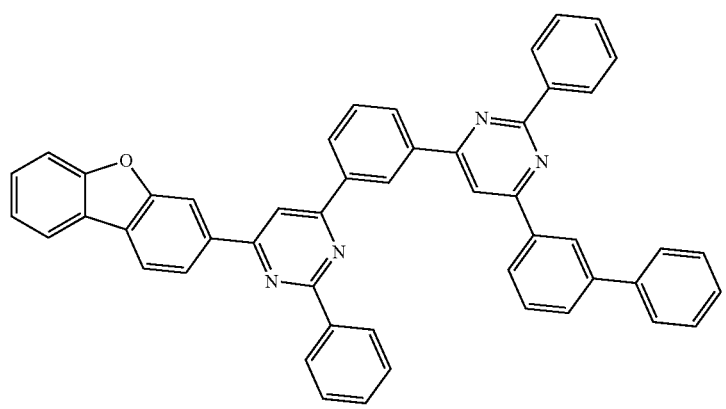

-continued
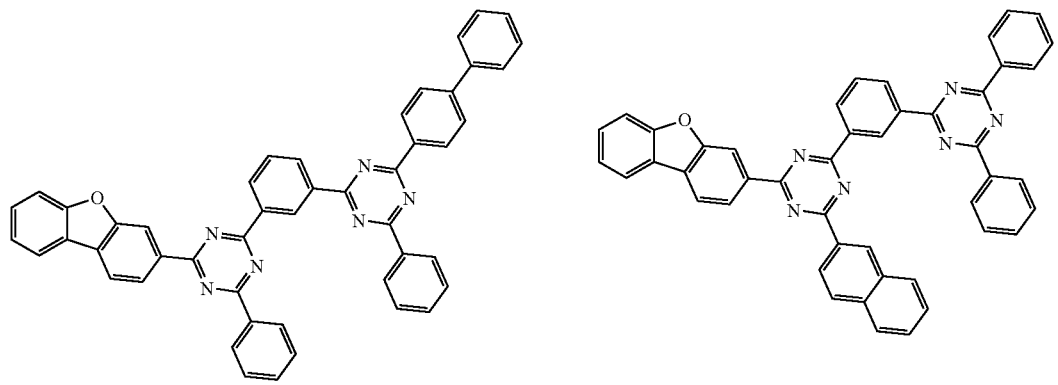
B-64
B-65
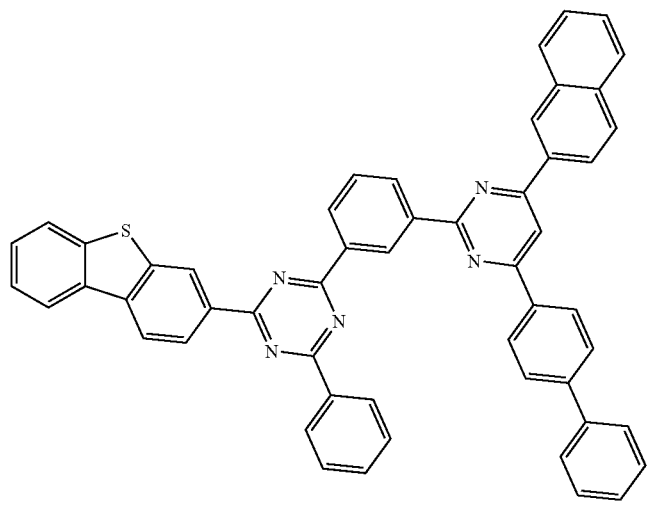
B-66
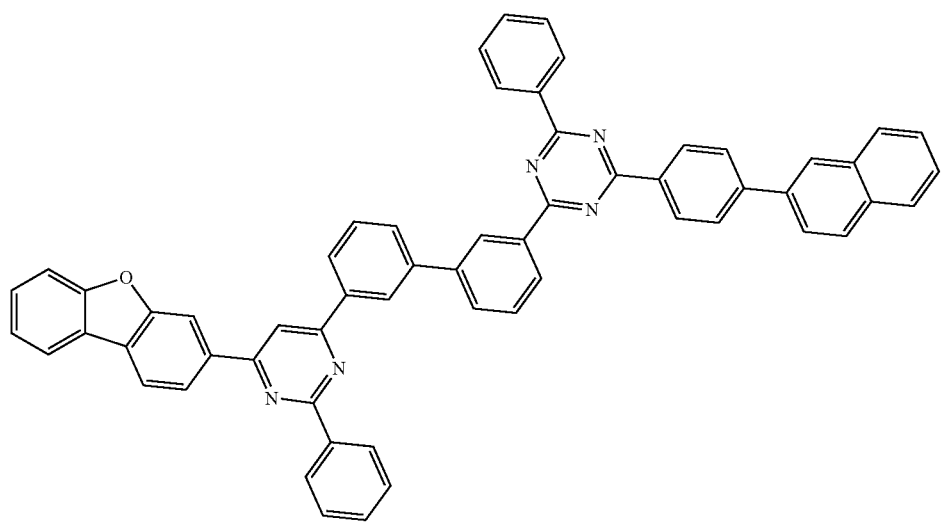
B-67

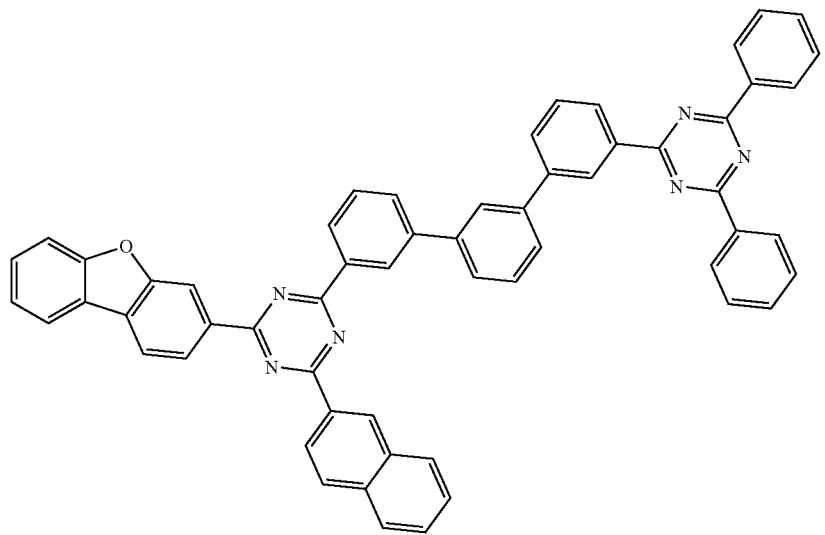
B-68
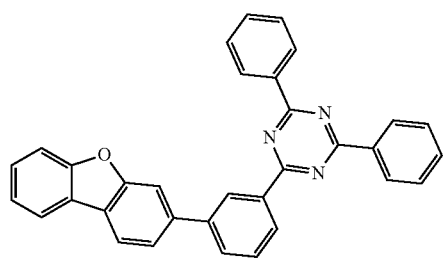
B-69
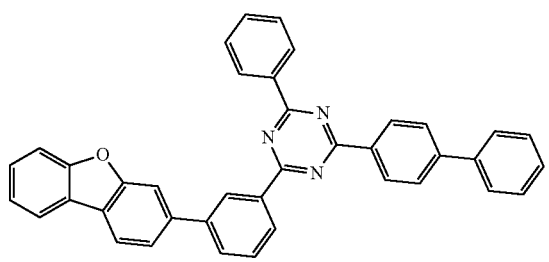
B-70
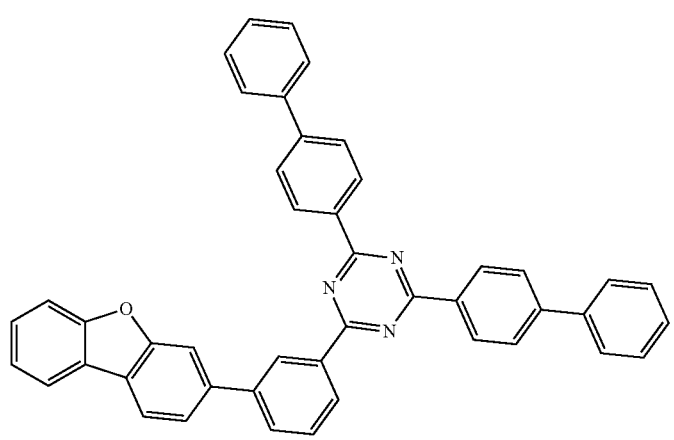
B-71

B-72
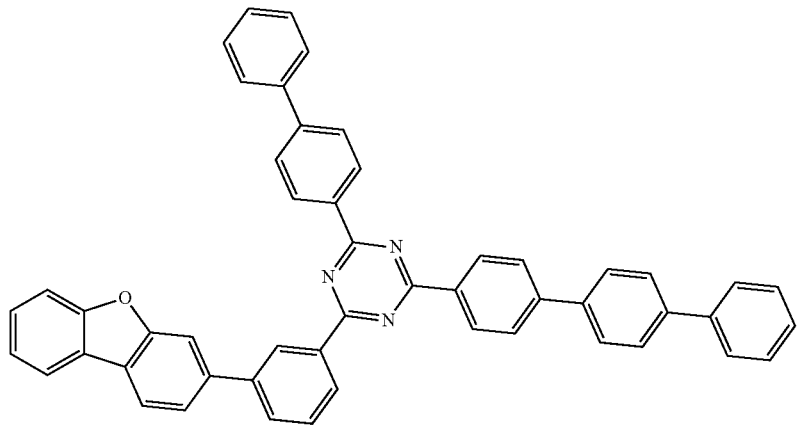
B-73
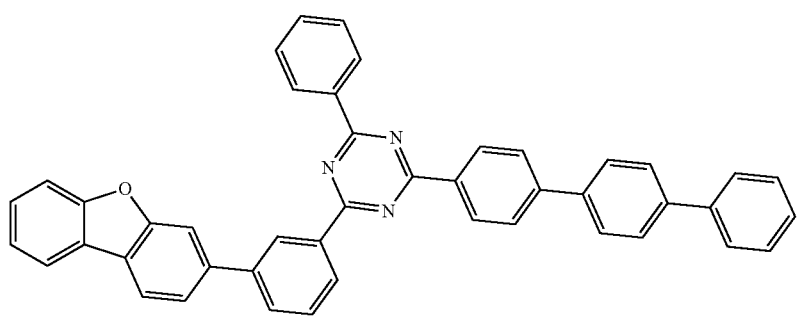
B-74
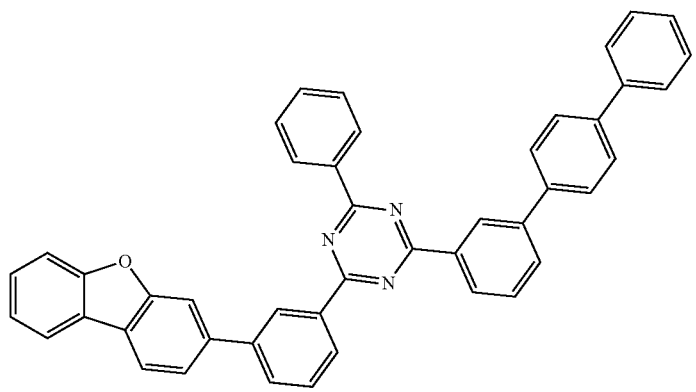
B-75
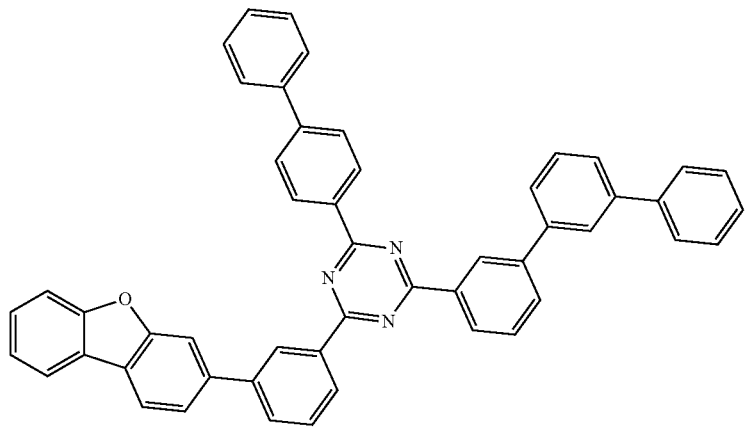

-continued
B-76
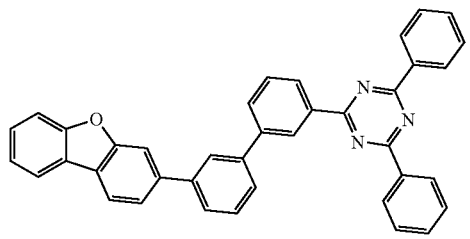
B-77
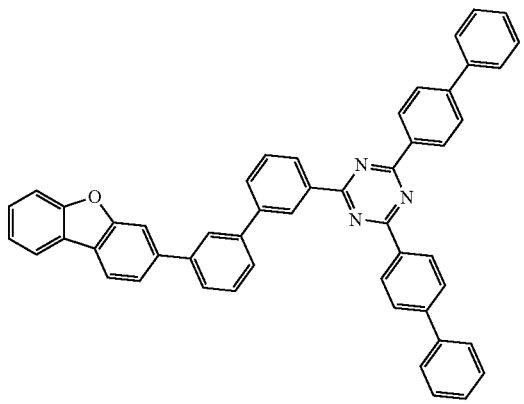
B-78
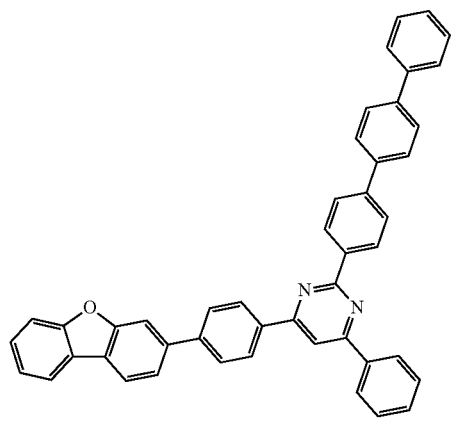
B-79
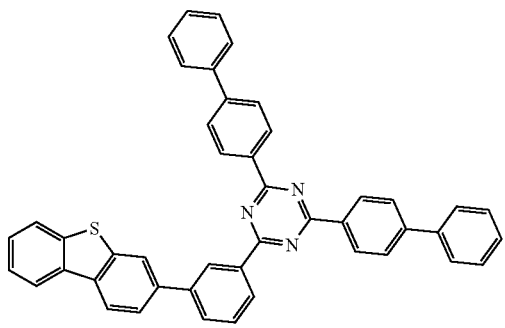
B-80
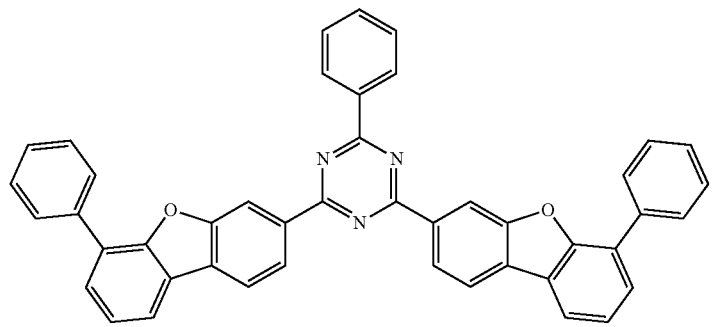
B-81
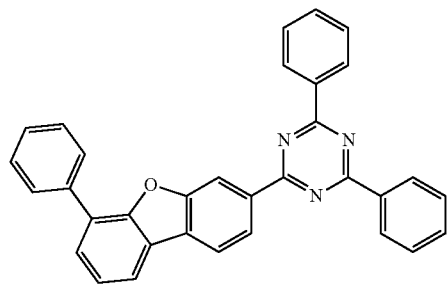
B-82
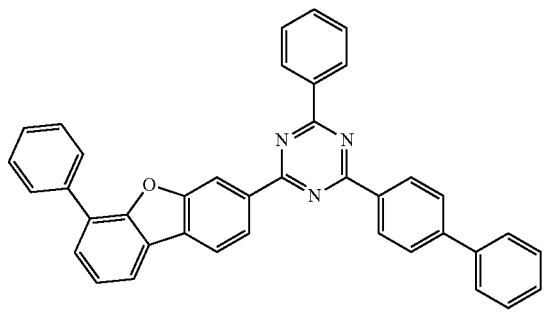

-continued
B-83
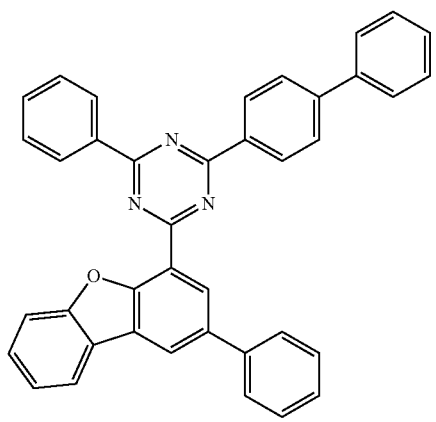
B-84
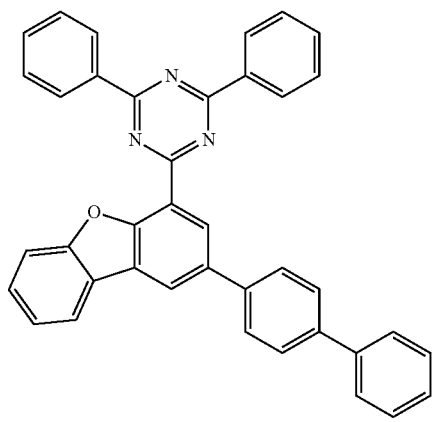
B-85
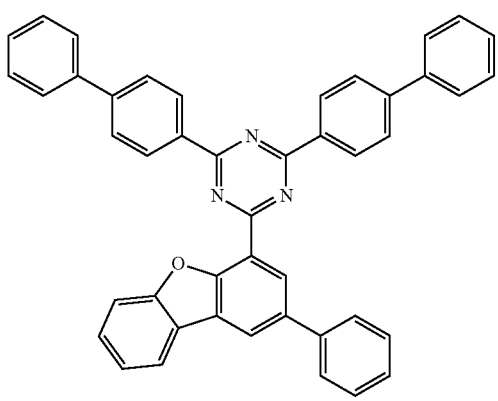
B-86
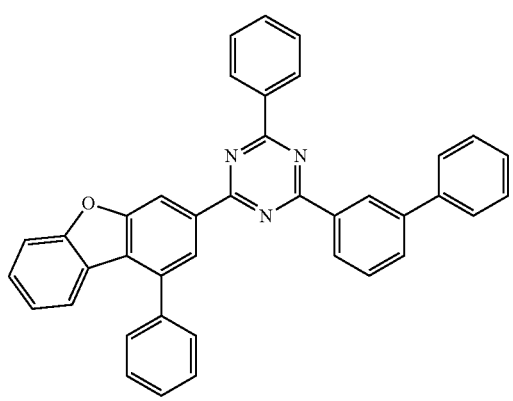
B-87
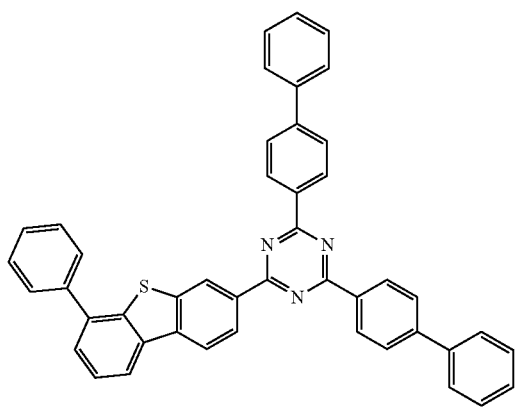
B-88
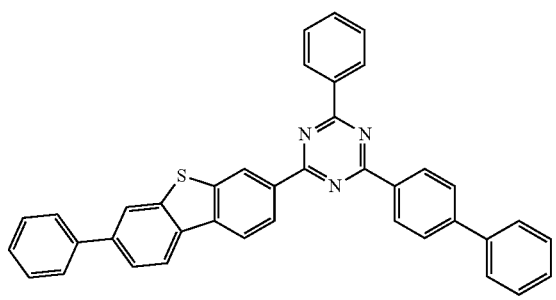

-continued
B-89
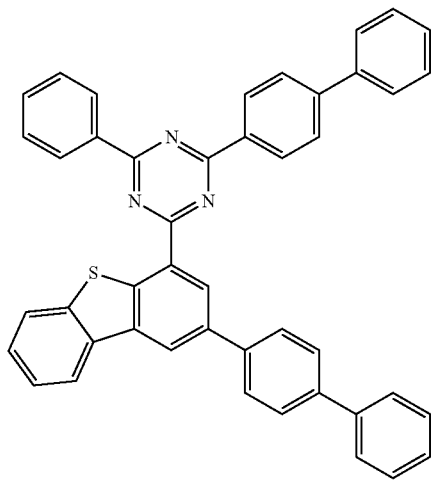
B-90
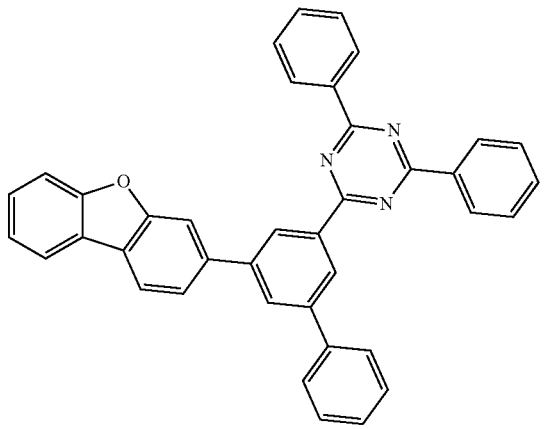
B-91
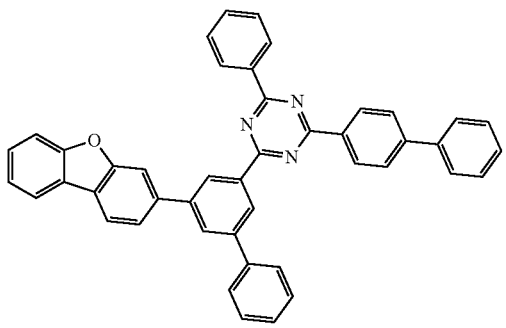
B-92
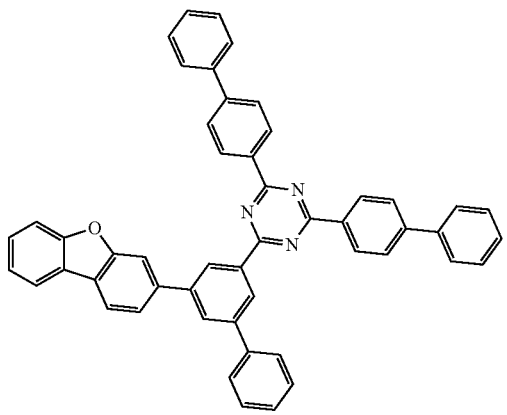
B-93
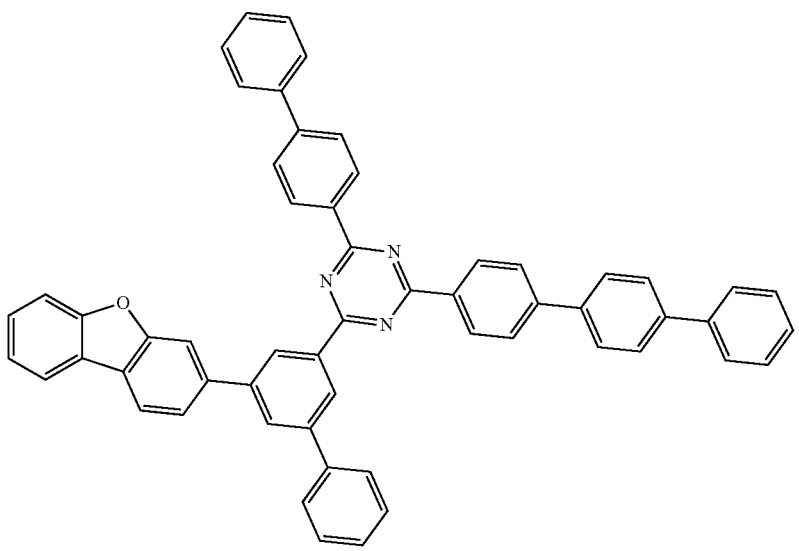

-continued
B-94
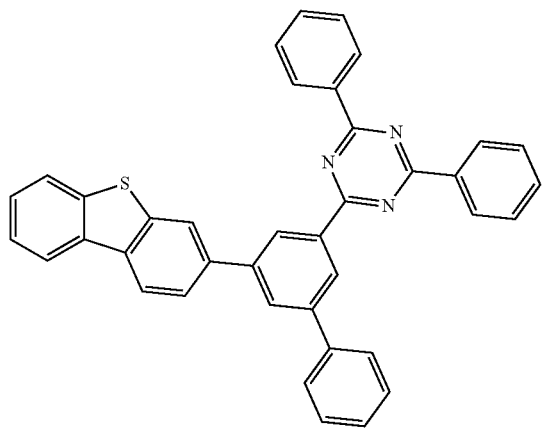
B-95
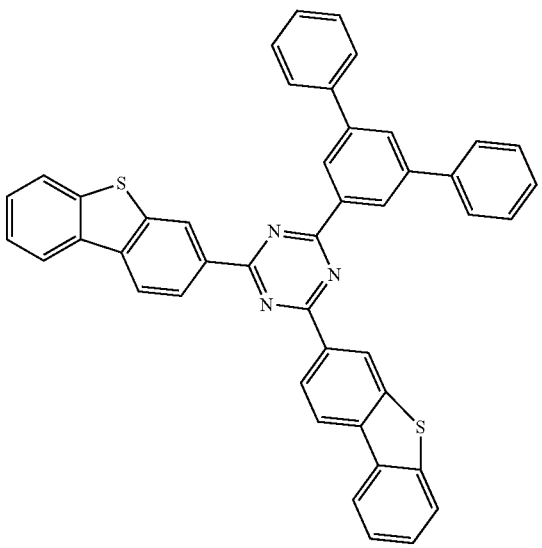
B-96
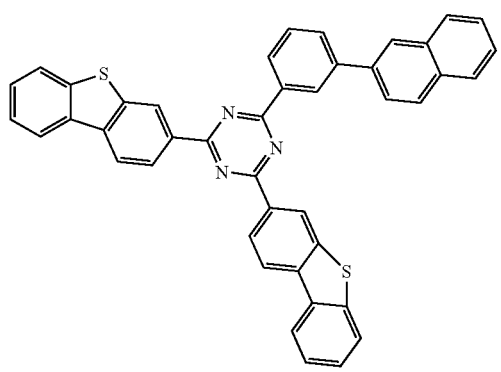
B-97
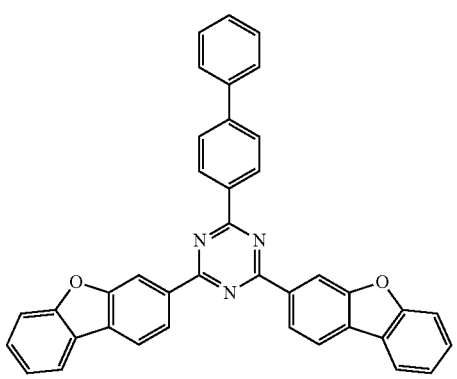
B-98
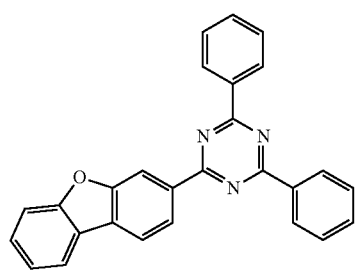
B-99
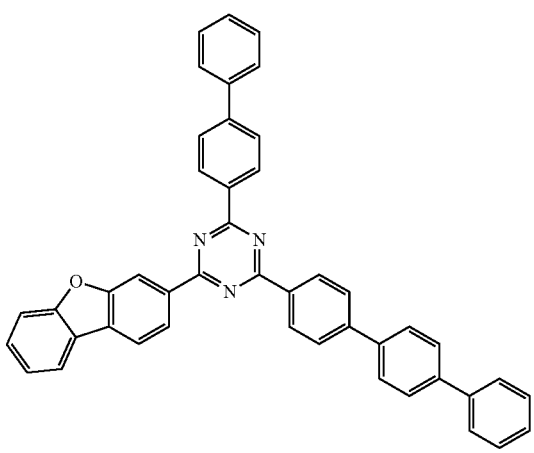

-continued
B-100
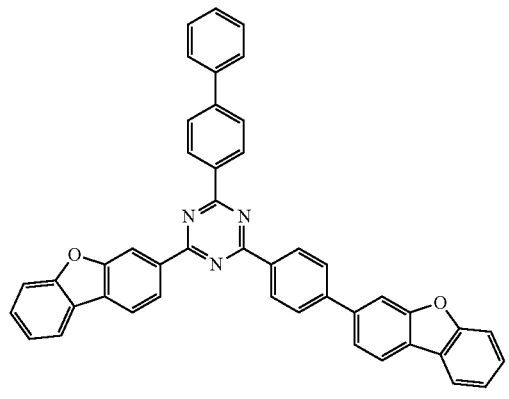
B-101
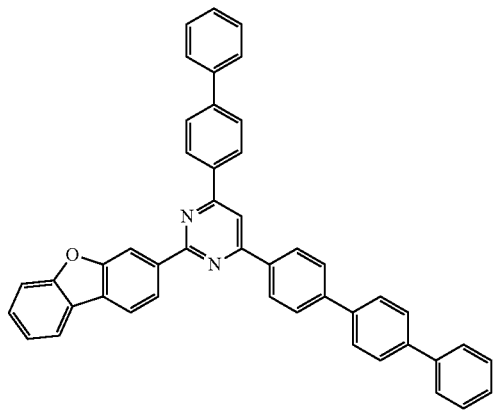
B-102
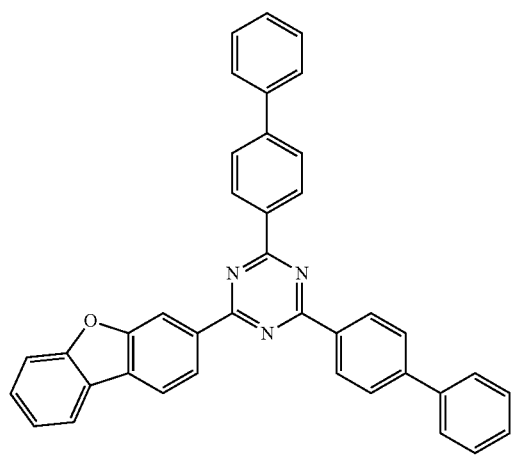
B-103
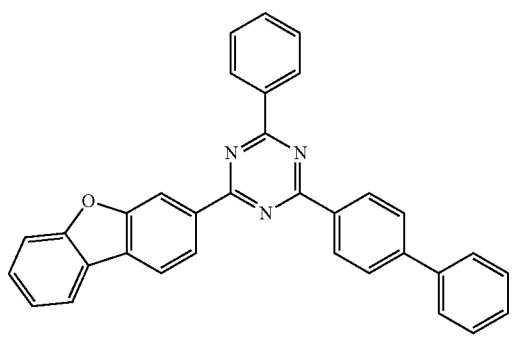
B-104
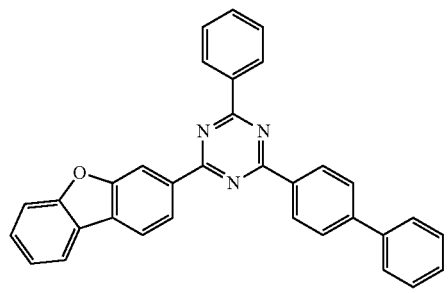
B-105
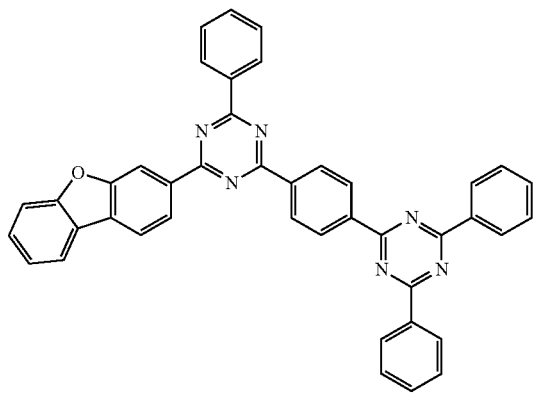

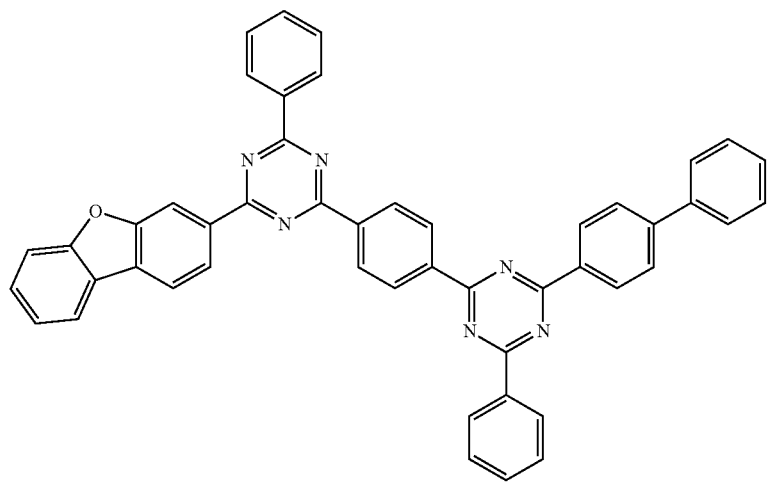
B-106
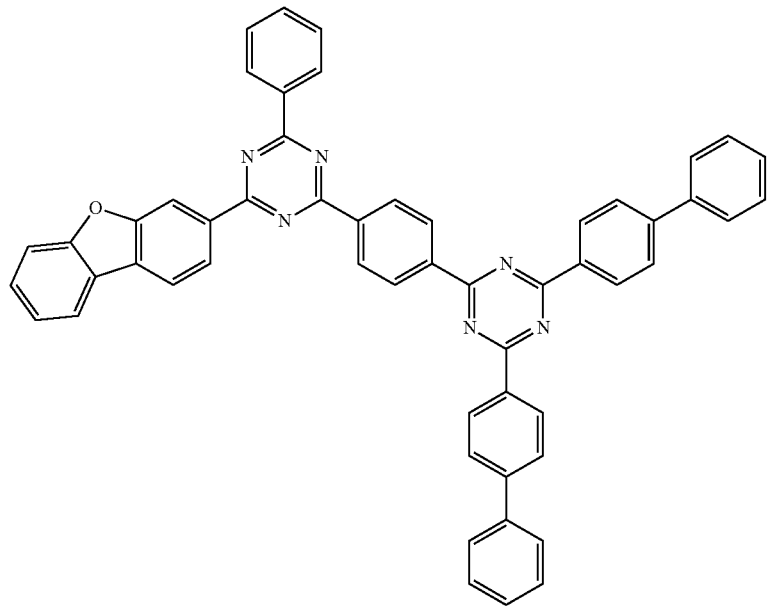
B-107
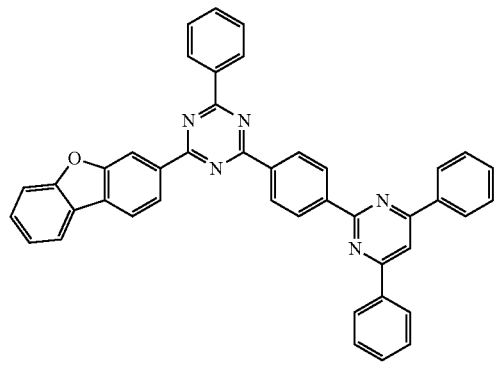
B-108
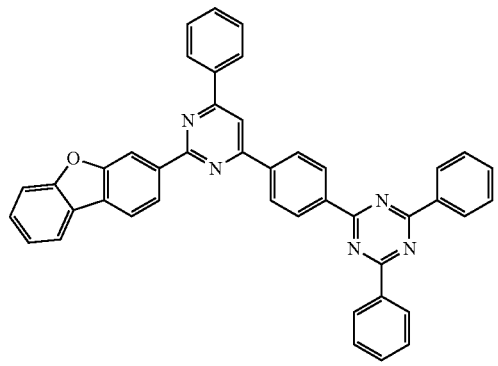
B-109

B-110
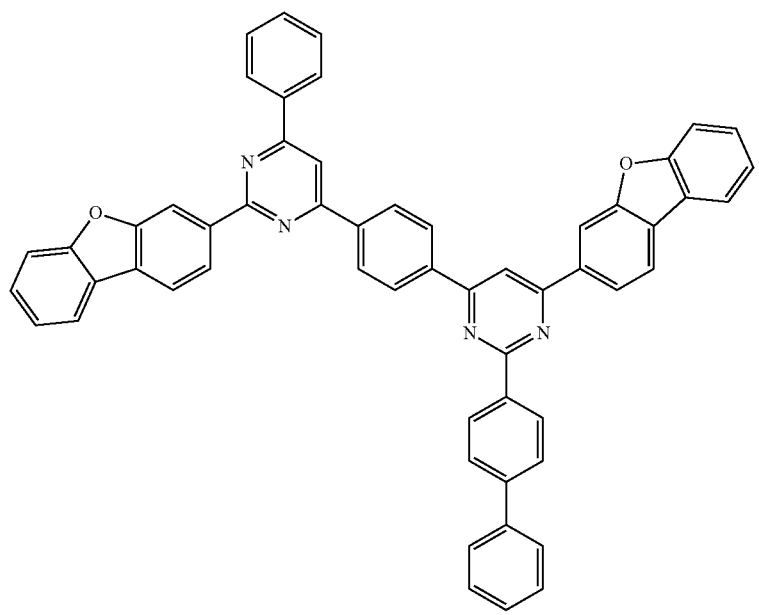
B-111
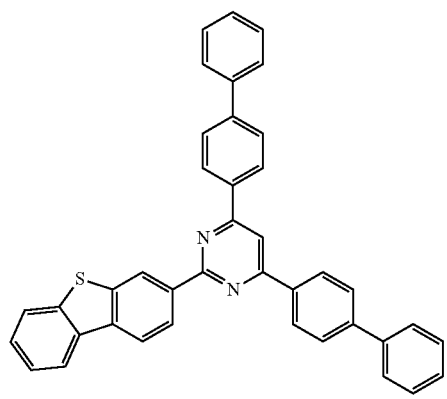
B-112
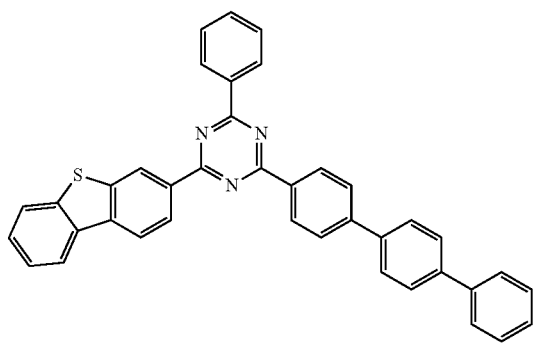
B-113
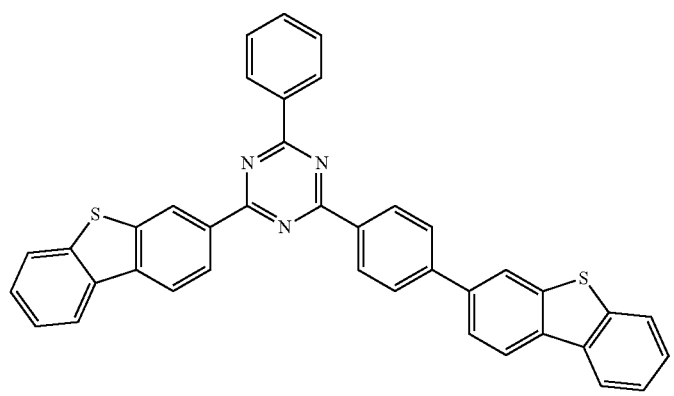

-continued
B-114
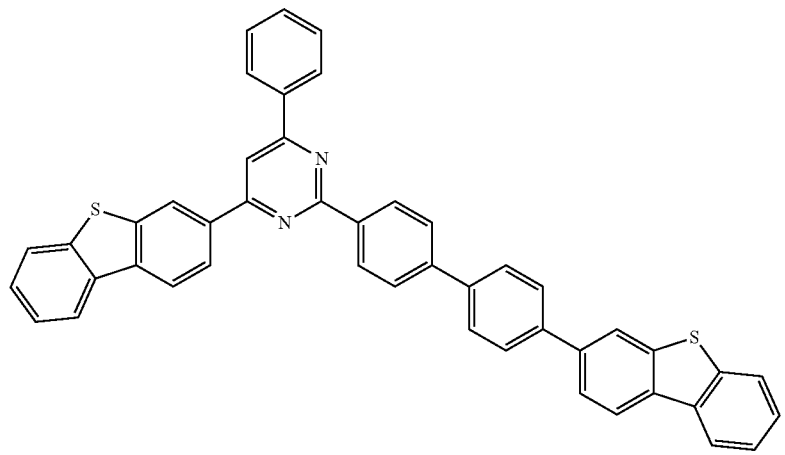
B-115
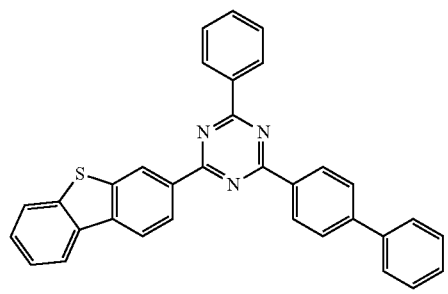
B-116
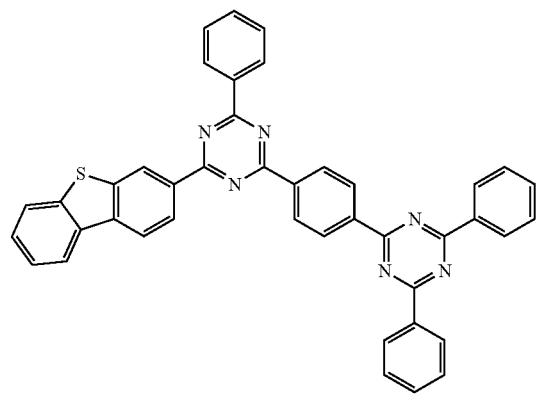
B-117
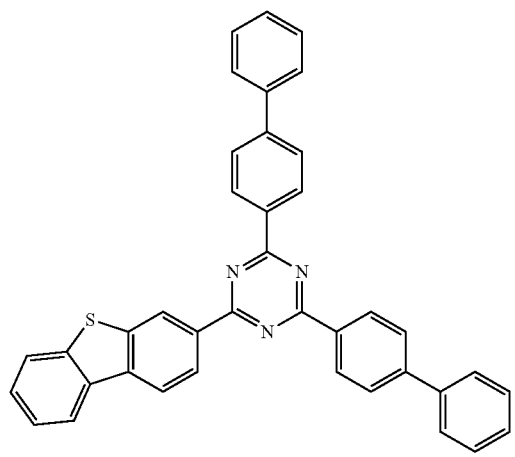
B-118
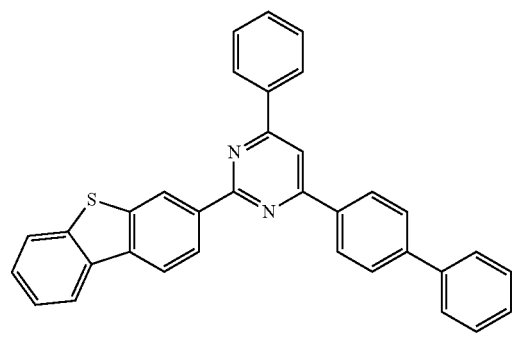

B-119
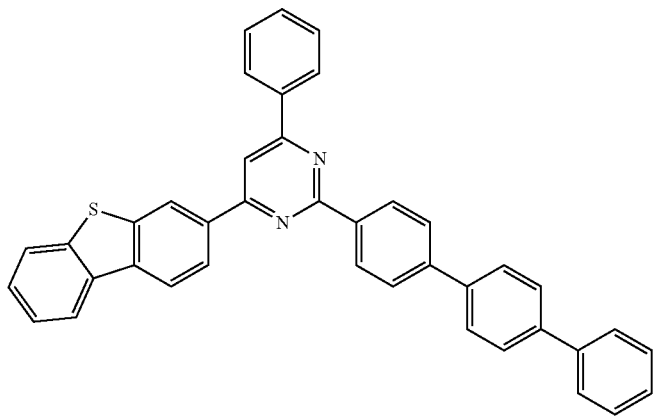
B-120
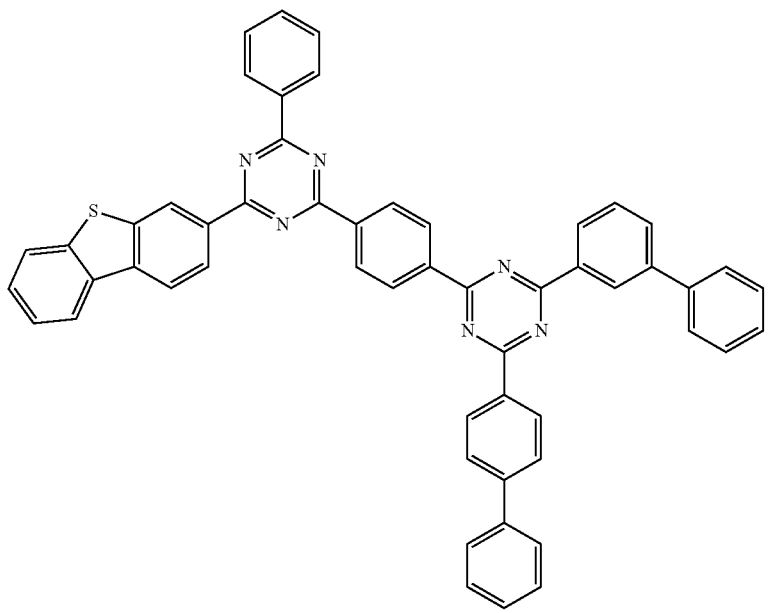
B-121
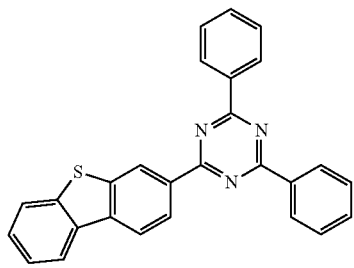
B-122
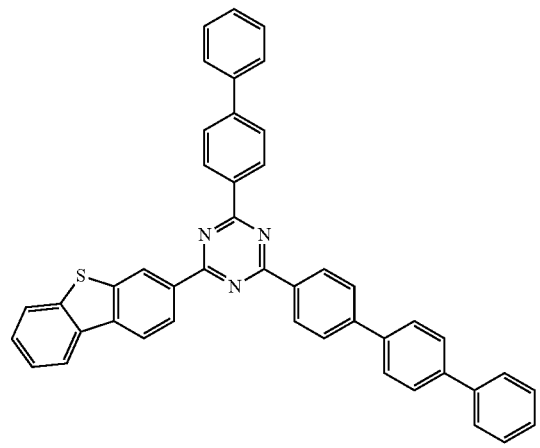

-continued
B-123
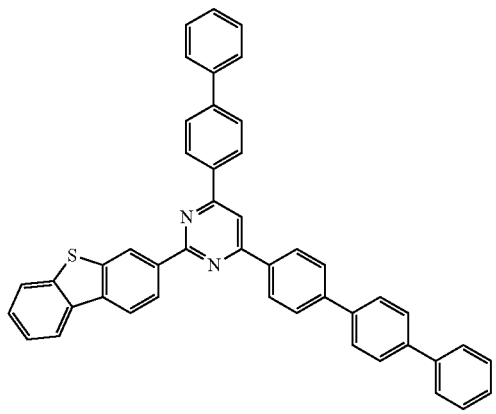
B-124
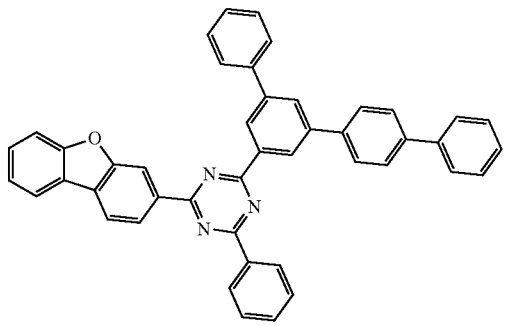
B-125
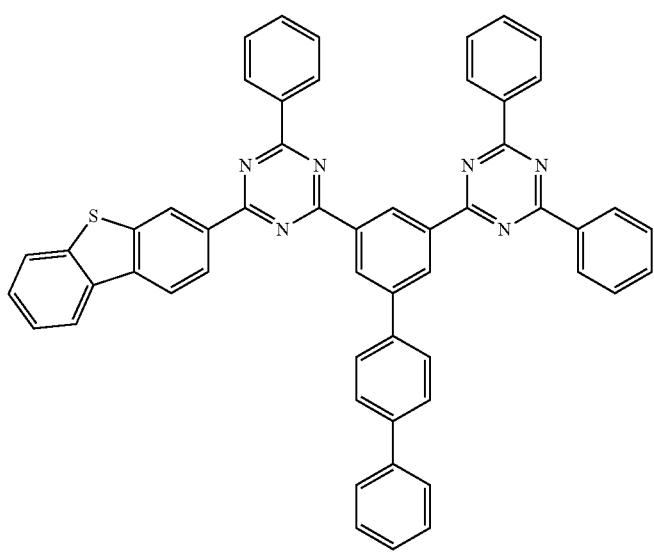
B-126
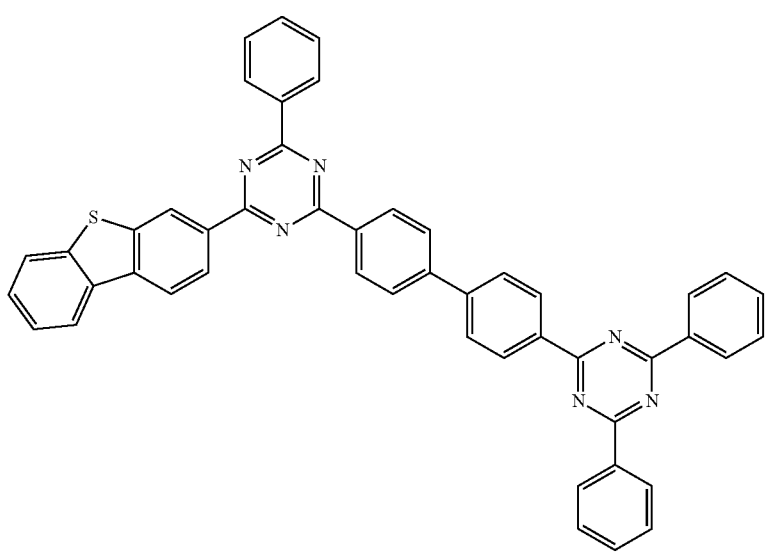

-continued
B-127
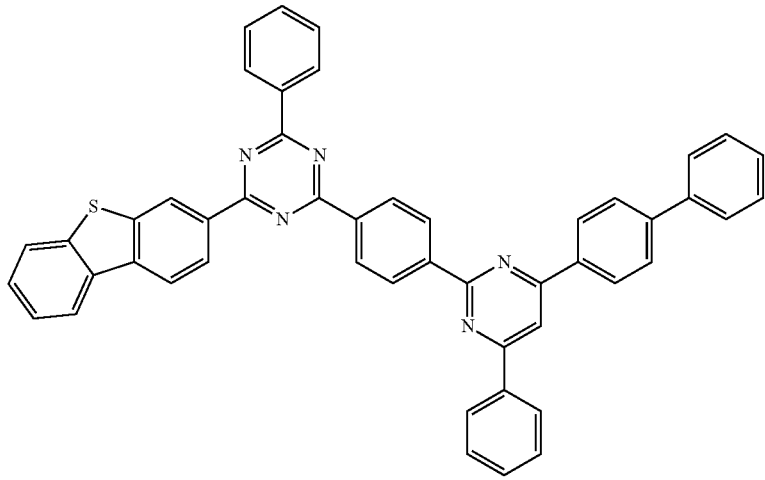
B-128
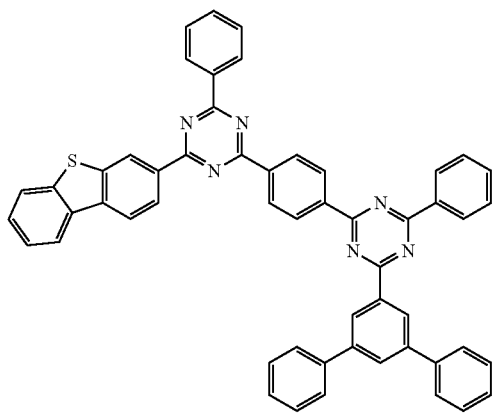
B-129
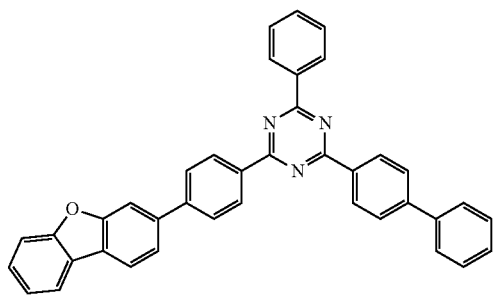
B-130
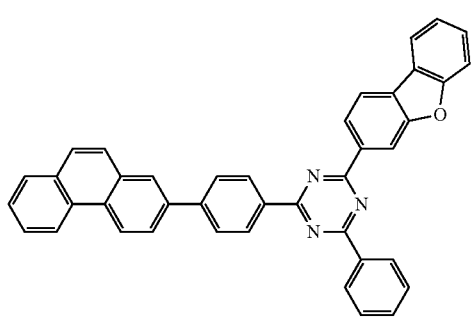
B-131
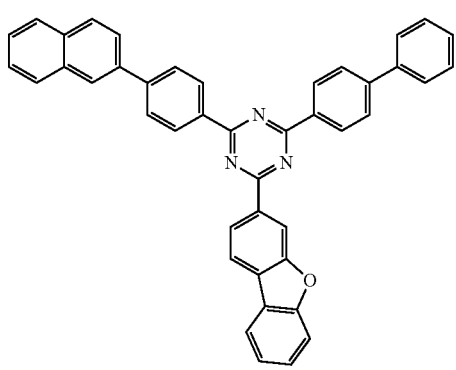
B-132
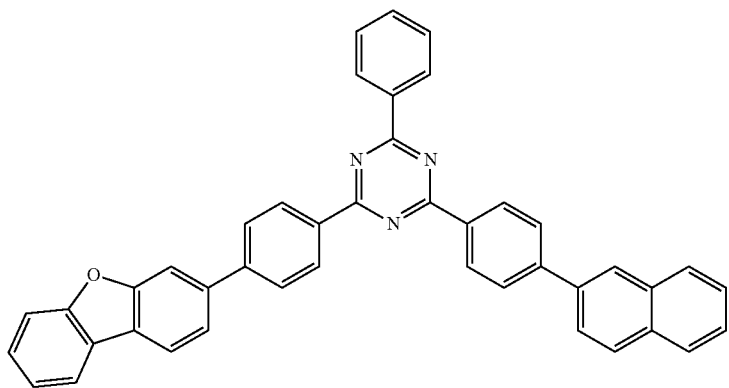

-continued
B-133
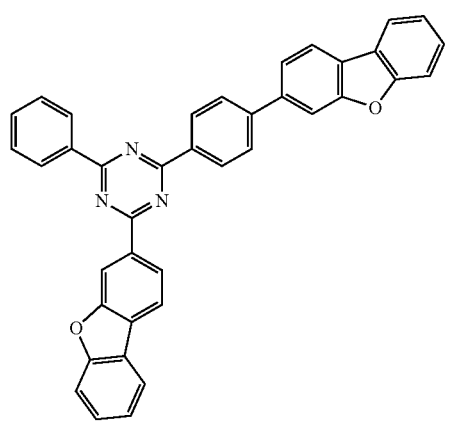
B-134
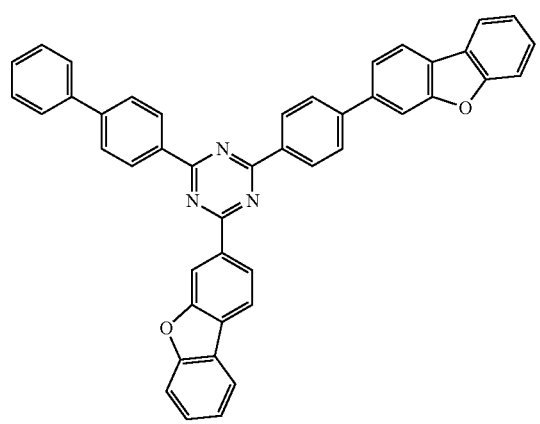
B-135
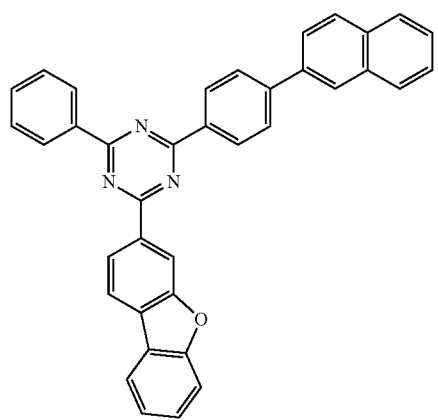
B-136
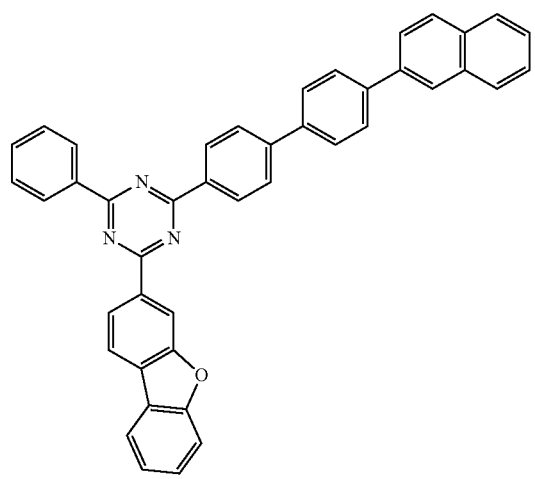
B-137
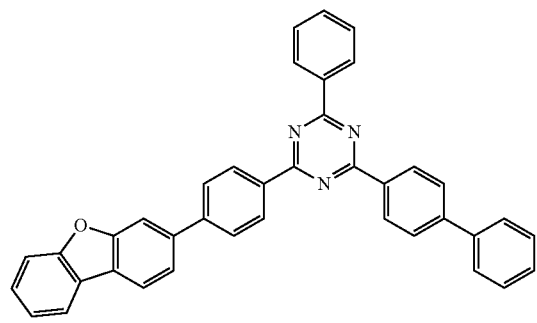
B-138
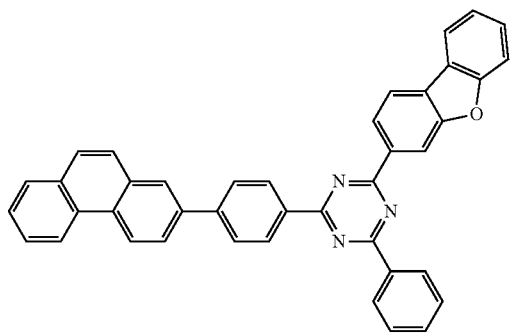

-continued
B-139
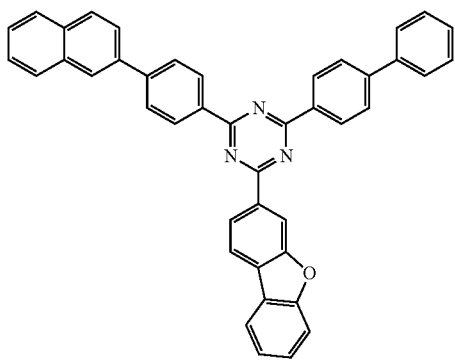
B-140
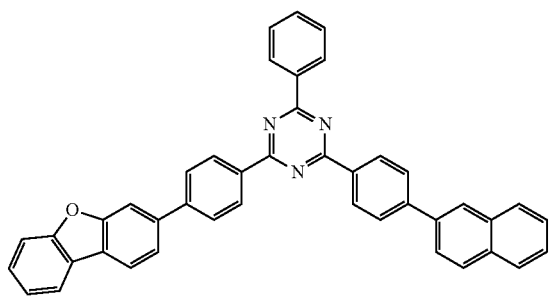
B-141
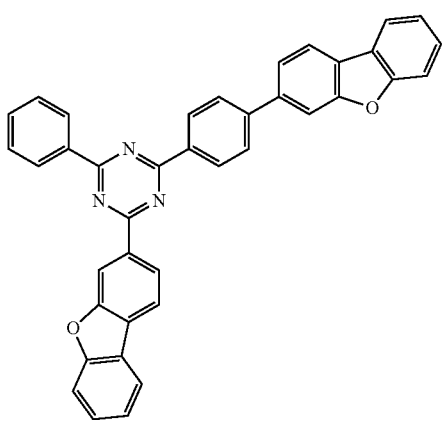
B-142
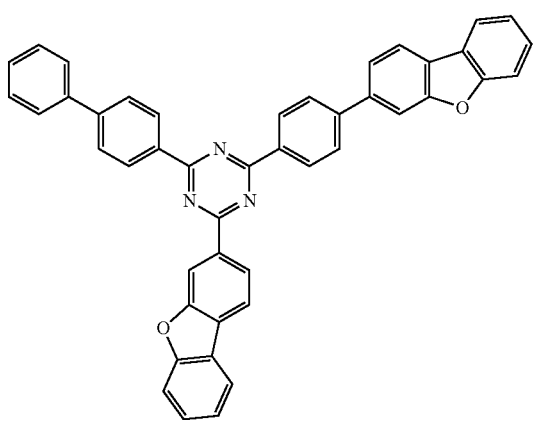
B-143
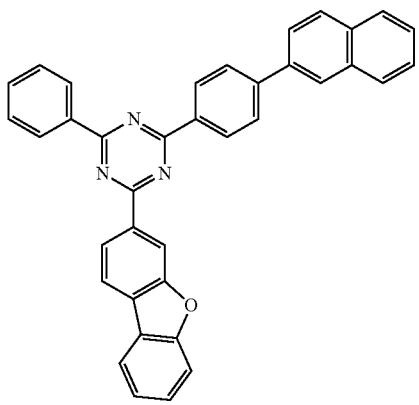
B-144
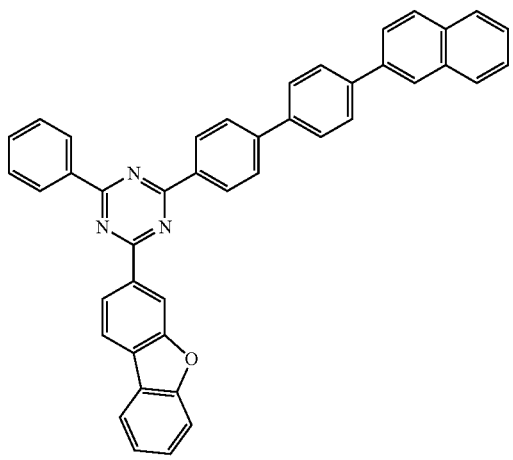
B-145
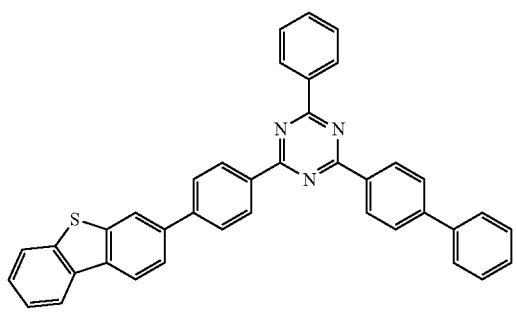
B-146
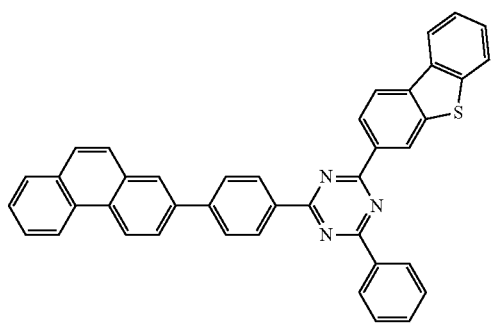

-continued
B-147
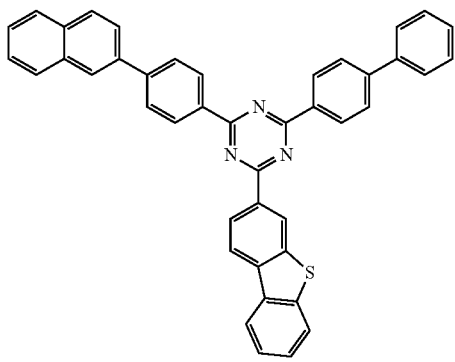
B-148
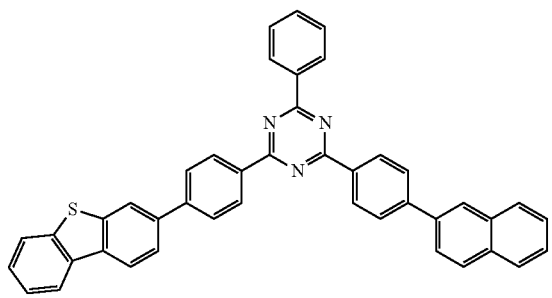
B-149
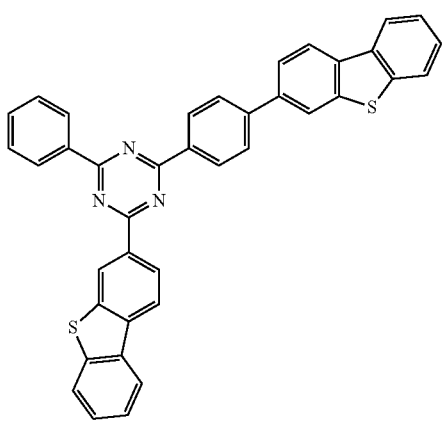
B-150
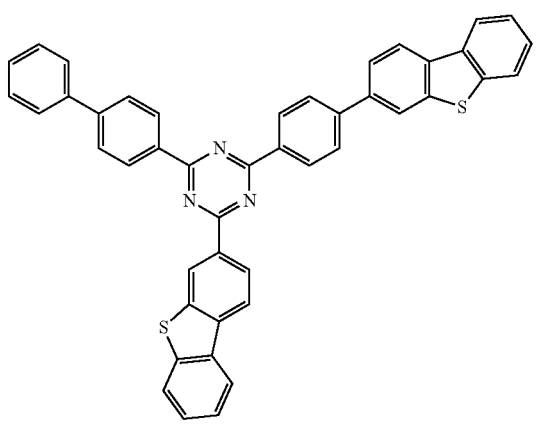
B-151
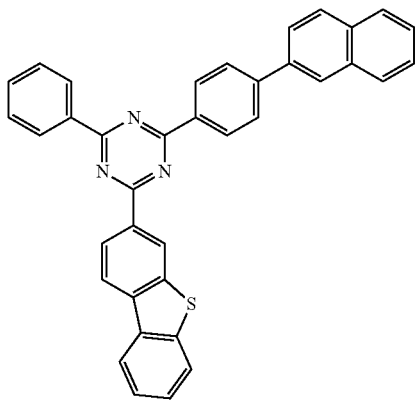
B-152
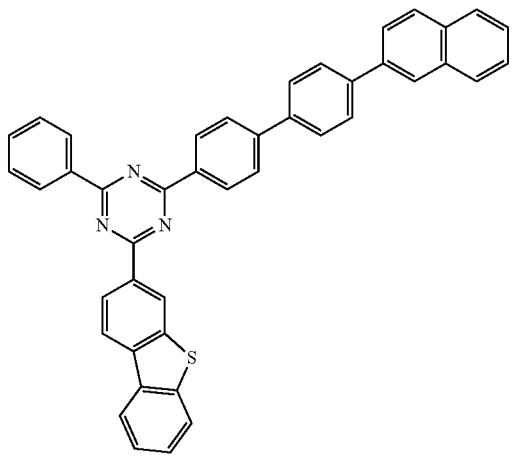
B-153
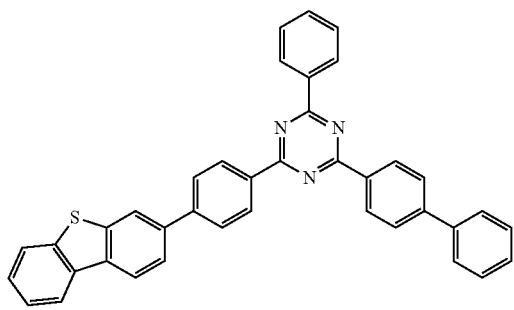
B-154
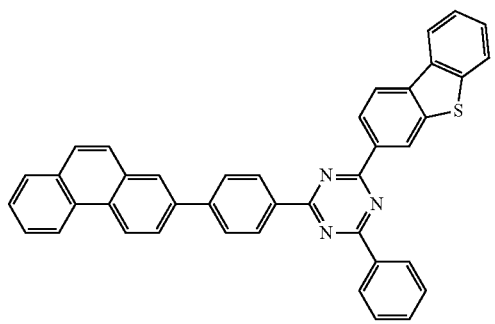

-continued
B-155
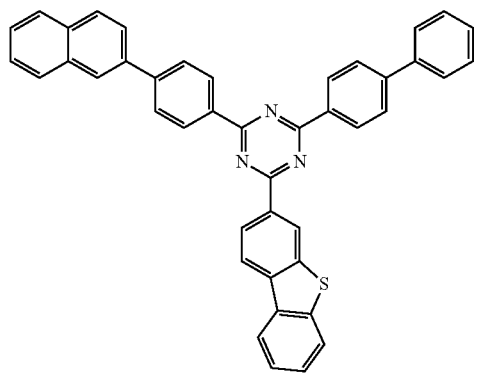
B-156
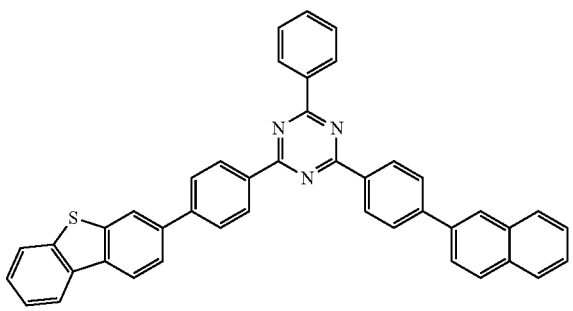
B-157
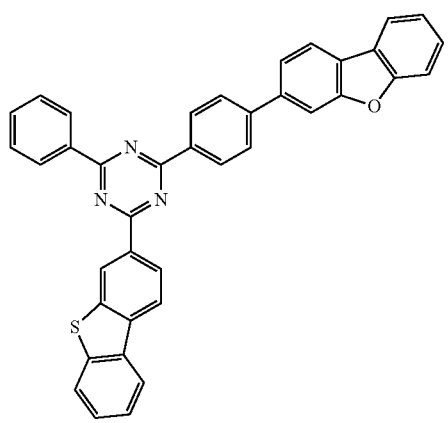
B-158
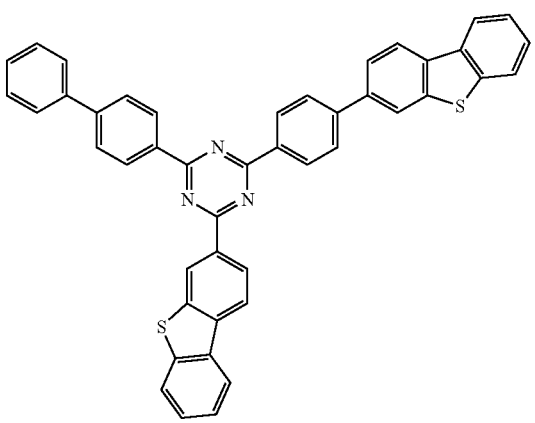
B-159
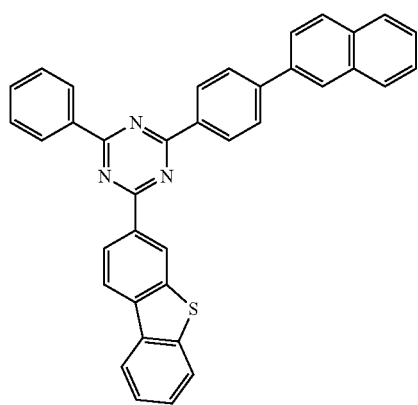
B-160
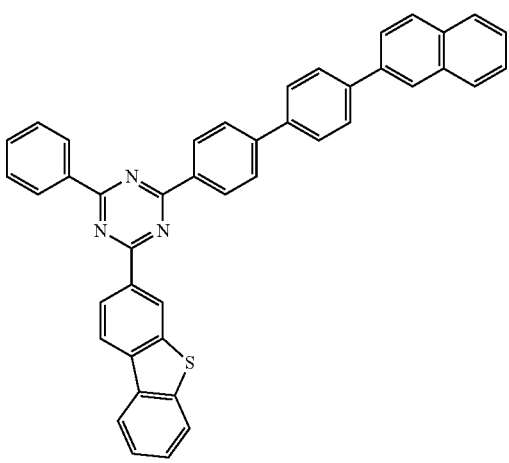

-continued
B-161
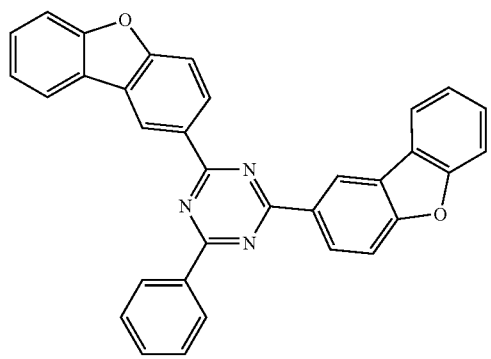
B-162
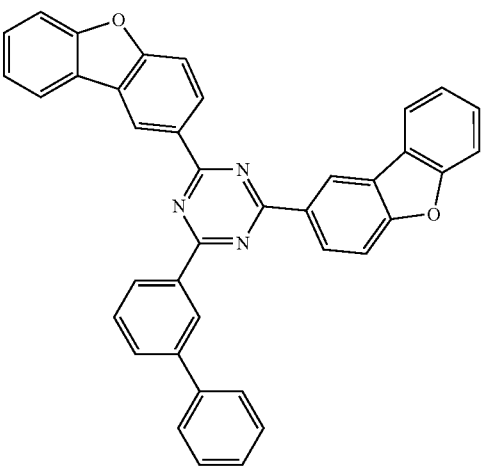
B-163
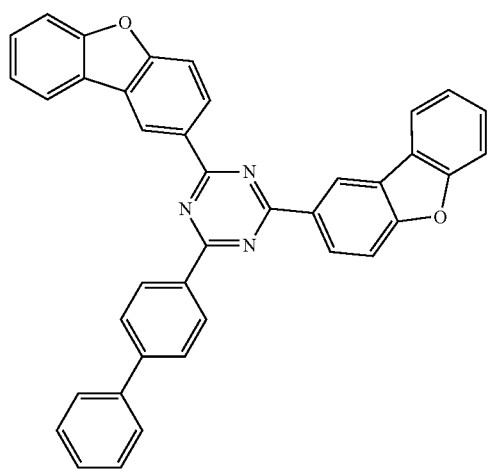
B-164
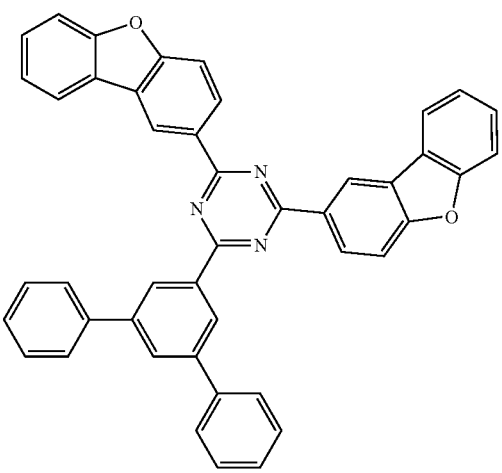
B-165
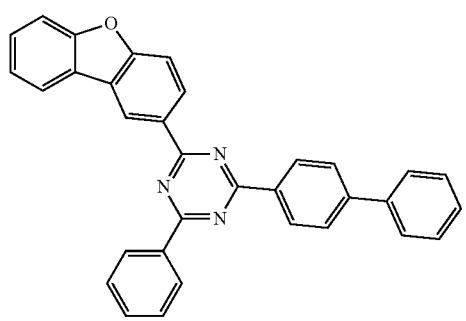
B-166
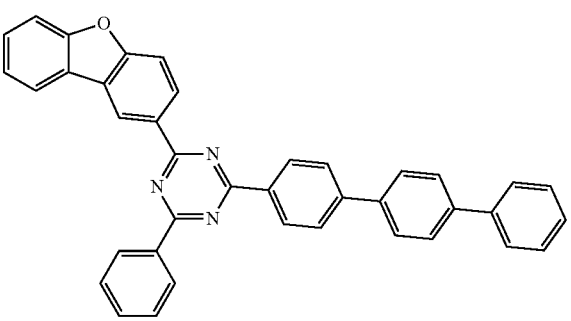

-continued
B-167
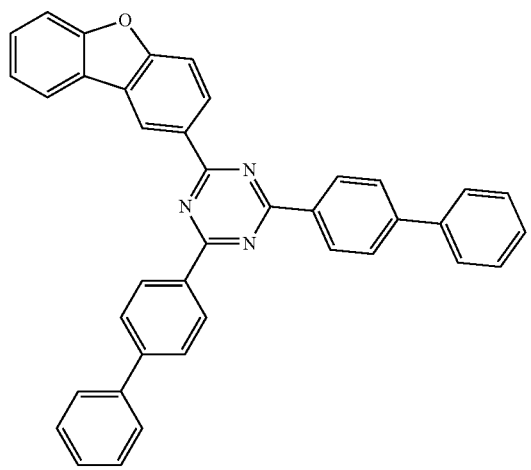
B-168
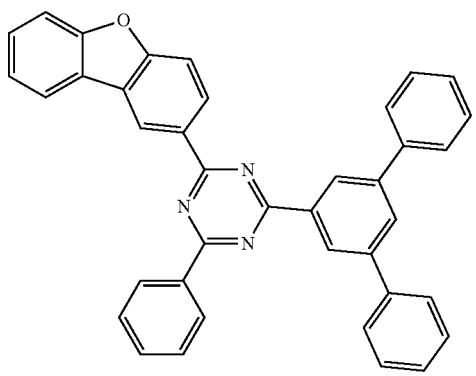
B-169
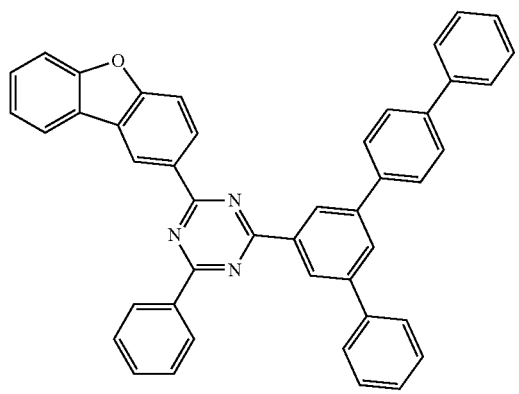
B-170
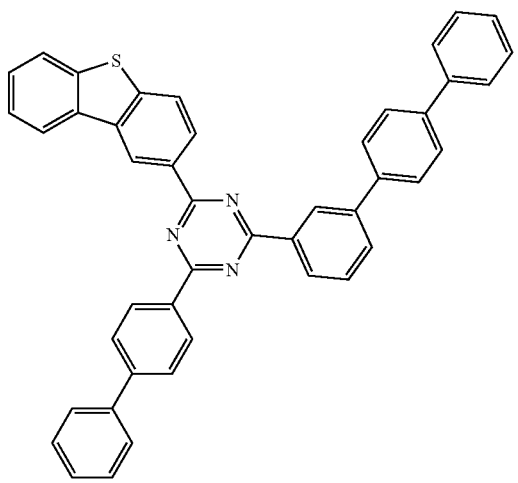
B-171
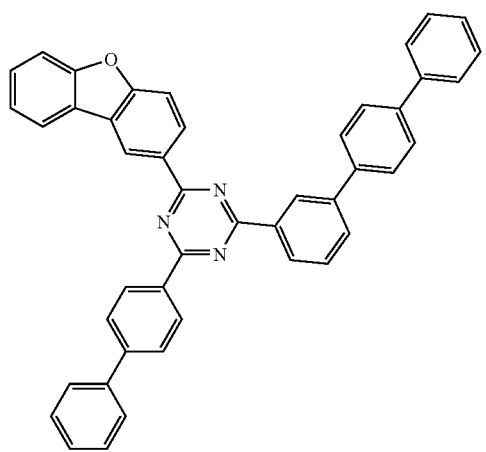
B-172
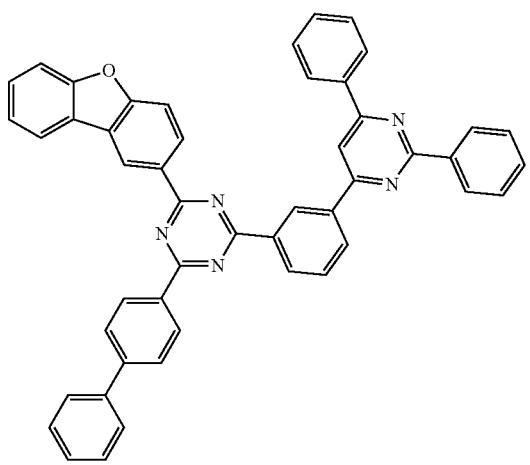

B-173
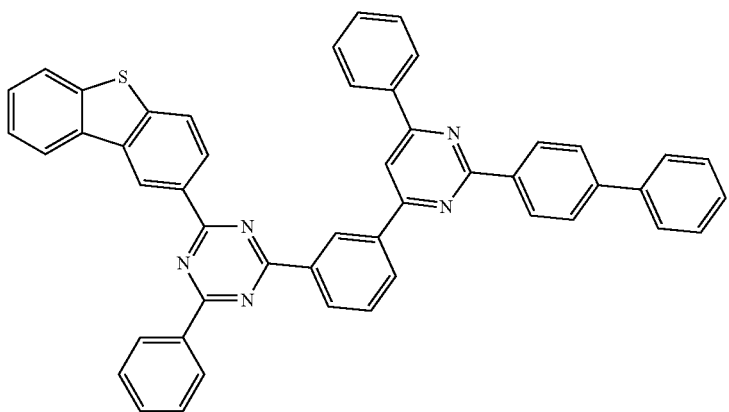
B-174
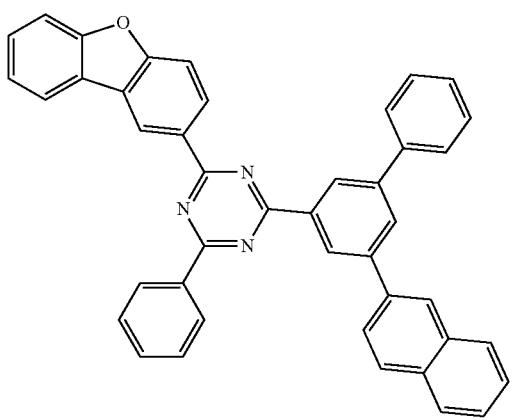
B-175
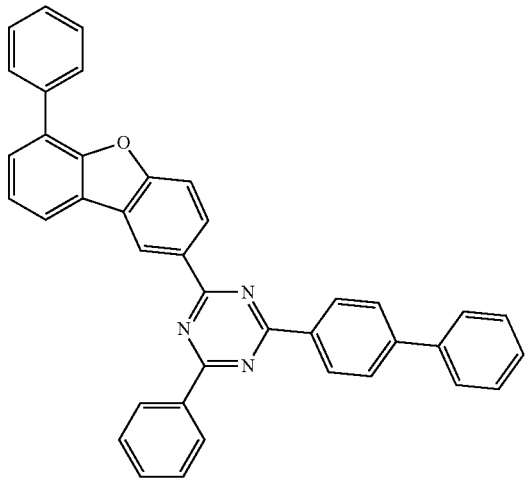
B-176
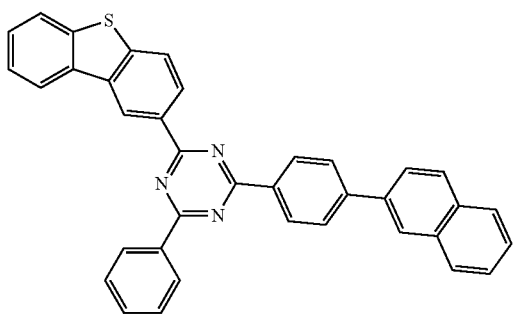
B-177
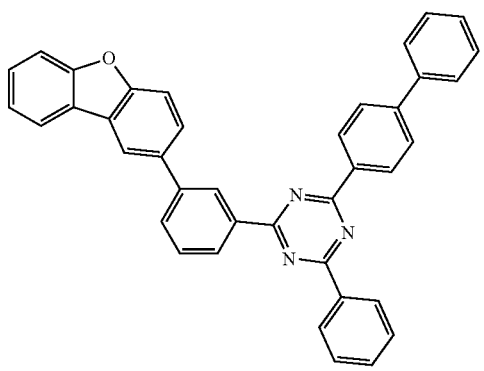

-continued
B-178
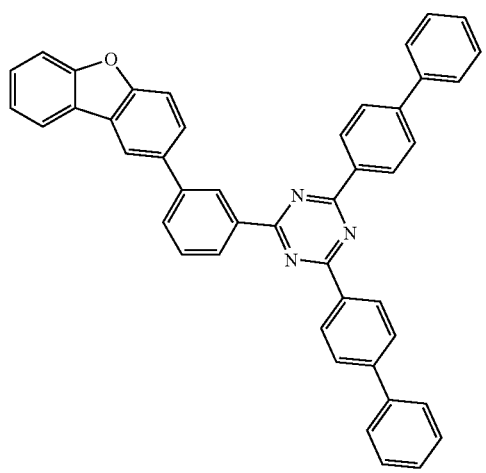
B-179
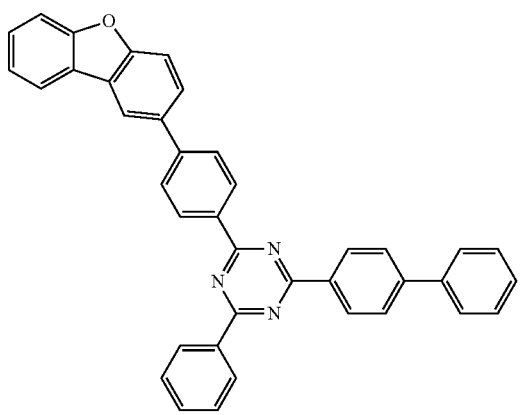
B-180
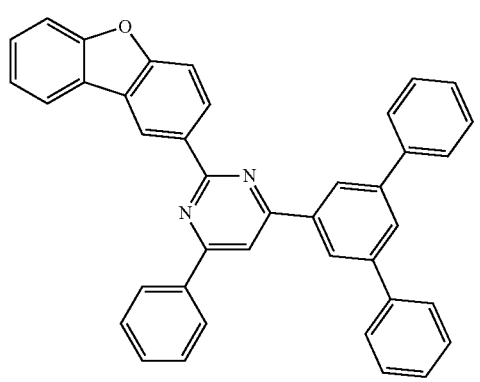
B-181
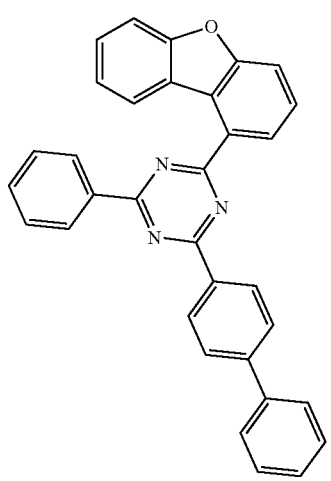
B-182
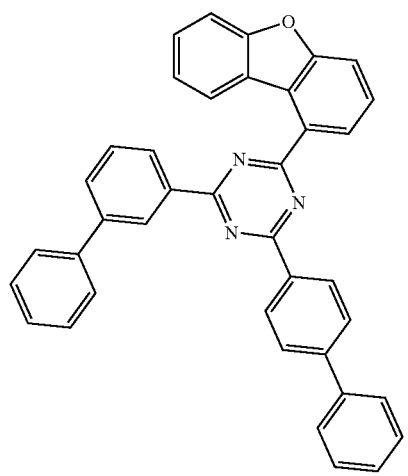
B-183
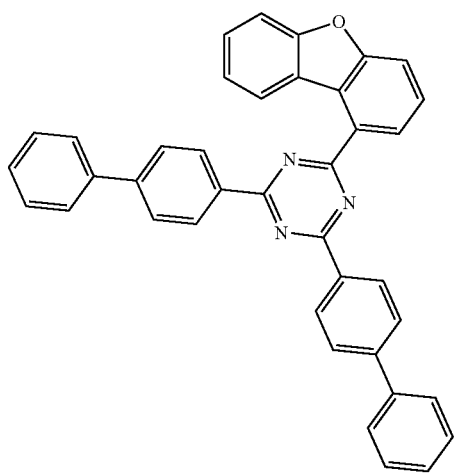

-continued
B-184
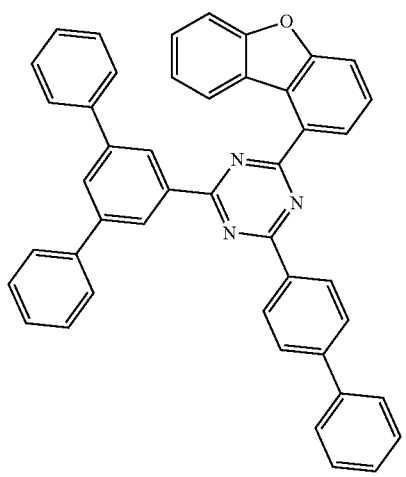
B-185
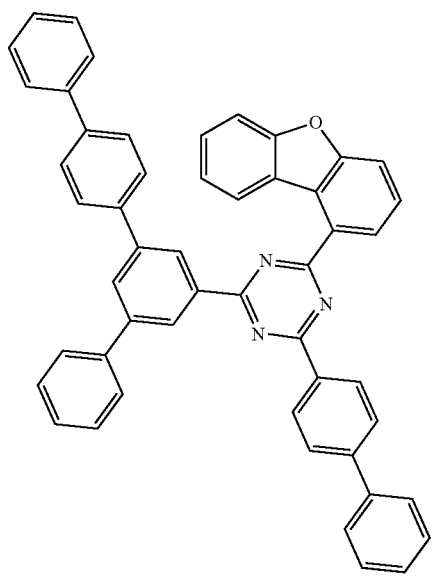
B-186
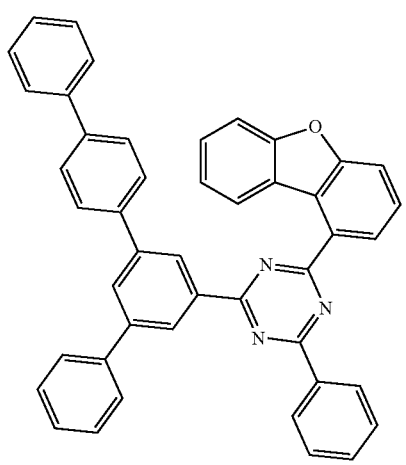
B-187
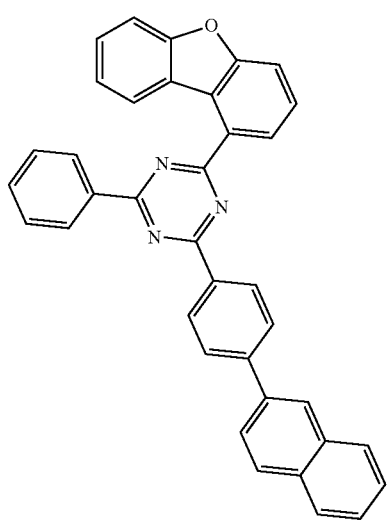
B-188
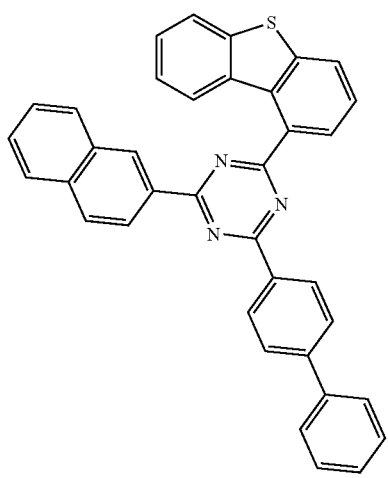
B-189
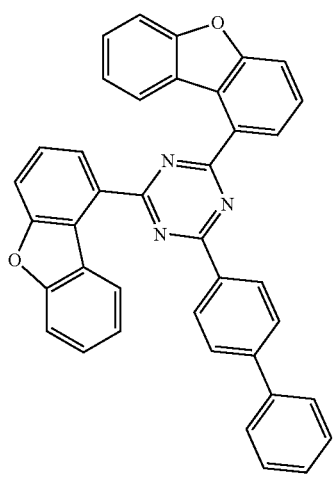

-continued
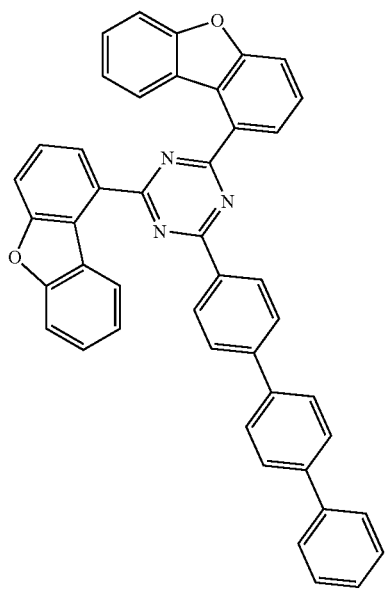
B-190
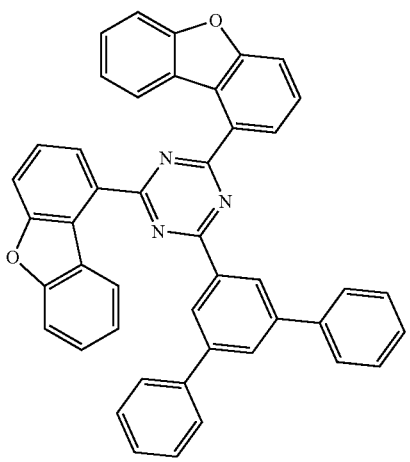
B-191
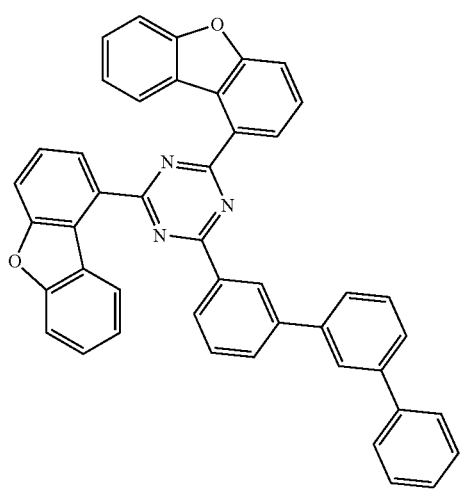
B-192
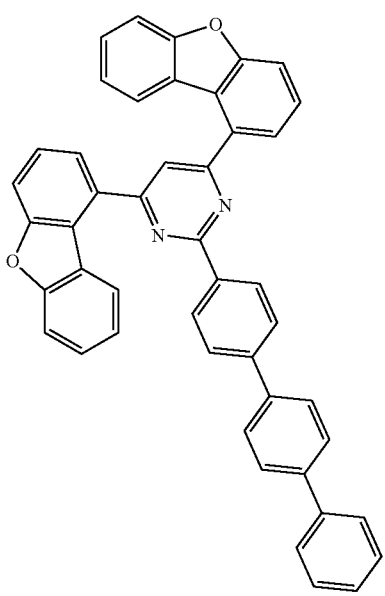
B-193

-continued
B-194
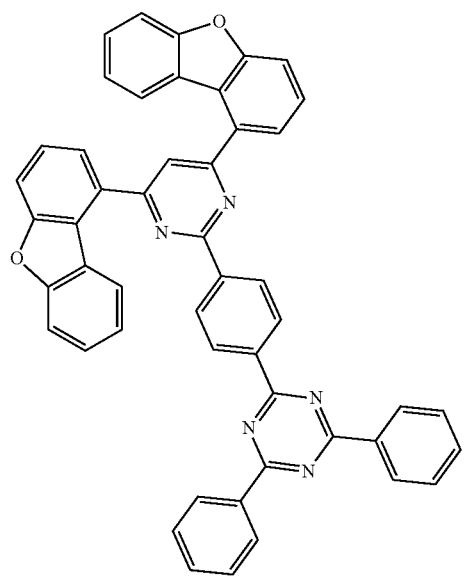
B-195
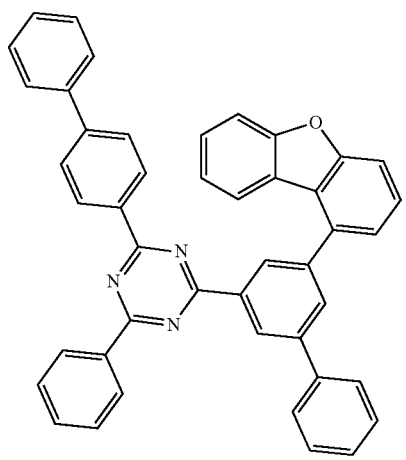
B-196
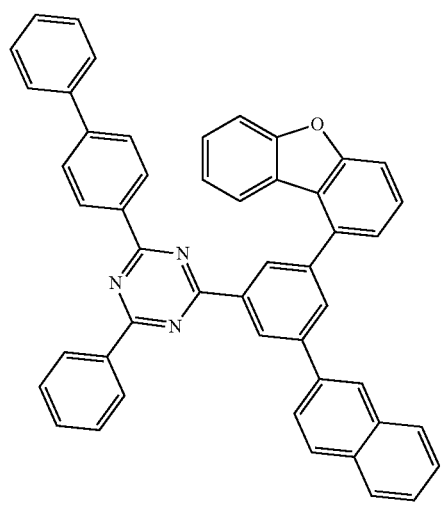
B-197
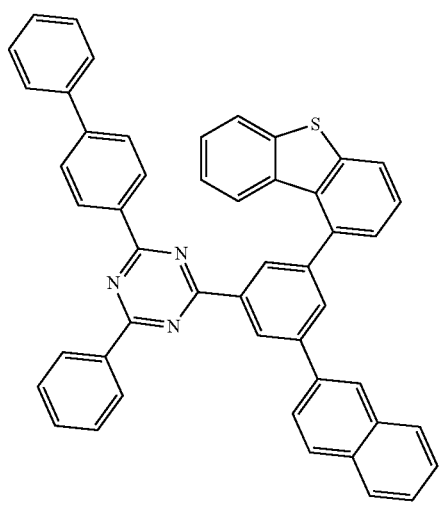
B-198
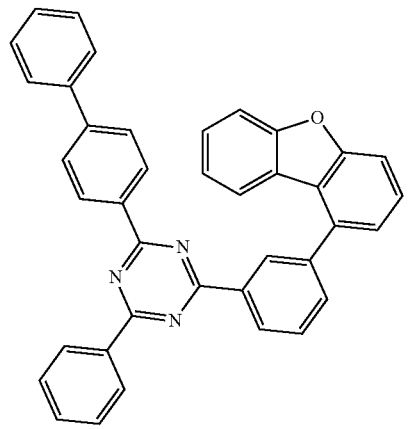
B-199
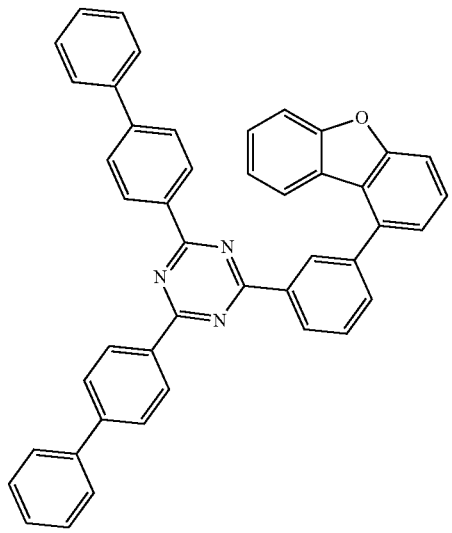

-continued
B-200
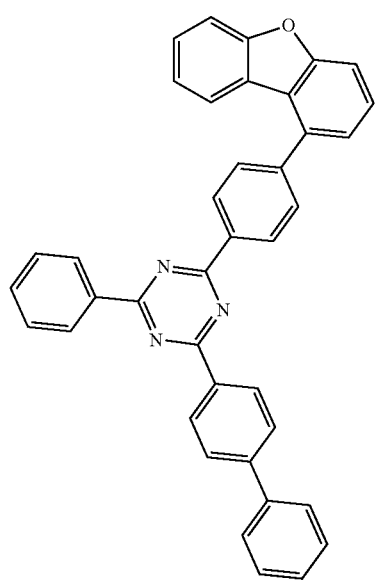
B-201
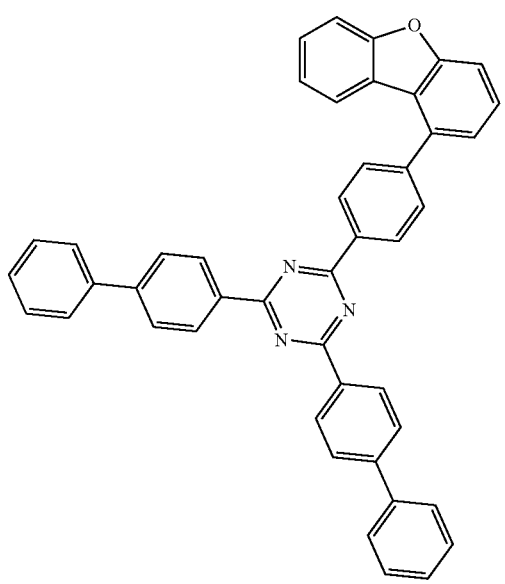
B-202
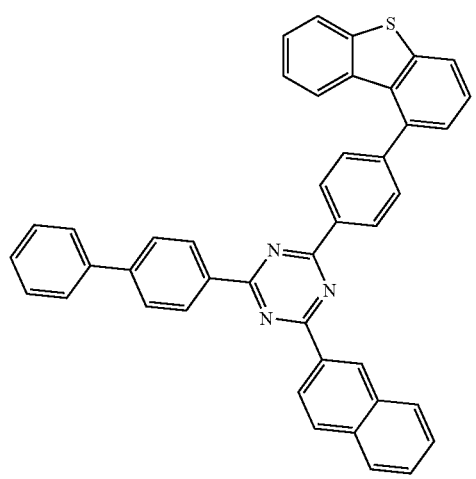
B-203
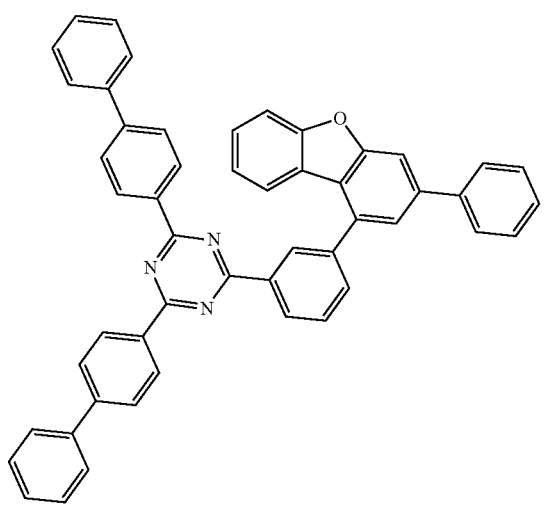
B-204
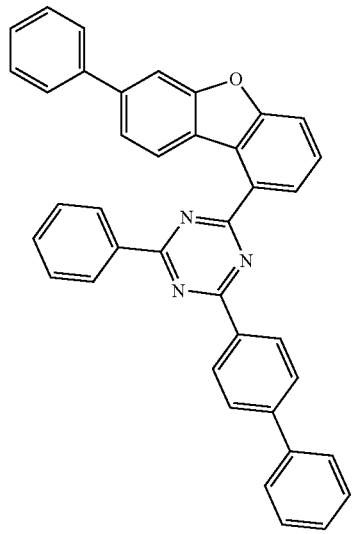
B-205
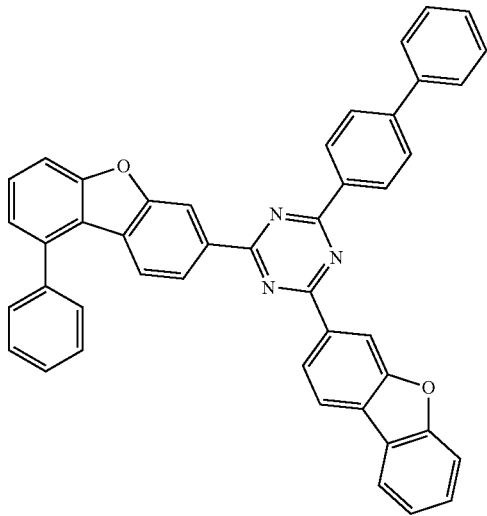

-continued
B-206
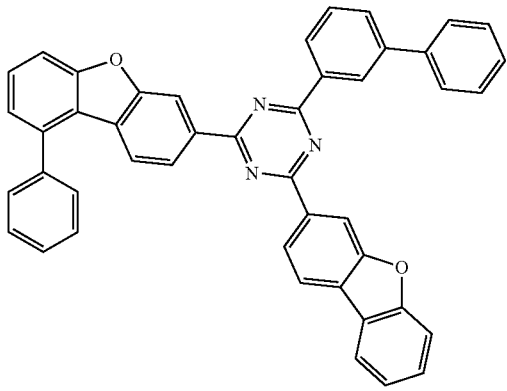
B-207
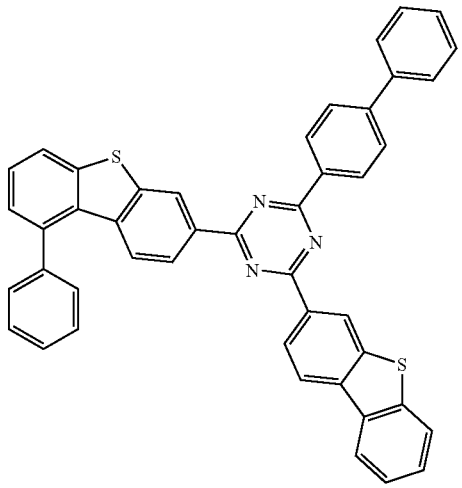
B-208
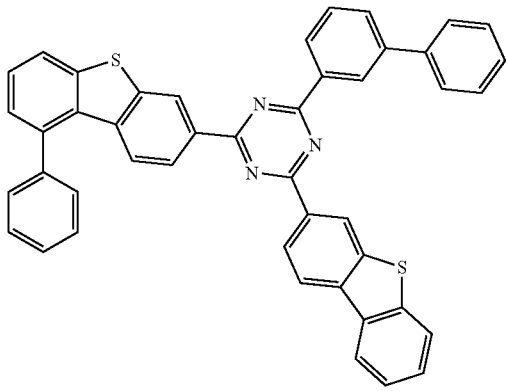
B-209
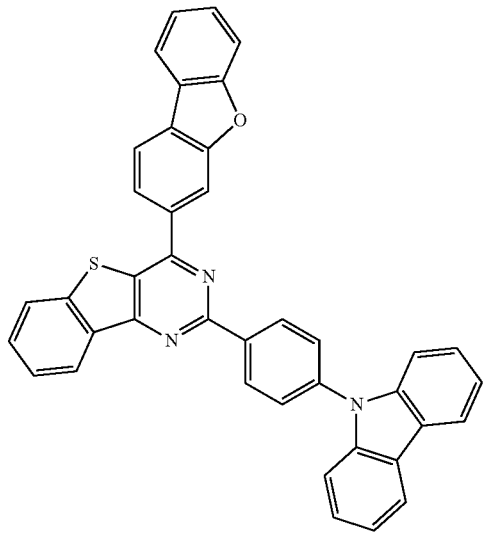
C-1
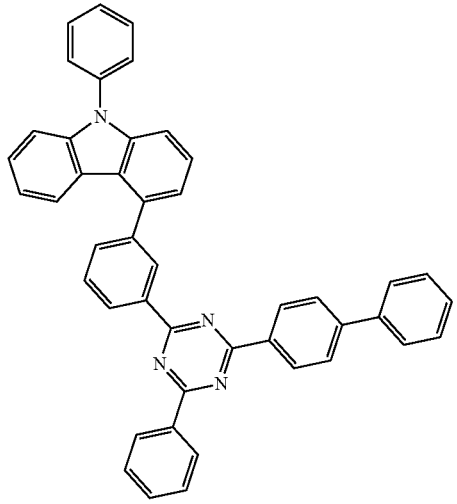
C-2
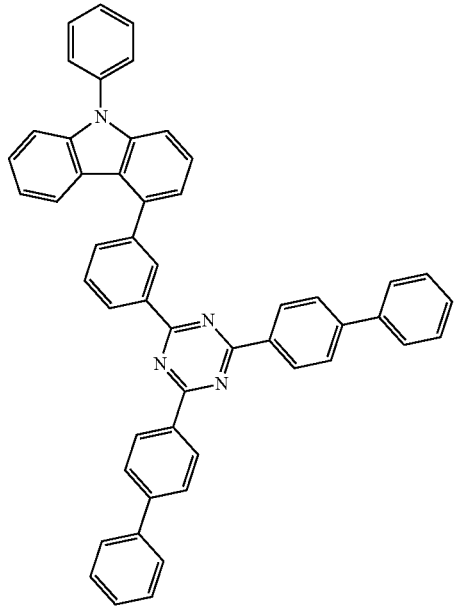

-continued
C-3
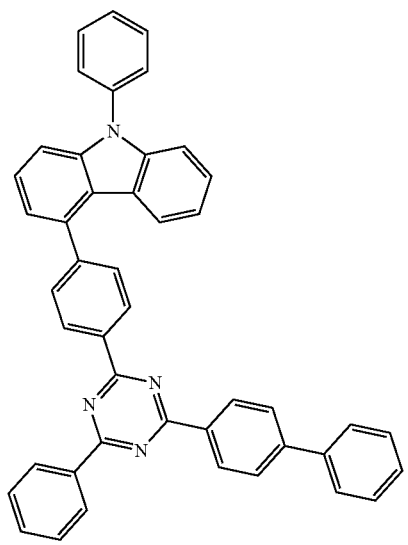
C-4
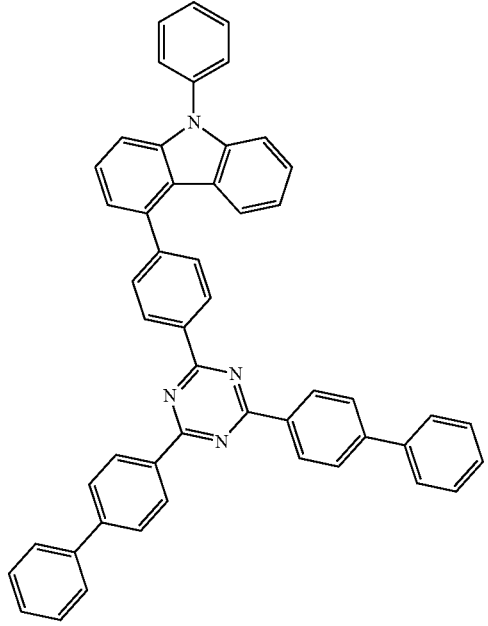
C-5
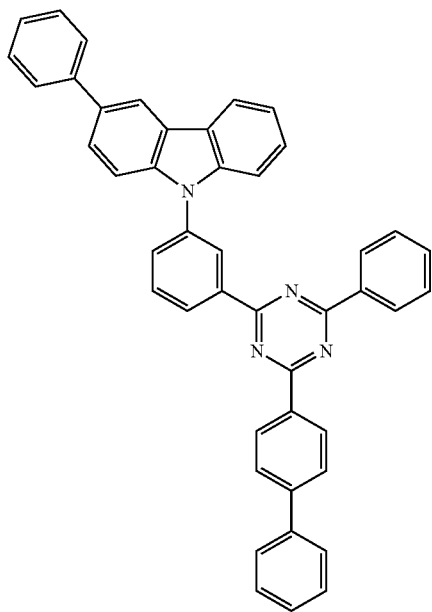
C-6
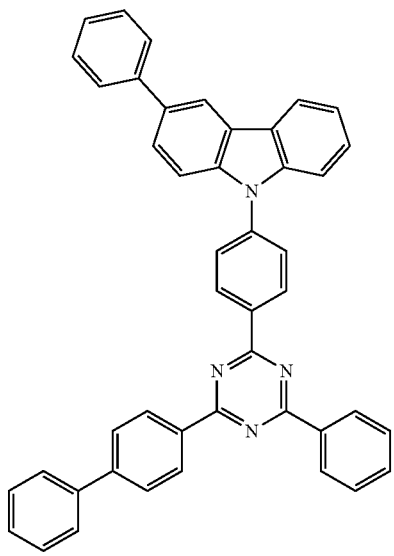

-continued
C-7
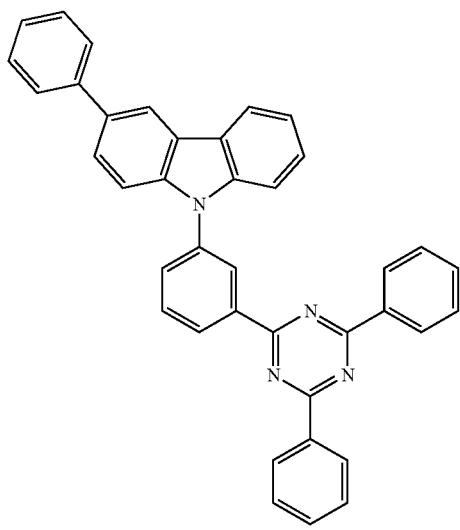
C-8
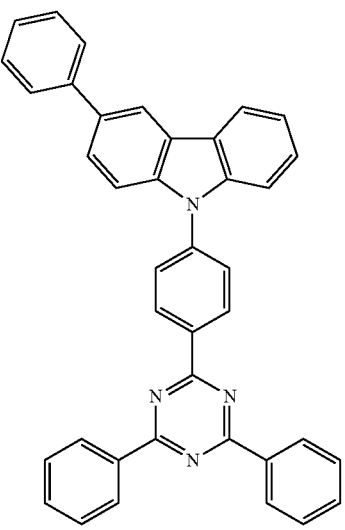
C-9
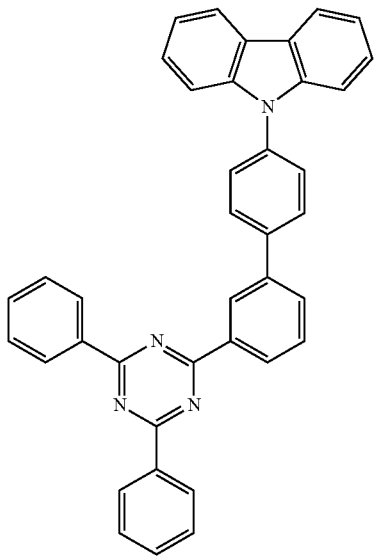
C-10
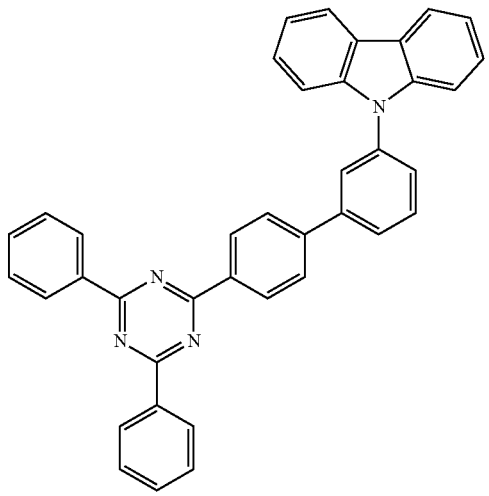

-continued
C-11
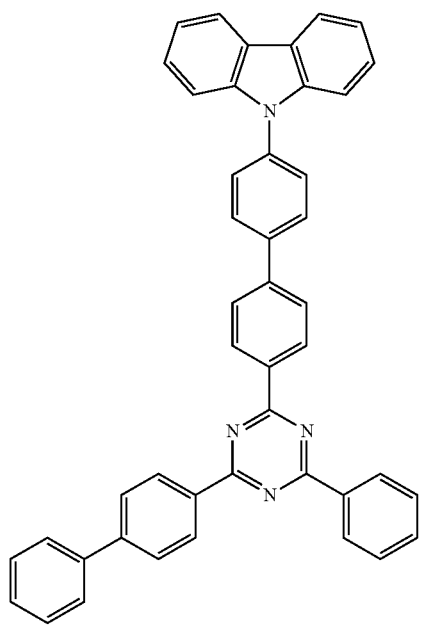
C-12
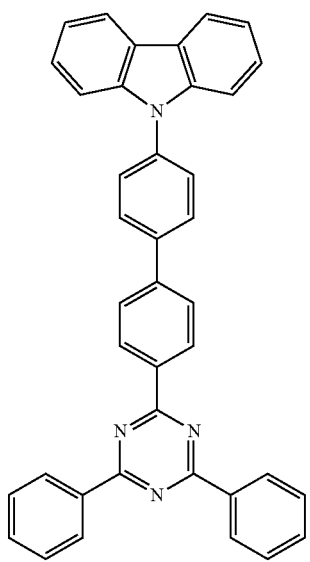
C-13
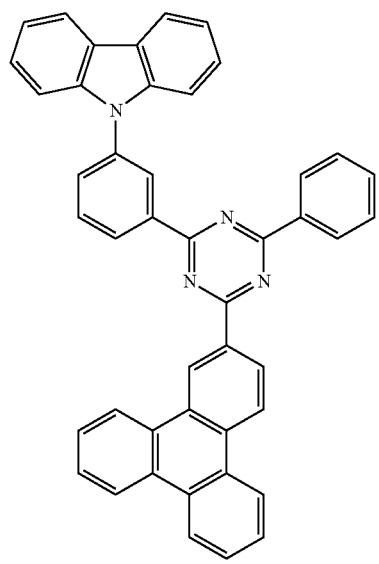
C-14
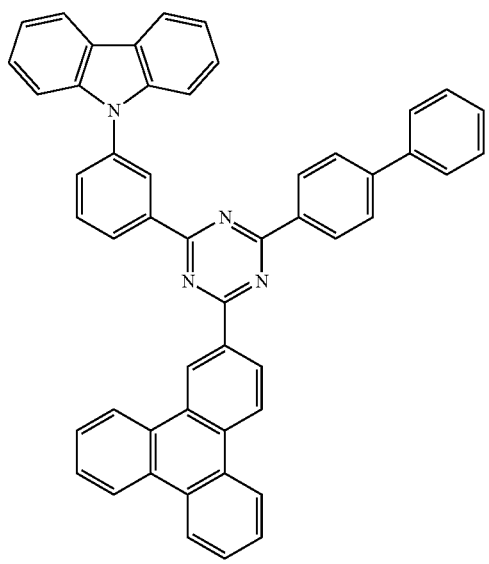

-continued
C-15
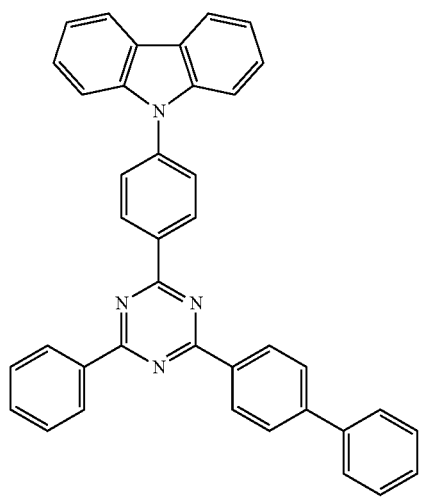
C-16
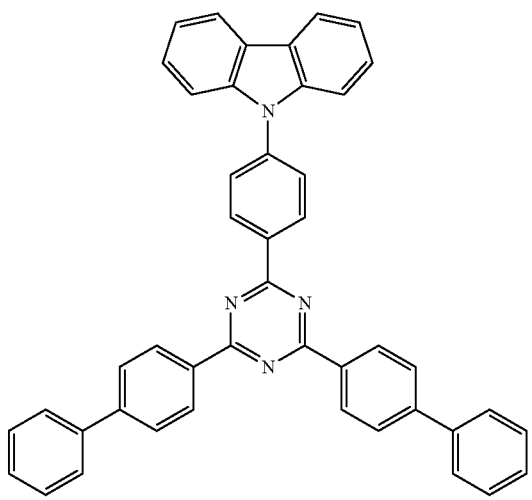
C-17
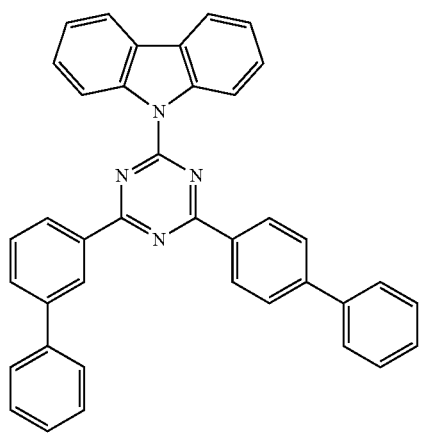
C-18
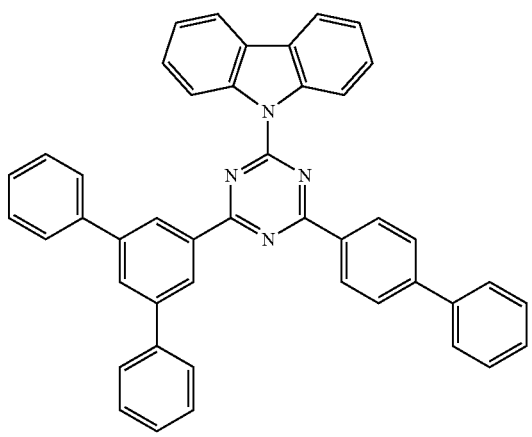
C-19
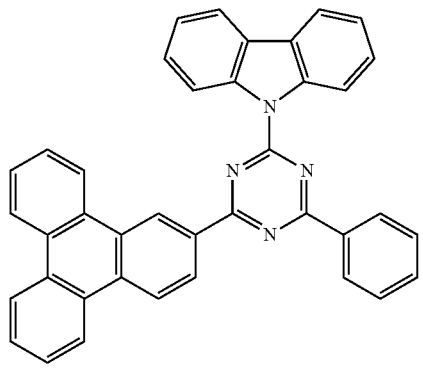
C-20
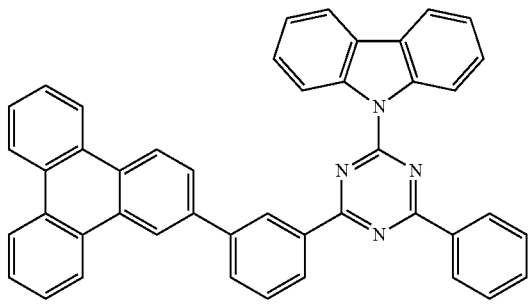

-continued
C-21
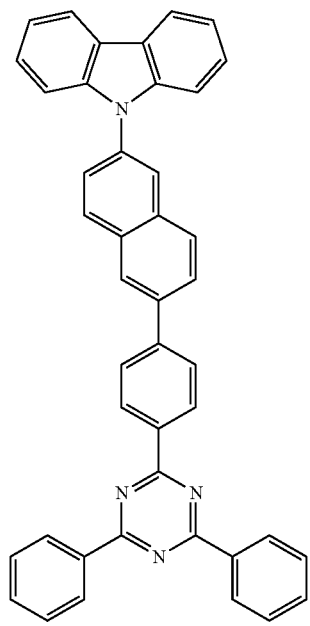
C-22
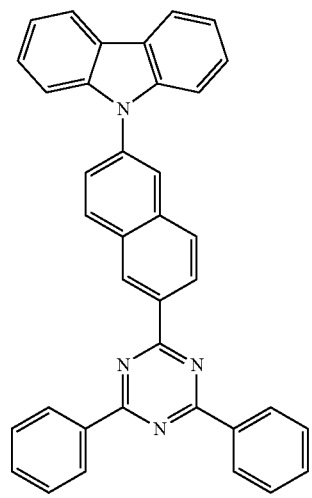
C-23
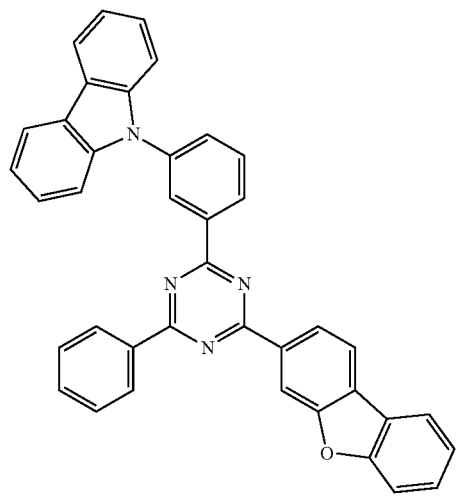
C-24
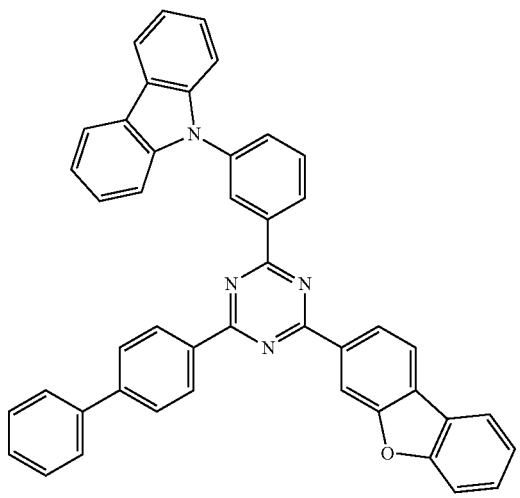

-continued
C-25
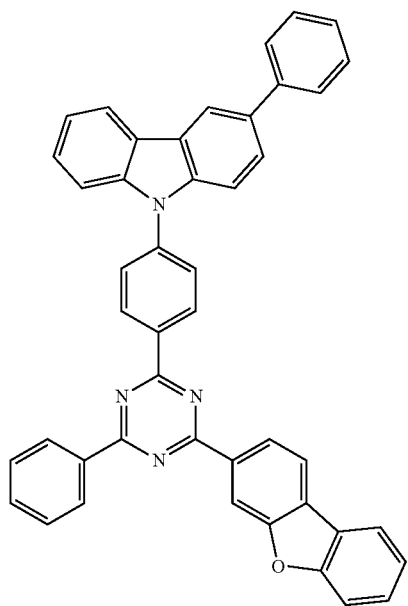
C-26
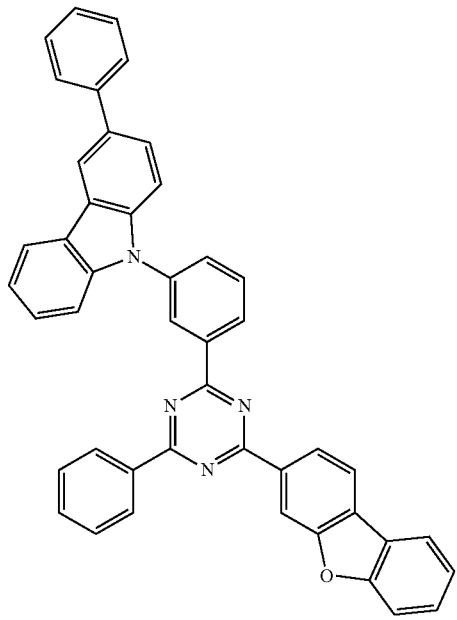
C-27
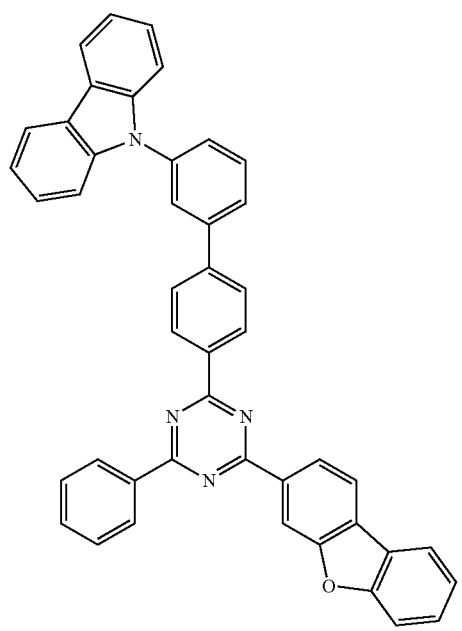
C-28
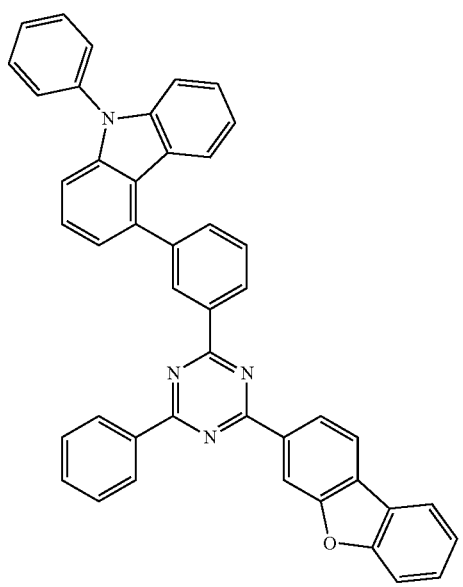

-continued
C-29
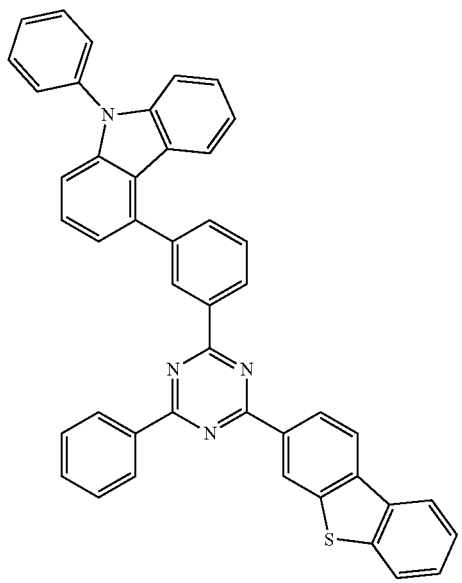
C-30
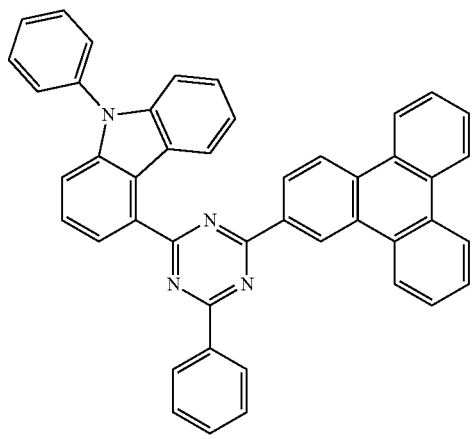
C-31
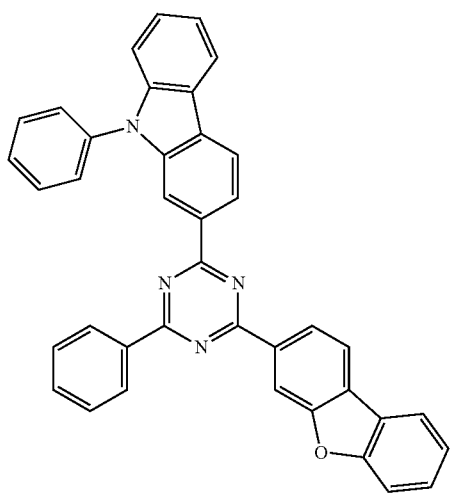
C-32
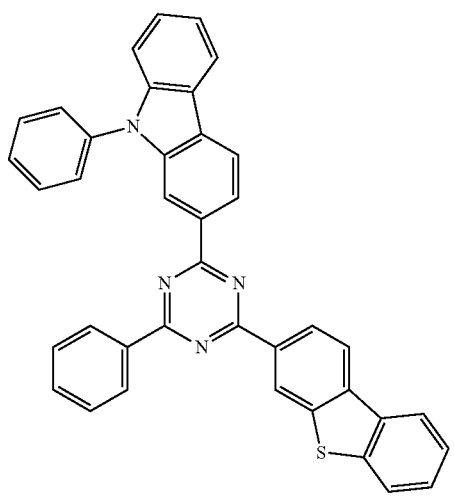
C-33
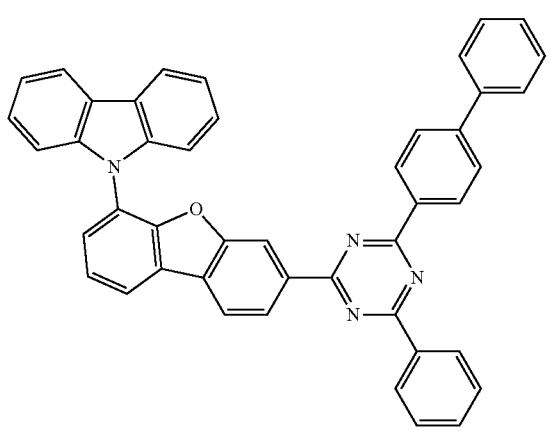
C-34
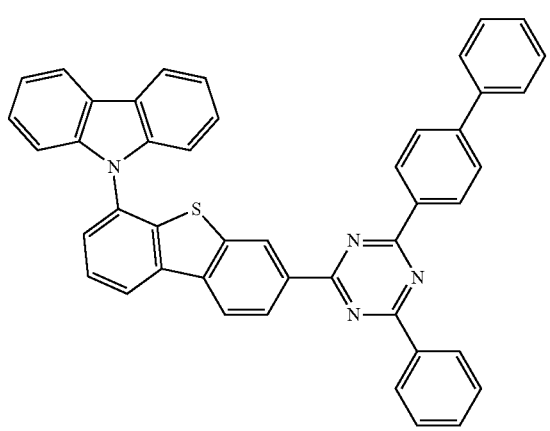

-continued
C-35
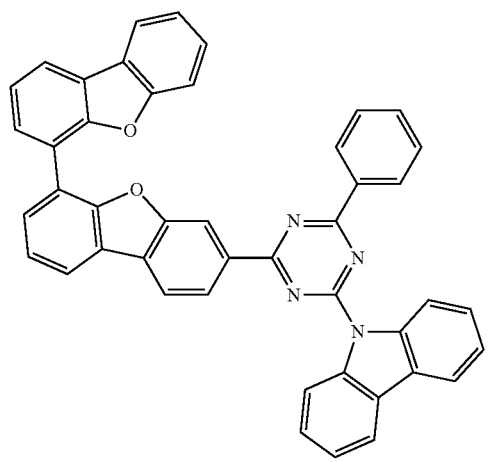
C-36
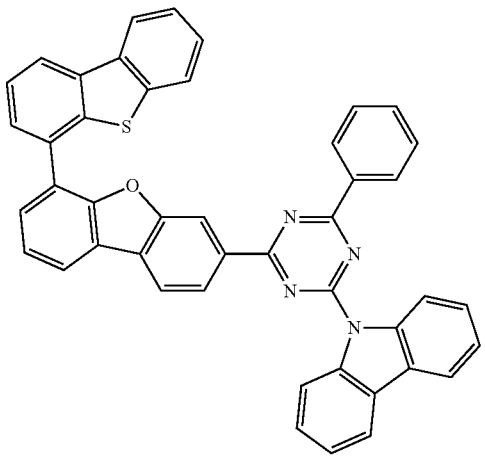
C-37
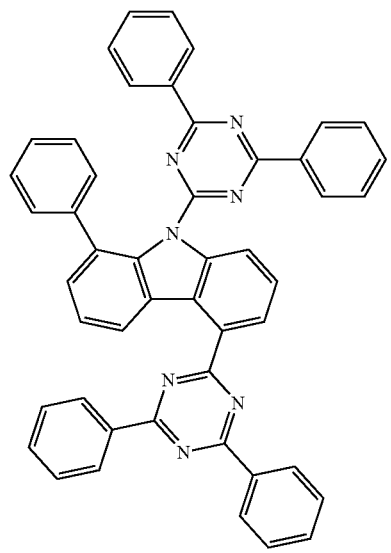
C-38
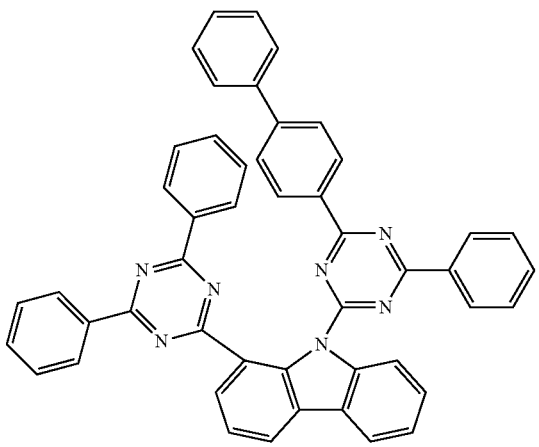
C-39
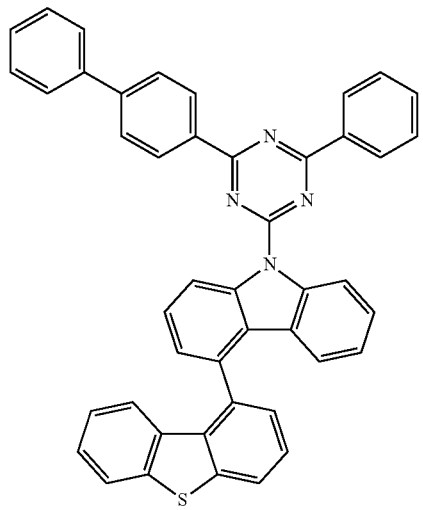
C-40
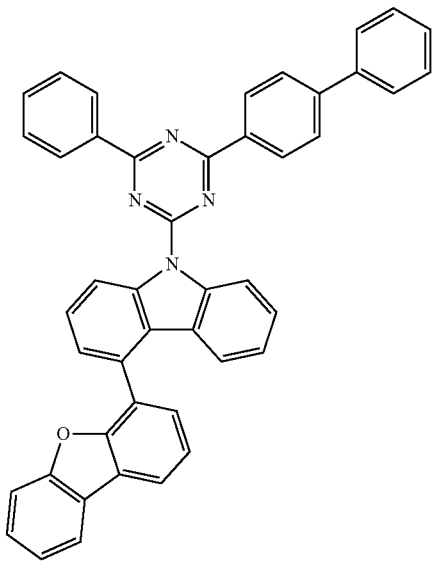

-continued
C-41
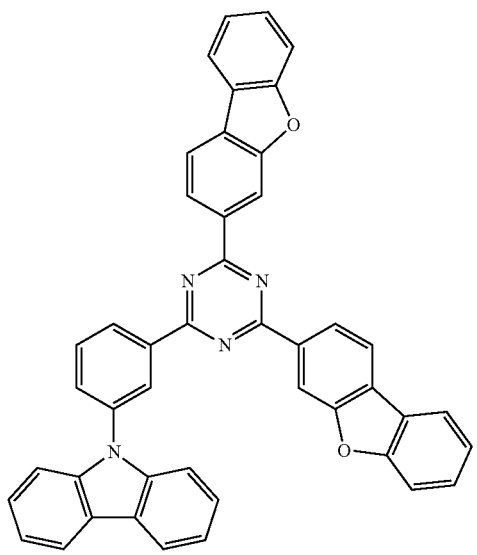
C-42
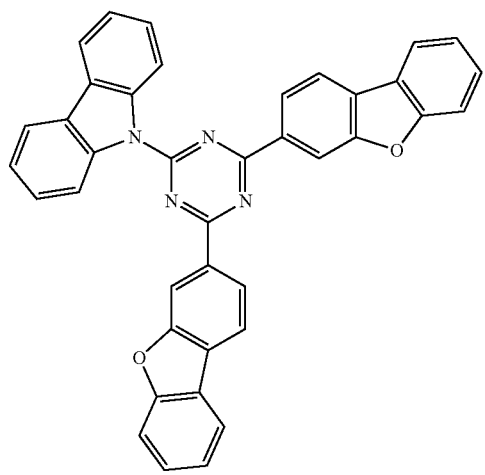
C-43
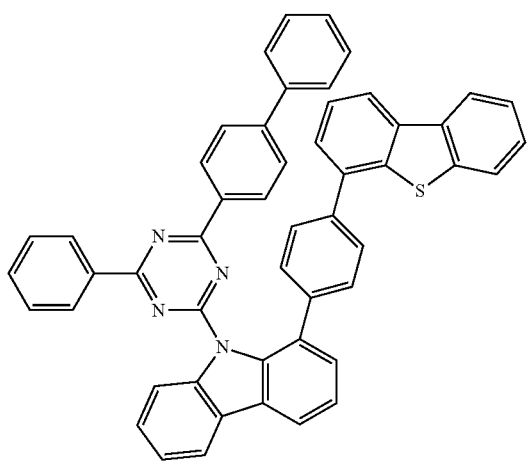
C-44
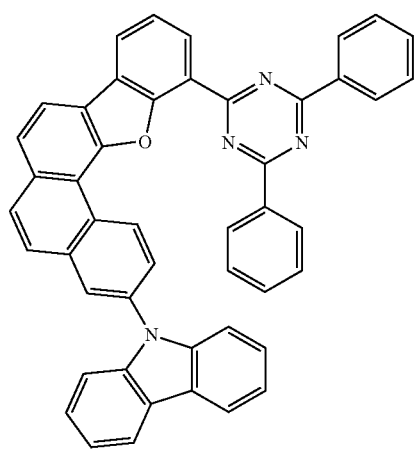
C-45
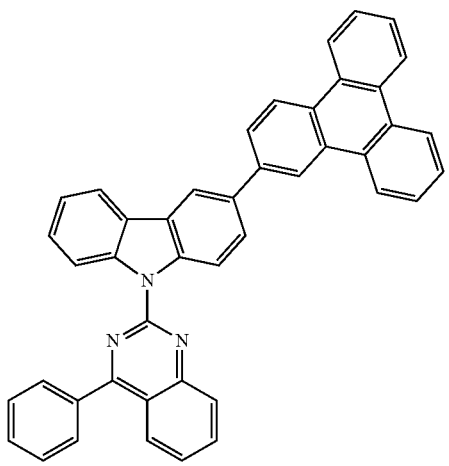
C-46
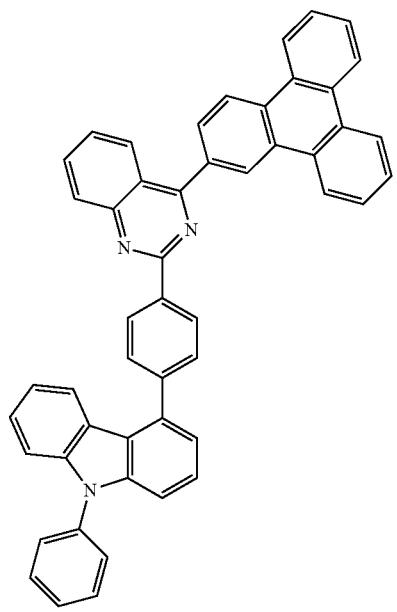

C-47
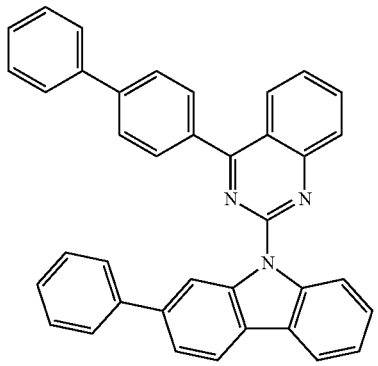
C-48
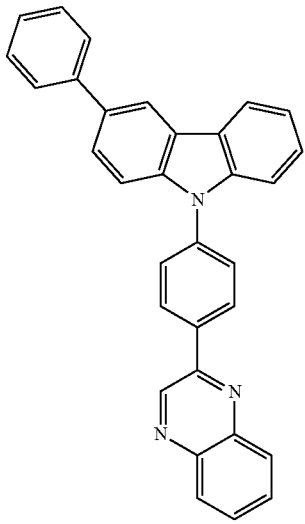
C-49
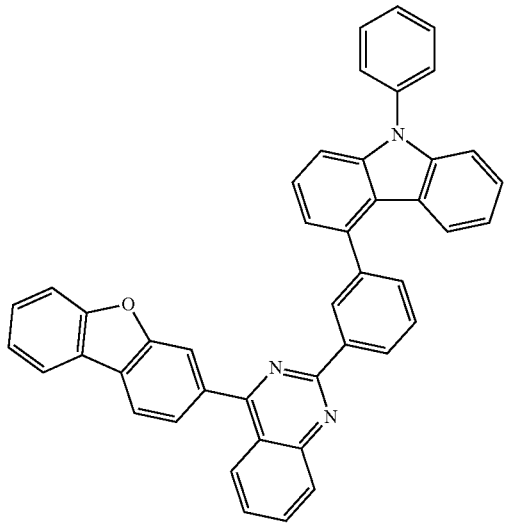
C-50
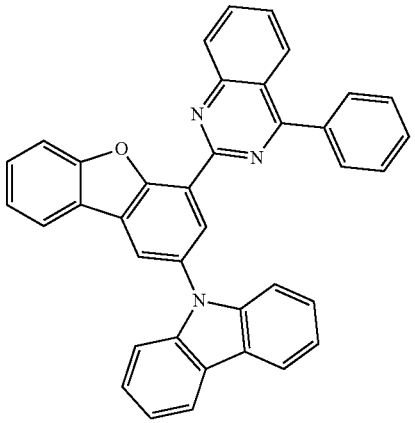
C-51
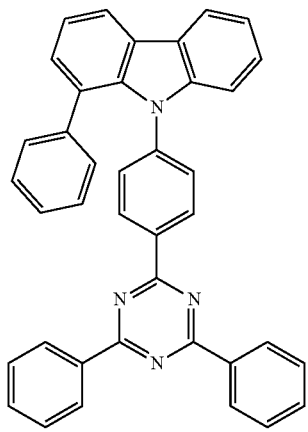
C-52
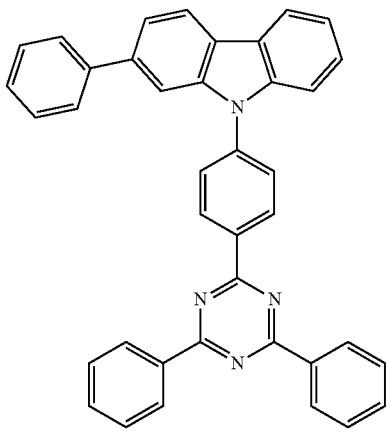

-continued
C-53
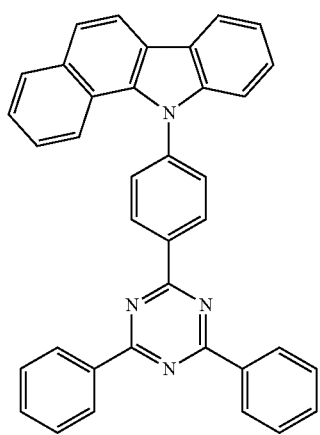
C-54
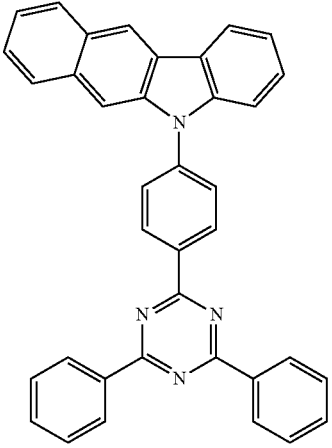
C-55
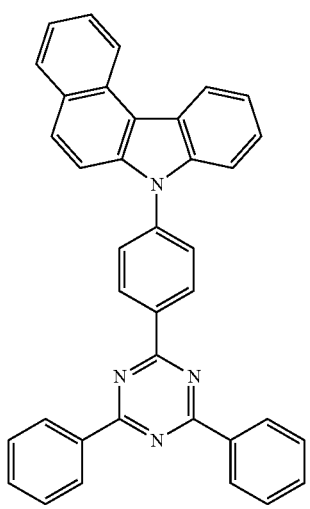
C-56
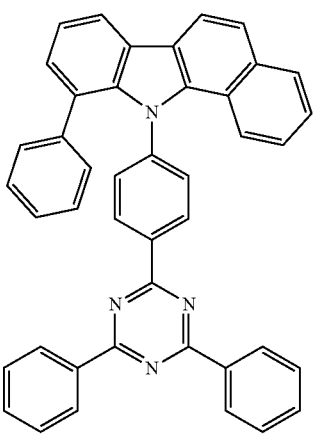
C-57
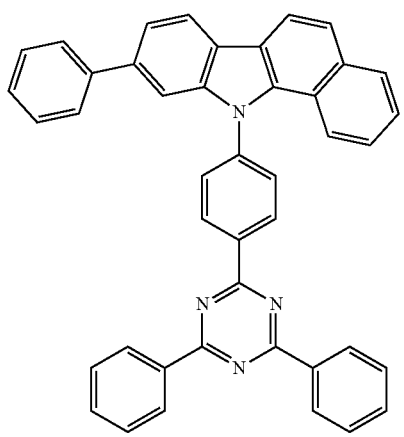
C-58
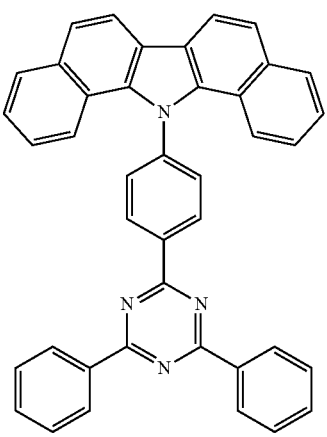

-continued
C-59
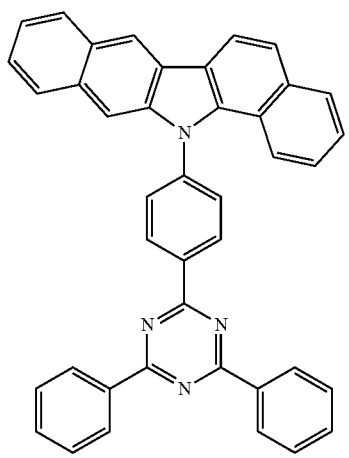
C-60
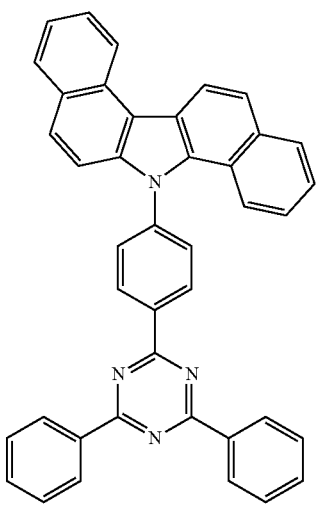
C-61
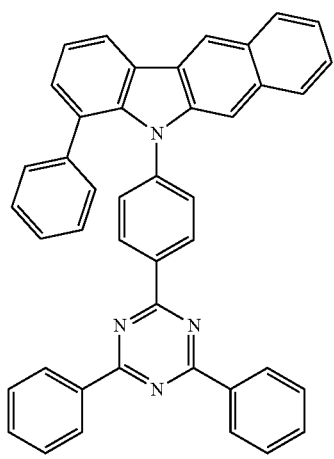
C-62
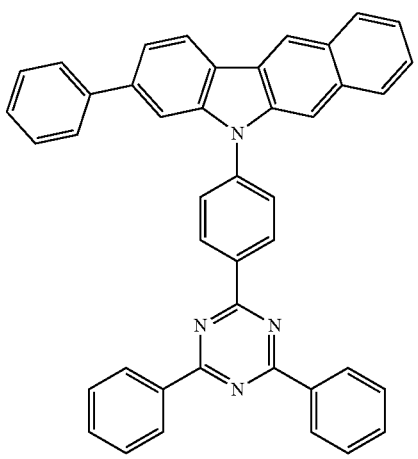
C-63
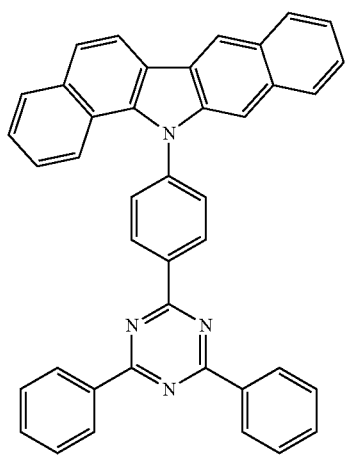
C-64
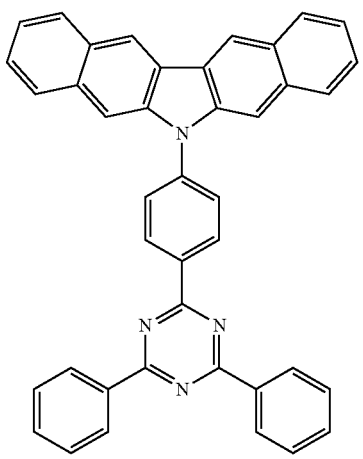

-continued
C-65
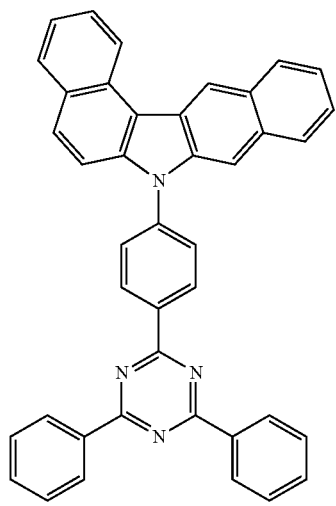
C-66
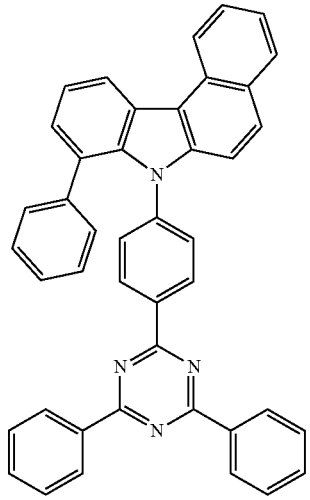
C-67
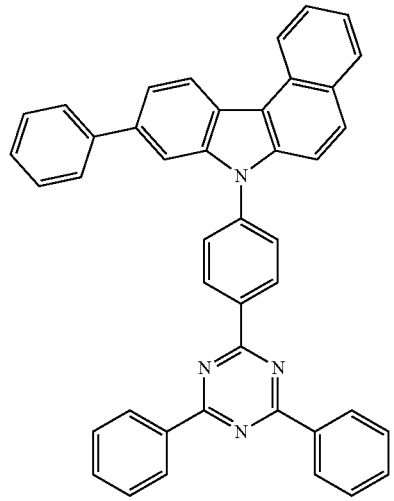
C-68
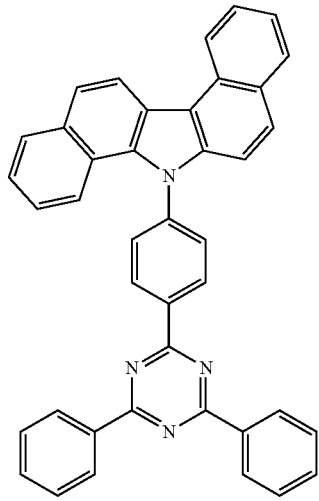
C-69
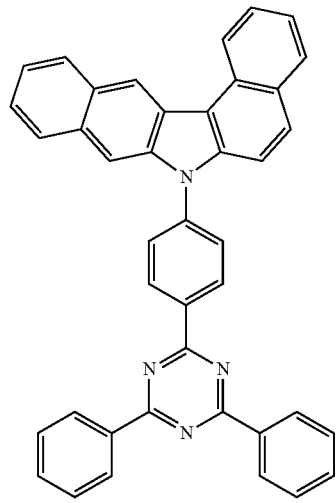
C-70
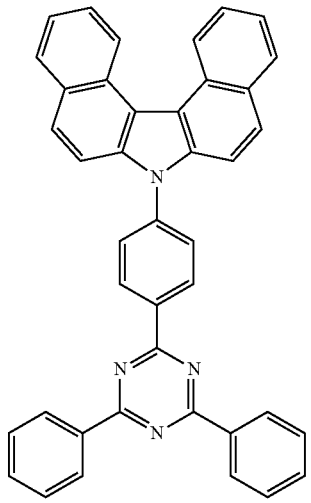

-continued
C-71
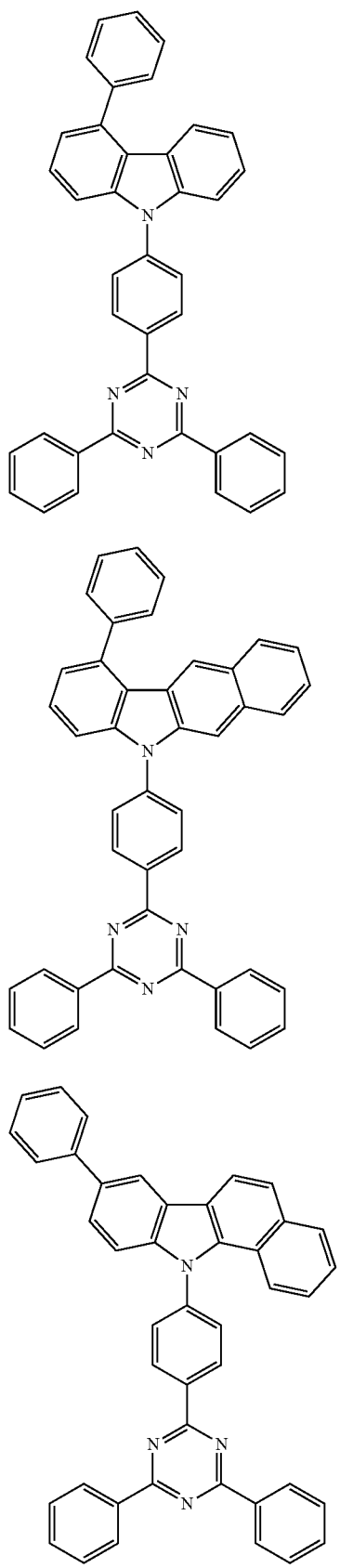
C-72
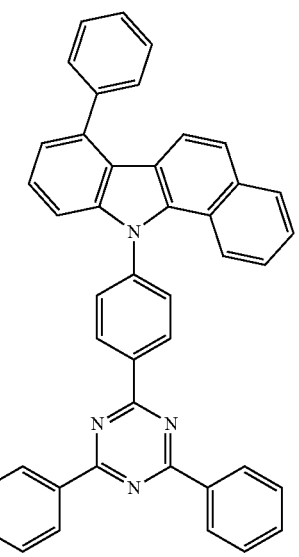
C-73
C-74
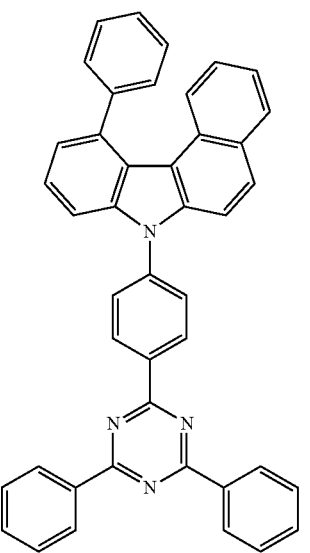
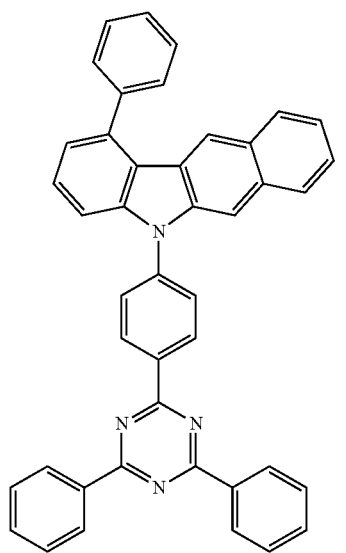
C-75
C-76
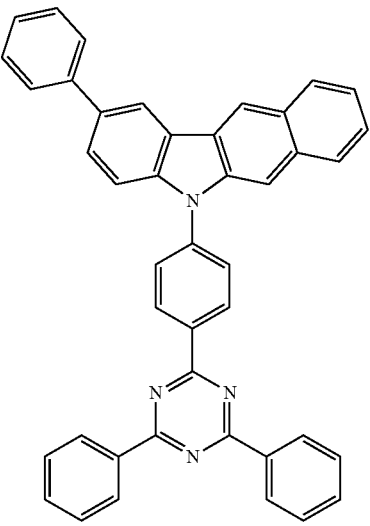

C-77
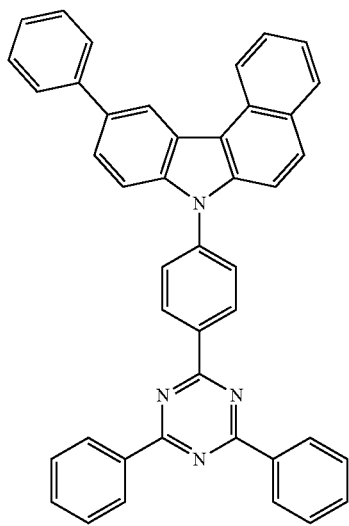
C-78
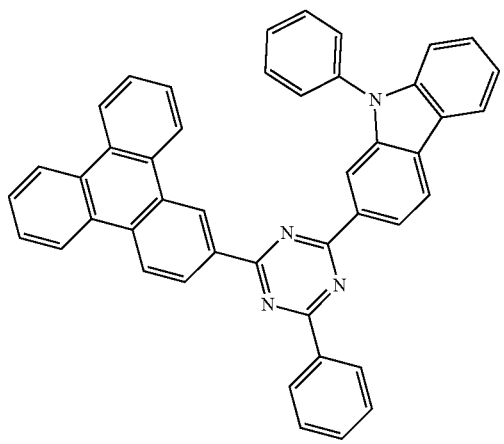
D-1
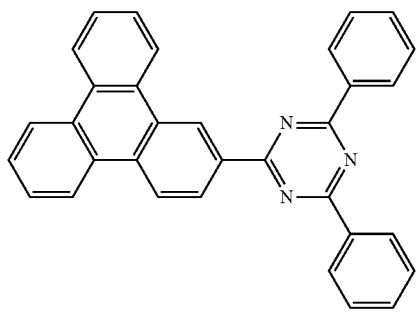
D-2
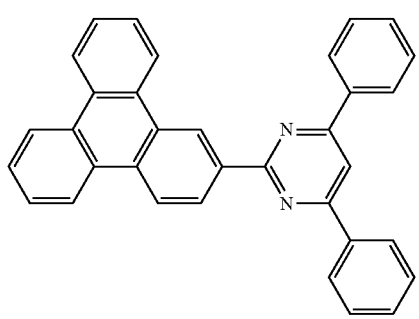
D-4
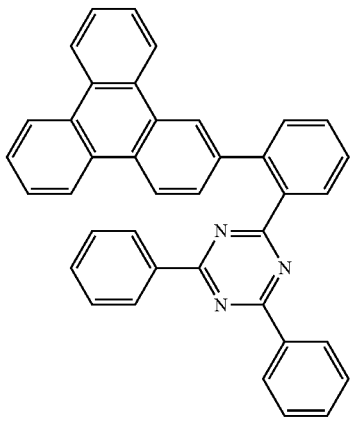
D-3
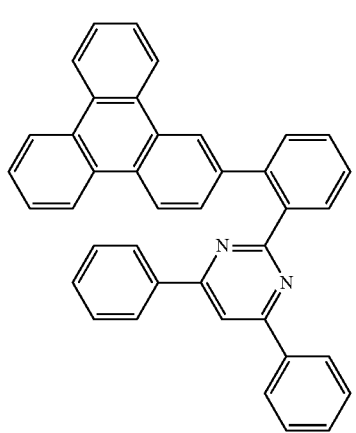
D-5
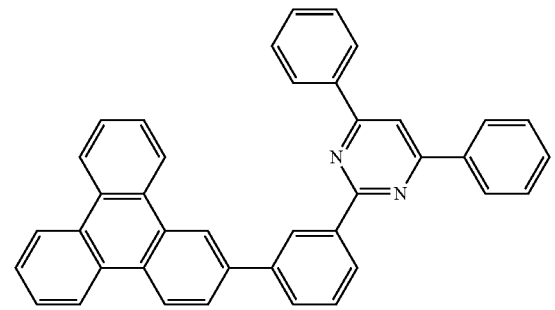

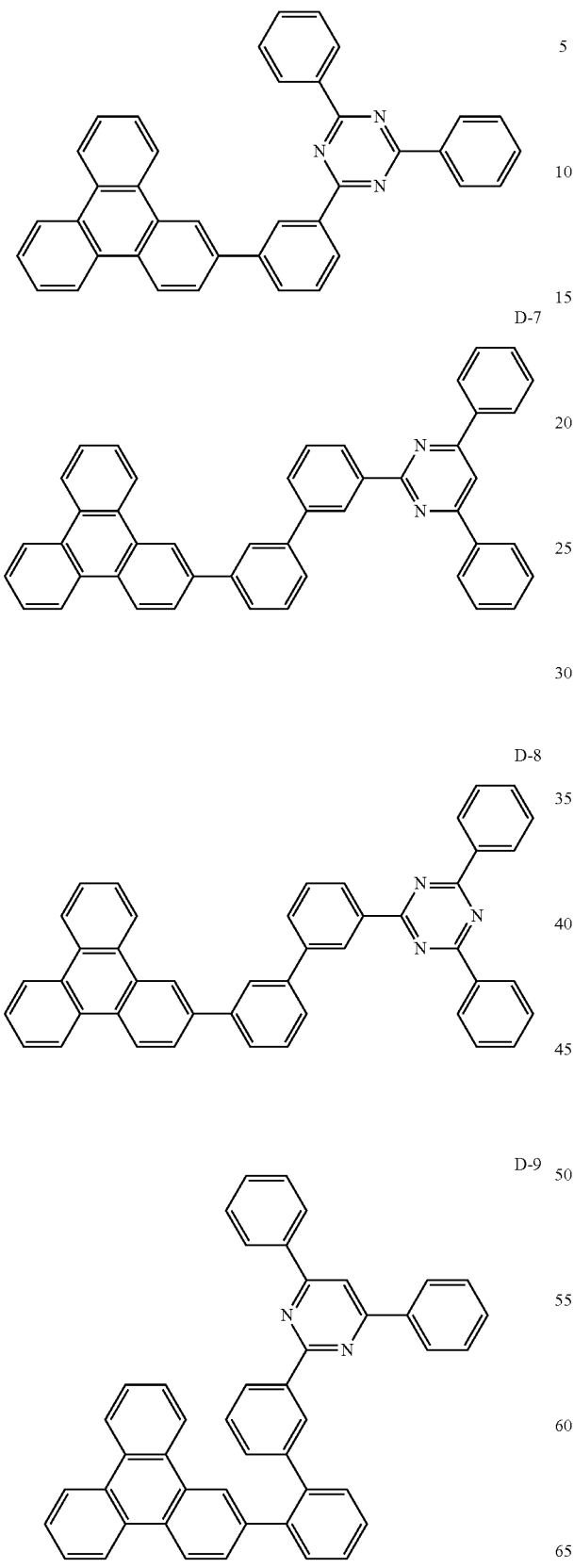
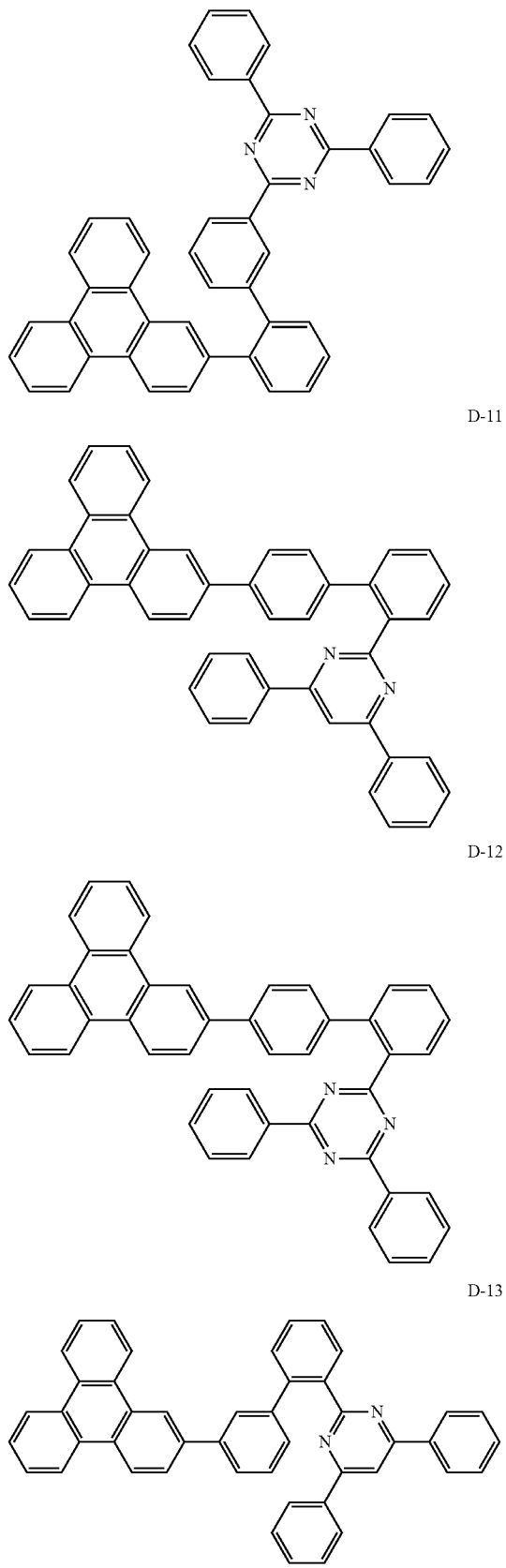

D-14
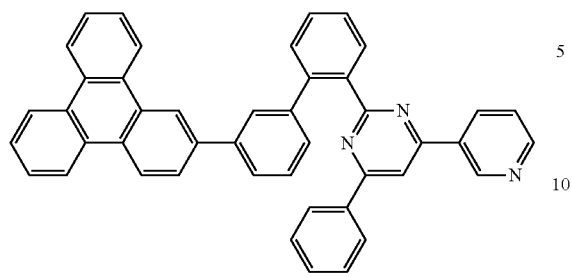
D-15
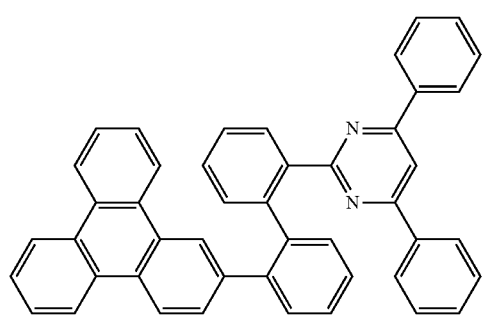
D-16
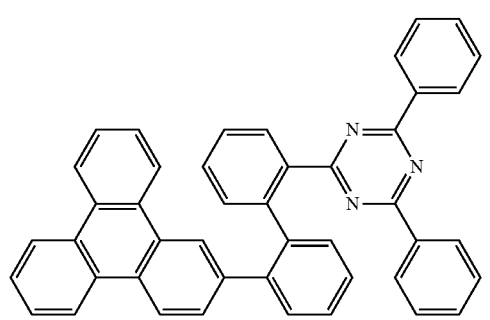
D-17
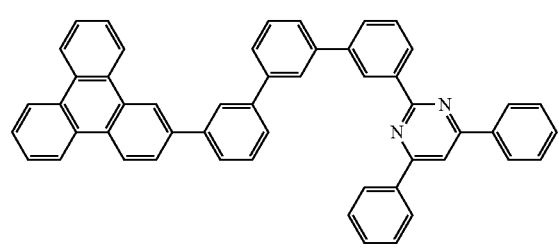
D-18
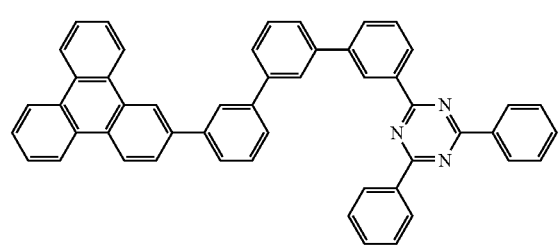
D-19
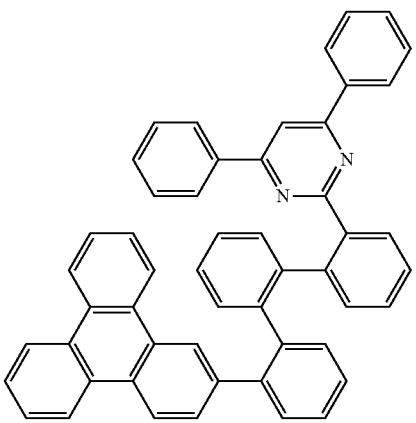
D-20
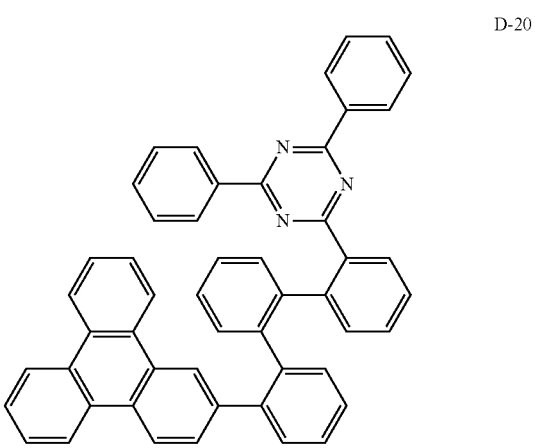
D-21
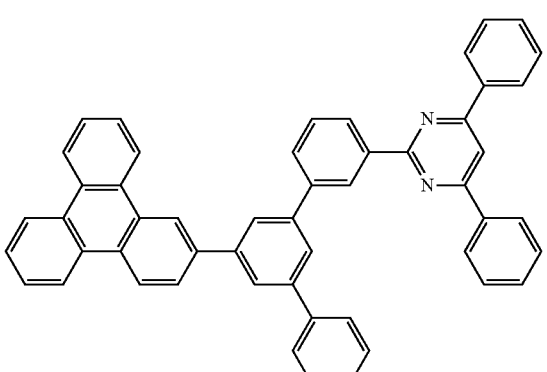
D-22
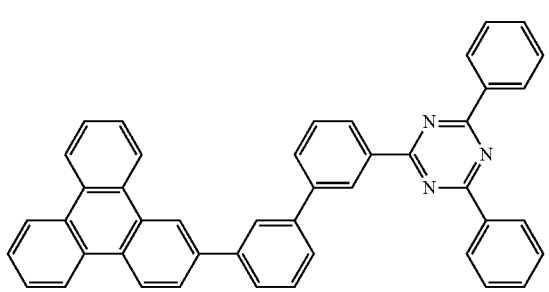

D-23
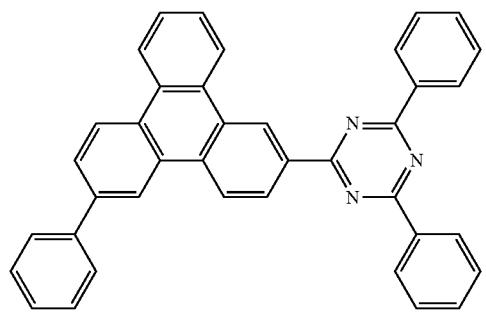
D-24
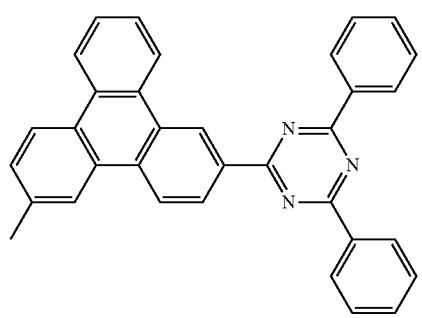
D-25
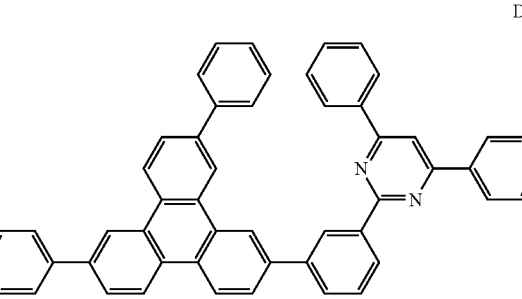
D-26
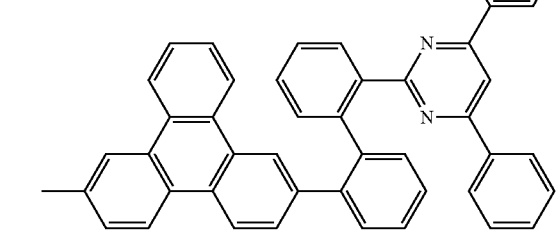
D-27
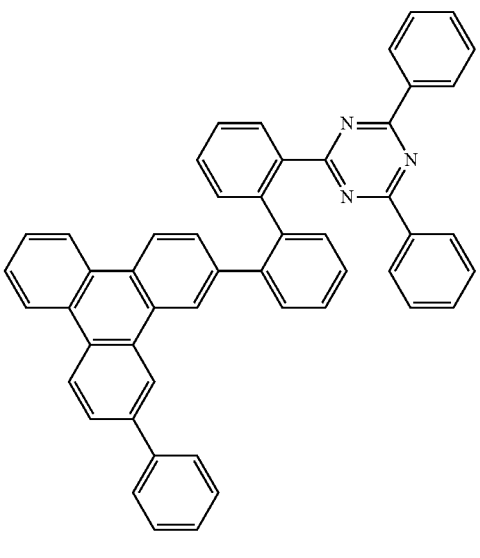
D-28
D-29
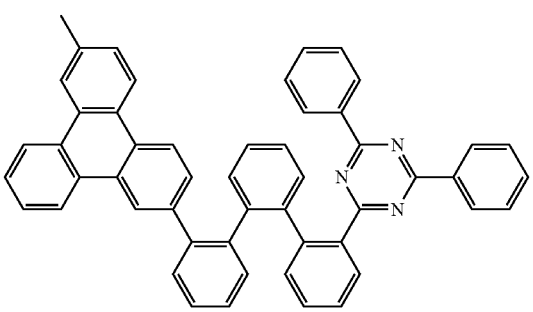
D-30

D-31
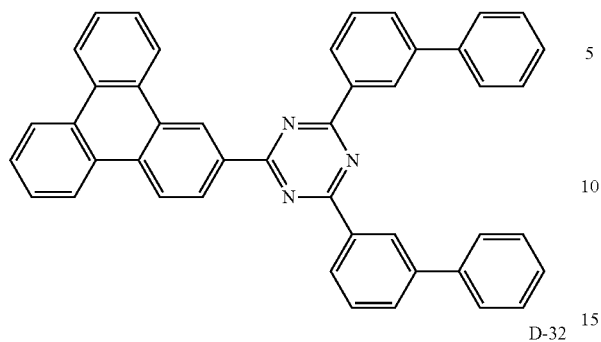
D-32
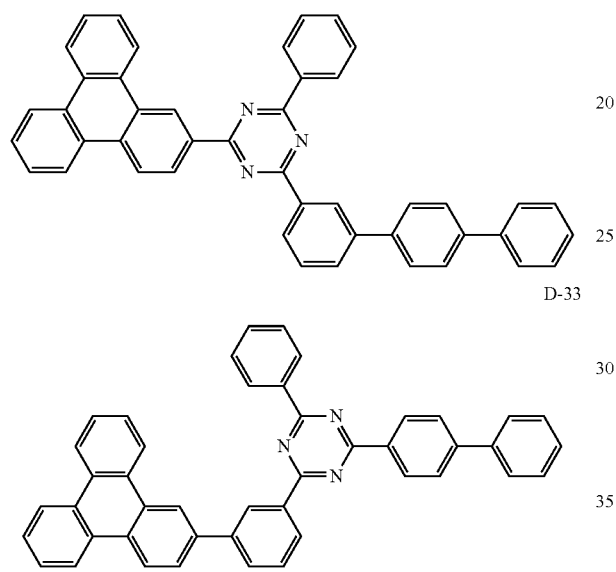
D-33
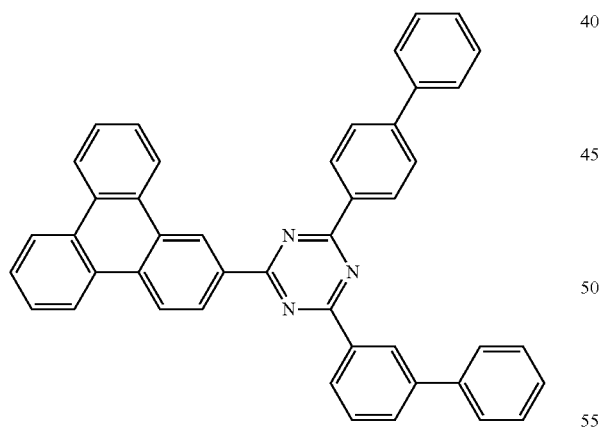
D-34
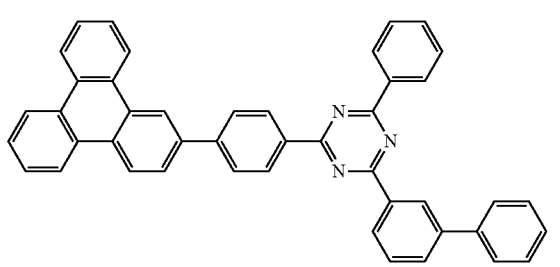
D-35
D-36
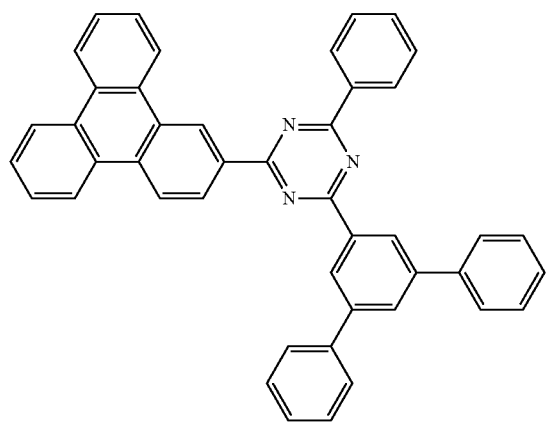
D-37
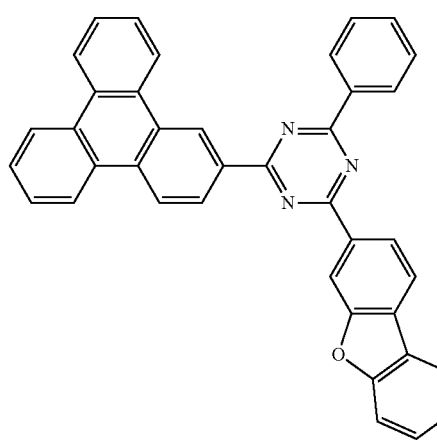
D-38
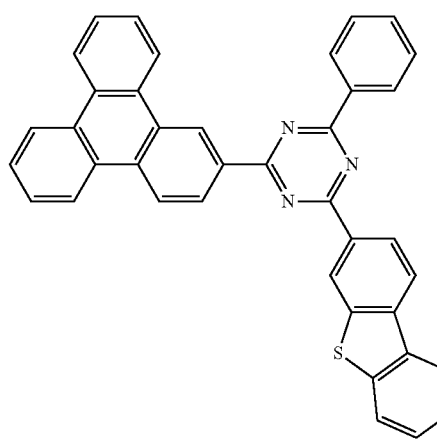

D-39
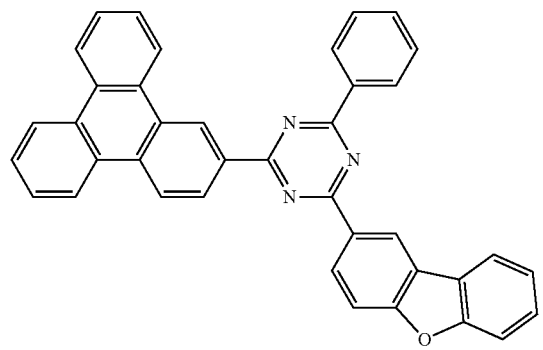
D-40
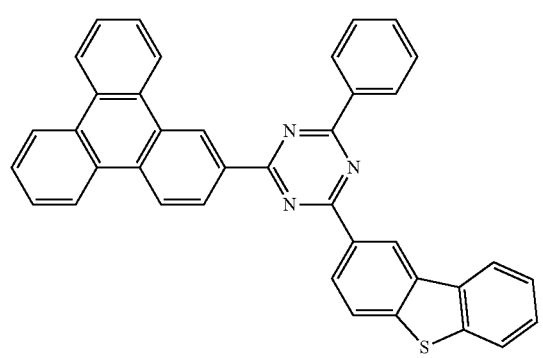
D-41
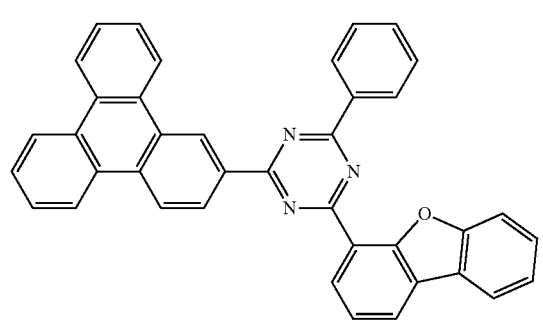
D-42
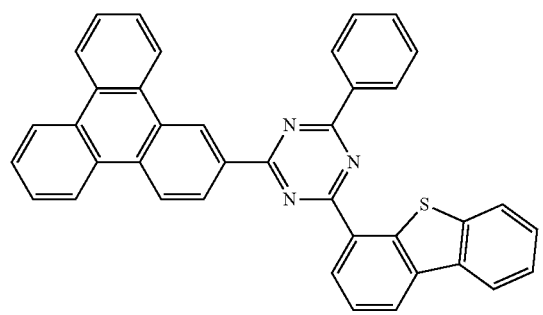
D-43
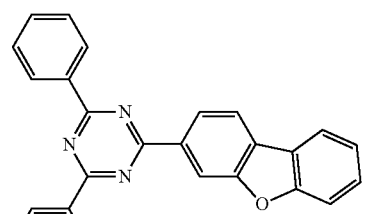
D-44
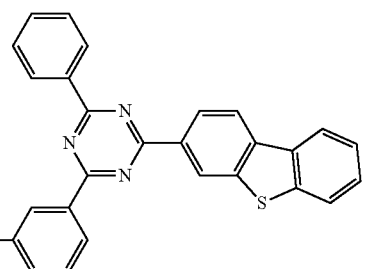
D-45
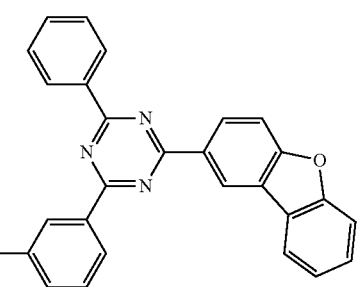
D-46
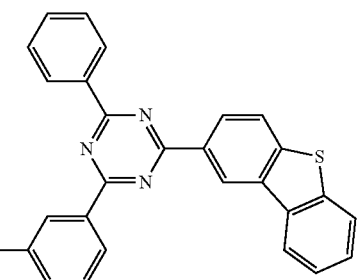
D-47
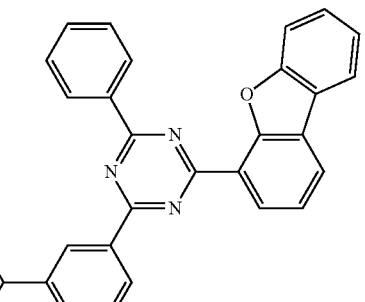

-continued
D-48
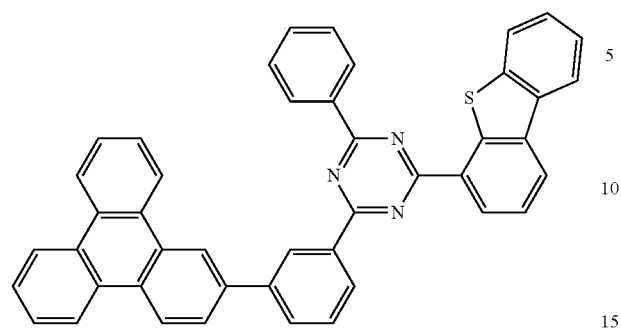
D-49
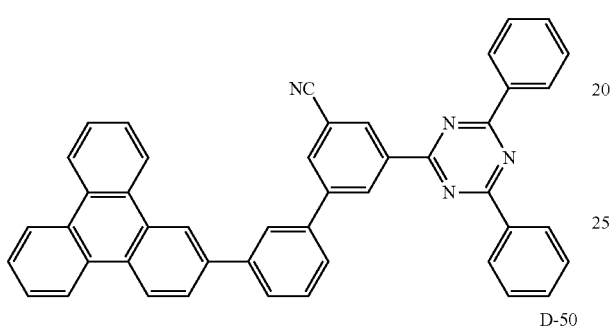
D-50
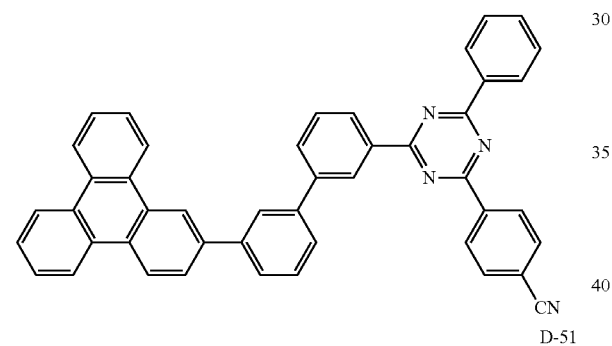
D-51
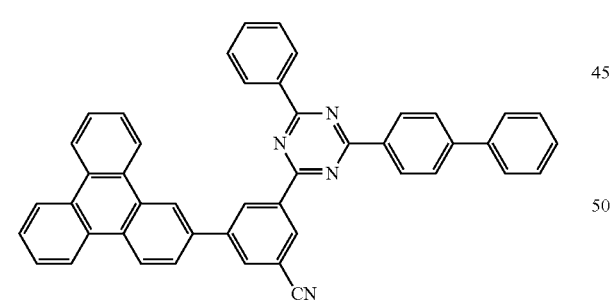
D-52
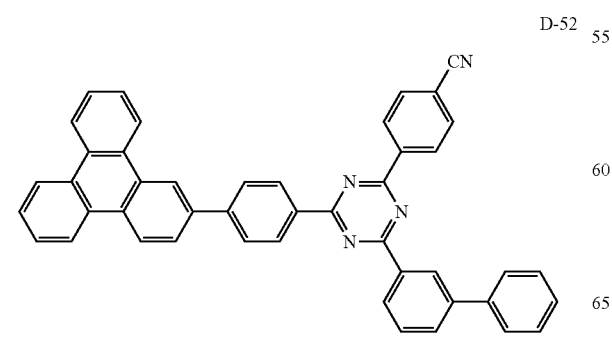
-continued
D-53
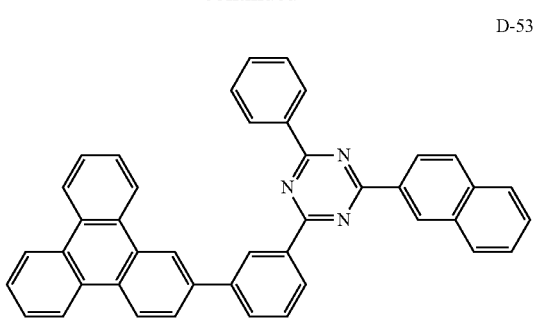
D-54
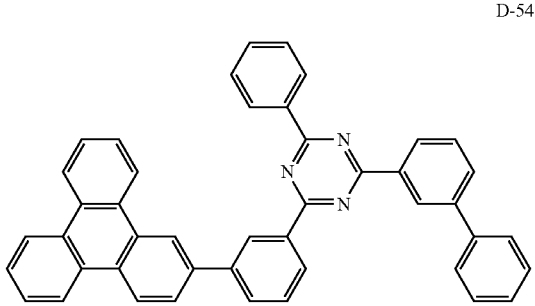
D-55
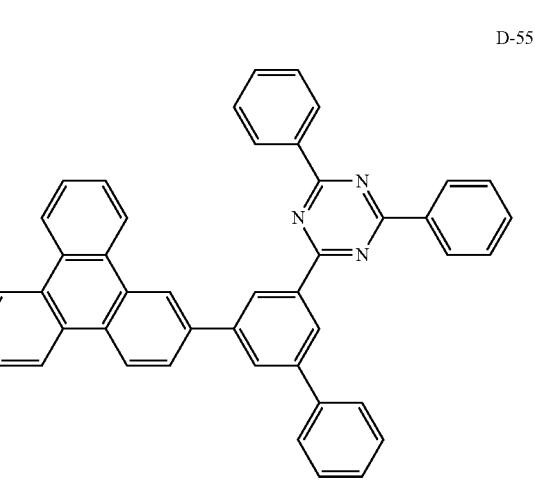
D-56
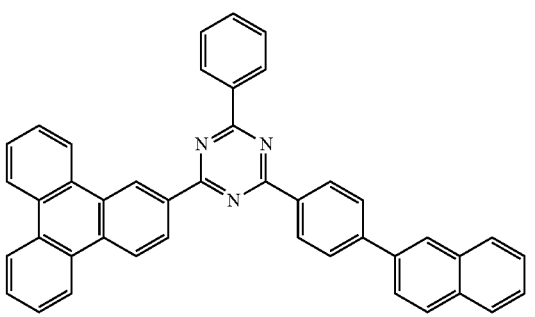

-continued

D-57

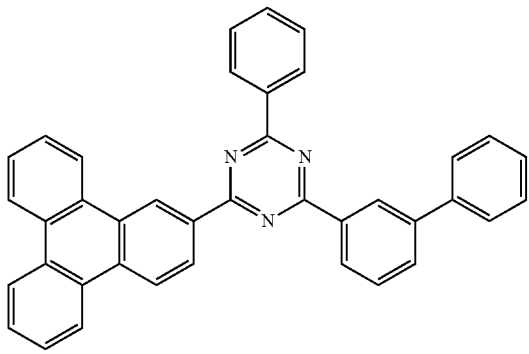

The first compound for an organic optoelectronic device and the second compound for an organic optoelectronic device may be for example included in a weight ratio of 1:99 to 99:1. Within the range, a desirable weight ratio may be adjusted using an electron transport capability of the first compound for an organic optoelectronic device and a hole transport capability of the second compound for an organic optoelectronic device to realize bipolar characteristics and thus to improve efficiency and a life-span. Within the range, they may be for example included in a weight ratio of about 10:90 to 90:10, about 20:80 to 80:20, about 30:70 to 70:30, about 40:60 to 60:40, or about 50:50. For example, they may be for example included in a weight ratio of 50:50 to 60:40, for example, 60:40.

For example, the composition for an organic optoelectronic device according to an embodiment of the present invention may include the compound represented by Chemical Formula 1A as the first compound for an organic optoelectronic device and the compound represented by Chemical Formula 2B-1, Chemical Formula 2B-4, or Chemical Formula 2D-1 as a second compound for an organic optoelectronic device.

For example, in Chemical Formula 1A, $Ar^1$ may be a substituted or unsubstituted phenyl group, or a substituted or unsubstituted biphenyl group, Are may be a substituted or unsubstituted phenyl group, or a substituted or unsubstituted naphthyl group, $L^1$ to $L^4$ may independently be a single bond or a substituted or unsubstituted phenylene group, and $Ar^3$ and $Ar^4$ may independently be a substituted or unsubstituted phenyl group, a substituted or unsubstituted biphenyl group, or a substituted or unsubstituted naphthyl group.

For example, Chemical Formula 2B-1 may be represented by Chemical Formula 2B-1-1 or Chemical Formula 2B-1-3.

For example, Chemical Formula 2B-4 may be represented by Chemical Formula 2B-4-3, and for specific examples may be represented by Chemical Formula 2B-4-3a.

For example, Chemical Formula 2D-1 may be represented by Chemical Formula 2D-1-1.

The composition may further include at least one compound in addition to the first compound for an organic optoelectronic device and/or the second compound for an organic optoelectronic device.

The compound for an organic optoelectronic device or the composition for an organic optoelectronic device may further include a dopant. The dopant may be for example a phosphorescent dopant, for example a red, green, or blue phosphorescent dopant, and may be for example a red phosphorescent dopant.

The dopant is a material mixed with the compound for an organic optoelectronic device or the composition for an organic optoelectronic device in a small amount to cause light emission and generally a material such as a metal complex that emits light by multiple excitation into a triplet or more. The dopant may be, for example an inorganic, organic, or organic/inorganic compound, and one or more kinds thereof may be used.

Examples of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$L^{12}MX^5$ [Chemical Formula Z]

In Chemical Formula Z, M is a metal, and $L^{12}$ and $X^5$ are the same or different and are a ligand to form a complex compound with M.

The M may be for example Ir, Pt, Os, Ti, Zr, Hf, Eu, Tb, Tm, Fe, Co, Ni, Ru, Rh, Pd, or a combination thereof and $L^8$ and $X^4$ may be for example a bidentate ligand.

The compound for an organic optoelectronic device or the composition for an organic optoelectronic device may be formed by a dry film formation method such as chemical vapor deposition (CVD).

Hereinafter, an organic optoelectronic device including the compound for an organic optoelectronic device or the composition for an organic optoelectronic device is described.

The organic optoelectronic device may be any device to convert electrical energy into photoenergy and vice versa without particular limitation, and may be for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views showing organic light emitting diodes according to embodiments.

Referring to FIG. 1, an organic light emitting diode 100 according to an embodiment includes an anode 120 and a cathode 110 and facing each other and an organic layer 105 disposed between the anode 120 and the cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al and $BaF_2$/Ca, but is not limited thereto.

The organic layer 105 includes a light emitting layer 130 including the compound or composition.

The light emitting layer 130 may include for example the composition.

The composition may be for example a red light emitting composition.

The light emitting layer 130 may include for example the first compound for an organic optoelectronic device and the second compound for an organic optoelectronic device as a phosphorescent host, respectively.

Referring to FIG. 2, an organic light emitting diode 200 further includes a hole auxiliary layer 140 in addition to the light emitting layer 130. The hole auxiliary layer 140 further increases hole injection and/or hole mobility and blocks electrons between the anode 120 and the light emitting layer 130.

The hole auxiliary layer 140 may include for example the compound for an organic optoelectronic device or the composition for an organic optoelectronic device, and may include at least one of a hole transport layer, a hole injection layer, and/or an electron blocking layer.

More specifically, the hole auxiliary layer 140 may include a hole transport layer between the anode 120 and the light emitting layer 130 and a hole transport auxiliary layer between the light emitting layer 130 and the hole transport layer, and the hole transport auxiliary layer may include the compound for an organic optoelectronic device.

In an embodiment, in FIG. 1 or 2, an organic light emitting diode may further include an electron transport layer, an electron injection layer, a hole injection layer, and the like as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

DETAILED DESCRIPTION OF THE EMBODIMENTS

Hereinafter, the embodiments are illustrated in more detail with reference to examples. However, these examples are exemplary, and the present scope is not limited thereto.

(Preparation of First Compound for Organic Optoelectronic Device)

Synthesis Example 1: Synthesis of Synthesis of Compound A-2

[Reaction Scheme 1]

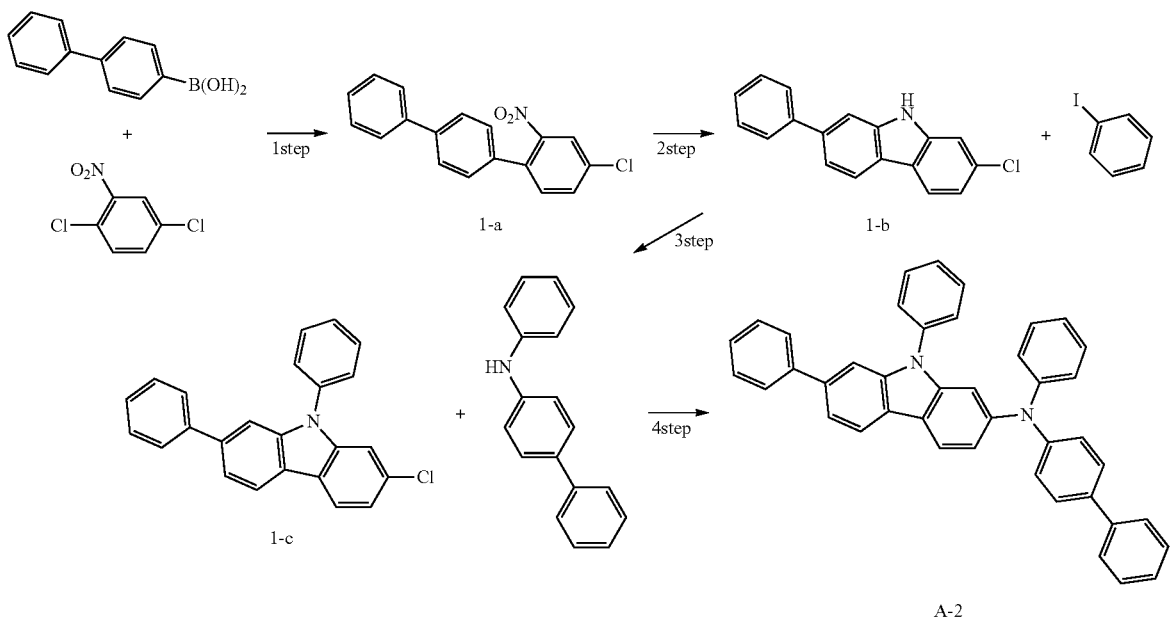

1 Step: Synthesis of Intermediate 1-a 1 equivalent (eq) (30.3 g) of 1,4-dichloro-2-nitrobenzene, 1 eq (31.3 g) of 4-biphenyl boronic acid, 5 mol % (9.1 g) of $Pd(PPh_3)_4$, and 2 eq (43.6 g) of $K_2CO_3$ were suspended in 310 ml of tetrahydrofuran and 220 ml of distilled water and then, refluxed and stirred under a nitrogen flow for 12 hours. When a reaction was complete, the resultant was treated with tetrahydrofuran and distilled water for an extraction, an organic layer therefrom was dried with magnesium sulfate ($MgSO_4$) and filtered, and a filtrate therefrom was concentrated under a reduced pressure. A solid therefrom was recrystallized with dichloromethane and hexane to obtain 37 g of Intermediate 1-a (yield: 74%).

2 Step: Synthesis of Intermediate 1-b 37 g of Intermediate 1-a and 100 g of triphenylphosphine were suspended in 400 ml of 1,2-dichlorobenzene and then, refluxed and stirred under a nitrogen flow for 18 hours. When a reaction was complete, a solvent was extracted therefrom, and an organic layer therefrom was recrystallized with 200 ml of acetone to obtain 20 g of Intermediate 1-b (yield: 61%).

3 Step: Synthesis of Intermediate 1-c 20 g of Intermediate 1-b, 45 g of iodobenzene, 2.7 g of 1,10-phenanthroline, 2.8 g of CuI, and 15.2 g of $K_2CO_3$ were suspended in 250 ml of dimethylformamide and then, refluxed and stirred under a nitrogen flow. When a reaction was complete, a solid was precipitated therefrom in methanol, filtered, dissolved in monochlorobenzene, silica-filtered, and recrystallized to obtain 18 g of Intermediate 1-c (yield: 69%).

4 Step: Synthesis of Compound A-2

1 eq (18 g) of Intermediate 1-c, 1 eq (12.5 g) of phenyl-(4-biphenyl)-amine, 2 eq (9.7 g) of sodium-t-butoxide, and 0.03 eq (1.4 g) of $Pd_2(dba)_3$ were suspended in 170 ml of toluene, 0.09 eq of tri-t-butylphosphine was added thereto, and the obtained mixture was refluxed and stirred for 12 hours. When a reaction was complete, the resultant was treated with toluene and distilled water for an extraction, and an organic layer therefrom was dried with magnesium sulfate and filtered, and a filtrate was concentrated under a reduced pressure. The concentrated product was silica gel columned with hexane:dichloromethane=8:2 (v/v, volume/volume) after removing an organic solution therefrom, and a solid therefrom was recrystallized with dichloromethane and acetone to obtain 21.2 g of Compound A-2 (yield: 74%).

LC-Mass measurement (theoretical value: 562.70 g/mol, measured value: Mass (M)=562.92 g/mol)

Synthesis Example 2: Synthesis of Compound A-3

1 eq (16.6 g) of Intermediate 1-c, 1 eq (15.1 g) of bis(4-biphenyl)-amine, 2 eq (9.0 g) of sodium-t-butoxide, and 0.03 eq (1.3 g) of $Pd_2(dba)_3$ were suspended in 200 ml of toluene, 0.09 eq of tri-t-butylphosphine was added thereto, and the mixture was refluxed and stirred for 12 hours. When a reaction was complete, the resultant was treated with toluene and distilled water for an extraction, an organic layer therefrom was dried with magnesium sulfate and filtered, and a filtrate therefrom was concentrated under a reduced pressure. After removing an organic solution therefrom, a solid therefrom was recrystallized with dichloromethane and acetone to obtain 24.3 g of Compound A-3 (yield: 84%).

LC-Mass measurement (theoretical value: 638.80 g/mol, measured value: M=639.15 g/mol)

Synthesis Example 3: Synthesis of Compound A-7

1 eq of Intermediate 1-c and 1 eq of phenyl-(4-terphenyl)-amine were reacted according to the same method as Synthesis Example 2 to obtain 23.5 g of Compound A-7 (yield: 78%).

LC-Mass measurement (theoretical value: 638.80 g/mol, measured value: M=639.40 g/mol)

Synthesis Example 4: Synthesis of Compound A-17

17.3 g of Intermediate 1-c and 14.5 g of 4-(2-naphthalenyl)-N-phenylbenzeneamine were reacted according to the same method as Synthesis Example 2 to obtain 22.6 g of Compound A-17 (yield: 75%).

LC-Mass measurement (theoretical value: 612.76 g/mol, measured value: M=613.76 g/mol)

Synthesis Example 5: Synthesis of Compound A-23

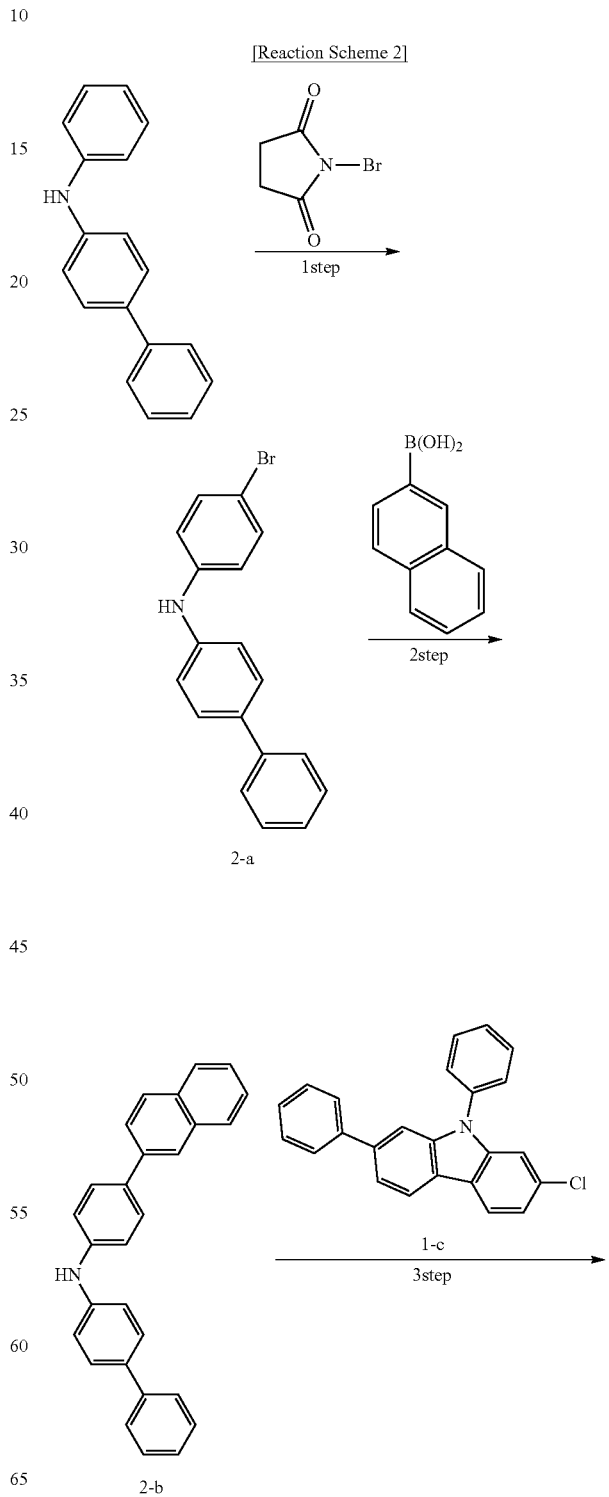

[Reaction Scheme 2]

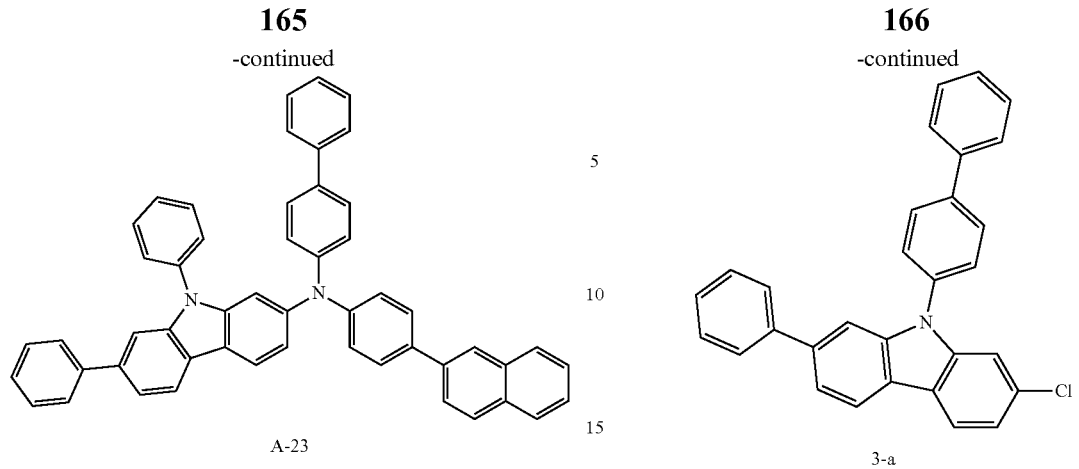

A-23

1 Step: Synthesis of Intermediate 2-a 1 eq (22.7 g) of phenyl-(4-biphenyl)-amine and 0.95 eq (15.7 g) of N-bromosuccinimide were dissolved in 300 ml of dichloromethane and then, refluxed and stirred at 0° C. for 8 hours. When a reaction was complete, the resultant was treated with distilled water for an extraction, and an organic layer therefrom was dried with magnesium sulfate and filtered, and a filtrate therefrom was concentrated under a reduced pressure and recrystallized with acetone to obtain 28.5 g of Intermediate 2-a (yield: 95%).

2 Step: Synthesis of Intermediate 2-b 1 eq (26.2 g) of Intermediate 2-a and 1 eq (13.9 g) of naphthalene-2-boronic acid along with 5 mol % (9.1 g) of Pd(PPh$_3$)$_4$ and 2 eq (43.6 g) of K$_2$CO$_3$ were suspended with 150 ml of tetrahydrofuran and 80 ml of distilled water and then, refluxed and stirred under a nitrogen flow for 12 hours. When a reaction was complete, the resultant was treated with tetrahydrofuran and distilled water for an extraction, an organic layer therefrom was dried with magnesium sulfate (MgSO$_4$) and filtered, and an filtrate was concentrated under a reduced pressure. A solid therefrom was recrystallized with dichloromethane and hexane to obtain 21 g of Intermediate 2-b (yield: 70%).

3 Step: Synthesis of Compound A-23

1 eq (15.4 g) of Intermediate 1-c and 1 eq (16.2 g) of Intermediate 2-b were reacted according to the same method as Synthesis Example 2 to obtain 23.0 g of Compound A-23 (yield: 77%).

LC-Mass measurement (theoretical value: 688.86 g/mol, measured value: M=689.86 g/mol)

Synthesis Example 6: Synthesis of Compound A-27

[Reaction Scheme 3]

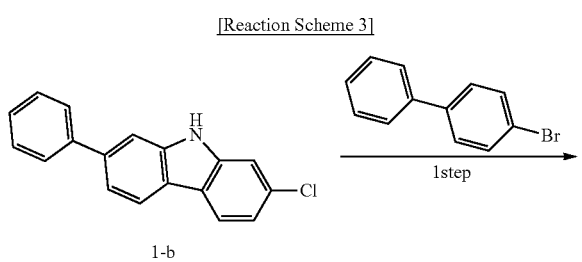

1 Step: Synthesis of Intermediate 3-a 16.1 g of Intermediate 1-b along with 41 g of 4-bromo-biphenyl, 2.1 g of 1,10-phenanthroline, 2.2 g of CuI, and 12.0 g of K$_2$CO$_3$ was suspended in 200 ml of dimethylformamide and then, refluxed and stirred under a nitrogen flow. When a reaction was complete, a solid was precipitated therefrom in methanol, filtered, dissolved in monochlorobenzene, silica-filtered, and recrystallized to obtain 15.7 g of Intermediate 3-a (yield: 63%).

2 Step: Synthesis of Compound A-27

1 eq (15.5 g) of Intermediate 3-a and 1 eq (8.8 g) of phenyl-(4-biphenyl)-amine along with 2 eq of sodium-t-butoxide and 0.03 eq of Pd$_2$(dba)$_3$ were suspended in 200 ml of xylene, 0.09 eq of tri-t-butylphosphine was added thereto, and the mixture was refluxed and stirred for 12 hours. When a reaction was complete, the resultant was treated with toluene and distilled water for an extraction, an organic layer was dried with magnesium sulfate and filtered, and a filtrate was concentrated under a reduced pressure. After removing an organic solution therefrom, a solid therefrom was silica gel columned with hexane:dichloromethane=8:2 (v/v) and recrystallized with dichloromethane and acetone to obtain 17.5 g of Compound A-27 (yield: 76%).

LC-Mass measurement (theoretical value: 638.80 g/mol, measured value: M=639.60 g/mol)

Synthesis Example 7: Synthesis of Compound A-33

[Reaction Scheme 4]

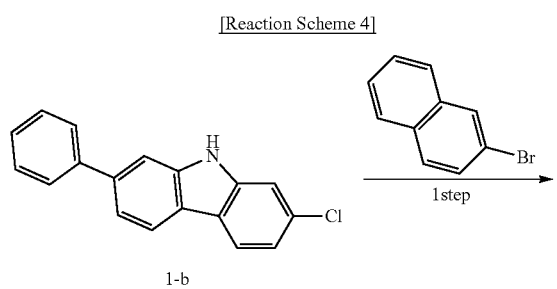

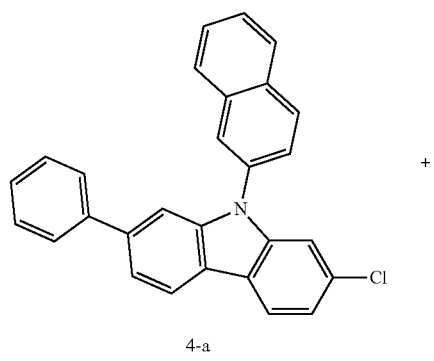

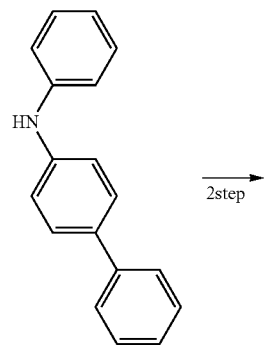

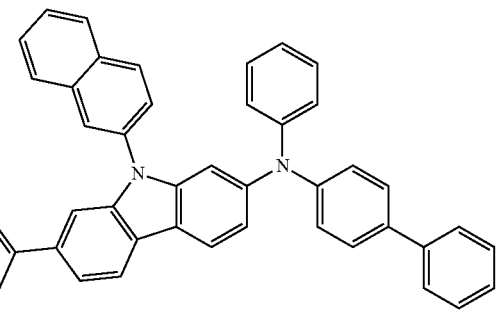

A-33

1 Step: Synthesis of Intermediate 4-a 17.2 g of Intermediate 1-b, 38.5 g of 2-bromonaphthalene, 2.2 g of 1,10-phenanthroline, 2.4 g of CuI, and 12.8 g of $K_2CO_3$ were suspended in 210 ml of dimethylformamide and then, refluxed and stirred under a nitrogen flow. When a reaction was complete, a solid was precipitated therefrom in methanol, filtered, dissolved in monochlorobenzene, silica-filtered, and recrystallized to obtain 18.5 g of Intermediate 4-a (yield: 74%).

2 Step: Synthesis of Compound A-33

1 eq (16.5 g) of Intermediate 4-a and 1 eq (10.0 g) of phenyl-(4-biphenyl)-amine along with 2 eq of sodium-t-butoxide, and 0.03 eq of $Pd_2(dba)_3$ were suspended in 180 ml of xylene, 0.09 eq of tri-t-butylphosphine was added thereto, and the mixture was refluxed and stirred for 12 hours. When a reaction was complete, the resultant was treated with toluene and distilled water for an extraction, and an organic layer was dried with magnesium sulfate, filtered, and concentrated under a reduced pressure. After removing an organic solution therefrom, a solid produced therein was silica gel columned with hexane:dichloromethane=8:2 (v/v) and recrystallized with dichloromethane and acetone to obtain 20.1 g of Compound A-33 (yield: 80%).

LC-Mass measurement (theoretical value: 612.76 g/mol, measured value: M=613.56 g/mol)

Synthesis Example 8: Synthesis of Compound A-47

[Reaction Scheme 5]

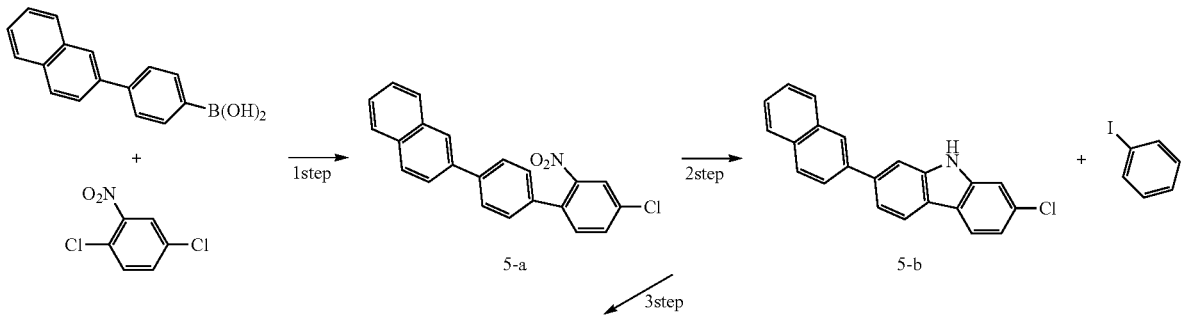

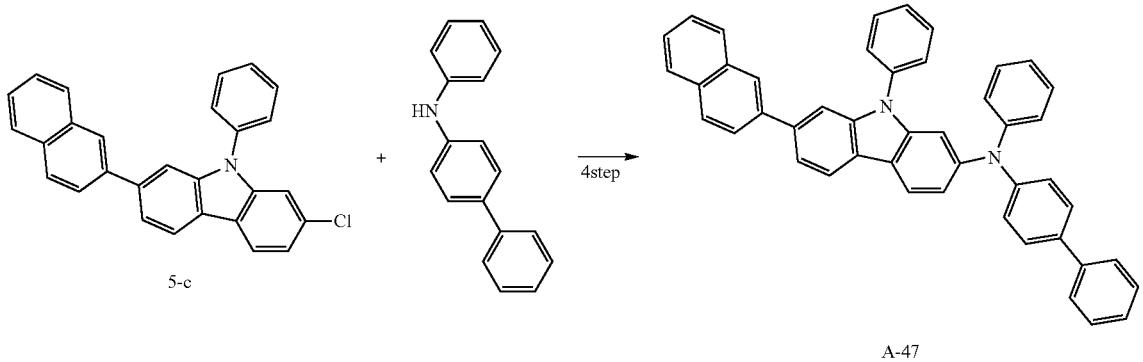

1 Step: Synthesis of Intermediate 5-a 1 eq (26.7 g) of 1,4-dichloro-2-nitrobenzene and 1 eq (34.5 g) of 4-(2-naphthalenyl)phenyl boronic acid along with 5 mol % (8.03 g) of Pd(PPh$_3$)$_4$ and 2 eq (38.4 g) of K$_2$CO$_3$ were suspended in 340 ml of tetrahydrofuran and 200 ml of distilled water and then, refluxed and stirred under a nitrogen flow for 12 hours. When a reaction was complete, the resultant was treated with tetrahydrofuran and distilled water for an extraction, an organic layer was dried with magnesium sulfate (MgSO$_4$) and filtered, and a filtrate was concentrated under a reduced pressure. A solid produced therein was recrystallized with dichloromethane and hexane to obtain 34 g of Intermediate 5-a (yield: 68%).

2 Step: Synthesis of Intermediate 5-b 34 g of Intermediate 5-a and 100 g of triphenylphosphine were suspended in 300 ml of 1,2-dichlorobenzene and then, refluxed and stirred under a nitrogen flow for 18 hours. When a reaction was complete, a solvent was extracted, and then, an organic layer therefrom was recrystallized with 150 ml of acetone to obtain 17 g of Intermediate 5-b (yield: 55%).

3 Step: Synthesis of Intermediate 5-c 17 g of Intermediate 5-b along with 36 g of iodobenzene, 1.9 g of 1,10-phenanthroline, 2.0 g of CuI, and 10.7 g of K$_2$CO$_3$ was suspended in 180 ml of dimethylformamide and then, refluxed and stirred under a nitrogen flow. When a reaction was complete, a solid was precipitated therefrom in methanol and filtered, dissolved in monochlorobenzene, silica-filtered, and then, recrystallized to obtain 16.4 g of Intermediate 5-c (yield: 78%).

4 Step: Synthesis of Compound A-47

1 eq (16.4 g) of Intermediate 5-c, 1 eq (10.0 g) of phenyl-(4-biphenyl)-amine, 2 eq (7.8 g) of sodium-t-butoxide, and 0.03 eq (1.12 g) of Pd$_2$(dba)$_3$ were suspended in 150 ml of xylene, 0.09 eq of tri-t-butylphosphine was added thereto, and the mixture was refluxed and stirred for 12 hours. When a reaction was complete, the resultant was treated with toluene and distilled water for an extraction, an organic layer therefrom was dried with magnesium sulfate and filtered, and a filtrate therefrom was concentrated under a reduced pressure. After removing an organic solution, a solid produced therein was silica gel columned with hexane:dichloromethane=8:2 (v/v) and recrystallized with dichloromethane and acetone to obtain 19.6 g of Compound A-47 (yield: 78%).

LC-Mass measurement (theoretical value: 612.76 g/mol, measured value: M=613.77 g/mol)

Comparative Synthesis Example 1: Synthesis of Compound V-1

[Reaction Scheme 6]

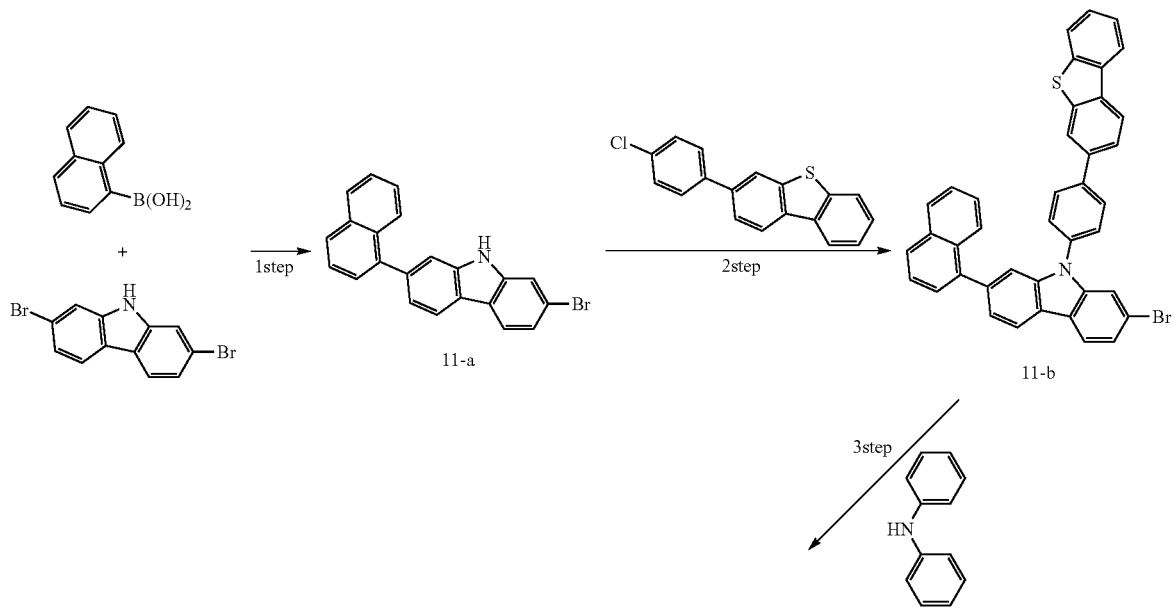

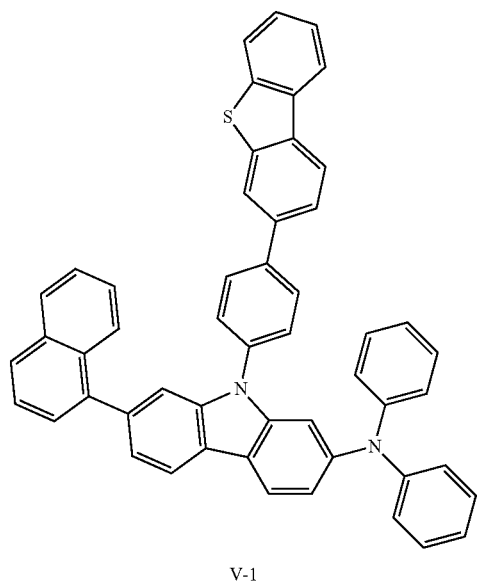

V-1

1 Step: Synthesis of Intermediate 11-a 1 eq (43.6 g) of 2,7-dibromo-9H-carbazole, 1 eq (23.1 g) of 1-naphthalene boronic acid, 5 mol % (7.8 g) of Pd(PPh$_3$)$_4$, and 2 eq (37.1 g) of K$_2$CO$_3$ were suspended in 300 ml of tetrahydrofuran and 150 ml of distilled water and then, refluxed and suspended under a nitrogen flow for 12 hours. When a reaction was complete, the resultant was treated with tetrahydrofuran and distilled water for an extraction, an organic layer was dried with magnesium sulfate (MgSO$_4$) and filtered, and a filtrate was concentrated under a reduced pressure. A solid produced therein was recrystallized with dichloromethane and hexane to obtain 26.4 g of Intermediate 11-a (yield: 53%).

2 Step: Synthesis of Intermediate 11-b 11.8 g of Intermediate 11-a, 28 g of 3-(4-chlorophenyl) dibenzothiophene, 1.14 g of 1,10-phenanthroline, 1.21 g of CuI, and 6.6 g of K$_2$CO$_3$ were suspended in 150 ml of dimethylformamide and then, refluxed and stirred under a nitrogen flow. When a reaction was complete, a solid was precipitated therefrom in methanol, filtered, dissolved in monochlorobenzene, silica-filtered, and recrystallized to obtain 14.7 g of Intermediate 11-b (yield: 74%).

3 Step: Synthesis of Compound V-1

1 eq of Intermediate 11-b and 1 eq of diphenylamine were reacted according to the same method as Synthesis Example 2 to obtain 11.9 g of Compound V-1 (yield: 79%).

LC-Mass measurement (theoretical value: 718.9 g/mol, measured value: M=719.60 g/mol)

Comparative Synthesis Example 2: Synthesis of Compound V-2

[Reaction Scheme 7]

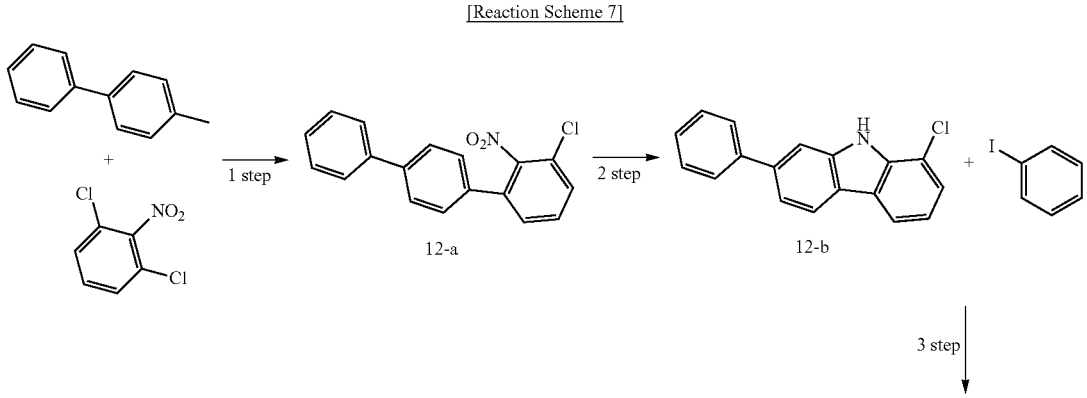

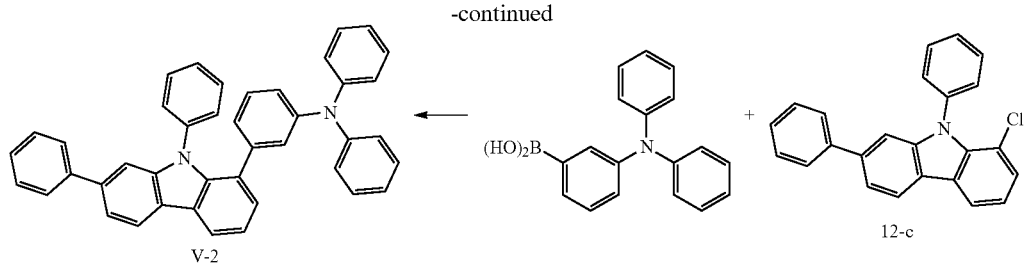

1 Step: Synthesis of Intermediate 12-a 1 eq (30.3 g) of 1,3-dichloro-2-nitrobenzene, 1 eq (31.3 g) of 4-biphenyl boronic acid, 5 mol % (9.1 g) of Pd(PPh$_3$)$_4$, and 2 eq (43.6 g) of K$_2$CO$_3$ were suspended in 310 ml of tetrahydrofuran and 220 ml of distilled water and then, refluxed and stirred under a nitrogen flow for 12 hours. When a reaction was complete, the resultant was treated with tetrahydrofuran and distilled water for an extraction, an organic layer therefrom was dried with magnesium sulfate (MgSO$_4$) and filtered, and a filtrate therefrom was concentrated under a reduced pressure. A solid produced therein was recrystallized with dichloromethane and hexane to obtain 23.5 g of Intermediate 12-a (yield: 47%).

2 Step: Synthesis of Intermediate 12-b 23.5 g of Intermediate 12-a and 60 g of triphenylphosphine were suspended in 250 ml of 1,2-dichlorobenzene and then, refluxed and stirred under a nitrogen flow for 24 hours. When a reaction was complete, a solvent was extracted therefrom, and an organic layer therefrom was recrystallized with 120 ml of acetone to obtain 10.8 g of Intermediate 12-b (yield: 51%).

3 Step: Synthesis of Intermediate 12-c 10.8 g of Intermediate 12-b, 24.4 g of iodobenzene, 1.4 g of 1,10-phenanthroline, 1.5 g of CuI, and 8.2 g of K$_2$CO$_3$ were suspended in 130 ml of dimethylformamide and then, refluxed and stirred under a nitrogen flow. When a reaction was complete, a solid was precipitated therefrom in methanol, filtered, dissolved in monochlorobenzene, silica filtered, and then, recrystallized to obtain 9.4 g of Intermediate 12-c (yield: 67%).

4 Step: Synthesis of Compound V-2

1 eq (9.4 g) of Intermediate 12-c, 1 eq (11.3 g) of 3-(diphenylamino)phenylboronic acid, 5 mol % (1.8 g) of Pd(PPh$_3$)$_4$, and 2 eq (8.8 g) of K$_2$CO$_3$ were suspended in 110 ml of tetrahydrofuran and 60 ml of distilled water and then, refluxed and stirred under a nitrogen flow for 12 hours. When a reaction was complete, the resultant was treated with tetrahydrofuran and distilled water for an extraction, an organic layer therefrom was dried with magnesium sulfate (MgSO$_4$) and filtered, and an filtrate therefrom was concentrated under a reduced pressure. A solid produced therein was recrystallized with dichloromethane and hexane to obtain 11.6 g of Compound V-2 (yield: 64%).

LC-Mass measurement (theoretical value: 562.70 g/mol, measured value: M=563.10 g/mol)

Comparative Synthesis Example 3: Synthesis of Compound V-3

1 eq of 9H-phenyl-carbazole and 1 eq of 4-(2-naphthalenyl)-N-phenylbenzeneamine were reacted according to the same method as Synthesis Example 2 to obtain 17.6 g of compound V-3 (yield: 88%).

LC-Mass measurement (theoretical value: 536.66 g/mol, measured value: M=537.06 g/mol)

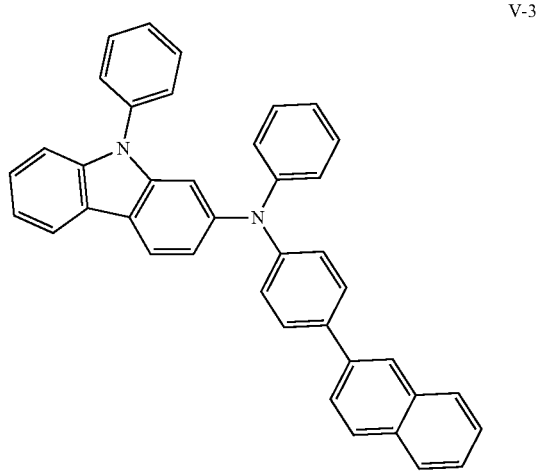 [SMILES: c1ccc(N(c2ccc(-c3ccc4ccccc4c3)cc2)c2ccc3c4ccccc4n(-c4ccccc4)c3c2)cc1]

Comparative Synthesis Example 4: Synthesis of Compound V-4

1 eq of Intermediate 1-c and 1 eq of 4-(3-dibenzothiophenyl)-2-naphthylamine were reacted according to the same method as Synthesis Example 2 to obtain 18.2 g of Compound V-4 (yield: 92%).

LC-Mass measurement (theoretical value: 718.90 g/mol, measured value: M=719.30 g/mol)

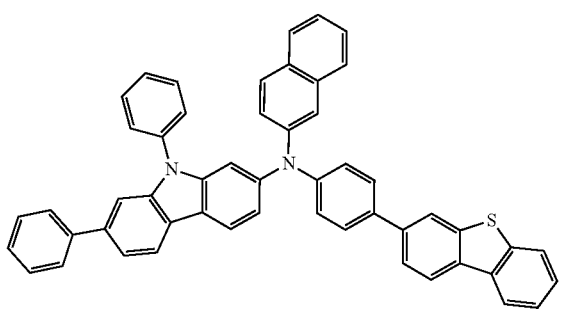

Comparative Synthesis Example 5: Synthesis of Compound V-5
[Reaction Scheme 8]
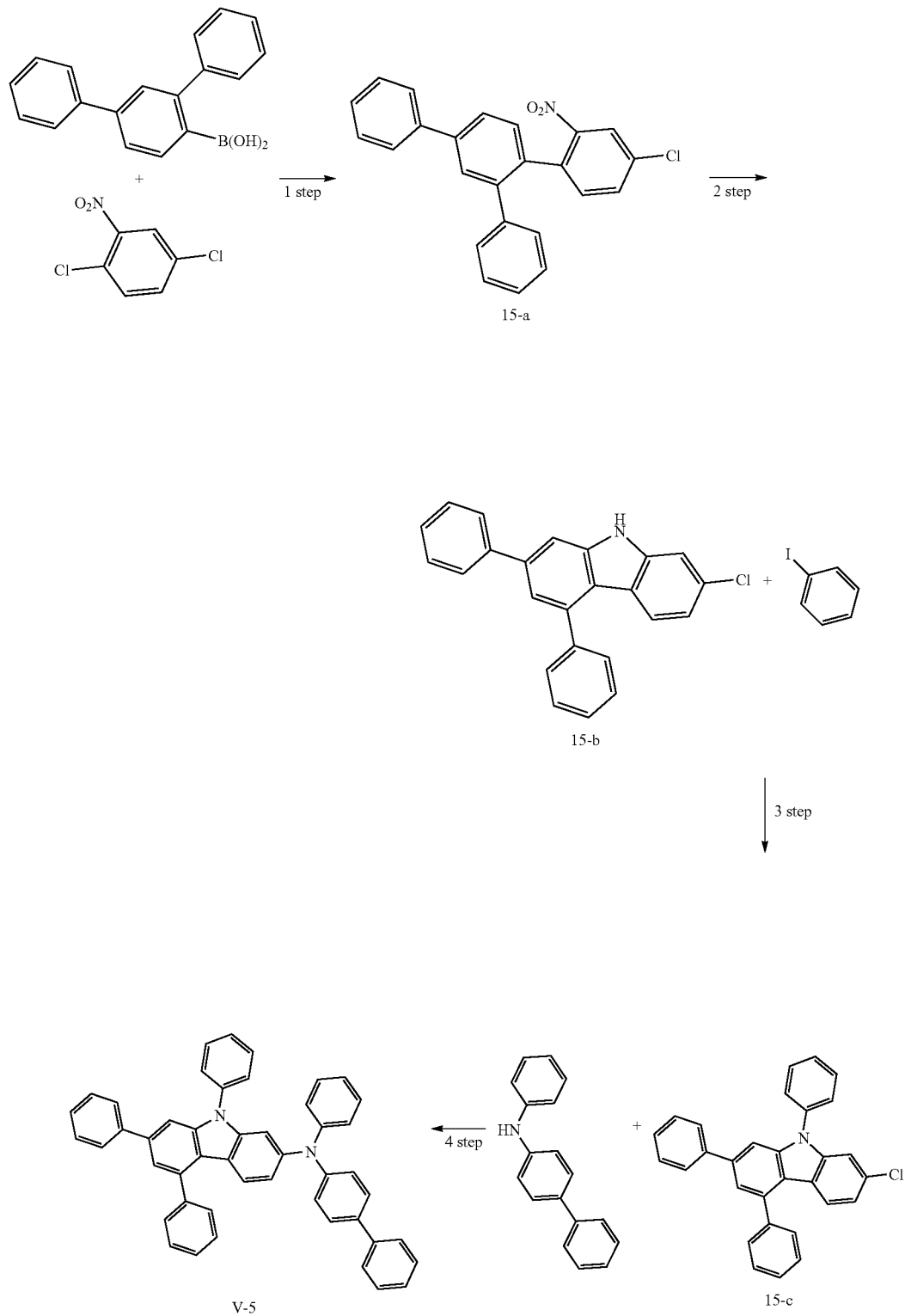

1 Step: Synthesis of Intermediate 15-a 1 eq (24.9 g) of 1,4-dichloro-2-nitrobenzene, 1 eq (35.5 g) of 2,4-(diphenyl)phenyl boronic acid, 5 mol % (7.5 g) of Pd(PPh$_3$)$_4$, and 2 eq (35.8 g) of K$_2$CO$_3$ were suspended in 310 ml of tetrahydrofuran and 220 ml of distilled water and then, refluxed and stirred under a nitrogen flow for 12 hours. When a reaction was complete, the resultant was treated with tetrahydrofuran and distilled water for an extraction, an organic layer therefrom was dried with magnesium sulfate (MgSO$_4$) and filtered, and a filtrate therefrom was concentrated under a reduced pressure. A solid produced therein was recrystallized with dichloromethane and hexane to obtain 30.4 g of Intermediate 15-a (yield: 61%).

2 Step: Synthesis of Intermediate 15-b 30.4 g of Intermediate 15-a and 62 g of triphenylphosphine were suspended in 250 ml of 1,2-dichlorobenzene and then, refluxed and stirred under a nitrogen flow for 24 hours. When a reaction was complete, a solvent was extracted therefrom, and an organic layer therefrom was recrystallized with 120 ml of acetone to obtain 18.1 g of Intermediate 15-b (yield: 65%).

3 Step: Synthesis of Intermediate 15-c 16.5 g of Intermediate 15-b, 28.5 g of iodobenzene, 1.7 g of 1,10-phenanthroline, 1.8 g of CuI, and 9.7 g of K$_2$CO$_3$ were suspended in 155 ml of dimethylformamide and then, refluxed and stirred under a nitrogen flow. When a reaction was complete, the resultant was precipitated in methanol, and a solid was filtered therefrom, dissolved in monochlorobenzene, silica filtered, and recrystallized to obtain 11.8 g of Intermediate 15-c (yield: 59%).

4 Step: Synthesis of Compound V-5

1 eq of Intermediate 15-c, 1 eq of 4-biphenyl-phenylamine, 5 mol % of Pd(PPh$_3$)$_4$, and 2 eq of K$_2$CO$_3$ were suspended in 110 ml of tetrahydrofuran and 60 ml of distilled water and then, refluxed and stirred under a nitrogen flow for 12 hours. When a reaction was complete, the resultant was treated with tetrahydrofuran and distilled water for an extraction, an organic layer therefrom was dried with magnesium sulfate (MgSO$_4$) and filtered, and an filtrate was concentrated under a reduced pressure. After removing an organic solution, the residue was silica gel columned with hexane:dichloromethane=8:2 (v/v), and a solid therein was recrystallized with dichloromethane and acetone to obtain 16.0 g of Compound V-5 (yield: 89%).

LC-Mass measurement (theoretical value: 638.80 g/mol, measured value: M=639.8 g/mol)

(Preparation of Compound for Organic Optoelectronic Device)

Synthesis Example 9: Synthesis of Compound B-17

[Reaction Scheme 9]

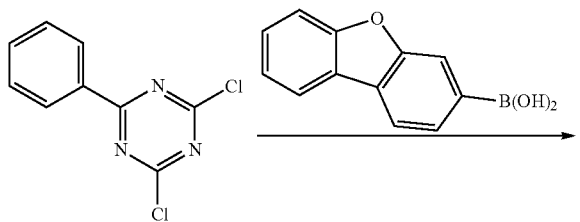

-continued

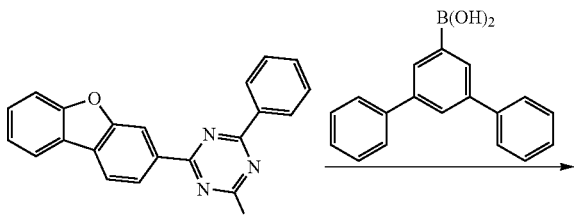

B-17-1

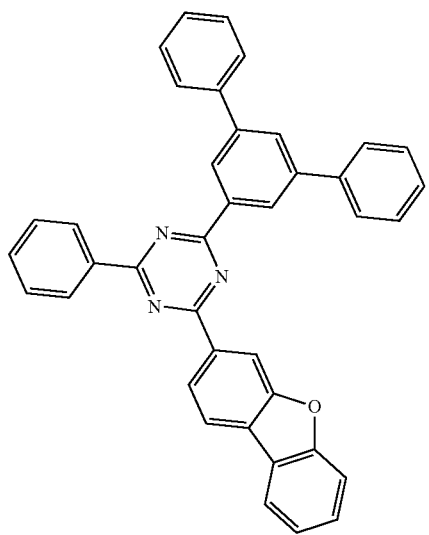

B-17

1 Step: Synthesis of Intermediate B-17-1

22.6 g (100 mmol) of 2,4-dichloro-6-phenyltriazine along with 100 mL of tetrahydrofuran, 100 mL of toluene, and 100 mL of distilled water was put in a 500 mL round-bottomed flask, 0.9 equivalent of dibenzofuran-3-boronic acid (CAS No.: 395087-89-5), 0.03 equivalent of tetrakistriphenylphosphine palladium, and 2 equivalent of potassium carbonate were added thereto, and the obtained mixture was heated and refluxed under a nitrogen atmosphere. After 6 hours, the reaction solution was cooled down, an aqueous layer was removed therefrom, and an organic layer therein was dried under a reduced pressure. A solid obtained therefrom was washed with water and hexane and recrystallized with 200 mL of toluene to obtain 21.4 g of Intermediate B-17-1 (yield: 60%).

2 step: SYNTHESIS of Compound B-17

Intermediate B-17-1 (56.9 mmol) along with 200 mL of tetrahydrofuran and 100 mL of distilled water was put in a 500 mL round-bottomed flask, 1.1 equivalent of 3,5-diphenylbenzeneboronic acid (CAS No.: 128388-54-5), 0.03 equivalent of tetrakistriphenylphosphine palladium, and 2 equivalent of potassium carbonate were added thereto, and the obtained mixture was heated and refluxed under a nitrogen atmosphere. After 18 hours, the reaction solution was cooled down, a solid precipitated therein was filtered and washed with 500 mL of water. The solid was recrystallized with 500 mL of monochlorobenzene to obtain Compound B-17.

LC/MS measurement (C39H25N3O, theoretical value: 555.1998 g/mol, measured value: 556.21 g/mol)

Synthesis Example 10: Synthesis of Compound B-135

[Reaction Scheme 10]

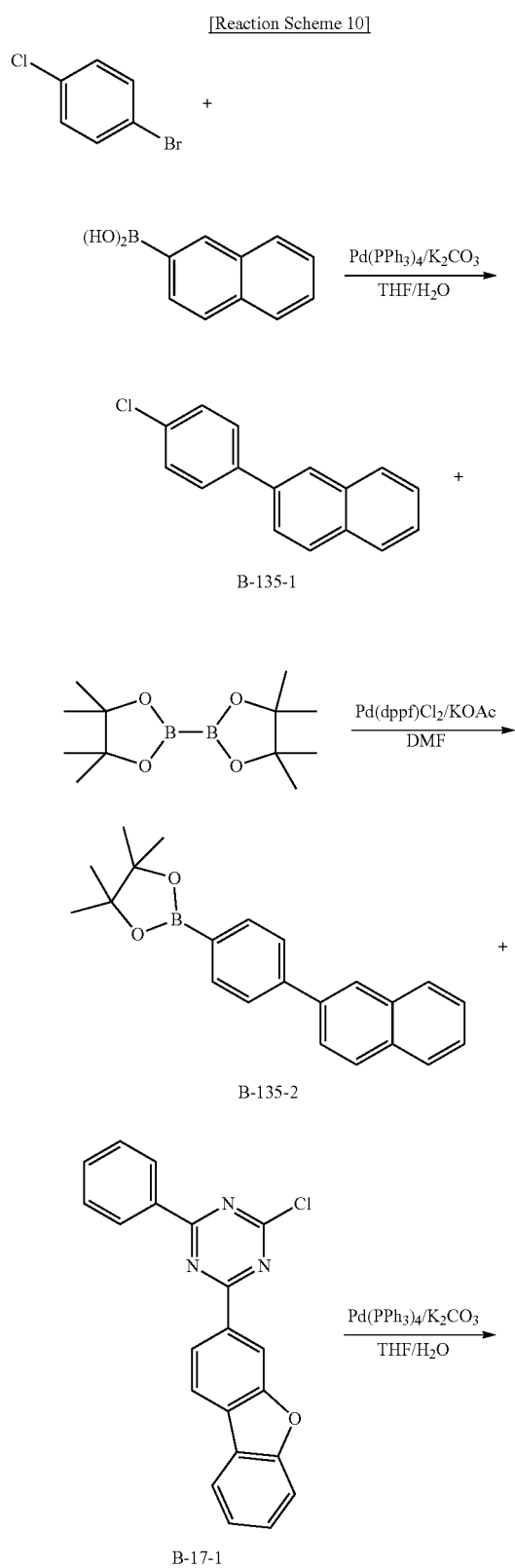

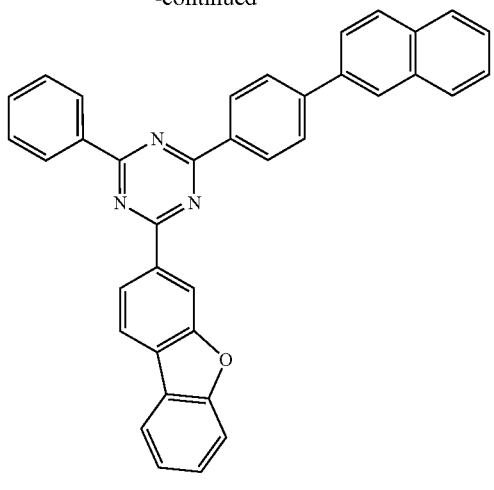

1 Step: Synthesis of Intermediate B-135-1

1-Bromo-4-chloro-benzene and 2-naphthalene boronic acid were respectively used in an amount of 1.0 equivalent according to the same method as the 1 step of Synthesis Example 9 to synthesize Intermediate B-135-1.

2 Step: Synthesis of Intermediate B-135-2

1 equivalent of Intermediate B-135-1 and 250 mL of DMF were put in a 500 mL round-bottomed flask, 0.05 equivalent of dichlorodiphenylphosphinoferrocene palladium, 1.2 equivalent of bispinacolato diboron, and 2 equivalent of potassium acetate were added thereto, and the mixture was heated and refluxed under a nitrogen atmosphere for 18 hours. The reaction solution was cooled down and dropped in 1 L of water to obtain a solid. The solid was dissolved in boiling toluene to treat activated carbon and then, filtered with silica gel, and a filtrate therefrom was concentrated. The concentrated solid was stirred with a small amount of hexane and then, filtered to synthesize Intermediate B-135-2.

3 Step: Synthesis of Compound B-135

Intermediate B-135-2 and Intermediate B-17-1 were respectively used in an amount of 1.0 equivalent according to the 2 step of Synthesis Example 9 to synthesize Compound B-135.

LC/MS measurement ($C_{37}H_{23}N_3O$, theoretical value: 525.18 g/mol, measured value: M=525.22 g/mol)

Synthesis Example 11: Synthesis of Compound B-205

[Reaction Scheme 11]

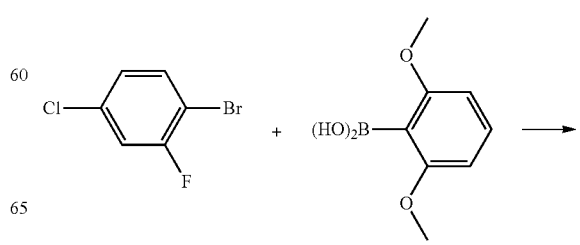

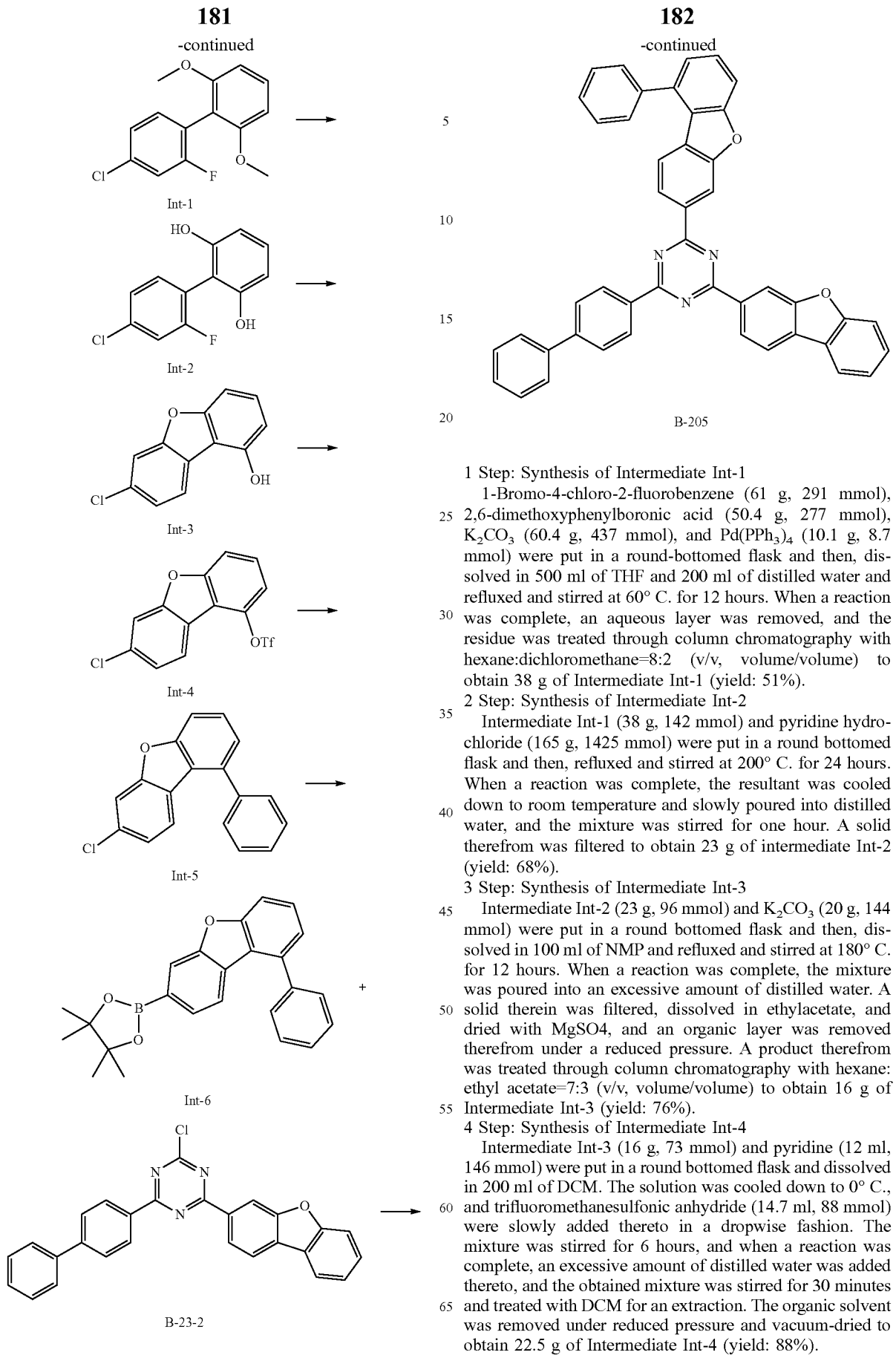

1 Step: Synthesis of Intermediate Int-1

1-Bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were put in a round-bottomed flask and then, dissolved in 500 ml of THF and 200 ml of distilled water and refluxed and stirred at 60° C. for 12 hours. When a reaction was complete, an aqueous layer was removed, and the residue was treated through column chromatography with hexane:dichloromethane=8:2 (v/v, volume/volume) to obtain 38 g of Intermediate Int-1 (yield: 51%).

2 Step: Synthesis of Intermediate Int-2

Intermediate Int-1 (38 g, 142 mmol) and pyridine hydrochloride (165 g, 1425 mmol) were put in a round bottomed flask and then, refluxed and stirred at 200° C. for 24 hours. When a reaction was complete, the resultant was cooled down to room temperature and slowly poured into distilled water, and the mixture was stirred for one hour. A solid therefrom was filtered to obtain 23 g of intermediate Int-2 (yield: 68%).

3 Step: Synthesis of Intermediate Int-3

Intermediate Int-2 (23 g, 96 mmol) and $K_2CO_3$ (20 g, 144 mmol) were put in a round bottomed flask and then, dissolved in 100 ml of NMP and refluxed and stirred at 180° C. for 12 hours. When a reaction was complete, the mixture was poured into an excessive amount of distilled water. A solid therein was filtered, dissolved in ethylacetate, and dried with MgSO4, and an organic layer was removed therefrom under a reduced pressure. A product therefrom was treated through column chromatography with hexane:ethyl acetate=7:3 (v/v, volume/volume) to obtain 16 g of Intermediate Int-3 (yield: 76%).

4 Step: Synthesis of Intermediate Int-4

Intermediate Int-3 (16 g, 73 mmol) and pyridine (12 ml, 146 mmol) were put in a round bottomed flask and dissolved in 200 ml of DCM. The solution was cooled down to 0° C., and trifluoromethanesulfonic anhydride (14.7 ml, 88 mmol) were slowly added thereto in a dropwise fashion. The mixture was stirred for 6 hours, and when a reaction was complete, an excessive amount of distilled water was added thereto, and the obtained mixture was stirred for 30 minutes and treated with DCM for an extraction. The organic solvent was removed under reduced pressure and vacuum-dried to obtain 22.5 g of Intermediate Int-4 (yield: 88%).

5 Step: Synthesis of Intermediate Int-5

Intermediate Int-4 (22.5 g, 64 mmol), phenylboronic acid (7.8 g, 64 mmol), $K_2CO_3$ (13.3 g, 96 mmol), and $Pd(PPh_3)_4$ (3.7 g, 3.2 mmol) were used according to the same method as Synthesis Example 1 to obtain 14.4 g of Intermediate Int-5 (yield: 81%).

6 Step: Synthesis of Intermediate Int-6

Intermediate Int-5 (22.5 g, 80 mmol), bis(pinacolato)diboron (24.6 g, 97 mmol), $Pd(dppf)Cl_2$ (2 g, 2.4 mmol), tricyclohexylphosphine (3.9 g, 16 mmol), and potassium acetate (16 g, 161 mmol) were put in a round bottomed flask and then, dissolved in 320 ml of DMF. The solution was refluxed and stirred at 120° C. for 10 hours. When a reaction was complete, the resultant was poured into an excessive amount of distilled water, and the obtained mixture was stirred for one hour. A solid produced therein was filtered and dissolved in DCM. After removing moisture with $MgSO_4$ therefrom, an organic solvent was filtered with a silica gel pad and removed under a reduced pressure. A solid therein was recrystallized with EA and hexane to obtain 26.9 g of Intermediate Int-6 (yield: 90%).

7 Step: Synthesis of Compound B-205

Intermediate B-23-2 (15 g, 35 mmol), Intermediate Int-6 (12.8 g, 35 mmol), $K_2CO_3$ (7.2 g, 52 mmol), and $Pd(PPh_3)_4$ (2 g, 1.7 mmol) were put in a round bottomed flask under a nitrogen condition and reacted according to the same method as the 2 step of Synthesis Example 9 to obtain 15.5 g of Compound B-205 (yield: 70%).

LC/MS measurement (C45H27N3O2, theoretical value: 641.21 g/mol, measured value: M=641.25 g/mol)

Synthesis Example 12: Synthesis of Compound B-183

[Reaction Scheme 12]

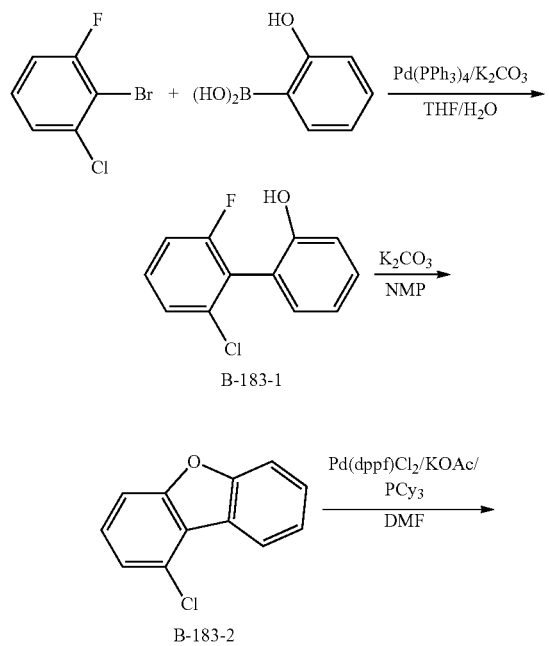

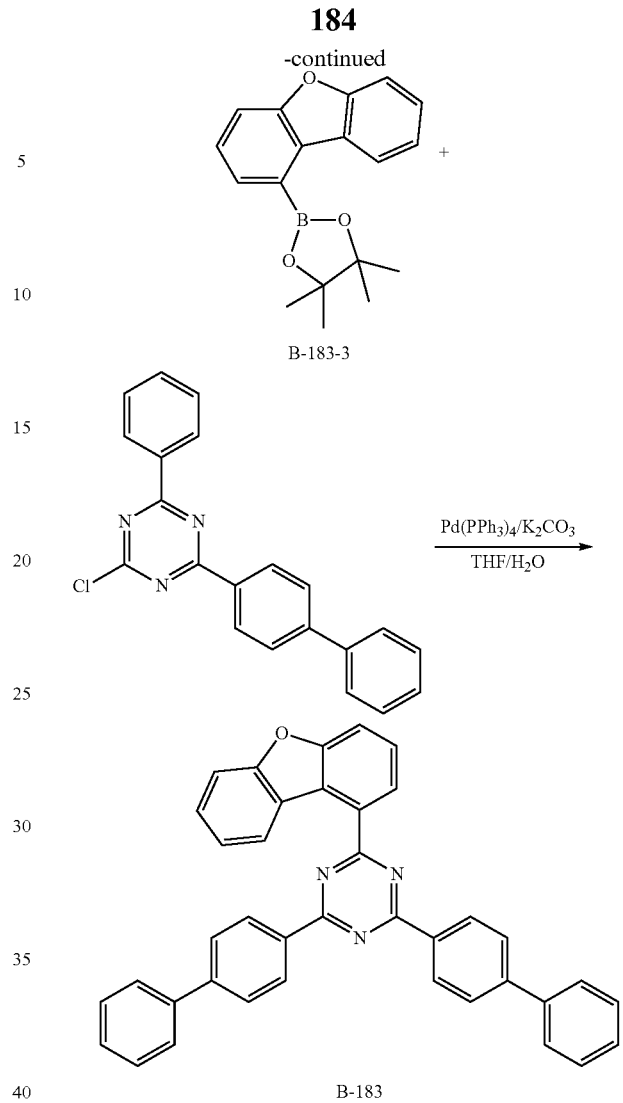

1 Step: Synthesis of Intermediate B-183-1

2-Bromo-1-chloro-3-fluoro-benzene and 2-hydroxyphenylboronic acid were respectively used in an amount of 1.0 equivalent according to the same method as the 1 step of Synthesis Example 11 to synthesize Intermediate B-183-1.

2 Step: Synthesis of Intermediate B-183-2

Intermediate B-183-1 and $K_2CO_3$ were used in an equivalent ratio of 1:1.5 according to the same method as the 3 step of Synthesis Example 11 to synthesize Intermediate B-183-2.

3 Step: Synthesis of Intermediate B-183-3

Intermediate D-3-2 and bis(pinacolato)diboron were used in an equivalent ratio of 1:1.2 according to the same method as the 6 step of Synthesis Example 11 to synthesize Intermediate B-183-3.

4 Step: Synthesis of Compound B-183

Intermediate B-183-3 and 2,4-bis([1,1'-biphenyl]-4-yl)-6-chloro-1,3,5-triazine were respectively used in an amount of 1.0 equivalent according to the same method as the 2 step of Synthesis Example 9 to synthesize Compound B-183.

LC/MS measurement (C39H25N3O theoretical value: 551.20 g/mol, measured value: M=551.24 g/mol)

Synthesis Example 13: Synthesis of Compound B-209

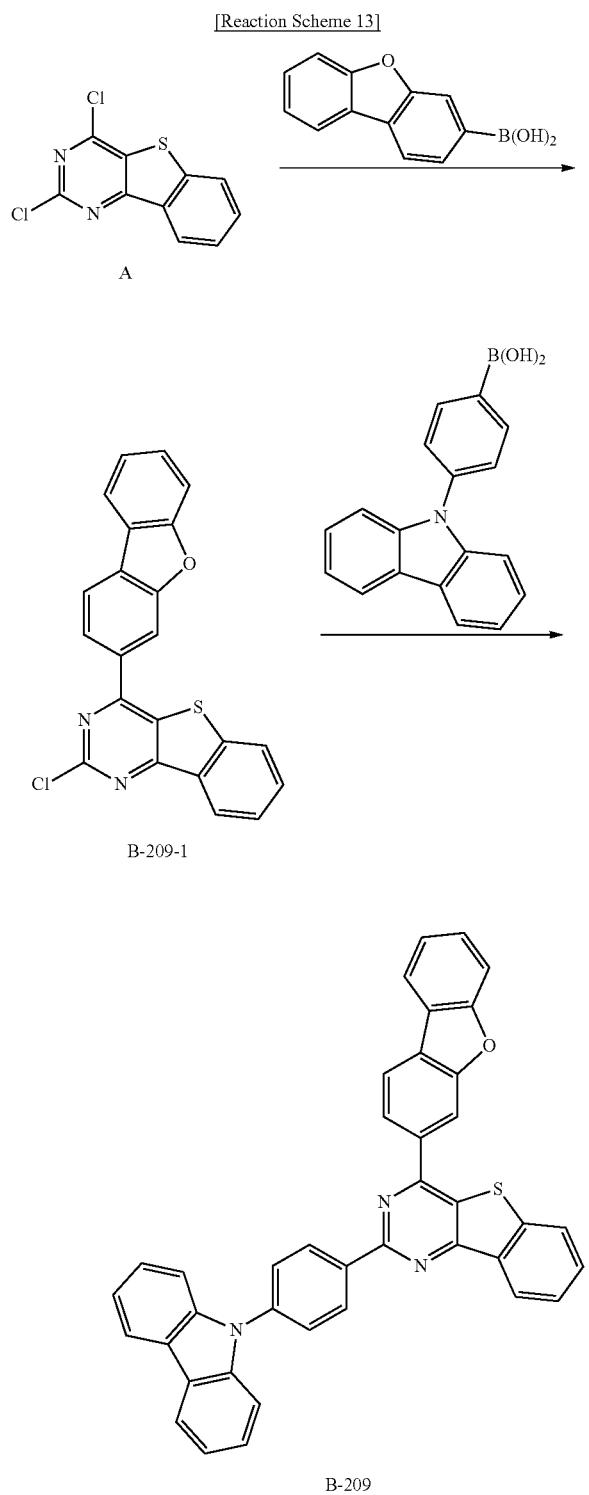

1 Step: Synthesis of Intermediate B-209-1

10.5 g of Intermediate A (refer to a synthesis method described in Korea Patent Laid-Open Publication No. 10-2017-0005637), 8.8 g of 3-dibenzofuran boronic acid, 11.4 g of potassium carbonate, and 2.4 g of tetrakis(triphenylphosphine) palladium (0) were added to 140 mL of 1,4-dioxane and 70 mL of water in a 500 mL flask and then, heated at 60° C. for 12 hours under a nitrogen flow. The mixture was added to 500 mL of methanol, a solid crystallized therein was filtered, dissolved in monochlorobenzene, filtered with silica gel/Celite, and then, after removing an appropriate amount of an organic solvent, recrystallized with methanol to obtain 10.7 g of Intermediate B-209-1 (yield: 67%).

2 Step: Synthesis of Compound B-209

10.4 g of Intermediate B-209-1, 7.8 g of 4-(9-carbazolyl)phenylboronic acid, 7.5 g of potassium carbonate, and 1.6 g of tetrakis(triphenylphosphine) palladium (0) were added to 90 mL of 1,4-dioxane and 45 mL of water in a 250 mL flask and then, heated at 70° C. under a nitrogen flow for 12 hours. The obtained mixture was added to 250 mL of methanol, a solid crystallized therein was filtered, dissolved in 1,2-dichlorobenzene, filtered with silica gel/Celite, and then, after removing an appropriate amount of an organic solvent, recrystallized with methanol to obtain 13.0 g of Compound B-209 (yield: 74%).

LC/MS measurement (C40H23N3OS, theoretical value: 593.16 g/mol, measured value: M=593.23 g/mol)

Synthesis Example 14: Synthesis of Compound C-25

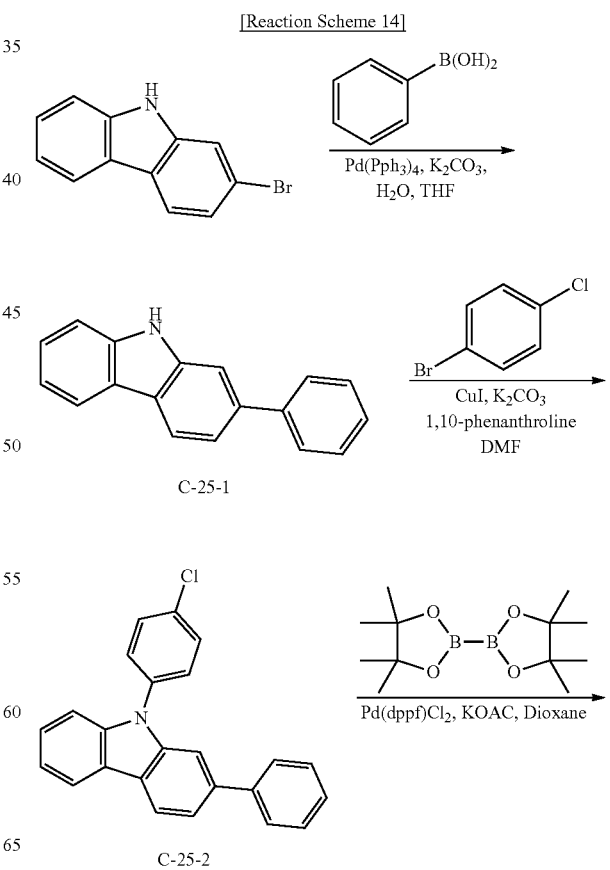

-continued

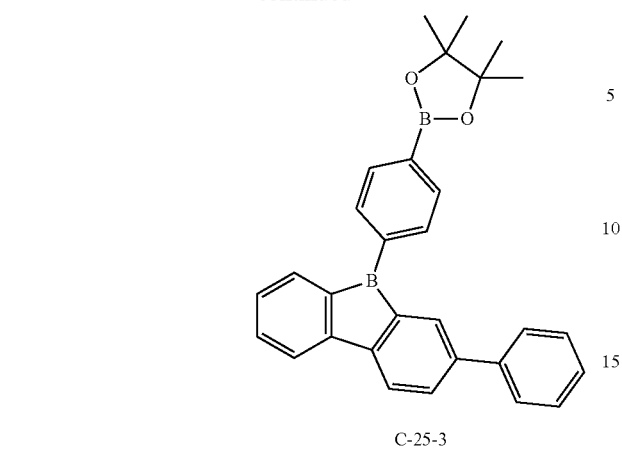

C-25-3

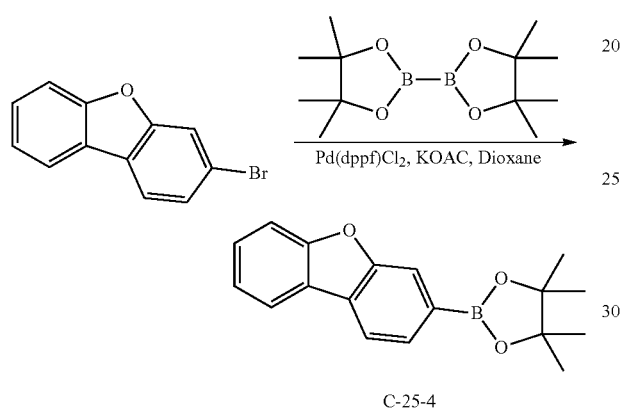

C-25-4

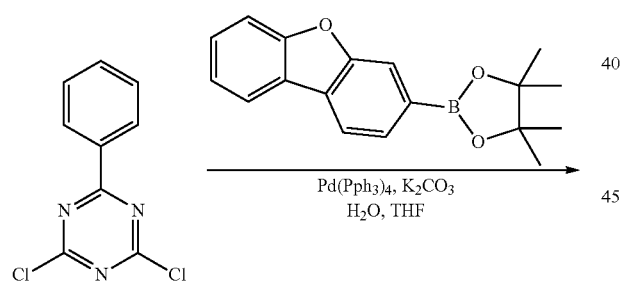

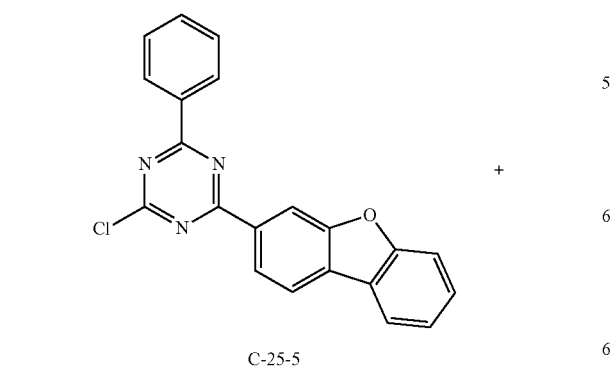

C-25-5

-continued

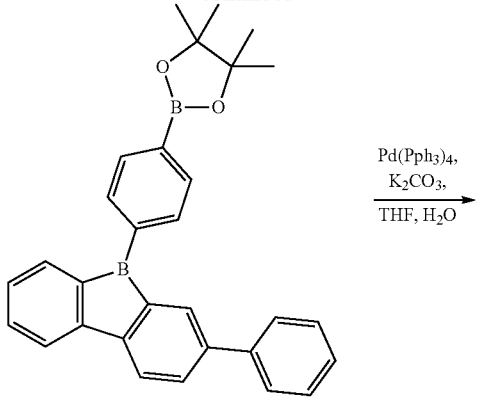

C-25-3

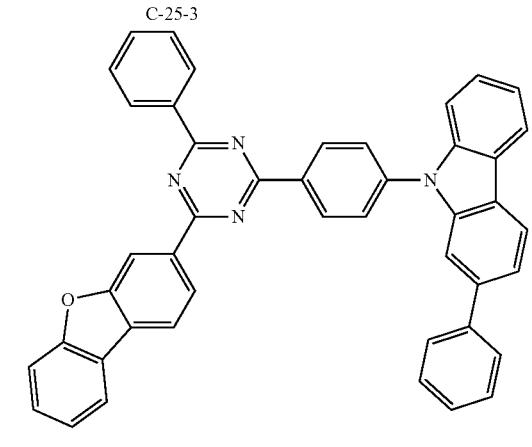

C-25

1 Step: Synthesis of Intermediate C-25-1

2-bromocarbazole (35 g, 142 mmol) was dissolved in 0.5 L of tetrahydrofuran (THF), phenyl boronic acid (17.3 g, 142 mmol) and tetrakis(triphenylphosphine)palladium (8.2 g, 7.1 mmol) were added thereto, and the mixture was stirred. Subsequently, potassium carbonate (49.1 g, 356 mmol) saturated in water was added thereto, and the obtained mixture was heated and refluxed at 80° C. for 12 hours. When a reaction was complete, water was added to the reaction solution, and an extract was obtained with dichloromethane (DCM), filtered after removing moisture therefrom with anhydrous magnesium sulfate, and concentrated under a reduced pressure. The obtained residue was separated and purified through flash column chromatography to obtain 22 g of Intermediate C-25-1 (yield: 63.6%).

2 Step: Synthesis of Intermediate C-25-2

Intermediate C-25-1 (22 g, 90.4 mmol), 1-bromo-4-chloro-benzene (25.96 g 135.61 mmol), CuI (1.71 g, 9 mmol), $K_2CO_3$ (18.74 g, 135.61 mmol), and 1,10-phenanthroline (1.62 g, 9 mmol) were put in a round bottomed flask and then, dissolved in 700 ml of DMF. The solution was stirred at 180° C. for 18 hours. When a reaction was complete, a product therefrom was dissolved in dichloromethane after removing the reaction solvent under a reduced pressure ant then, silica gel-filtered. The product was concentrated with dichloromethane and recrystallized with hexane to obtain 18 g of Intermediate C-25-2 (yield: 56.3%).

3 Step: Synthesis of Intermediate C-25-3

Intermediate C-25-2 (18 g, 51 mmol), bis(pinacolato) diboron (19.43 g, 76.5 mmol), Pd(dppf)Cl$_2$ (2.24 g, 8.64 mmol), tricyclohexylphosphine (2.86 g, 10.2 mmol), and potassium acetate (15.02 g, 153.01 mmol) were put in a round bottomed flask and then, dissolved in 720 ml of DMF. The mixture was refluxed and stirred at 120° C. for 12 hours. When a reaction was complete, the mixture was poured into an excessive amount of distilled water, and the obtained mixture was stirred for one hour. A solid therein was filtered and dissolved in DCM. After removing moisture therefrom with MgSO$_4$, an organic solvent was filtered with a silica gel pad and removed under a reduced pressure. A solid therefrom was recrystallized with EA and hexane to obtain 14.8 g of Intermediate C-25-3 (yield: 65.3%).

4 Step: Synthesis of Intermediate C-25-4

31 g of Intermediate C-25-4 was synthesized (yield: 65.1%) according to the same method as the 3 step of Synthesis Example 12 by using 3-bromo-dibenzofuran (40 g, 162 mmol) instead of Intermediate C-25-2.

5 Step: Synthesis of Intermediate C-25-5

Intermediate C-25-4 was dissolved in 0.3 L of tetrahydrofuran (THF), 2,4-chloro-6-phenyl-1,3,5-triazine (21 g, 93 mmol) and tetrakis(triphenylphosphine)palladium (5.38 g, 4.65 mmol) were added thereto, and the mixture was stirred. Subsequently, potassium carbonate (32.14 g, 232 mmol) saturated in water was added thereto, and the mixture was heated and refluxed at 80° C. for 12 hours. When a reaction was complete, water was added to the reaction solution, the obtained mixture was stirred for 30 minutes and filtered, a solid therefrom was dissolved in monochlorobenzene at 133° C., after removing moisture therefrom with anhydrous magnesium sulfate, the solution was filtered by using silica gel, and a filtrate therefrom was cooled down to room temperature and filtered. The obtained solid was repetitively purified by using monochlorobenzene to obtain 15 g of Intermediate C-25-5 (yield: 64.8%).

6 Step: Synthesis of Compound C-25

Intermediate C-25-5 (10.5 g, 29.3 mmol) and Intermediate C-25-3 (14.38 g, 32.28 mmol) were reacted according to the same method as the 4 step of Synthesis Example 12 to obtain 12.7 g of Compound C-25 (yield: 67.5%).

LC/MS measurement (C45H28NO, theoretical value: 640.23 g/mol, measured value: M=641.38 g/mol)

Synthesis Example 15: Synthesis of Compound C-23

[Reaction Scheme 15]

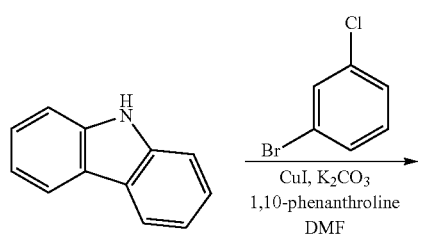

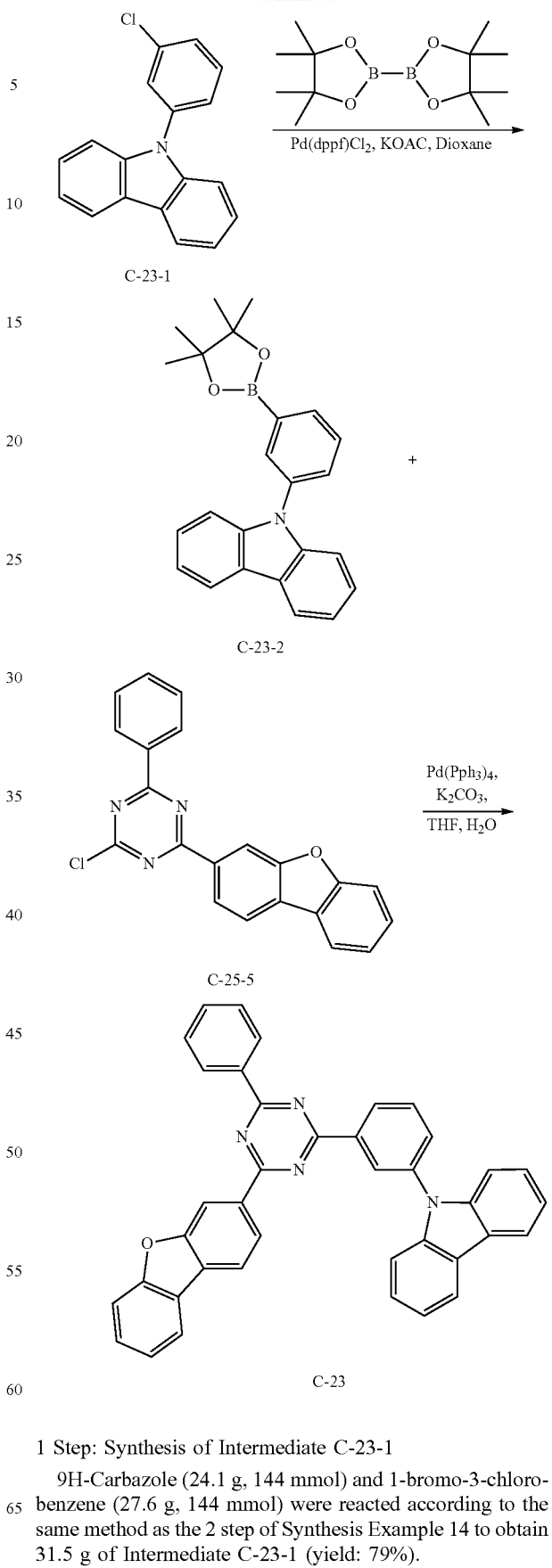

1 Step: Synthesis of Intermediate C-23-1

9H-Carbazole (24.1 g, 144 mmol) and 1-bromo-3-chlorobenzene (27.6 g, 144 mmol) were reacted according to the same method as the 2 step of Synthesis Example 14 to obtain 31.5 g of Intermediate C-23-1 (yield: 79%).

2 Step: Synthesis of Intermediate C-23-2

16.8 g of Intermediate C-23-2 (yield: 70%) was obtained according to the same method as the 3 step of Synthesis Example 14 except that Intermediate C-23-1 (18 g, 65 mmol) was used.

3 Step: Synthesis of Compound C-23

Intermediate C-23-2 (16.3 g, 44.3 mmol) and Intermediate C-25-3 (15.8 g, 44.3 mmol) were reacted according to the same method as the 6 step of Synthesis Example 14 to obtain 16.4 g of Compound C-23 (yield: 66%).

LC/MS measurement (C39H24N4O, theoretical value: 564.20 g/mol, measured value: M=565.36 g/mol)

Synthesis Example 16: Synthesis of Compound D-57

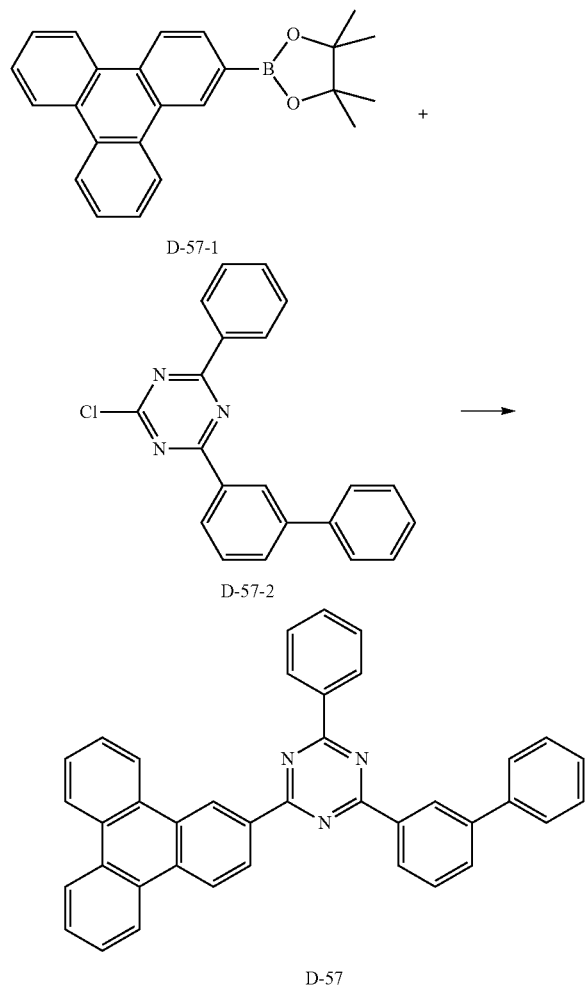

Intermediate D-57-1 and Intermediate D-57-2 were used with a reference to a synthesis method described in Korean Patent Laid-Open Publication No. 10-2014-0135524 to synthesize Compound D-57 (yield: 88%).

LC/MS measurement (C39H25N3, theoretical value: 535.20 g/mol, measured value: M=535.83 g/mol)

(Manufacture of Organic Light Emitting Diode I-Hole Auxiliary Layer)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 700 Å thick to form a hole transport layer. A 700 Å-thick hole transport auxiliary layer was formed on the hole transport layer by vacuum-depositing Compound A-3. A 400 Å-thick light emitting layer was formed on the hole transport auxiliary layer by vacuum-depositing Compound E as a host doped with 2 wt % of [Ir(piq)₂acac] as a dopant. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows:
a structure of ITO/Compound A (700 Å)/Compound B (50 Å)/Compound C (700 Å)/Compound A-3 (700 Å)/EML[Compound E: [Ir(piq)2acac] (2 wt %)] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Compound E: 9-phenyl-9'-(4-phenylquinazolin-2-yl)-9H, 9'H-3,3'-bicarb azole Examples 2 to 5

Organic light emitting diodes were respectively manufactured according to the same method as Example 1 except for using the compositions in Table 1.

Comparative Examples 1 to 5

Organic light emitting diodes were respectively manufactured according to the same method as Example 1 except for using the compositions in Table 1.

(Manufacture of Organic Light Emitting Diode II-Host)

Example 6

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 700 Å thick to form a hole transport layer. A 400 Å-thick hole transport auxiliary layer was formed on the hole transport layer by vacuum-depositing Compound C-1. A 400 Å-thick light emitting layer was formed on the hole transport auxiliary layer by vacuum-depositing Compounds A-3 and B-135 simultaneously as hosts doped with 2 wt % of [Ir(piq)$_2$acac] as a dopant. A 400 Å-thick light emitting layer was formed on the hole transport auxiliary layer by vacuum-depositing Compound A-3 and Compound B-135 in a weight ratio of 6:4, and their ratios of the following examples were separately described. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows:

a structure of ITO/Compound A (700 Å)/Compound B (50 Å)/Compound C (700 Å)/Compound C-1 (400 Å)/EML[Compound A-3: B-135: [Ir(piq)$_2$acac] (2 wt %)] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound C-1: N,N-di([1,1'-biphenyl]-4-yl)-7,7-dimethyl-7H-fluoreno[4,3-b]benzofuran-10-amine Compound D: 8-(4-(4,6-di(naphthalen-2-yl)-1,3,5-triazin-2-yl)phenyl)quinoline Examples 7 to 22

Organic light emitting diodes were respectively manufactured according to the same method as Example 6 except for using the compositions in Table 2.

Comparative Examples 6 to 11

Organic light emitting diodes were respectively manufactured according to the same method as Example 2-1 except for using the compositions in Table 2.

Evaluation

Single characteristics of materials were evaluated using diodes according to Examples 1 to 5 and Comparative Examples 1 to 5, and power efficiency depending on use of hosts of the organic light emitting diodes was evaluated using the diodes according to Examples 6 to 22 and Comparative Examples 6 to 11.

Specific measurement methods are as follows, and the results are shown in Table 1 and Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Power Efficiency

Power efficiency (cd/A) at the same current density (10 mA/cm$^2$) were calculated by using the luminance, current density, and voltages (V) from the items (1) and (2).

(4) Measurement of Life-Span

The results were obtained by measuring a time when current efficiency (cd/A) was decreased down to 97%, while luminance (cd/m$^2$) was maintained to be 9000 cd/m$^2$.

(5) Measurement of Driving Voltage

A driving voltage of each diode was measured using a current-voltage meter (Keithley 2400) at 15 mA/cm$^2$ to obtain the results.

TABLE 1

| | Hole transport auxiliary layer | Color | Driving voltage (V) | Life-span (h) |
|---|---|---|---|---|
| Example 1 | A-3 | red | 3.75 | 100 |
| Example 2 | A-17 | red | 3.80 | 105 |
| Example 3 | A-23 | red | 3.79 | 103 |
| Example 4 | A-27 | red | 3.85 | 93 |
| Example 5 | A-47 | red | 3.83 | 97 |
| Comparative Example 1 | V-1 | red | 4.20 | 32 |
| Comparative Example 2 | V-2 | red | 4.35 | 15 |
| Comparative Example 3 | V-3 | red | 3.85 | 4 |
| Comparative Example 4 | V-4 | red | 4.10 | 37 |
| Comparative Example 5 | V-5 | red | 4.17 | 42 |

TABLE 2

| | First host | Second host | First host:second host ratio (wt:wt) | Color | Power efficiency (cd/A) | Driving voltage (V) | Life-span T97 (h) |
|---|---|---|---|---|---|---|---|
| Example 6 | A-3 | B-135 | 6:4 | red | 20.2 | 3.90 | 95 |
| Example 7 | A-3 | B-183 | 6:4 | red | 20.4 | 3.91 | 96 |
| Example 8 | A-3 | B-209 | 6:4 | red | 20.8 | 3.95 | 88 |
| Example 9 | A-3 | C-23 | 6:4 | red | 21.1 | 3.84 | 92 |
| Example 10 | A-3 | D-57 | 6:4 | red | 20.2 | 3.91 | 117 |
| Example 11 | A-17 | B-135 | 6:4 | red | 20.3 | 3.89 | 96 |
| Example 12 | A-23 | B-135 | 6:4 | red | 20.1 | 3.89 | 99 |
| Example 13 | A-27 | B-135 | 6:4 | red | 19.7 | 3.94 | 92 |

TABLE 2-continued

| | First host | Second host | First host:second host ratio (wt:wt) | Color | Power efficiency (cd/A) | Driving voltage (V) | Life-span T97 (h) |
|---|---|---|---|---|---|---|---|
| Example 14 | A-33 | B-135 | 6:4 | red | 19.7 | 3.93 | 94 |
| Example 15 | A-47 | B-135 | 6:4 | red | 20.1 | 3.96 | 97 |
| Example 16 | A-17 | B-209 | 6:4 | red | 20.8 | 3.95 | 88 |
| Example 17 | A-33 | B-209 | 6:4 | red | 20.5 | 3.97 | 85 |
| Example 18 | A-17 | C-25 | 6:4 | red | 21.4 | 3.84 | 108 |
| Example 19 | A-17 | C-23 | 6:4 | red | 21.4 | 3.87 | 115 |
| Example 20 | A-33 | C-23 | 6:4 | red | 21.2 | 3.88 | 92 |
| Example 21 | A-17 | D-57 | 6:4 | red | 20.4 | 3.89 | 115 |
| Example 22 | A-47 | D-57 | 6:4 | red | 20.1 | 3.92 | 112 |
| Comparative Example 6 | V-1 | B-135 | 6:4 | red | 17.7 | 4.42 | 55 |
| Comparative Example 7 | V-2 | B-135 | 6:4 | red | 17.4 | 4.40 | 43 |
| Comparative Example 8 | V-3 | B-135 | 6:4 | red | 19.4 | 4.03 | 2 |
| Comparative Example 9 | V-4 | B-135 | 6:4 | red | 18.2 | 4.24 | 31 |
| Comparative Example 10 | V-5 | B-135 | 6:4 | red | 16.3 | 4.51 | 14 |
| Comparative Example 11 | V-3 | C-23 | 6:4 | red | 18.9 | 4.07 | 5 |

Referring to Table 1, the organic light emitting diodes according to Examples 1 to 5 showed a remarkably improved driving voltage and life-span compared with the organic light emitting diodes according to Comparative Examples 1 to 5.

In addition, referring to Table 2, the organic light emitting diodes according to Examples 6 to 22 showed improved driving voltage, efficiency, and life-span and particularly, remarkably life-span characteristics compared with the organic light emitting diodes according to Comparative Examples 6 to 11.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

The invention claimed is:

1. A compound for an organic optoelectronic device represented by Chemical Formula 1:

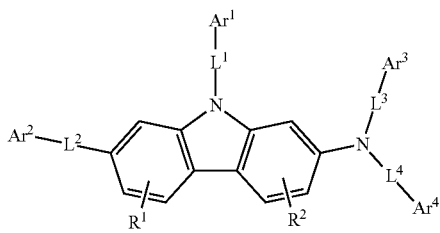

[Chemical Formula 1]

wherein, in Chemical Formula 1,

Ar$^1$ is an unsubstituted C6 aryl group or a substituted or unsubstituted C7 to C12 aryl group, Ar$^2$ is a substituted or unsubstituted C6 to C12 aryl group, Ar$^3$ and Ar$^4$ are independently a substituted or unsubstituted C6 to C30 aryl group, L$^1$ is a single bond or a phenylene group, L$^2$ to L$^4$ are independently a single bond or a substituted or unsubstituted C6 to C12 arylene group, and R$^1$ and R$^2$ are independently hydrogen, deuterium, a cyano group, or a substituted or unsubstituted C1 to C10 alkyl group.

2. The compound for an organic optoelectronic device of claim 1, wherein Chemical Formula 1 is represented by Chemical Formula 1A:

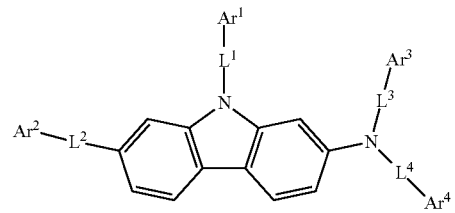

[Chemical Formula 1A]

wherein, in Chemical Formula 1A,

Ar$^1$ is an unsubstituted C6 aryl group or a substituted or unsubstituted C7 to C12 aryl group, Ar$^2$ is a substituted or unsubstituted C6 to C12 aryl group, Ar$^3$ and Ar$^4$ are independently a substituted or unsubstituted C6 to C30 aryl group, L$^1$ is a single bond or a phenylene group, and L$^2$ to L$^4$ are independently a single bond or a substituted or unsubstituted C6 to C12 arylene group.

3. The compound for an organic optoelectronic device of claim 1, wherein:

Ar$^1$ is an unsubstituted phenyl group, a substituted or unsubstituted biphenyl group, or a substituted or unsubstituted naphthyl group, and Ar$^2$ is a substituted or unsubstituted phenyl group, a substituted or unsubstituted biphenyl group, or a substituted or unsubstituted naphthyl group.

4. The compound for an organic optoelectronic device of claim 1, wherein Ar$^3$ and Ar$^4$ are independently a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, or a substituted or unsubstituted phenanthrenyl group.

5. The compound for an organic optoelectronic device of claim 1, wherein the compound is a compound of Group 1:
[Group 1]
A-1
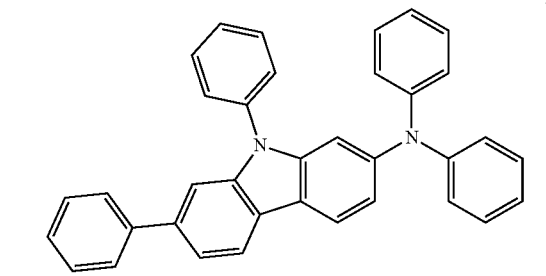
A-2
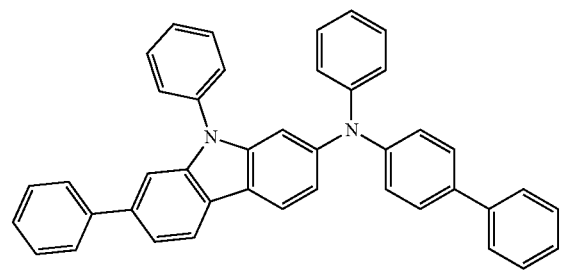
A-3
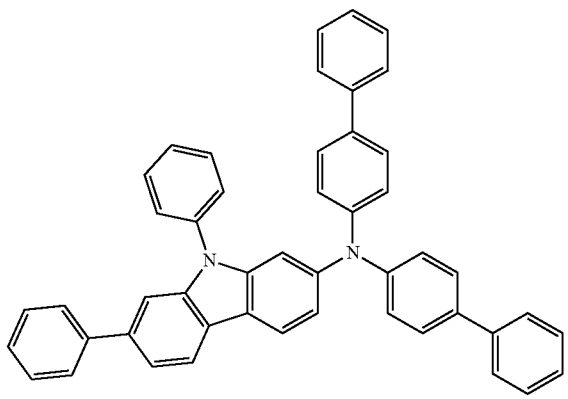
A-4
A-5
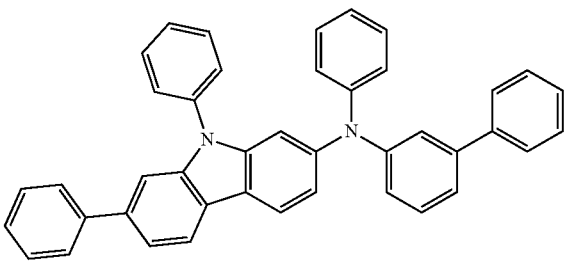
A-6
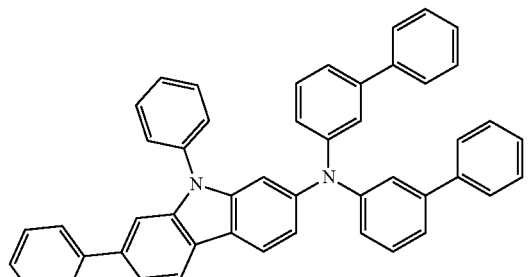
A-7
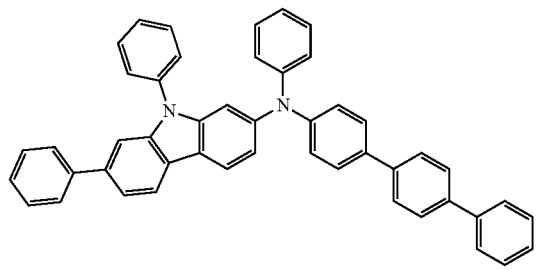
A-8
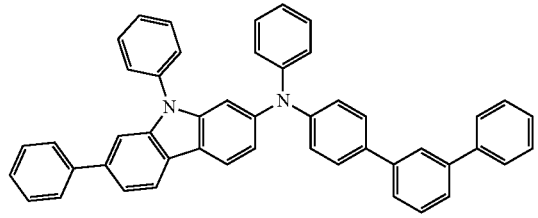
A-9
A-10
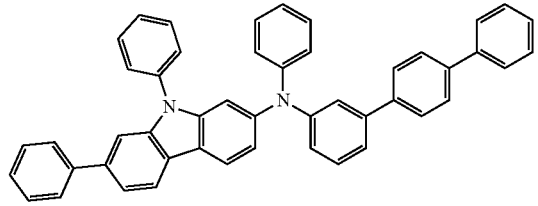

A-11
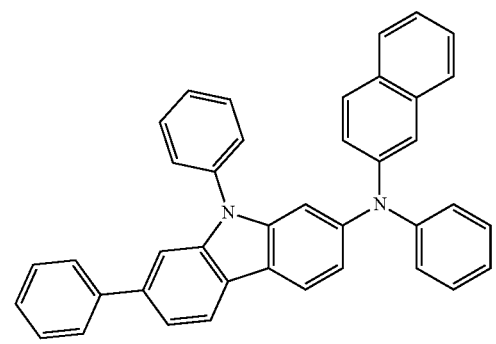
A-12
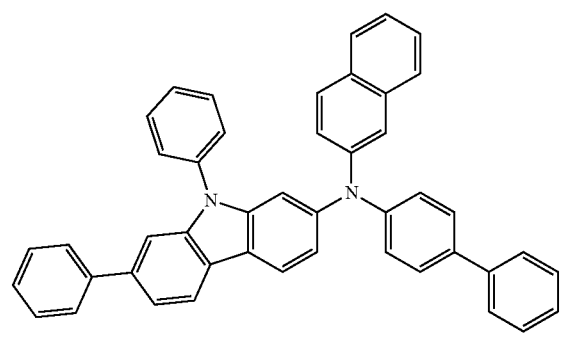
A-13
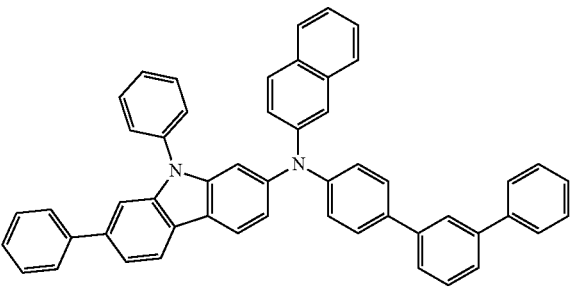
A-14
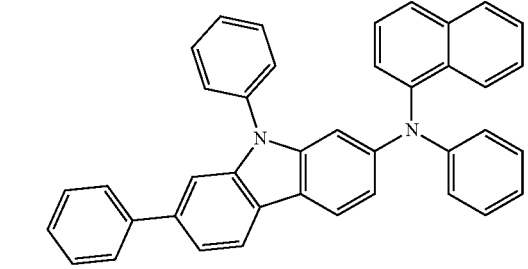
A-15
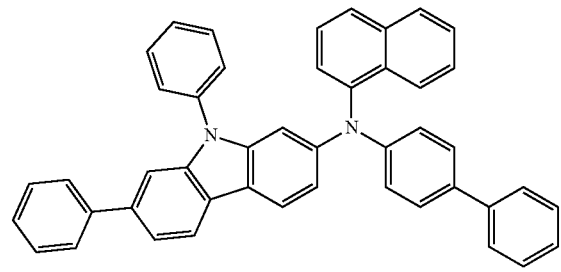
A-16
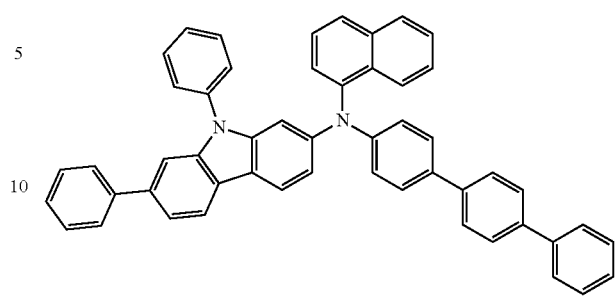
A-17
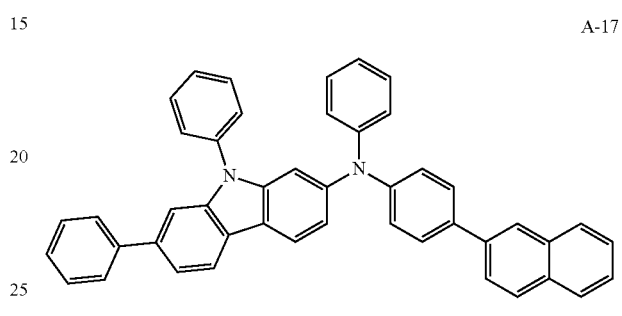
A-18
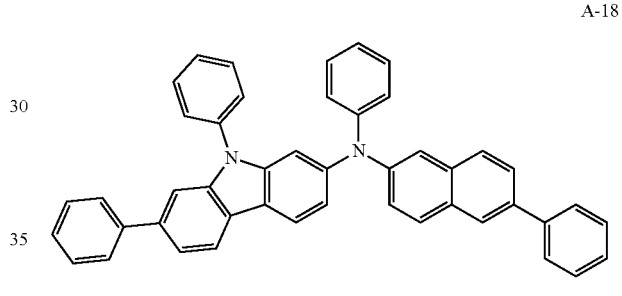
A-19
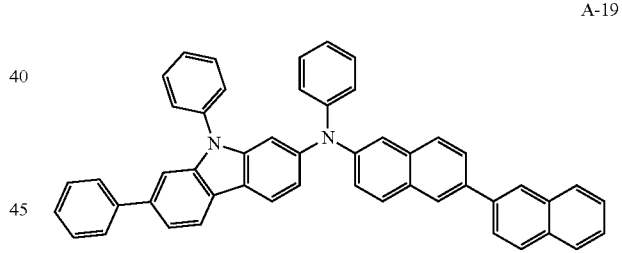
A-20
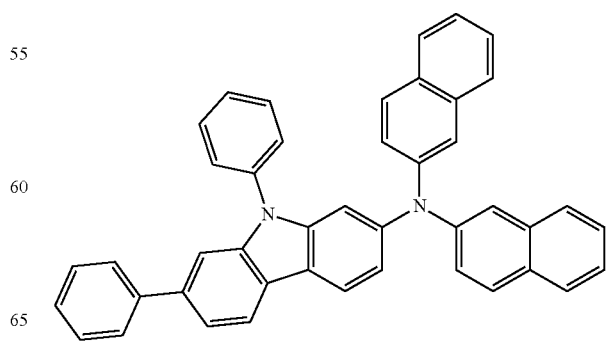

-continued
A-21
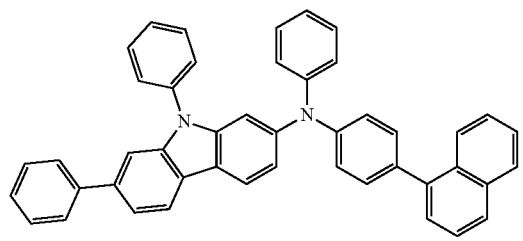
A-22
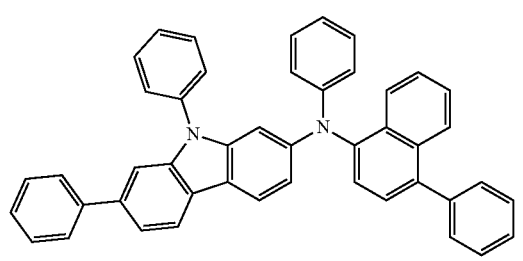
A-23
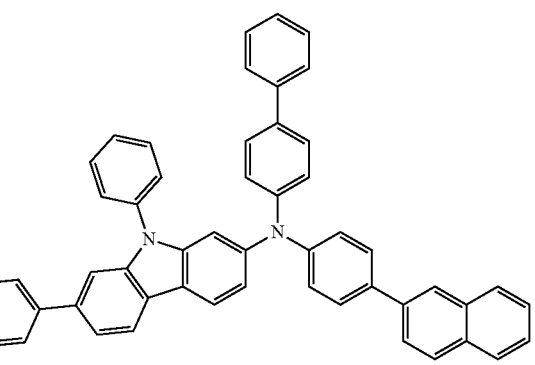
A-24
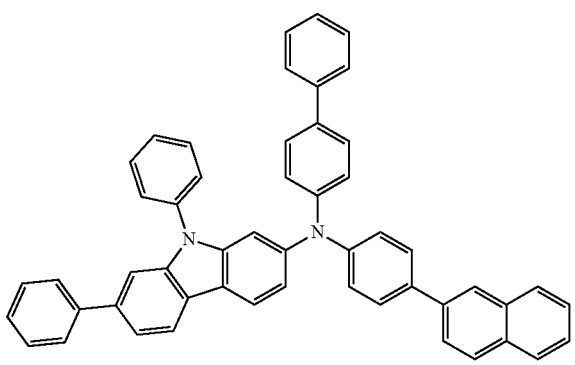
A-25
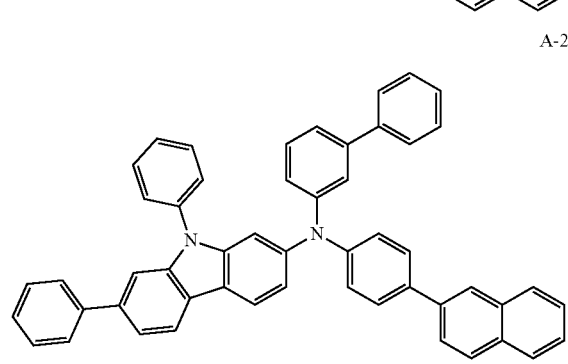
-continued
A-26
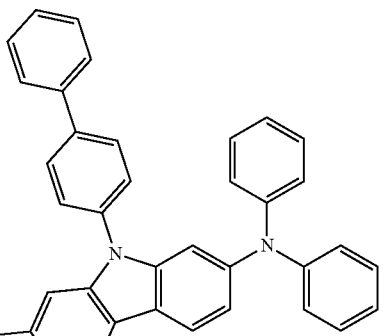
A-27
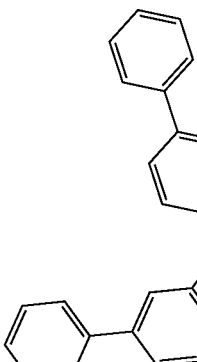
A-28
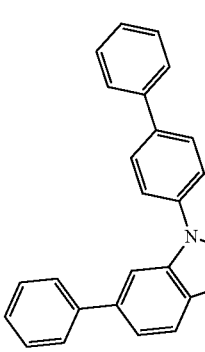
A-29
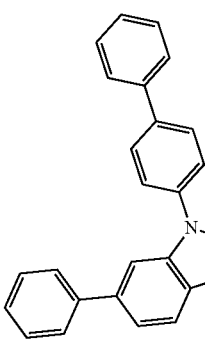

A-30
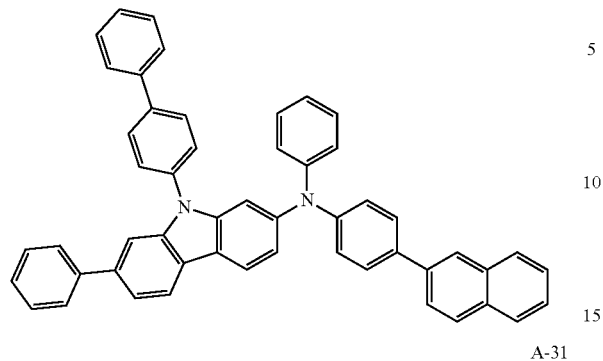
A-31
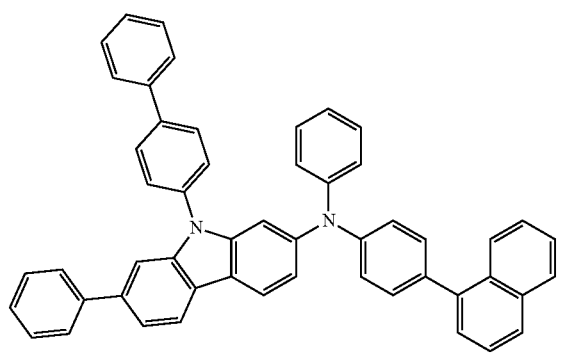
A-32
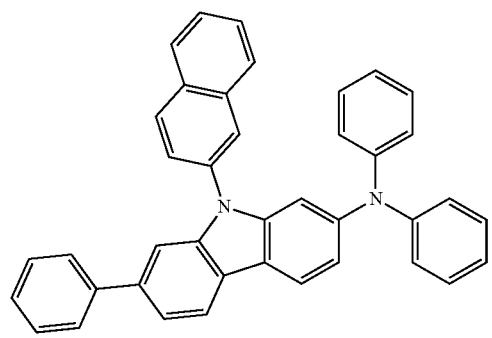
A-33
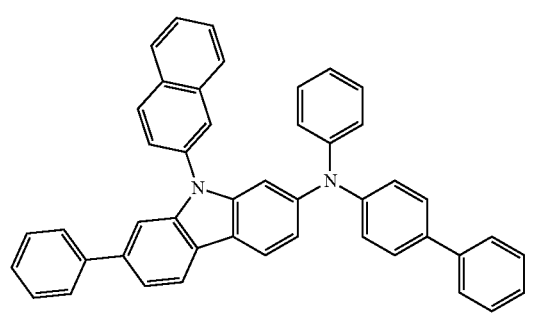
A-34
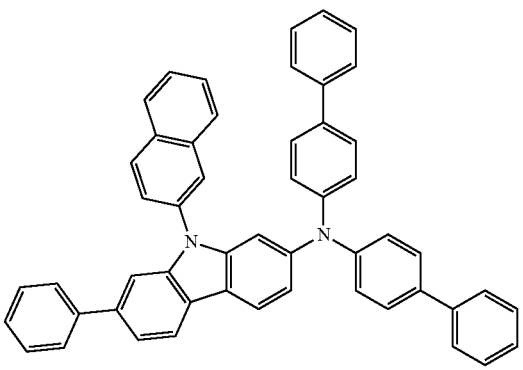
A-35
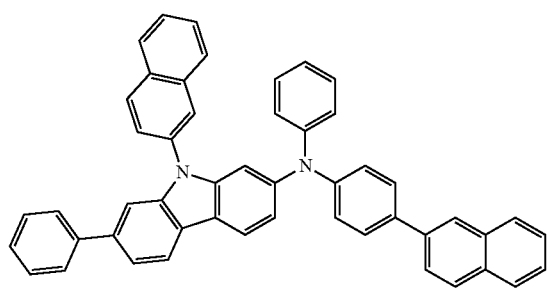
A-36
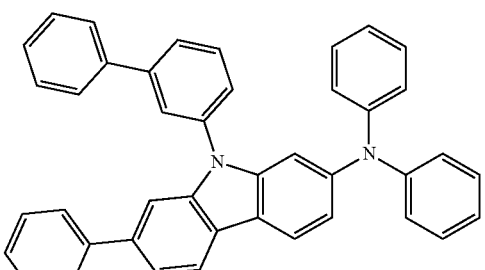
A-37
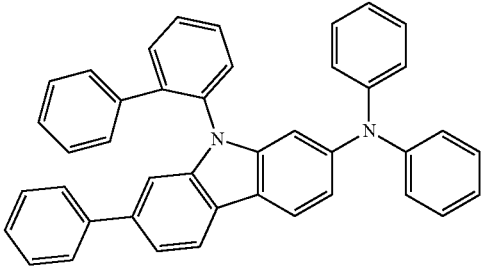
A-38

A-39
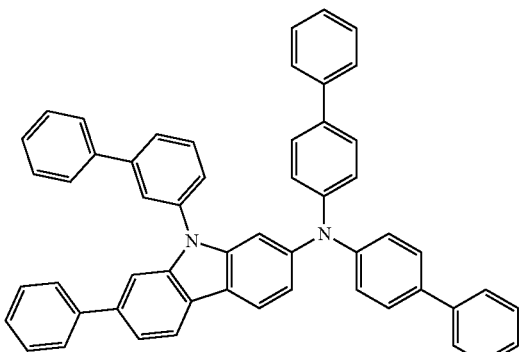
A-40
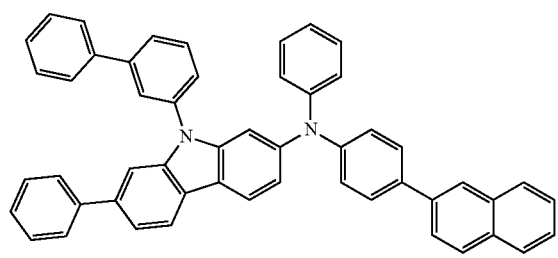
A-41
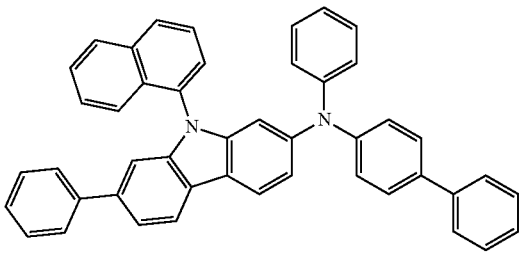
A-42
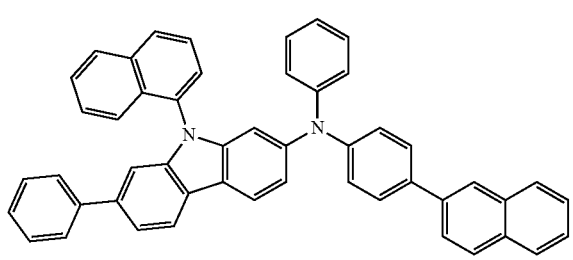
A-43
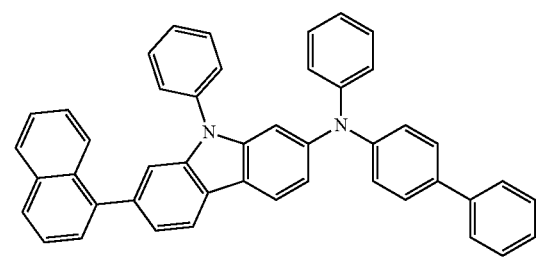
A-44
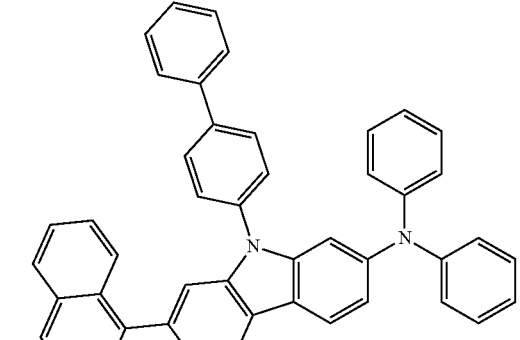
A-45
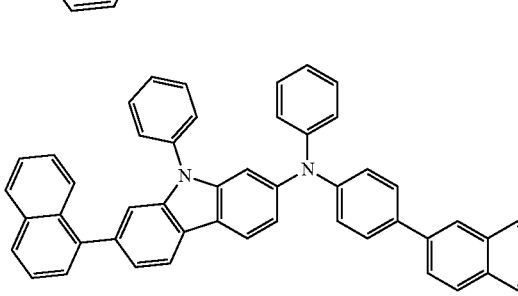
A-46
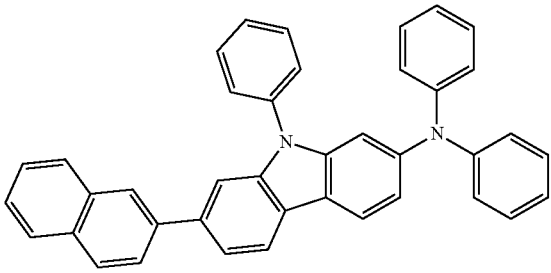
A-47
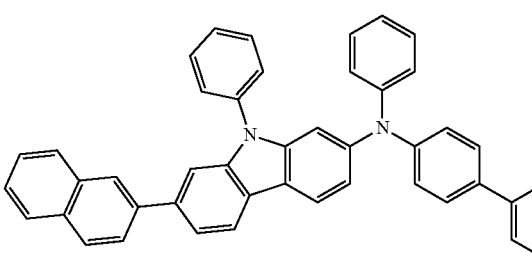
A-48
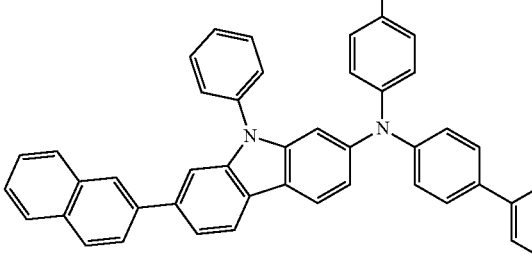

-continued

A-49

A-50

A-51

A-52

A-53

-continued

A-54

A-55

A-56

A-57

A-58
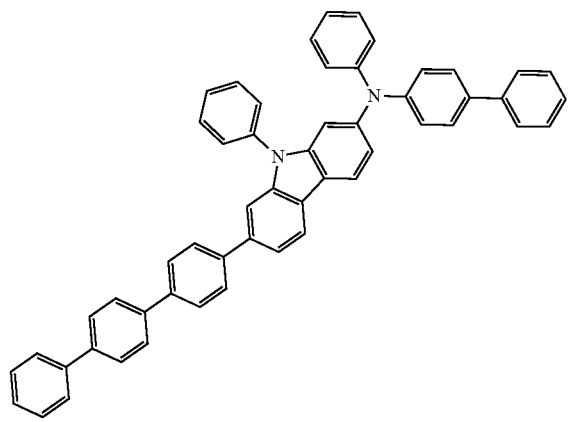
A-59
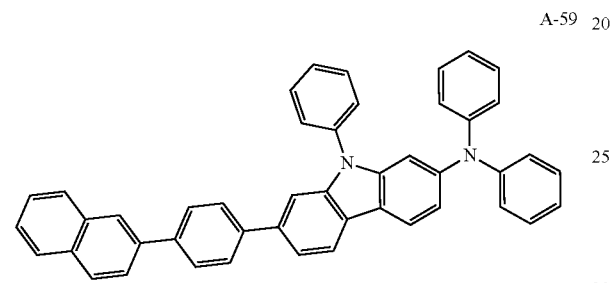
A-60
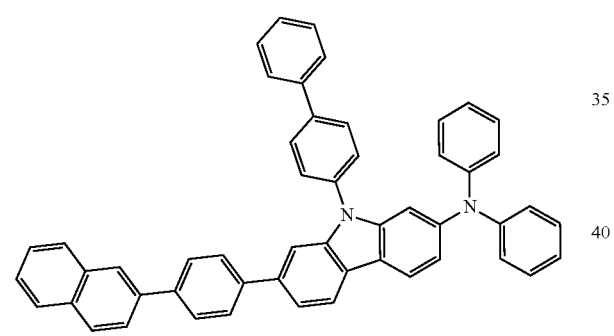
A-61
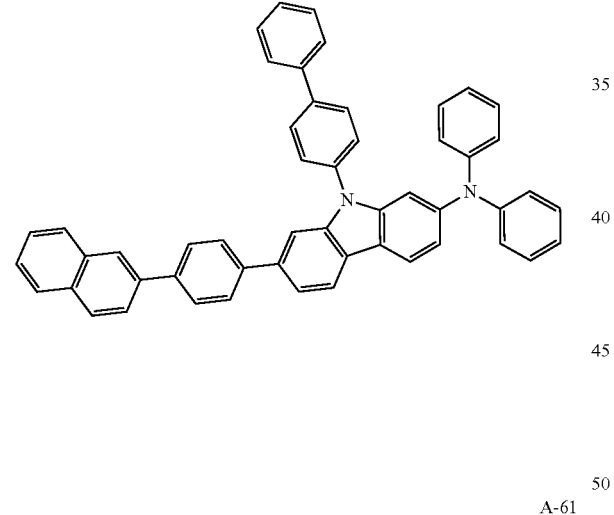
A-62
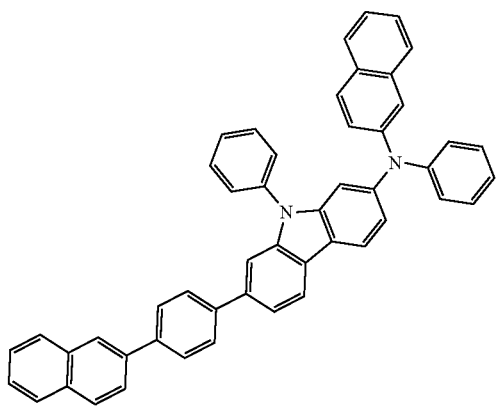
A-63
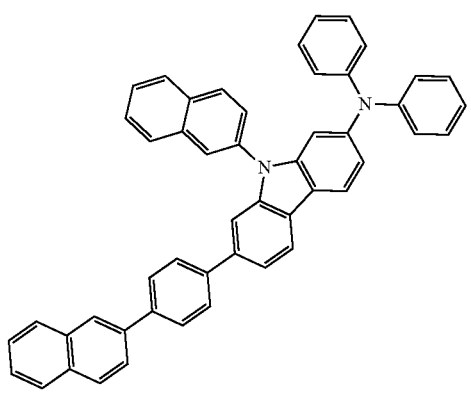
A-64
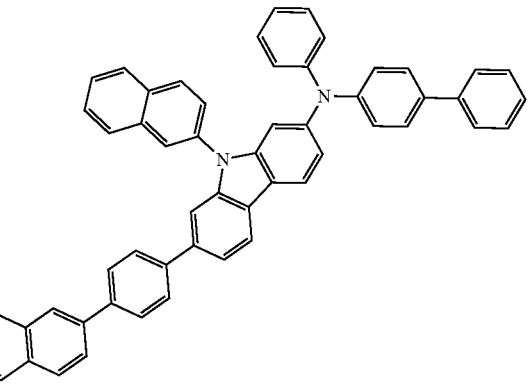
A-65
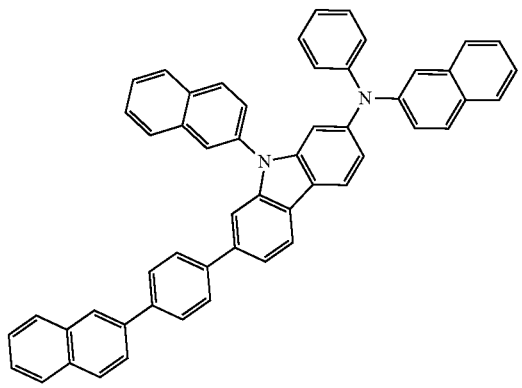

A-66
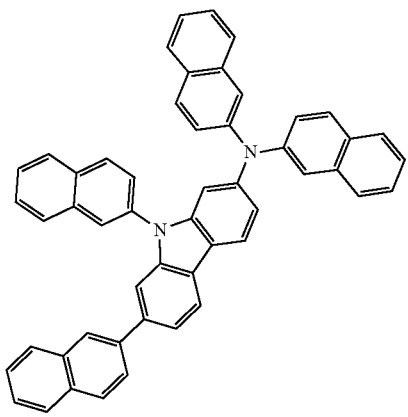

A-67
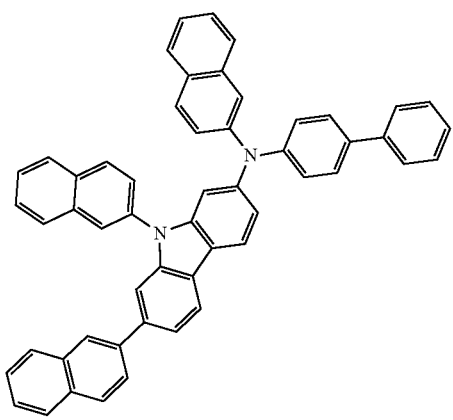

A-68
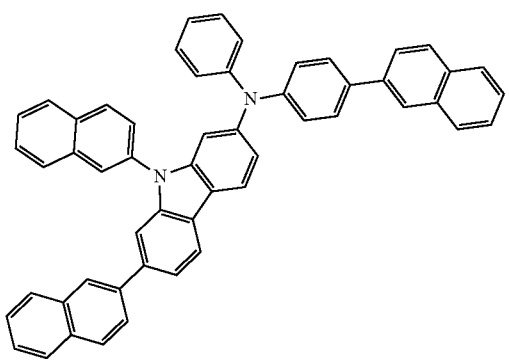

A-69
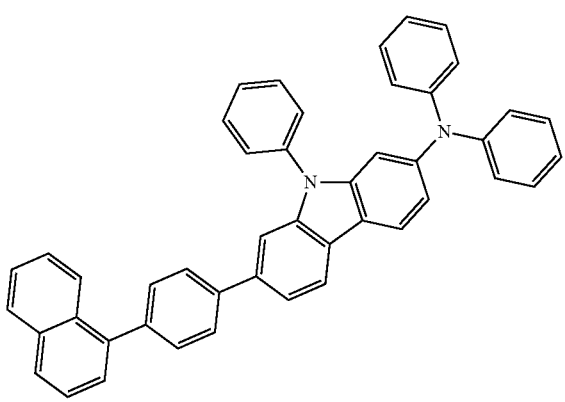

A-70
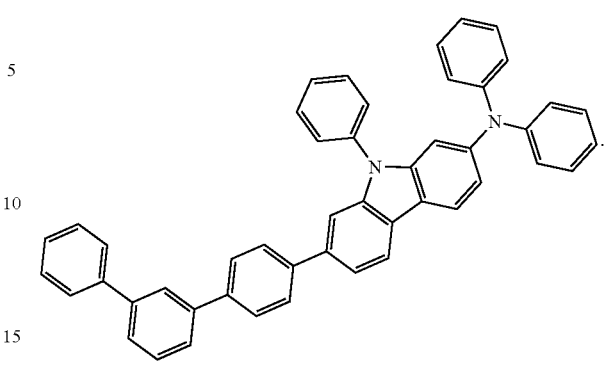

6. A composition for an organic optoelectronic device, comprising:
a first compound, the first compound being the compound for an organic optoelectronic device of claim 1, and
a second compound for an organic optoelectronic device represented by Chemical Formula 2:

[Chemical Formula 2]

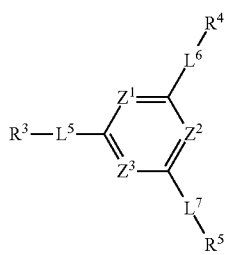

wherein, in Chemical Formula 2,
$Z^1$ to $Z^3$ are independently N or $CR^a$,
at least two of $Z^1$ to $Z^3$ are N,
$R^a$ is hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof,
$L^5$ to $L^7$ are independently a single bond, a substituted or unsubstituted C6 to C20 arylene group, a substituted or unsubstituted C2 to C20 heterocyclic group, or a combination thereof,
$R^3$ to $R^5$ are independently substituted or unsubstituted C6 to C30 aryl group, a substituted or unsubstituted C2 to C30 heterocyclic group, or a combination thereof,
at least one of $R^3$ to $R^5$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group, and
$R^a$ and $R^3$ to $R^5$ are independently present or adjacent groups thereof are linked with each other to form a substituted or unsubstituted aliphatic, aromatic, or heteroaromatic monocyclic or polycyclic ring.

7. The composition for an organic optoelectronic device of claim 6, wherein the second compound for an organic optoelectronic device is represented by one of Chemical Formula 2B-1 to Chemical Formula 2B-4:

[Chemical Formula 2B-1]

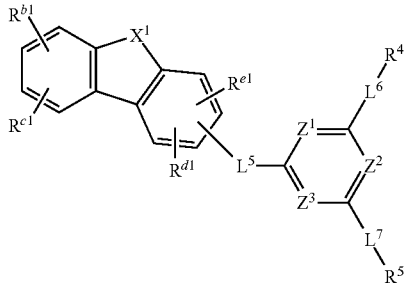

[Chemical Formula 2B-2]

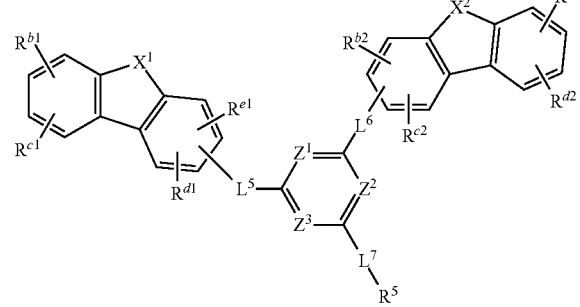

[Chemical Formula 2B-3]

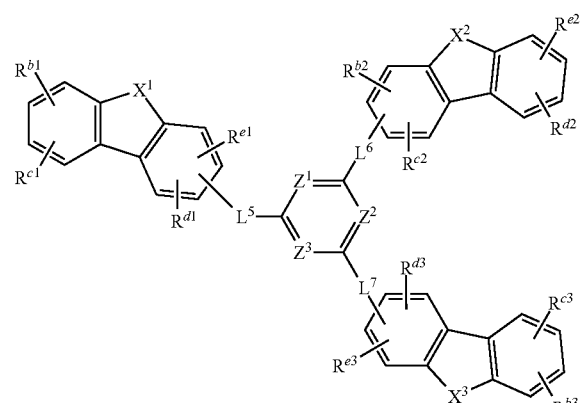

[Chemical Formula 2B-4]

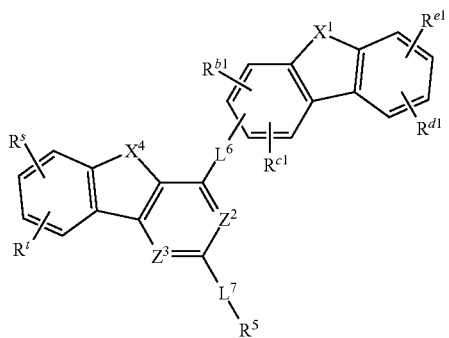

wherein, in Chemical Formulae 2B-1 to 2B-4, $Z^1$ to $Z^3$ are independently N or $CR^a$, at least two of $Z^1$ to $Z^3$ are N, $R^a$ is hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof, $R^4$ and $R^5$ are independently substituted or unsubstituted C6 to C30 aryl group, a substituted or unsubstituted C2 to C30 heterocyclic group, or a combination thereof, $L^5$ to $L^7$ are independently a single bond, a substituted or unsubstituted C6 to C20 arylene group, a substituted or unsubstituted C2 to C20 heterocyclic group, or a combination thereof, $X^1$ to $X^4$ are independently O or S, and $R^{b1}$ to $R^{b3}$, $R^{c1}$ to $R^{c3}$, $R^{d1}$ to $R^{d3}$, and $R^{e1}$ to $R^{e3}$, $R^s$, and $R^t$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

8. The composition for an organic optoelectronic device of claim 6, wherein the second compound for an organic optoelectronic device is represented by one of Chemical Formula 2C-1 to Chemical Formula 2C-12:

[Chemical Formula 2C-1]

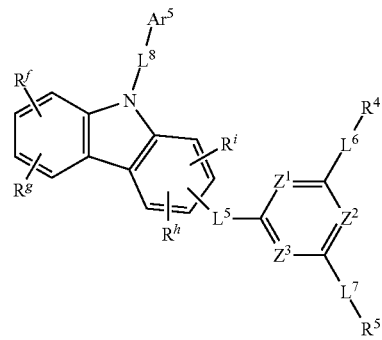

[Chemical Formula 2C-2]

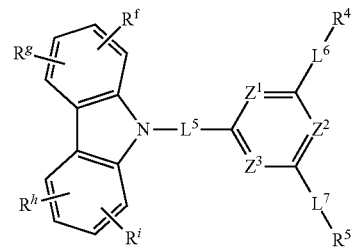

[Chemical Formula 2C-3]
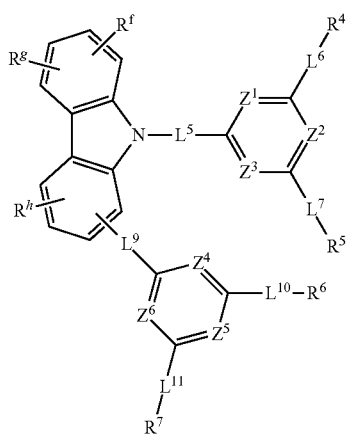
[Chemical Formula 2C-4]
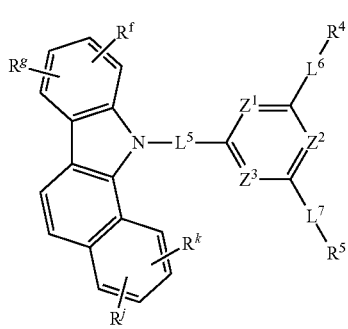
[Chemical Formula 2C-5]
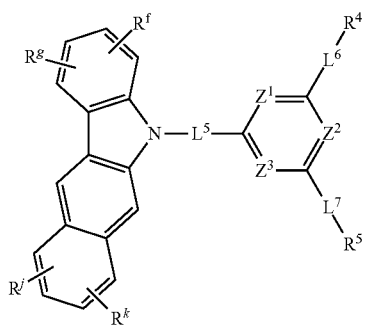
[Chemical Formula 2C-6]
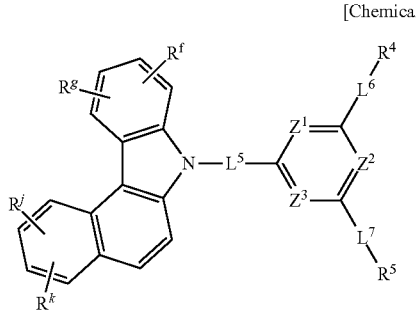
[Chemical Formula 2C-7]
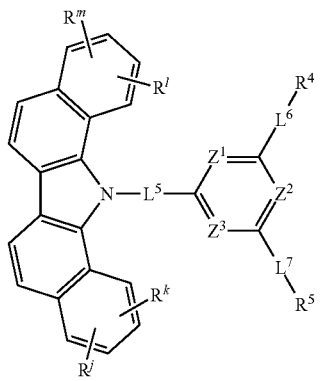
[Chemical Formula 2C-8]
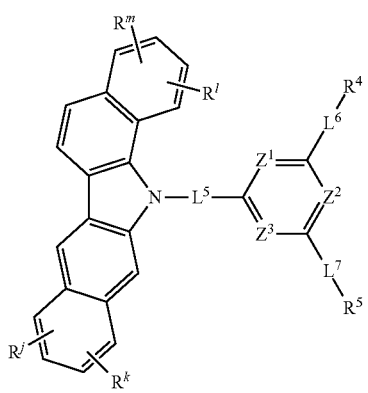
[Chemical Formula 2C-9]
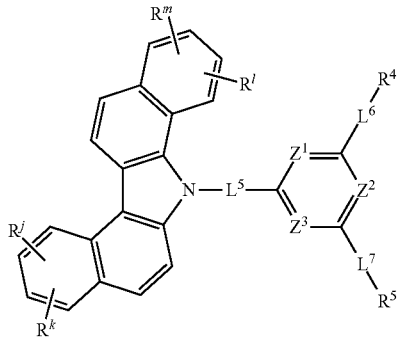
[Chemical Formula 2C-10]
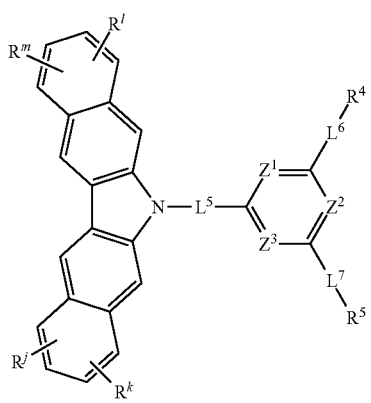

[Chemical Formula 2C-11]

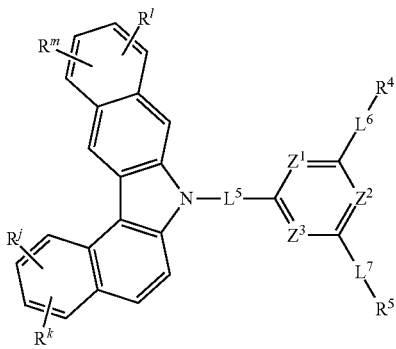

[Chemical Formula 2C-12]

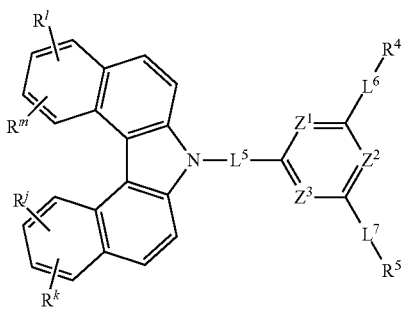

[Chemical Formula 2D-1]

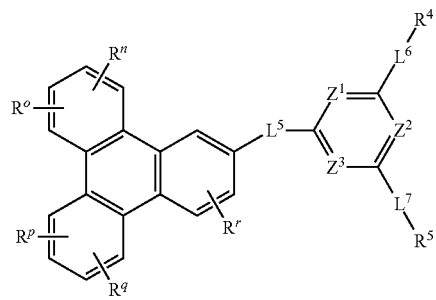

[Chemical Formula 2D-2]

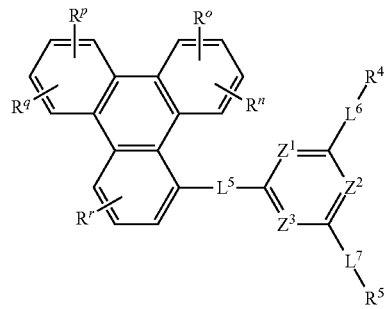

wherein, in Chemical Formula 2C-1 to Chemical Formula 2C-12,
$Z^1$ to $Z^6$ are independently N or $CR^a$,
at least two of $Z^1$ to $Z^3$ are N,
at least two of $Z^4$ to $Z^6$ are N,
$R^a$ is hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof,
$R^4$ to $R^7$ are independently substituted or unsubstituted C6 to C30 aryl group, a substituted or unsubstituted C2 to C30 heterocyclic group, or a combination thereof,
$R^a$ and $R^4$ to $R^7$ are independently present or adjacent groups thereof are linked with each other to form a substituted or unsubstituted aliphatic, aromatic, or heteroaromatic monocyclic or polycyclic ring,
$R^f$, $R^g$, $R^h$, $R^i$, $R^j$, $R^k$, $R^l$, and $R^m$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof,
$L^5$ to $L^{11}$ are independently a single bond, a substituted or unsubstituted C6 to C20 arylene group, a substituted or unsubstituted C2 to C20 heterocyclic group, or a combination thereof, and
$Ar^5$ is a substituted or unsubstituted C6 to C30 aryl group, a substituted or unsubstituted C2 to C30 heterocyclic group, or a combination thereof.

9. The composition for an organic optoelectronic device of claim 6, wherein the second compound for an organic optoelectronic device is represented by Chemical Formula 2D-1 or Chemical Formula 2D-2:

wherein, in Chemical Formula 2D-1 and Chemical Formula 2D-2,
$Z^1$ to $Z^3$ are independently N or $CR^a$,
at least two of $Z^1$ to $Z^3$ are N,
$R^a$ is hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof,
$R^4$ and $R^5$ are independently substituted or unsubstituted C6 to C30 aryl group, a substituted or unsubstituted C2 to C30 heterocyclic group, or a combination thereof,
$R^a$, $R^4$, and $R^5$ are independently present or adjacent groups thereof are linked with each other to form a substituted or unsubstituted aliphatic, aromatic, or heteroaromatic monocyclic or polycyclic ring,
$L^5$ to $L^7$ are independently a single bond, a substituted or unsubstituted C6 to C20 arylene group, a substituted or unsubstituted C2 to C20 heterocyclic group, or a combination thereof, and
$R^n$, $R^o$, $R^p$, $R^q$, and $R^r$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

10. The composition for an organic optoelectronic device of claim 6, wherein the second compound for an organic optoelectronic device is represented by one of Chemical Formula 2B-1-1, Chemical Formula 2B-1-3, Chemical Formula 2B-4-3, and Chemical Formula 2D-1-1:

[Chemical Formula 2B-1-1]

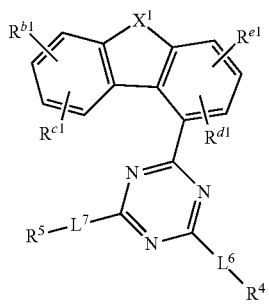

[Chemical Formula 2B-1-3]

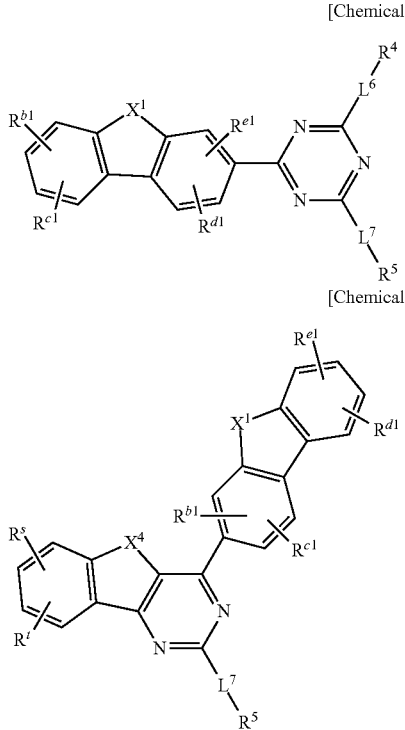

[Chemical Formula 2B-4-3]

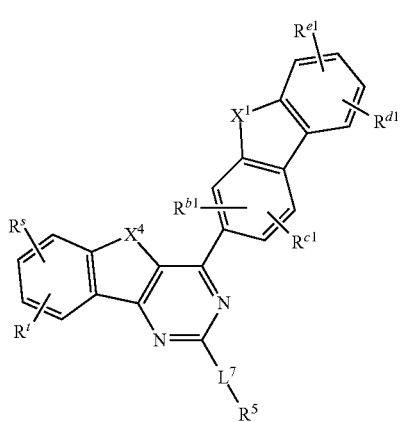

[Chemical Formula 2D-1-1]

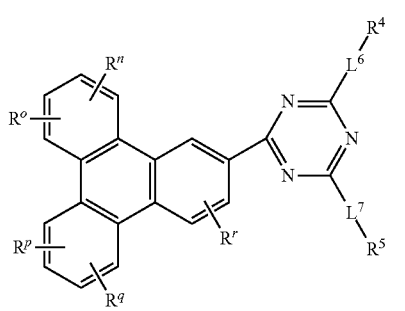

wherein, in Chemical Formula 2B-1-1, Chemical Formula 2B-1-3, Chemical Formula 2B-4-3, and Chemical Formula 2D-1-1, $X^1$ and $X^4$ are independently O or S, $R^4$ and $R^5$ are independently a substituted or unsubstituted phenyl group, a substituted or unsubstituted biphenyl group, a substituted or unsubstituted terphenyl group, a substituted or unsubstituted naphthyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, or a substituted or unsubstituted dibenzothiophenyl group, $L^6$ and $L^7$ are independently a single bond or a substituted or unsubstituted C6 to C20 arylene group, and $R^{b1}$, $R^{c1}$, $R^{d1}$, $R^{e1}$, $R^n$, $R^o$, $R^p$, $R^q$, $R^r$, $R^s$, and $R^t$ are independently hydrogen, deuterium, a substituted or unsubstituted C1 to C30 alkyl group, or a substituted or unsubstituted C6 to C30 aryl group.

11. The composition for an organic optoelectronic device of claim 10, wherein Chemical Formula 2B-4-3 is represented by Chemical Formula 2B-4-3a:

[Chemical Formula 2B-4-3a]

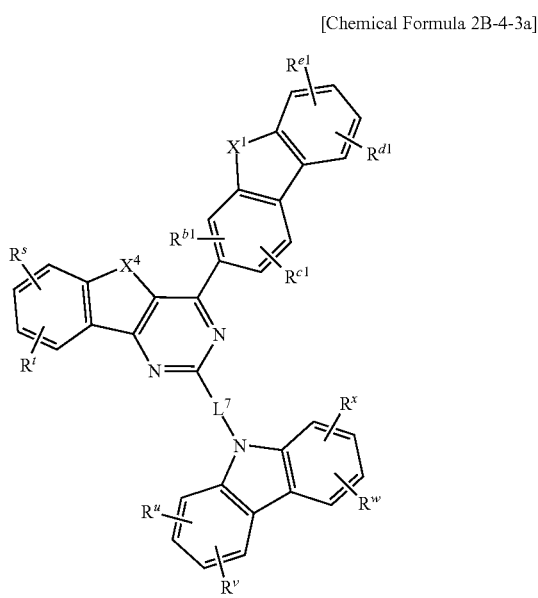

wherein, in Chemical Formula 2B-4-3a, $X^1$ and $X^4$ are independently O or S, $L^7$ is independently a single bond or a substituted or unsubstituted C6 to C20 arylene group, and $R^{b1}$, $R^{c1}$, $R^{d1}$, $R^{e1}$, $R^s$, $R^t$ $R^u$, $R^v$, $R^w$, and $R^x$ are independently hydrogen, deuterium, a substituted or unsubstituted C1 to C30 alkyl group, or a substituted or unsubstituted C6 to C30 aryl group.

12. The composition for an organic optoelectronic device of claim 6, which further comprises a dopant.

13. An organic optoelectronic device, comprising:

an anode and a cathode facing each other, and at least one organic layer disposed between the anode and the cathode, wherein the at least one organic layer comprises the compound for an organic optoelectronic device of claim 1.

14. The organic optoelectronic device of claim 13, wherein:

the at least one organic layer comprises a light emitting layer, and the light emitting layer comprises the compound for an organic optoelectronic device.

15. An organic optoelectronic device, comprising:

an anode and a cathode facing each other, and at least one organic layer disposed between the anode and the cathode, wherein:

the at least one organic layer includes a light emitting layer and a hole transport auxiliary layer between the anode and the light emitting layer, and the hole transport auxiliary layer includes a compound represented by Chemical Formula 1:

[Chemical Formula 1]

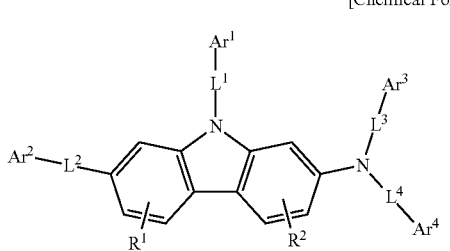

in Chemical Formula 1,

Ar$^1$ and Ar$^2$ are independently a substituted or unsubstituted C6 to C12 aryl group, Ar$^3$ and Ar$^4$ are independently a substituted or unsubstituted C6 to C30 aryl group, L$^1$ is a single bond or a phenylene group, L$^2$ to L$^4$ are independently a single bond or a substituted or unsubstituted C6 to C12 arylene group, and R$^1$ and R$^2$ are independently hydrogen, deuterium, a cyano group, or a substituted or unsubstituted C1 to C10 alkyl group.

16. A display device comprising the organic optoelectronic device of claim 13.

17. The organic optoelectronic device of claim 16, wherein the first compound for an organic optoelectronic device and the second compound for an organic optoelectronic device are phosphorescent hosts of the light emitting layer.

18. An organic optoelectronic device, comprising:
an anode and a cathode facing each other, and
at least one organic layer disposed between the anode and the cathode,
wherein the organic layer comprises the composition for an organic optoelectronic device of claim 6.

19. A display device comprising the organic optoelectronic device of claim 18.

* * * * *